US009951125B2

(12) United States Patent
Barghorn et al.

(10) Patent No.: US 9,951,125 B2
(45) Date of Patent: *Apr. 24, 2018

(54) Aβ CONFORMER SELECTIVE ANTI-Aβ GLOBULOMER MONOCLONAL ANTIBODIES

(71) Applicants: ABBVIE INC., North Chicago, IL (US); ABBVIE DEUTSCHLAND GMBH & CO. KG, Wiesbaden (DE)

(72) Inventors: Stefan Barghorn, Mannheim (DE); Heinz Hillen, Hassloch (DE); Andreas R. Striebinger, Speyer (DE); Boris Labkovsky, Wales, MA (US); Ulrich Ebert, Mannheim (DE); Patrick Keller, Darmstadt (DE)

(73) Assignees: ABBVIE INC., North Chicago, IL (US); ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,739

(22) Filed: May 16, 2016

(65) Prior Publication Data
US 2016/0326238 A1  Nov. 10, 2016

Related U.S. Application Data

(62) Division of application No. 14/513,837, filed on Oct. 14, 2014, now Pat. No. 9,394,360, which is a division of application No. 13/102,713, filed on May 6, 2011, now Pat. No. 8,877,190, which is a division of application No. 11/945,124, filed on Nov. 26, 2007, now Pat. No. 8,455,626.

(60) Provisional application No. 60/872,156, filed on Nov. 30, 2006.

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *C07K 2317/10* (2013.01); *C07K 2317/14* (2013.01); *C07K 2317/24* (2013.01); *C07K 2317/34* (2013.01); *C07K 2317/565* (2013.01); *C07K 2317/92* (2013.01); *G01N 2800/2821* (2013.01)

(58) Field of Classification Search
CPC .............. C07K 16/18; C07K 2317/10; C07K 2317/14; C07K 2317/24; C07K 2317/34; C07K 2317/56; C07K 2317/565; C07K 2317/92; G01N 33/6896; G01N 2800/2821
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,526,039 A | 7/1985 | Ceccon et al. |
| 4,582,788 A | 4/1986 | Erlich |
| 4,634,665 A | 1/1987 | Axel et al. |
| 4,666,829 A | 5/1987 | Glenner et al. |
| 4,683,194 A | 7/1987 | Saiki et al. |
| 4,683,202 A | 7/1987 | Mullis |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,107,065 A | 4/1992 | Shewmaker et al. |
| 5,128,326 A | 7/1992 | Balazs et al. |
| 5,134,062 A | 7/1992 | Blass |
| 5,168,062 A | 12/1992 | Stinski |
| 5,179,017 A | 1/1993 | Axel et al. |
| 5,218,100 A | 6/1993 | Mueller-Hill et al. |
| 5,223,409 A | 6/1993 | Ladner et al. |
| 5,225,539 A | 7/1993 | Winter |
| 5,231,000 A | 7/1993 | Majocha et al. |
| 5,231,020 A | 7/1993 | Jorgensen et al. |
| 5,231,170 A | 7/1993 | Averback |
| 5,234,814 A | 8/1993 | Card et al. |
| 5,258,498 A | 11/1993 | Huston et al. |
| 5,262,332 A | 11/1993 | Selkoe |
| 5,290,540 A | 3/1994 | Prince et al. |
| 5,403,484 A | 4/1995 | Ladner et al. |

(Continued)

FOREIGN PATENT DOCUMENTS

| | | |
|---|---|---|
| AU | 2007200047 A1 | 1/2007 |
| CA | 2541522 A1 | 9/2007 |

(Continued)

OTHER PUBLICATIONS

Britschgi M et al. Neuroprotective natural antibodies to assemblies of amyloidogenic peptides decrease with normal aging and advancing Alzheimer's disease. Proc. Natl. Acad. Sci. USA, 2009, 106(29):12145-12150.*
Acha-Orbea H., "Anti-T-Cell Receptor V Beta Antibodies in Autoimmunity," Immunology series, 1993, vol. 59, pp. 193-202.
Aisen P.S., "The Development of Anti-Amyloid Therapy for Alzheimer's Disease : From Secretase Modulators to Polymerisation Inhibitors," CNS Drugs, 2005, vol. 19 (12), pp. 989-996.
Albert S.E., et al., "Time-Dependent Induction of Protective Anti-Influenza Immune Responses in Human Peripheral Blood Lymphocyte/SCID Mice," Journal of Immunology, 1997, vol. 159 (3), pp. 1393-1403.

(Continued)

*Primary Examiner* — Kimberly Ballard
(74) *Attorney, Agent, or Firm* — Neal, Gerber & Eisenberg LLP

(57) ABSTRACT

The subject invention relates to monoclonal antibodies that may be used in the treatment and diagnosis of Alzheimer's Disease. In particular, the present invention relates to monoclonal antibodies referred to as 10F4 and 3C5 and to other monoclonal antibodies (e.g., murine, human or humanized) having similar properties thereto.

19 Claims, 16 Drawing Sheets

(56) References Cited

U.S. PATENT DOCUMENTS

| | | |
|---|---|---|
| 5,427,908 A | 6/1995 | Dower et al. |
| 5,441,870 A | 8/1995 | Seubert et al. |
| 5,455,169 A | 10/1995 | Mullan |
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,665,355 A | 9/1997 | Primi |
| 5,679,377 A | 10/1997 | Bernstein et al. |
| 5,679,531 A | 10/1997 | Koenig et al. |
| 5,693,753 A | 12/1997 | Koenig et al. |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Koenig et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Krafft et al. |
| 6,284,221 B1 | 9/2001 | Schenk et al. |
| 6,287,793 B1 | 9/2001 | Schenk et al. |
| 6,294,171 B2 | 9/2001 | McMichael |
| 6,309,892 B1 | 10/2001 | Averback |
| 6,323,218 B1 | 11/2001 | Bush et al. |
| 6,333,034 B1 | 12/2001 | Gupta-Bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk et al. |
| 6,761,888 B1 | 7/2004 | Schenk |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler et al. |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B2 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La Monte et al. |
| 7,238,488 B2 | 7/2007 | Maresh et al. |
| 7,238,788 B2 | 7/2007 | Lee |
| 7,247,301 B2 | 7/2007 | Van De Winkel et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |
| 7,375,190 B2 | 5/2008 | Cheng et al. |
| 7,413,884 B2 | 8/2008 | Raso |

(56) References Cited

U.S. PATENT DOCUMENTS

| | | |
|---|---|---|
| 7,427,342 B2 | 9/2008 | Barber |
| 7,625,560 B2 | 12/2009 | Basi et al. |
| 7,772,375 B2 | 8/2010 | Greferath et al. |
| 7,892,544 B2 | 2/2011 | Pfeifer et al. |
| 7,902,328 B2 | 3/2011 | Hillen et al. |
| 2001/0029293 A1 | 10/2001 | Gallatin et al. |
| 2002/0009445 A1 | 1/2002 | Du et al. |
| 2002/0015941 A1 | 2/2002 | Kim et al. |
| 2002/0086014 A1 | 7/2002 | Korman et al. |
| 2002/0086847 A1 | 7/2002 | Chain |
| 2002/0094335 A1 | 7/2002 | Chalifour et al. |
| 2002/0132758 A1 | 9/2002 | Shell |
| 2002/0137134 A1 | 9/2002 | Gerngross |
| 2002/0162129 A1 | 10/2002 | Lannfelt et al. |
| 2002/0182644 A1 | 12/2002 | Diamandis |
| 2002/0182660 A1 | 12/2002 | Fong |
| 2002/0188106 A1 | 12/2002 | Mandelkow et al. |
| 2002/0197258 A1 | 12/2002 | Ghanbari et al. |
| 2003/0065141 A1 | 4/2003 | Carter et al. |
| 2003/0068316 A1 | 4/2003 | Klein et al. |
| 2003/0073655 A1 | 4/2003 | Chain |
| 2003/0077278 A1 | 4/2003 | Gallatin et al. |
| 2003/0077757 A1 | 4/2003 | Andrews |
| 2003/0086938 A1 | 5/2003 | Jensen et al. |
| 2003/0100011 A1 | 5/2003 | Jackowski et al. |
| 2003/0100058 A1 | 5/2003 | Roschke et al. |
| 2003/0108551 A1 | 6/2003 | Nicolau et al. |
| 2003/0114510 A1 | 6/2003 | Ingram et al. |
| 2003/0147882 A1 | 8/2003 | Solomon et al. |
| 2003/0148356 A1 | 8/2003 | Cruts et al. |
| 2003/0157117 A1 | 8/2003 | Rasmussen et al. |
| 2003/0180722 A1 | 9/2003 | Godbole et al. |
| 2003/0185826 A1 | 10/2003 | Tobinick |
| 2003/0185827 A1 | 10/2003 | Rodriguez et al. |
| 2003/0186333 A1 | 10/2003 | Loring et al. |
| 2003/0186374 A1 | 10/2003 | Hufton et al. |
| 2003/0190689 A1 | 10/2003 | Crosby et al. |
| 2003/0194403 A1 | 10/2003 | Van De Winkel et al. |
| 2003/0195347 A1 | 10/2003 | Baker et al. |
| 2003/0228307 A1 | 12/2003 | Ramakrishnan et al. |
| 2003/0229907 A1 | 12/2003 | Hsiao et al. |
| 2003/0232758 A1 | 12/2003 | St. George-Hyslop et al. |
| 2004/0013647 A1 | 1/2004 | Solomon et al. |
| 2004/0013680 A1 | 1/2004 | Bush et al. |
| 2004/0018590 A1 | 1/2004 | Gerngross et al. |
| 2004/0043418 A1 | 3/2004 | Holtzman et al. |
| 2004/0053371 A1 | 3/2004 | Maresh et al. |
| 2004/0058414 A1 | 3/2004 | Queen et al. |
| 2004/0081657 A1 | 4/2004 | Schenk |
| 2004/0116337 A1 | 6/2004 | Kapurniotu et al. |
| 2004/0127471 A1 | 7/2004 | Reisberg |
| 2004/0138296 A1 | 7/2004 | Robertson et al. |
| 2004/0142872 A1 | 7/2004 | Poduslo et al. |
| 2004/0146512 A1 | 7/2004 | Rosenthal et al. |
| 2004/0157267 A1 | 8/2004 | Huang |
| 2004/0157779 A1 | 8/2004 | Schenk |
| 2004/0166119 A1 | 8/2004 | Schenk |
| 2004/0170641 A1 | 9/2004 | Schenk |
| 2004/0175394 A1 | 9/2004 | Schenk |
| 2004/0185039 A1 | 9/2004 | Kohler et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0223970 A1 | 11/2004 | Afar et al. |
| 2004/0228865 A1 | 11/2004 | Schenk |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265308 A1 | 12/2004 | Schenk |
| 2004/0265919 A1 | 12/2004 | Vanderstichele et al. |
| 2005/0009110 A1 | 1/2005 | Chang |
| 2005/0014821 A1 | 1/2005 | Tsai et al. |
| 2005/0019330 A1 | 1/2005 | Schenk |
| 2005/0019343 A1 | 1/2005 | Schenk |
| 2005/0031651 A1 | 2/2005 | Gervais et al. |
| 2005/0037026 A1 | 2/2005 | Schenk |
| 2005/0042664 A1 | 2/2005 | Wu et al. |
| 2005/0048584 A1 | 3/2005 | Lamping et al. |
| 2005/0053614 A1 | 3/2005 | Schenk |
| 2005/0057813 A1 | 3/2005 | Hasei et al. |
| 2005/0059591 A1 | 3/2005 | Schenk et al. |
| 2005/0059802 A1 | 3/2005 | Schenk et al. |
| 2005/0090439 A1 | 4/2005 | Chalifour et al. |
| 2005/0112543 A1 | 5/2005 | Bush et al. |
| 2005/0118651 A1 | 6/2005 | Basi et al. |
| 2005/0123544 A1 | 6/2005 | Schenk et al. |
| 2005/0124016 A1 | 6/2005 | Ladu et al. |
| 2005/0129691 A1 | 6/2005 | Gerlai |
| 2005/0129695 A1 | 6/2005 | Mercken et al. |
| 2005/0142131 A1 | 6/2005 | Hinton et al. |
| 2005/0142132 A1 | 6/2005 | Schenk et al. |
| 2005/0147613 A1 | 7/2005 | Raso |
| 2005/0153381 A1 | 7/2005 | Marusich et al. |
| 2005/0163744 A1 | 7/2005 | Rasmussen et al. |
| 2005/0163788 A1 | 7/2005 | Schenk |
| 2005/0169925 A1 | 8/2005 | Bardroff et al. |
| 2005/0175626 A1 | 8/2005 | Delacourte et al. |
| 2005/0249725 A1 | 11/2005 | Schenk et al. |
| 2005/0249727 A1 | 11/2005 | Schenk |
| 2005/0255122 A1 | 11/2005 | Schenk |
| 2005/0272025 A1 | 12/2005 | Suo et al. |
| 2006/0008458 A1 | 1/2006 | Solomon |
| 2006/0029603 A1 | 2/2006 | Ellis et al. |
| 2006/0029611 A1 | 2/2006 | Schenk |
| 2006/0034858 A1 | 2/2006 | Schenk |
| 2006/0039906 A1 | 2/2006 | Holtzman et al. |
| 2006/0057646 A1 | 3/2006 | Wiltfang et al. |
| 2006/0057701 A1 | 3/2006 | Rosenthal et al. |
| 2006/0057702 A1 | 3/2006 | Rosenthal et al. |
| 2006/0062786 A1 | 3/2006 | Salcedo et al. |
| 2006/0073149 A1 | 4/2006 | Bales et al. |
| 2006/0099211 A1 | 5/2006 | Monthe et al. |
| 2006/0104968 A1 | 5/2006 | Bookbinder et al. |
| 2006/0105394 A1 | 5/2006 | Pomara |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0141541 A1 | 6/2006 | McIntyre |
| 2006/0160161 A1 | 7/2006 | Pavliakova et al. |
| 2006/0165682 A1 | 7/2006 | Basi et al. |
| 2006/0166275 A1 | 7/2006 | Krafft et al. |
| 2006/0166311 A1 | 7/2006 | Okochi et al. |
| 2006/0188505 A1 | 8/2006 | Skurkovich et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0234947 A1 | 10/2006 | Gazit |
| 2006/0240007 A1 | 10/2006 | Sanders |
| 2006/0241038 A1 | 10/2006 | Watanabe et al. |
| 2006/0246075 A1 | 11/2006 | Mercken et al. |
| 2006/0257396 A1 | 11/2006 | Jacobsen |
| 2006/0257420 A1 | 11/2006 | Zimmerman |
| 2006/0257882 A1 | 11/2006 | Shimkets et al. |
| 2006/0280733 A1 | 12/2006 | Kayed et al. |
| 2006/0292152 A1 | 12/2006 | Rosenthal et al. |
| 2007/0009931 A1 | 1/2007 | Kirsch |
| 2007/0010435 A1 | 1/2007 | Frangione et al. |
| 2007/0010657 A1 | 1/2007 | Klocke et al. |
| 2007/0015217 A1 | 1/2007 | Durham et al. |
| 2007/0015218 A1 | 1/2007 | Cao et al. |
| 2007/0021345 A1 | 1/2007 | Gazit |
| 2007/0031416 A1 | 2/2007 | Shoji et al. |
| 2007/0036789 A1 | 2/2007 | Chung et al. |
| 2007/0036794 A1 | 2/2007 | Devaux et al. |
| 2007/0042424 A1 | 2/2007 | Ebinuma et al. |
| 2007/0048312 A1 | 3/2007 | Klein et al. |
| 2007/0071675 A1 | 3/2007 | Wu et al. |
| 2007/0072307 A1 | 3/2007 | Godavarti et al. |
| 2007/0081998 A1 | 4/2007 | Kinney et al. |
| 2007/0082350 A1 | 4/2007 | Landfield et al. |
| 2007/0086994 A1 | 4/2007 | Wallach et al. |
| 2007/0098721 A1 | 5/2007 | Hillen et al. |
| 2007/0105092 A1 | 5/2007 | Paul et al. |

(56) References Cited

U.S. PATENT DOCUMENTS

| | | |
|---|---|---|
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |
| 2007/0134247 A9 | 6/2007 | Solomon |
| 2007/0135337 A2 | 6/2007 | Chalifour et al. |
| 2007/0140966 A1 | 6/2007 | Chang et al. |
| 2007/0148167 A1 | 6/2007 | Strohl |
| 2007/0160616 A1 | 7/2007 | Rosenthal et al. |
| 2007/0167522 A1 | 7/2007 | Imawaka et al. |
| 2007/0190046 A1 | 8/2007 | DeMaattos et al. |
| 2007/0196367 A1 | 8/2007 | Dinu |
| 2007/0213512 A1 | 9/2007 | Krafft et al. |
| 2007/0218069 A1 | 9/2007 | Gordon et al. |
| 2007/0218499 A1 | 9/2007 | Lambert et al. |
| 2007/0231331 A1 | 10/2007 | Dewji et al. |
| 2007/0248606 A1 | 10/2007 | Lannfelt et al. |
| 2007/0264276 A1 | 11/2007 | Chalifour et al. |
| 2007/0280953 A1 | 12/2007 | Rosenberg et al. |
| 2007/0292410 A1 | 12/2007 | Cashman et al. |
| 2007/0292895 A1 | 12/2007 | Shi et al. |
| 2008/0009467 A1 | 1/2008 | Henderson |
| 2008/0014194 A1 | 1/2008 | Schenk et al. |
| 2008/0014596 A1 | 1/2008 | Jerecic et al. |
| 2008/0025988 A1 | 1/2008 | Yamaguchi et al. |
| 2008/0029911 A1 | 2/2008 | Jeon et al. |
| 2008/0044356 A1 | 2/2008 | Lesne et al. |
| 2008/0044406 A1 | 2/2008 | Johnson-Wood et al. |
| 2008/0051690 A1 | 2/2008 | Mattner et al. |
| 2008/0057053 A1 | 3/2008 | Stolen |
| 2008/0057593 A1 | 3/2008 | Vanderstichele et al. |
| 2008/0058276 A1 | 3/2008 | Lu et al. |
| 2008/0058330 A1 | 3/2008 | Paris et al. |
| 2008/0089885 A1 | 4/2008 | Smith et al. |
| 2008/0096818 A1 | 4/2008 | Schenk et al. |
| 2008/0107601 A1 | 5/2008 | Lauwereys et al. |
| 2008/0107649 A1 | 5/2008 | Zurbriggen |
| 2008/0113444 A1 | 5/2008 | Pray |
| 2008/0131422 A1 | 6/2008 | Sugimura et al. |
| 2008/0199879 A1 | 8/2008 | Takayama et al. |
| 2008/0220449 A1 | 9/2008 | Vasan et al. |
| 2008/0292639 A1 | 11/2008 | Shen et al. |
| 2008/0299111 A1 | 12/2008 | Delacourte et al. |
| 2009/0018084 A1 | 1/2009 | Krafft et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2010/0028333 A1 | 2/2010 | Getty et al. |
| 2010/0173828 A1 | 7/2010 | Hillen et al. |
| 2010/0209346 A1 | 8/2010 | Hillen et al. |
| 2011/0092445 A1 | 4/2011 | Barghorn et al. |
| 2011/0212109 A1 | 9/2011 | Barghorn et al. |
| 2011/0256138 A1 | 10/2011 | Barghorn et al. |
| 2011/0287005 A1 | 11/2011 | Hillen et al. |
| 2012/0034166 A1 | 2/2012 | Hillen et al. |

FOREIGN PATENT DOCUMENTS

| | | |
|---|---|---|
| CN | 1396183 A | 2/2003 |
| CN | 1446581 A | 10/2003 |
| CN | 1673369 A | 9/2005 |
| CN | 1721437 A | 1/2006 |
| CN | 1803842 A | 7/2006 |
| CN | 101058608 A | 10/2007 |
| CN | 101084909 A | 12/2007 |
| CN | 101152576 A | 4/2008 |
| DE | 19902550 A1 | 7/2000 |
| DE | 10055703 A1 | 5/2002 |
| DE | 10303974 A1 | 8/2004 |
| DE | 102004039326 A1 | 2/2006 |
| EP | 45665 A1 | 2/1982 |
| EP | 0050424 B1 | 9/1985 |
| EP | 50424 B1 | 9/1985 |
| EP | 0237362 A1 | 9/1987 |
| EP | 0239400 A2 | 9/1987 |
| EP | 285159 A1 | 10/1988 |
| EP | 341491 A2 | 11/1989 |
| EP | 0084796 B1 | 5/1990 |
| EP | 84796 B1 | 5/1990 |
| EP | 0368684 A1 | 5/1990 |
| EP | 391714 A2 | 10/1990 |
| EP | 411974 A1 | 2/1991 |
| EP | 415801 A1 | 3/1991 |
| EP | 237362 B1 | 3/1992 |
| EP | 0201184 B1 | 12/1992 |
| EP | 201184 B1 | 12/1992 |
| EP | 0519596 A1 | 12/1992 |
| EP | 229246 B1 | 8/1993 |
| EP | 368684 B1 | 3/1994 |
| EP | 0592106 A1 | 4/1994 |
| EP | 239400 B1 | 8/1994 |
| EP | 613007 A2 | 8/1994 |
| EP | 0623675 A1 | 11/1994 |
| EP | 557270 B1 | 5/1995 |
| EP | 519598 B1 | 6/1995 |
| EP | 440619 B1 | 1/1996 |
| EP | 304013 B1 | 6/1996 |
| EP | 589877 B1 | 11/1996 |
| EP | 0589877 B1 | 11/1996 |
| EP | 436597 B1 | 4/1997 |
| EP | 0436597 B1 | 4/1997 |
| EP | 258017 B1 | 6/1997 |
| EP | 783104 A1 | 7/1997 |
| EP | 444856 B1 | 9/1997 |
| EP | 816492 A1 | 1/1998 |
| EP | 592127 B1 | 4/1998 |
| EP | 0274826 B1 | 8/1998 |
| EP | 274826 B1 | 8/1998 |
| EP | 527839 B1 | 12/1998 |
| EP | 1038958 A1 | 9/2000 |
| EP | 1094080 A2 | 4/2001 |
| EP | 1130032 A1 | 9/2001 |
| EP | 1172378 A1 | 1/2002 |
| EP | 1176195 B1 | 1/2002 |
| EP | 877939 B1 | 6/2002 |
| EP | 683234 B1 | 5/2003 |
| EP | 1308461 A2 | 5/2003 |
| EP | 1408333 A2 | 4/2004 |
| EP | 1420032 A1 | 5/2004 |
| EP | 1270592 B1 | 9/2004 |
| EP | 1467212 A1 | 10/2004 |
| EP | 0592106 B1 | 11/2004 |
| EP | 1200470 B1 | 11/2004 |
| EP | 519596 B1 | 2/2005 |
| EP | 1538163 A2 | 6/2005 |
| EP | 1632242 A2 | 3/2006 |
| EP | 1092767 B1 | 10/2006 |
| EP | 1717250 A1 | 11/2006 |
| EP | 998495 B1 | 12/2006 |
| EP | 1731913 A2 | 12/2006 |
| EP | 1049712 B1 | 1/2007 |
| EP | 1741783 A1 | 1/2007 |
| EP | 1346041 B1 | 2/2007 |
| EP | 1752472 A2 | 2/2007 |
| EP | 1592476 B1 | 4/2007 |
| EP | 970203 B1 | 5/2007 |
| EP | 1787998 A1 | 5/2007 |
| EP | 948536 B1 | 6/2007 |
| EP | 1160256 B1 | 6/2007 |
| EP | 1379546 B1 | 6/2007 |
| EP | 1792991 A1 | 6/2007 |
| EP | 1842859 A2 | 10/2007 |
| EP | 1861422 A2 | 12/2007 |
| EP | 1878751 A2 | 1/2008 |

(56) References Cited

FOREIGN PATENT DOCUMENTS

| | | |
|---|---|---|
| EP | 1434053 B1 | 3/2008 |
| EP | 1521831 B1 | 4/2008 |
| EP | 1778837 B1 | 4/2008 |
| EP | 1911765 A2 | 4/2008 |
| EP | 911398 B1 | 6/2008 |
| EP | 2009445 A1 | 12/2008 |
| EP | 1781644 B1 | 5/2009 |
| EP | 1623719 B1 | 7/2009 |
| EP | 1681566 B1 | 8/2009 |
| EP | 1861422 B1 | 2/2010 |
| EP | 1766396 B1 | 8/2010 |
| EP | 1720909 B1 | 11/2011 |
| EP | 1176195 B1 | 5/2013 |
| EP | 1976877 B1 | 1/2014 |
| FR | 2740454 A1 | 4/1997 |
| FR | 2741881 A1 | 6/1997 |
| GB | 1495159 A | 12/1977 |
| GB | 2371303 A | 7/2002 |
| GR | 1005016 B | 10/2005 |
| JP | S63240797 A | 10/1988 |
| JP | H04252195 A | 9/1992 |
| JP | H04320694 A | 11/1992 |
| JP | H07209295 A | 8/1995 |
| JP | H07209296 A | 8/1995 |
| JP | H07238096 A | 9/1995 |
| JP | H07309900 A | 11/1995 |
| JP | H08245700 A | 9/1996 |
| JP | H0967397 A | 3/1997 |
| JP | H1075781 A | 3/1998 |
| JP | H10210982 A | 8/1998 |
| JP | 2000050885 A | 2/2000 |
| JP | 2000354487 A | 12/2000 |
| JP | 2001231578 A | 8/2001 |
| JP | 2002040023 A | 2/2002 |
| JP | 2002253252 A | 9/2002 |
| JP | 2004107260 A | 4/2004 |
| JP | 2005185281 A | 7/2005 |
| JP | 2006166879 A | 6/2006 |
| JP | 2006213621 A | 8/2006 |
| JP | 2006265189 A | 10/2006 |
| JP | 2007077103 A | 3/2007 |
| JP | 2007300856 A | 11/2007 |
| JP | 2007319127 A | 12/2007 |
| JP | 2008096311 A | 4/2008 |
| KR | 100806914 B1 | 2/2008 |
| WO | WO-8803951 A1 | 6/1988 |
| WO | WO-8906689 A1 | 7/1989 |
| WO | WO-8907657 A1 | 8/1989 |
| WO | WO-9002809 A1 | 3/1990 |
| WO | WO-9005144 A1 | 5/1990 |
| WO | WO-9012870 A1 | 11/1990 |
| WO | WO-9014424 A1 | 11/1990 |
| WO | WO-9014430 A1 | 11/1990 |
| WO | WO-9014443 A1 | 11/1990 |
| WO | WO-9219244 A2 | 11/1990 |
| WO | WO-9105548 A1 | 5/1991 |
| WO | WO-9109967 A1 | 7/1991 |
| WO | WO-9110737 A1 | 7/1991 |
| WO | WO-9110741 A1 | 7/1991 |
| WO | WO-9117271 A1 | 11/1991 |
| WO | WO-9200969 A1 | 1/1992 |
| WO | WO-9201047 A1 | 1/1992 |
| WO | WO-9202551 A1 | 2/1992 |
| WO | WO-9209690 A2 | 6/1992 |
| WO | WO-9211018 A1 | 7/1992 |
| WO | WO-9215679 A1 | 9/1992 |
| WO | WO-9218619 A1 | 10/1992 |
| WO | WO-9220791 A1 | 11/1992 |
| WO | WO-9222324 A1 | 12/1992 |
| WO | WO-9301288 A1 | 1/1993 |
| WO | WO-9308302 A1 | 4/1993 |
| WO | WO-9311236 A1 | 6/1993 |
| WO | WO-9402602 A1 | 2/1994 |
| WO | WO-9417197 A1 | 8/1994 |
| WO | WO-9507707 A1 | 3/1995 |
| WO | WO-9511311 A1 | 4/1995 |
| WO | WO-9511994 A1 | 5/1995 |
| WO | WO-9515982 A2 | 6/1995 |
| WO | WO-9516787 A1 | 6/1995 |
| WO | WO-9520401 A1 | 8/1995 |
| WO | WO-9620218 A1 | 7/1996 |
| WO | WO-9620698 A2 | 7/1996 |
| WO | WO-9628187 A1 | 9/1996 |
| WO | WO-9633735 A1 | 10/1996 |
| WO | WO-9634096 A1 | 10/1996 |
| WO | WO-9639512 A2 | 12/1996 |
| WO | WO-9640731 A1 | 12/1996 |
| WO | WO-9708320 A1 | 3/1997 |
| WO | WO-9710505 A1 | 3/1997 |
| WO | WO-9718476 A1 | 5/1997 |
| WO | WO-9729131 A1 | 8/1997 |
| WO | WO-97029131 A1 | 8/1997 |
| WO | WO-9732572 A2 | 9/1997 |
| WO | WO-9744013 A1 | 11/1997 |
| WO | WO-9746678 A1 | 12/1997 |
| WO | WO-9805350 A1 | 2/1998 |
| WO | WO-9807850 A2 | 2/1998 |
| WO | WO-9813490 A2 | 4/1998 |
| WO | WO-9816654 A1 | 4/1998 |
| WO | WO-9822120 A1 | 5/1998 |
| WO | WO-9824893 A2 | 6/1998 |
| WO | WO-9828445 A1 | 7/1998 |
| WO | WO-9831346 A1 | 7/1998 |
| WO | WO-9831700 A1 | 7/1998 |
| WO | WO-9833815 A1 | 8/1998 |
| WO | WO-9841201 A1 | 9/1998 |
| WO | WO-9847343 A2 | 10/1998 |
| WO | WO-98047343 A2 | 10/1998 |
| WO | WO-9849286 A1 | 11/1998 |
| WO | WO-9850433 A2 | 11/1998 |
| WO | WO-9851793 A1 | 11/1998 |
| WO | WO-9905175 A2 | 2/1999 |
| WO | WO-9909150 A1 | 2/1999 |
| WO | WO-9912870 A1 | 3/1999 |
| WO | WO-9913908 A1 | 3/1999 |
| WO | WO-9915154 A1 | 4/1999 |
| WO | WO-9920253 A1 | 4/1999 |
| WO | WO-9922024 A1 | 5/1999 |
| WO | WO-9925044 A1 | 5/1999 |
| WO | WO-9927944 A1 | 6/1999 |
| WO | WO-9927949 A1 | 6/1999 |
| WO | WO-9933815 A1 | 7/1999 |
| WO | WO-9936569 A1 | 7/1999 |
| WO | WO-9940909 A1 | 8/1999 |
| WO | WO-9945031 A2 | 9/1999 |
| WO | WO-9945962 A1 | 9/1999 |
| WO | WO-9953049 A1 | 10/1999 |
| WO | WO-9955842 A1 | 11/1999 |
| WO | WO-9958157 A1 | 11/1999 |
| WO | WO-9958564 A1 | 11/1999 |
| WO | WO-9959571 A1 | 11/1999 |
| WO | WO-9962505 A1 | 12/1999 |
| WO | WO-9966903 A2 | 12/1999 |
| WO | WO-0009560 A2 | 2/2000 |
| WO | WO-2000017345 A1 | 3/2000 |
| WO | WO-2000018805 A1 | 4/2000 |
| WO | WO-2000029446 A1 | 5/2000 |
| WO | WO-0037504 A2 | 6/2000 |
| WO | WO-2000032805 A1 | 6/2000 |
| WO | WO-2000035939 A2 | 6/2000 |
| WO | WO-0056772 A1 | 9/2000 |
| WO | WO-0058344 A1 | 10/2000 |
| WO | WO-2000058344 A1 | 10/2000 |
| WO | WO-0077178 A1 | 12/2000 |
| WO | WO-0078807 A1 | 12/2000 |
| WO | WO-2000072870 A1 | 12/2000 |
| WO | WO-2000072876 A1 | 12/2000 |
| WO | WO-2000072880 A2 | 12/2000 |
| WO | WO-2000075328 A1 | 12/2000 |
| WO | WO-2000077178 A1 | 12/2000 |
| WO | WO-0110900 A2 | 2/2001 |
| WO | WO-0116364 A2 | 3/2001 |
| WO | WO-0118169 A2 | 3/2001 |
| WO | WO-2001018169 A2 | 3/2001 |

(56) References Cited

FOREIGN PATENT DOCUMENTS

| | | |
|---|---|---|
| WO | WO-0132712 A2 | 5/2001 |
| WO | WO-2001032712 A2 | 5/2001 |
| WO | WO-2001039796 A2 | 6/2001 |
| WO | WO-2001042306 A2 | 6/2001 |
| WO | WO-0162801 A2 | 8/2001 |
| WO | WO-2001062284 A2 | 8/2001 |
| WO | WO-2001068860 A1 | 9/2001 |
| WO | WO-0183525 A2 | 11/2001 |
| WO | WO-0185093 A2 | 11/2001 |
| WO | WO-2001083519 A1 | 11/2001 |
| WO | WO-2001090182 A2 | 11/2001 |
| WO | WO-2001098361 A2 | 12/2001 |
| WO | WO-0203911 A2 | 1/2002 |
| WO | WO-2002000245 A1 | 1/2002 |
| WO | WO 2002021141 A2 | 3/2002 |
| WO | WO-2002030980 A2 | 4/2002 |
| WO | WO-0236614 A2 | 5/2002 |
| WO | WO-2002034777 A1 | 5/2002 |
| WO | WO-2002036614 A2 | 5/2002 |
| WO | WO-0246237 A2 | 6/2002 |
| WO | WO-02055552 A2 | 7/2002 |
| WO | WO-02059155 A2 | 8/2002 |
| WO | WO-02062851 A1 | 8/2002 |
| WO | WO-02074240 A2 | 9/2002 |
| WO | WO-02081505 A2 | 10/2002 |
| WO | WO-02085922 A2 | 10/2002 |
| WO | WO-02088306 A2 | 11/2002 |
| WO | WO-02088307 A2 | 11/2002 |
| WO | WO-02094870 A2 | 11/2002 |
| WO | WO-02094985 A2 | 11/2002 |
| WO | WO-02096350 A2 | 12/2002 |
| WO | WO-02096937 A2 | 12/2002 |
| WO | WO-03000714 A2 | 1/2003 |
| WO | WO-03008626 A2 | 1/2003 |
| WO | WO-03014162 A1 | 2/2003 |
| WO | WO-03014329 A2 | 2/2003 |
| WO | WO-03015617 A2 | 2/2003 |
| WO | WO-03015691 A2 | 2/2003 |
| WO | WO-03015812 A2 | 2/2003 |
| WO | WO-03016466 A2 | 2/2003 |
| WO | WO-03016467 A2 | 2/2003 |
| WO | WO-2008022349 A2 | 2/2003 |
| WO | WO-03020212 A2 | 3/2003 |
| WO | WO-03028668 A2 | 4/2003 |
| WO | WO-03031475 A2 | 4/2003 |
| WO | WO-03035835 A2 | 5/2003 |
| WO | WO-03039467 A2 | 5/2003 |
| WO | WO-03045128 A2 | 6/2003 |
| WO | WO-03046012 A1 | 6/2003 |
| WO | WO-03047499 A2 | 6/2003 |
| WO | WO-03051374 A2 | 6/2003 |
| WO | WO-03070760 A2 | 8/2003 |
| WO | WO-03074004 A2 | 9/2003 |
| WO | WO-03074081 A1 | 9/2003 |
| WO | WO-03074569 A2 | 9/2003 |
| WO | WO-03074715 A2 | 9/2003 |
| WO | WO-03076455 A2 | 9/2003 |
| WO | WO-03077858 A2 | 9/2003 |
| WO | WO-03080672 A1 | 10/2003 |
| WO | WO-03089460 A1 | 10/2003 |
| WO | WO-03090772 A1 | 11/2003 |
| WO | WO-03091734 A1 | 11/2003 |
| WO | WO-03095429 A1 | 11/2003 |
| WO | WO-03100419 A1 | 12/2003 |
| WO | WO-03104437 A2 | 12/2003 |
| WO | WO-03105658 A2 | 12/2003 |
| WO | WO-2004001422 A2 | 12/2003 |
| WO | WO-2004003019 A2 | 1/2004 |
| WO | WO-2004003563 A2 | 1/2004 |
| WO | WO-2004006861 A2 | 1/2004 |
| WO | WO-2004009776 A2 | 1/2004 |
| WO | WO-2004011674 A1 | 2/2004 |
| WO | WO-2004011943 A1 | 2/2004 |
| WO | WO-2004013172 A2 | 2/2004 |
| WO | WO-2004014296 A2 | 2/2004 |
| WO | WO-2004014367 A2 | 2/2004 |
| WO | WO-2004016282 A1 | 2/2004 |
| WO | WO-2004016655 A1 | 2/2004 |
| WO | WO-2004018997 A2 | 3/2004 |
| WO | WO-2004019045 A2 | 3/2004 |
| WO | WO-2004024090 A2 | 3/2004 |
| WO | WO-2004029093 A2 | 4/2004 |
| WO | WO-2004029630 A1 | 4/2004 |
| WO | WO-2004031241 A1 | 4/2004 |
| WO | WO-2004031400 A2 | 4/2004 |
| WO | WO-2004032868 A2 | 4/2004 |
| WO | WO-2004033397 A2 | 4/2004 |
| WO | WO-2004038411 A2 | 5/2004 |
| WO | WO-2004041067 A2 | 5/2004 |
| WO | WO-2004043989 A2 | 5/2004 |
| WO | WO-2004044204 A2 | 5/2004 |
| WO | WO-2006047254 A1 | 5/2004 |
| WO | WO-2004045525 A2 | 6/2004 |
| WO | WO-2004050707 A2 | 6/2004 |
| WO | WO-2004050850 A2 | 6/2004 |
| WO | WO 2004050876 A1 | 6/2004 |
| WO | WO-2004056318 A2 | 7/2004 |
| WO | WO-2004058239 A1 | 7/2004 |
| WO | WO-2004058258 A1 | 7/2004 |
| WO | WO-2004058820 A1 | 7/2004 |
| WO | WO-2004062556 A2 | 7/2004 |
| WO | WO-04067561 A1 | 8/2004 |
| WO | WO-2004065419 A1 | 8/2004 |
| WO | WO-2004065569 A2 | 8/2004 |
| WO | WO-2004067561 A1 | 8/2004 |
| WO | WO-2004068931 A2 | 8/2004 |
| WO | WO-2004069182 A2 | 8/2004 |
| WO | WO-2004071408 A2 | 8/2004 |
| WO | WO-2004072286 A1 | 8/2004 |
| WO | WO-04078140 A2 | 9/2004 |
| WO | WO-2004074837 A1 | 9/2004 |
| WO | WO-2004078140 A2 | 9/2004 |
| WO | WO-04090544 A2 | 10/2004 |
| WO | WO-2004085712 A2 | 10/2004 |
| WO | WO-2004087733 A2 | 10/2004 |
| WO | WO-2004087735 A2 | 10/2004 |
| WO | WO-2004095031 A1 | 11/2004 |
| WO | WO-2004098631 A1 | 11/2004 |
| WO | WO-2004104597 A1 | 12/2004 |
| WO | WO-2004108895 A2 | 12/2004 |
| WO | WO-2004111250 A1 | 12/2004 |
| WO | WO-2005000897 A2 | 1/2005 |
| WO | WO-2005005638 A2 | 1/2005 |
| WO | WO-2005011599 A2 | 2/2005 |
| WO | WO-2005012330 A2 | 2/2005 |
| WO | WO-2005014618 A2 | 2/2005 |
| WO | WO-2005016236 A2 | 2/2005 |
| WO | WO-05028511 A2 | 3/2005 |
| WO | WO-2005018424 A2 | 3/2005 |
| WO | WO-2005018536 A2 | 3/2005 |
| WO | WO-2005025516 A2 | 3/2005 |
| WO | WO-2005025592 A2 | 3/2005 |
| WO | WO-2005025616 A1 | 3/2005 |
| WO | WO-2005026360 A1 | 3/2005 |
| WO | WO-2005027965 A1 | 3/2005 |
| WO | WO-05037209 A2 | 4/2005 |
| WO | WO-2005033145 A2 | 4/2005 |
| WO | WO-05041650 A1 | 5/2005 |
| WO | WO-2005040212 A2 | 5/2005 |
| WO | WO-2005044306 A2 | 5/2005 |
| WO | WO-2005046605 A2 | 5/2005 |
| WO | WO-2005047484 A2 | 5/2005 |
| WO | WO-2005047860 A2 | 5/2005 |
| WO | WO-2005051998 A2 | 6/2005 |
| WO | WO-2005052002 A2 | 6/2005 |
| WO | WO-2005053604 A2 | 6/2005 |
| WO | WO-2005058815 A2 | 6/2005 |
| WO | WO-2005058940 A2 | 6/2005 |
| WO | WO-2005070965 A2 | 8/2005 |
| WO | WO-2005072777 A2 | 8/2005 |
| WO | WO-2005080986 A1 | 9/2005 |
| WO | WO-2005081872 A2 | 9/2005 |
| WO | WO-2005090971 A1 | 9/2005 |
| WO | WO-2005095457 A2 | 10/2005 |

(56) References Cited

FOREIGN PATENT DOCUMENTS

| | | |
|---|---|---|
| WO | WO-2005096730 A2 | 10/2005 |
| WO | WO-2005100584 A2 | 10/2005 |
| WO | WO-2005105841 A2 | 11/2005 |
| WO | WO-2005105847 A2 | 11/2005 |
| WO | WO-2005105998 A1 | 11/2005 |
| WO | WO-2005108378 A2 | 11/2005 |
| WO | WO-2005110056 A2 | 11/2005 |
| WO | WO-05123775 A1 | 12/2005 |
| WO | WO-2005120571 A2 | 12/2005 |
| WO | WO-2005123776 A1 | 12/2005 |
| WO | WO-2006005588 A1 | 1/2006 |
| WO | WO-2006005707 A2 | 1/2006 |
| WO | WO-2006014478 A1 | 2/2006 |
| WO | WO-2006014638 A2 | 2/2006 |
| WO | WO-2006015976 A1 | 2/2006 |
| WO | WO-2006016644 A1 | 2/2006 |
| WO | WO-2006033688 A2 | 3/2006 |
| WO | WO-06037604 A1 | 4/2006 |
| WO | WO-2006036291 A2 | 4/2006 |
| WO | WO-2006038729 A1 | 4/2006 |
| WO | WO-2006039327 A2 | 4/2006 |
| WO | WO-2006039470 A2 | 4/2006 |
| WO | WO-2006040153 A2 | 4/2006 |
| WO | WO-2006041934 A2 | 4/2006 |
| WO | WO-2006047670 A2 | 5/2006 |
| WO | WO-2006050041 A2 | 5/2006 |
| WO | WO-2006050667 A1 | 5/2006 |
| WO | WO-2006052924 A2 | 5/2006 |
| WO | WO-2006053428 A1 | 5/2006 |
| WO | WO-2006055178 A2 | 5/2006 |
| WO | WO-06066049 A2 | 6/2006 |
| WO | WO-06066171 A1 | 6/2006 |
| WO | WO-2006066089 A1 | 6/2006 |
| WO | WO-2006066118 A2 | 6/2006 |
| WO | WO-2006066171 A1 | 6/2006 |
| WO | WO-2006066233 A1 | 6/2006 |
| WO | WO-2006067792 A2 | 6/2006 |
| WO | WO-2006069081 A2 | 6/2006 |
| WO | WO-2006069202 A2 | 6/2006 |
| WO | WO-2006081171 A1 | 8/2006 |
| WO | WO-2006083533 A2 | 8/2006 |
| WO | WO-2006083689 A2 | 8/2006 |
| WO | WO-2006087550 A2 | 8/2006 |
| WO | WO-2006094192 A2 | 9/2006 |
| WO | WO-2006094724 A2 | 9/2006 |
| WO | WO-2006095041 A1 | 9/2006 |
| WO | WO-2006096529 A2 | 9/2006 |
| WO | WO-2006096653 A2 | 9/2006 |
| WO | WO-2006099543 A2 | 9/2006 |
| WO | WO-2006100679 A2 | 9/2006 |
| WO | WO-2006103116 A1 | 10/2006 |
| WO | WO-2006110748 A2 | 10/2006 |
| WO | WO-06121656 A2 | 11/2006 |
| WO | WO-06128163 A2 | 11/2006 |
| WO | WO-2006116369 A2 | 11/2006 |
| WO | WO-2006118959 A2 | 11/2006 |
| WO | WO-2006119449 A2 | 11/2006 |
| WO | WO-2006125830 A2 | 11/2006 |
| WO | WO-2006133164 A2 | 12/2006 |
| WO | WO-2006137354 A1 | 12/2006 |
| WO | WO-2007005358 A2 | 1/2007 |
| WO | WO-2007005359 A1 | 1/2007 |
| WO | WO-2007008547 A2 | 1/2007 |
| WO | WO-2007011639 A2 | 1/2007 |
| WO | WO-2007011834 A2 | 1/2007 |
| WO | WO-2007017686 A2 | 2/2007 |
| WO | WO-2007019620 A1 | 2/2007 |
| WO | WO-2007021886 A2 | 2/2007 |
| WO | WO-2007022416 A2 | 2/2007 |
| WO | WO-2007040437 A1 | 4/2007 |
| WO | WO-2007042261 A2 | 4/2007 |
| WO | WO-2007047967 A2 | 4/2007 |
| WO | WO-2007047995 A2 | 4/2007 |
| WO | WO-2007050359 A2 | 5/2007 |
| WO | WO-2007053661 A2 | 5/2007 |
| WO | WO-2007059135 A2 | 5/2007 |
| WO | WO-2007059203 A2 | 5/2007 |
| WO | WO-2007062088 A1 | 5/2007 |
| WO | WO-2007062852 A2 | 6/2007 |
| WO | WO-2007064917 A2 | 6/2007 |
| WO | WO-2007064919 A2 | 6/2007 |
| WO | WO-2007064972 A2 | 6/2007 |
| WO | WO-2007067512 A2 | 6/2007 |
| WO | WO-2007068411 A2 | 6/2007 |
| WO | WO-2007068412 A2 | 6/2007 |
| WO | WO-2007068429 A1 | 6/2007 |
| WO | WO-2007082750 A1 | 7/2007 |
| WO | WO-2007068412 A3 | 8/2007 |
| WO | WO-2007088399 A1 | 8/2007 |
| WO | WO-2007088712 A1 | 8/2007 |
| WO | WO-2007090872 A2 | 8/2007 |
| WO | WO-2007092861 A2 | 8/2007 |
| WO | WO-2007096076 A2 | 8/2007 |
| WO | WO-2007097251 A1 | 8/2007 |
| WO | WO-2007098417 A2 | 8/2007 |
| WO | WO-2007103788 A2 | 9/2007 |
| WO | WO-2007106617 A2 | 9/2007 |
| WO | WO-2007108756 A1 | 9/2007 |
| WO | WO-2007109107 A2 | 9/2007 |
| WO | WO-2007109749 A2 | 9/2007 |
| WO | WO-2007112288 A2 | 10/2007 |
| WO | WO-2007113172 A2 | 10/2007 |
| WO | WO-2007118984 A1 | 10/2007 |
| WO | WO-2007119685 A1 | 10/2007 |
| WO | WO-2007123345 A1 | 11/2007 |
| WO | WO-2007125351 A1 | 11/2007 |
| WO | WO-2007127393 A2 | 11/2007 |
| WO | WO-2007127448 A2 | 11/2007 |
| WO | WO-2007129457 A1 | 11/2007 |
| WO | WO-2007144198 A2 | 12/2007 |
| WO | WO-2007149032 A1 | 12/2007 |
| WO | WO-2008002893 A2 | 1/2008 |
| WO | WO-2008008939 A2 | 1/2008 |
| WO | WO-2008011348 A2 | 1/2008 |
| WO | WO-2008012101 A1 | 1/2008 |
| WO | WO-2008015384 A1 | 2/2008 |
| WO | WO-2008021296 A2 | 2/2008 |
| WO | WO-2008027526 A1 | 3/2008 |
| WO | WO-2008028939 A1 | 3/2008 |
| WO | WO-2008030251 A1 | 3/2008 |
| WO | WO-2008030973 A2 | 3/2008 |
| WO | WO-2008031911 A1 | 3/2008 |
| WO | WO-2008045962 A2 | 4/2008 |
| WO | WO-2008047111 A1 | 4/2008 |
| WO | WO-2008051017 A1 | 5/2008 |
| WO | WO-2008051326 A2 | 5/2008 |
| WO | WO-2008057240 A2 | 5/2008 |
| WO | WO-2008060364 A2 | 5/2008 |
| WO | WO-2008061795 A2 | 5/2008 |
| WO | WO-2008064244 A2 | 5/2008 |
| WO | WO-2008067464 A2 | 6/2008 |
| WO | WO-2008070229 A2 | 6/2008 |
| WO | WO-2008071394 A1 | 6/2008 |
| WO | WO-2008084402 A2 | 7/2008 |
| WO | WO-2008104385 A1 | 9/2008 |
| WO | WO-2008104386 A2 | 9/2008 |
| WO | WO-2008107677 A2 | 9/2008 |
| WO | WO-2008110885 A2 | 9/2008 |
| WO | WO-2008122441 A2 | 10/2008 |
| WO | WO-2008124940 A1 | 10/2008 |
| WO | WO-2008129023 A2 | 10/2008 |
| WO | WO-2008130449 A2 | 10/2008 |
| WO | WO-2008131298 A2 | 10/2008 |
| WO | WO-2008134034 A1 | 11/2008 |
| WO | WO-2008143708 A2 | 11/2008 |
| WO | WO-2008150467 A1 | 12/2008 |
| WO | WO-2008150946 A1 | 12/2008 |
| WO | WO-2008150949 A1 | 12/2008 |
| WO | WO-2008156621 A1 | 12/2008 |
| WO | WO-2008156622 A1 | 12/2008 |
| WO | WO-2009008890 A1 | 1/2009 |
| WO | WO-2009008891 A1 | 1/2009 |
| WO | WO-2009009768 A2 | 1/2009 |
| WO | WO-2009044160 A1 | 4/2009 |

(56) References Cited

FOREIGN PATENT DOCUMENTS

| WO | WO-2009048537 A2 | 4/2009 |
|---|---|---|
| WO | WO-2009048538 A2 | 4/2009 |
| WO | WO-2009048539 A2 | 4/2009 |
| WO | WO-2009134711 A1 | 11/2009 |
| WO | WO-2010011947 A2 | 1/2010 |
| WO | WO-2010097012 A1 | 9/2010 |
| WO | WO-2012024187 A1 | 2/2012 |
| WO | WO-2005033142 A2 | 4/2014 |

OTHER PUBLICATIONS

Almquist R. G. et al., "Synthesis and biological activity of a ketomethylene analogue of a tripeptide inhibitor of angiotensin converting enzyme," J Med Chem, 1980, vol. 23, pp. 1392-1398.

Altschul S.F., et al., "Gapped BLAST and PSI-BLAST: A New Generation of Protein Database Search Programs," Nucleic Acids Research, 1997, 25 (17), 3389-3402.

Ames R.S., et al., "Conversion of Murine Fabs Isolated from a Combinatorial Phage Display Library to Full Length Immunoglobulins," Journal of Immunological Methods, 1995, vol. 184 (2), pp. 177-186.

Anderson D.H., et al., "Characterization of Beta Amyloid Assemblies in Drusen: The Deposits Associated With Aging and Age-Related Macular Degeneration," Experimental Eye Research, 2004, vol. 78 (2), pp. 243-256.

Arai K., et al., "An ELISA to Determine the Biodistribution of Human Monoclonal Antibody in Tumor-Xenografted SCID Mice," Journal of Immunological Methods, 1998, vol. 217 (1-2), pp. 79-85.

Ardaillou R., "An Ang II Antagonist Improves the Alzheimer's Disease of the Mouse," Medecine/Sciences, 2008, vol. 24 (1), pp. 41.

Arispe N., et al., "Alzheimer Disease Amyloid B Protein Forms Calcium Channels in Bilayer Membranes: Blockade by Tromethamine and Aluminum ," The Proceedings of the National Academy of Sciences of the United States of America, 1993, vol. 90, pp. 567-571.

Armstrong, J. et al., "Familial Alzheimer disease associated with A713T mutation in APP, XP004607340 ," Neuroscience Letters, Limerick, IE, vol. 370 (2-3), pp. 241-243, 2004.

Asakura K., et al., "P/Q-type Ca2+ Channelblocker Gama-agatoxin IVA Protects Againstbrain Injury After Focal Ischemia in Rats," Brain Research, 1997, vol. 776 (1-2), 140-145.

Asakura K., et al.,"Alpha-Eudesmol, a PA-type Ca2+ Channel Blocker, Inhibits Neurogenic Vasodilatation and Extravasation Following Electrical Stimulation of Trigeminal Ganglion," Brain Research, 2000, vol. 873 (1), 94-101.

Askanas V., et al., "Inclusion-Body Myositis: A Myodegenerative Conformational Disorder Associated with Abeta, Protein Misfolding, and Proteasome Inhibition," Neurology, 2006, vol. 66 (2 Suppl. 1), pp. S39-S48.

Askanas V., et al., "Molecular Pathology and Pathogenesis of Inclusion-Body Myositis," Microscopy Research and Technique, 2005, vol. 67 (3-4), pp. 114-120.

Askanas V., et al., "Proposed Pathogenetic Cascade of Inclusion-Body Myositis: Importance of Amyloid-Beta. Misfolded Proteins, Predisposing Genes, and Aging," Current Opinion in Rheumatology, 2003, vol. 15 (6), pp. 737-744.

Atherton et al., "The Fluorenylmethoxycarbonyl Amino Protecting Group," The Peptides: Analysis, Synthesis, Biology, 1987, vol. 9, Academic Press, pp. 1-38.

Ausubel, et al., Current Protocols in Molecular Biology, 1993, 6.3.1-6.3.6,2.10.1-2.10.1-2.10.16.

Ausubel et al., Current Protocols in Molecular Biology, 1993, Table of Contents.

Ausubel F.M., et al., "A Compendium of Methods from Current Protocols in Molecular Biology" in: Short Protocols in Molecular Biology, John Wiely & Sons, 1989, Table of Contents.

Ausubel F.M., et al., eds., Current Protocols in Molecular Biology, vol. 1, Green Publishing Associates, Inc., and John Wiley & Sons, Inc., 1989, pp. 6.3.1-6.3.6 and 2.10.3.

Ausubel F.M., et al., Eds., Short Protocols in Molecular Biology: A Compendium of Methods from Current Protocols in Molecular Biology, 3rd Edition, John Wiley and Sons, Inc., 1995, Table of Contents.

Author Guidelines, Journal of Neurochemistry, Version 13, Jun. 2012, 14 pages.

Auvynet C., et al., "Structural Requirements for Antimicrobial Versus Chemoattractant Activities for Dermaseptin S9," FEBS Journal, 2008, vol. 275 (16), pp. 4134-4151.

Awasthi A., et al., "Amloid-Beta Causes Apoptosis of Newronal Cells Via Caspase Cascade, which can be Prevented by Amyloid-Beta-Derived Short Peptides," Experimental Neurology, 2005, vol. 196 (2), pp. 282-289.

Azzazy H.M., et al., "Phage Display Technology: Clinical Applications and Recent Innovations," Clinical Biochemistry, 2002, vol. 35 (6), pp. 425-445.

Babcook J.S., et al., "A Novel Strategy for Generating Monoclonal Antibodies from Single, Isolated Lymphocytes Producing Antibodies of Defined Specificities," Proceedings of the National Academy of Sciences, 1996, vol. 93 (15), pp. 7843-7848.

Bagriantsev S., et al., "Modulation of Abeta42 Low-n Oligomerization Using a Novel Yeast Reporter System," BMC Biology, 2006, vol. 4:32.

Banker, G. A. & Cowan, W. M., Rat hippocampal neurons in dispersed cell culture, Brain Research, 1977, 126 (3), 397-425.

Barany G., et al., "Solid-Phase Peptide Synthesis," in the Peptides: Analysis, Synthesis, Biology, 1980, Academic Press, Gross editor, vol. 2, pp. 1-284.

Barbas C.F., et al., "Assembly of Combinatorial Antibody Libraries on Phage Surfaces: The Gene III Site," Proceedings of the National Academy of Sciences, 1991, vol. 88 (18), pp. 7978-7982.

Bard F., et al., "Epitope and Isotype Specificities of Antibodies to Beta-Amyloid Peptide for Protection against Alzheimer's Disease-Like Neuropathology," PNAS, Proceedings of the National Academy of Sciences, 2003, vol. 100 (4), pp. 2023-2028.

Bard F., et al., "Peripherally Administered Antibodies Against Amyloid Beta-Peptide Enter the Central Nervous System and Reduce Pathology in a Mouse Model of Alzheimer Disease.," Nature Medicine, 2000, vol. 6 (8), pp. 916-919.

Barghorn S., et al., "Abeta-Oligomer Selective Antibody A-887755 Exhibits a Favorable Profile for Alzheimer's Disease Immunotherapy Compared to Abeta-Peptide Unselective Antibodies," Alzheimer's & Dementia: The Journal of the Alzheimer's & Association, 2009, vol. 5 (4), pp. P424.

Barghorn S., et al., "Globular Amyloid [beta7-peptidel-42 oligorner—A Homogenous and Stable Neuropathological Protein in Alzheimer's Disease.," Journal of Neurochemistry, 2005, vol. 95 (3), pp. 834-847.

Barrow C.J., et al., "Solution Conformations and Aggregational Properties of Synthetic Amyloid Beta-Peptides of Alzheimer's Disease. Analysis of Circular Dichroism Spectra," Journal of Molecular Biology, 1992, vol. 225 (4), pp. 1075-1093.

Bartolini M., et al., "Insight into the Kinetic of Amyloid Beta (1-42) Peptide Self-Aggregation: Elucidation of Inhibitors' Mechanism of Action," Chembiochem, 2007, vol. 8 (17), pp. 2152-2161.

Bateman D., et al., "Specific Binding of Alzheimer Amyloid Peptides to the Cell Surface Implicates the Presence of a Membrane Receptor," Neurobiol. of Aging, 2004, 9th International Conference on Alzheimers Disease and Related Disorders, Philadelphia, PA, Jul. 17-22, 2004.

Bateman R.J., et al., "Human Amyloid-Beta Synthesis and Clearance Rates as Measured in Cerebrospinal Fluid In Vivo," Nature Medicine, 2006, vol. 12 (7), pp. 856-861.

Bates K.A., et al., "Clearance Mechanisms of Alzheimer's Amyloid-Beta Peptide: Implications for Therapeutic Design and Diagnostic Tests," Molecular Psychiatry, 2009, vol. 14 (5), pp. 469-486.

Bayer T.A., et al., "Review on the APP/PS1KI Mouse Model: Intraneuronal Abeta Accumulation Triggers Axonopathy, Neuron Loss and Working Memory Impairment," Genes, Brain and Behavior, 2008, vol. 7 (Suppl 1), pp. 6-11.

(56) References Cited

OTHER PUBLICATIONS

Bedzyk W.D., et al., "Active Site Structure and Antigen Binding Properties of Idiotypically Cross-Reactive Anti-Fluorescein Monoclonal Antibodies," The Journal of Biological Chemistry, 1990, vol. 265 (1), pp. 133-138.
Bell K.A., et al., "MAPK Recruitment by Beta-Amyloid in Organotypid Hippocampal Slice Cultures Depends on Physical State and Exposure Time," Journal of Neurochemistry , 2004, vol. 91 (2), pp. 349-361.
Belokon Y. N. et al., "Improved Procedures for the Synthesis of (S)-24n-(N'-Benzyl-Prolyl)Amino]Benzophenoe (Bpb) and Ni(II) Complexes of Schiff S Bases Derived from BPB and Amino Acida," Tetrahedron: Asymmetry, 1998, vol. 9, pp. 4249-4252.
Bendig M.M., "Humanization of Rodent Monoclonal Antibodies by CDR Grafting," Methods: A Companion to Methods in Enzymology, 1995, vol. 8, pp. 83-93.
Benevenuti M., et al., "Crystallization of Soluble Proteins in Vapor Diffusion for X-Ray Crystallography," Nature Protocols, 2007, vol. 2 (7), pp. 1633-1651.
Bennett D.A., et al., "Immunization Therapy for Alzheimer Disease", Neurology, 2005, vol. 64, pp. 10-12.
Berman D.E., et al., "Oligomeric Amyloid-Beta Peptide Disrupts Phosphatidylinositol-4,5-Bisphosphate Metabolism," Nature Neuroscience, 2008, vol. 11 (5), pp. 547-554.
Bernstein S.L., et al., "Amyloid Beta-Protein: Monomer Structure and Early Aggregation States of Abeta42 and its Pro19 Alloform," Journal of the American Chemical Society, 2005, vol. 127 (7), pp. 2075-2084.
Bernstein S.L., et al., "Amyloid-β Protein Oligomerization and the Importance of Tetramers and Dodecamers in the Aetiology of Alzheimer's Disease," Nature Chemistry, 2009, vol. 1 (4), pp. 326-331.
Better M., et al. "*Escherichia coli* Secretion of an Active Chimeric Antibody Fragment," Science, 1988, vol. 240 (4855), pp. 1041-1043.
Bezprozvanny I., et al., "Neuronal Calcium Mishandling and the Pathogenesis of Alzheimer's Disease," Trends in Neurosciences, 2008, vol. 31 (9), pp. 454-463.
Bharadwaj P., et al., "A New Method to Measure Cellular Toxicity of Non-Fibrillar and Fibrillar Alzheimer's Abeta using Yeast," Journal of Alzheimer's Disease, 2008, vol. 13 (2), pp. 147-150.
Bhaskar K., et al., "The PI3K-Akt-mTOR Pathway Regulates Abeta Oligomer Induced Neuronal Cell Cycle Events," Molecular Neurodegeneration, 2009, vol. 4:14, 18 pages.
Bieniarz C. et al. , "Extended Length Heterobifunctional Coupling Agents for Protein Conjugations," Bioconjug chem, 1996, vol. 7 (1), pp. 88-95.
Bird R.E., et al., "Single-Chain Antigen-Binding Proteins," Science, 1988, vol. 242 (4877), pp. 423-426.
Birren B., et al., eds., Genome Analysis—A Laboratory Manual, vol. 1 & 2, Cold Spring Harbor Laboratory Press, 1998, Table of Contents.
Bitan G., et al., "A Molecular Switch in Amyloid Assembly: Met35 and Amyloid Beta-Protein Oligomerization," Journal of the American Chemical Society, 2003, vol. 125 (50), pp. 15359-15365.
Bitan G., et al., "Amyloid Beta-Protein (Abeta) Assembly: Abeta40 and Abeta42 Oligomerize Through Distinct Pathways ," The Proceedings of the National Academy of Sciences of the United States of America, 2003, vol. 100 (1), pp. 330-335.
Bitan G., et al., "Primary-Quaternary Structure Relationships Controlling Erarly ABeta Oligomerization" in: Peptide Revolution: Genomics, Proteomics & Therapeutics, Chorev M., et al., Eds., 18th American Peptide Symposium, 2003, pp. 765-767.
Bitan G., et al., "Towards Inhibition of Amyloid Beta-Protein Oligomerization," Biopolymers (2005) 80573, 19th American Peptide Symposium, San Diego, CA Jun. 18-23, 2005.
Bobich J.A., et al., "Incubation of Nerve Endings with a Physiological Concentration of Abeta1-42 Activates CaV2.2(N-Type)-Voltage Operated Calcium Channels and Acutely Increases Glutamate and Noradrenaline Release," Journal of Alzheimer's Disease, 2004, vol. 6 (3), pp. 243-255.
Bocher W.O., et al. "Antigen-specific B and T cells in Human/ mouse Radiation Chimera Following Immunization in Vivo," Immunology, 1999, vol. 96 (4), pp. 634-641.
Bombil F., et al., "A Promising Model of Primary Human Immunization in Human-Scid Mouse ," Immunobiology, 1996, vol. 195 (3), pp. 360-375.
Boridy S., et al., "The Binding of Pullulan Modified Cholesteryl Nanogels to Abeta Oligomers and their Suppression of Cytotoxicity," Biomaterials, 2009, vol. 30 (29), pp. 5583-5591.
Boss M.A., et al., "Genetically Engineered Antibodies," Immunology Today, 1985, vol. 6 (1), pp. 12-13.
Boutaud O., et al., "PGH2-Derived Levuglandin Adducts Increase the Neurotoxicity of Amyloid Beta1-42," Journal of Neurochemistry, 2006, vol. 96 (4), pp. 917-923.
Boutaud O., et al., "Prostaglandin H2 (PGH2) Accelerates Formation of Amyloid Beta1-42 Oligomers," Journal of Neurochemistry, 2002, vol. 82 (4), pp. 1003-1006.
Boyd-Kimball D., et al., "Neurotoxicity and Oxidative Stress in D1M-Substituted Alzheimer's a Beta(1-42): Relevance to N-Terminal Methionine Chemistry in Small Model Peptides," Peptides, 2005, vol. 26 (4), pp. 665-673.
Bravo R., et al., "Sulfated Polysaccharides Promote the Assembly of Amyloid Beta(1-42) Peptide into Stable Fibrils of Reduced Cytotoxicity," The Journal of Biological Chemistry, 2008, vol. 283 (47), pp. 32471-32483.
Brettschneider S., et al., "Decreased Serum Amyloid Beta(1-42) Autoantibody Levels in Alzheimer's Disease, Determined by a Newly Developed Immuno-Precipitation Assay with Radiolabeled Amyloid Beta(1-42) Peptide," Biological Psychiatry, 2005, vol. 57 (7), pp. 813-816.
Brinkley M. A., "A survey of methods for preparing protein conjugates with dyes, haptens and crosslinking reagents.," Bioconjugate Chem, 1992, vol. 3 , pp. 2-13.
Brinkmann U., et al., "Phage Display of Disulfide-stabilized Fv Fragments," Journal of Immunological Methods , 1995, vol. 182 (1), pp. 41-50.
Britschgi M., et al., "Neuroprotective natural antibodies to assemblies of amyloidogenic peptides decrease with normal aging and advancing Alzheimer's disease," Proceedings of the National Academy of Sciences, 2009, vol. 106 (29), pp. 12145-12150.
Brorson K., et al., "Mutational Analysis of Avidity and Fine Specificity of Anti-Levan Antibodies," The Journal of Immunology, 1999, vol. 163 (12), pp. 6694-6701.
Brown J.P., et al., "Protein Antigens of Normal and Malignant Human Cells Identified by Immunoprecipitatin with Monoclonal Antibodies ," The Journal of Biological Chemistry, 1980, vol. 255 (11), pp. 4980-4983.
Brown J.P., et al., "Structural Characterization of Human Melanoma-Associated Antigen p97 with Monoclonal Antibodies ," The Journal of Immunology, 1981, vol. 127 (2), pp. 539-546.
Brown M., et al., "Tolerance of Single, but not Multiple, Amino Acid Replacements in Antibody VH CDR 2: a means of Minimizing B Cell Wastage from Somatic Hypermutation?," Journal of Immunology, 1996, vol. 156 (9), pp. 3285-3291.
Brummell D.A., et al., "Probing the Combining Site of an Anti-Carbohydrate Antibody by Saturation-Mutagenesis: Role of the Heavy-Chain CDR3 Residues," Biochemistry, 1993, vol. 32 (4), pp. 1180-1187.
Brunger A.T., et al., "Crystallography & NMR System: A New Software Suite for Macromolecular Structure Determination," Acta Crystallographica Section D: Biological Crystallography, 1998, vol. 54 (Pt 5), pp. 905-921.
Brutlag, D., "Computational Molecular Biology Multiple Sequence Alignment," Departments of Biochemistry and Medicine standford University School of Medicine, 2007, pp. 1-54.
Buchwald H., et al., "Long-term, Continuous Intravenous Heparin Administration by an Implantable Infusion Pump in Ambulatory Patients with Recurrent Venous Thrombosis," Surgery, 1980, vol. 88 (4), pp. 507-516.

(56) References Cited

OTHER PUBLICATIONS

Buraei Z., et al., "Roscovitine Differentially Affects CaV2 and Kv Channels by Binding to the Open State," Neuropharmacology, 2007, vol. 52 (3), pp. 883-894.
Burks E.A., et al., "In Vitro Scanning Saturation Mutagenesis of an Antibody Binding Pocket," Proceedings of the National Academy of Sciences, 1997, vol. 94 (2), pp. 412-417.
Burton D.R., et al., "Human Antibodies from Combinatorial Libraries," Advances in Immunology, 1994, vol. 57, pp. 191-280.
Butler D., et al., "Cellular Responses to Protein Accumulation Involve Autophagy and Lysosomal Enzyme Activation," Rejuvenation Research, 2005, vol. 8 (4), pp. 227-237.
Campbell., Monoclonal Antibody Technology, 1984, pp. 1-32.
Carlsson J., et al., "Protein Thiolation and Reversible Protein-Protein Conjugation. N-Succinimidyl 3-(2-pyridyldithio)propionate, a New Heterobifunctional Reagent," Biochemical Journal, 1978, vol. 173 (3), pp. 723-737.
Carter D.A., et al., "More Missense in Amyloid Gene," Nature Genetics, 1992, vol. 2 (4), pp. 255-256.
Carter P., et al., "Humanization of an Anti-p185 HER2 Antibody for Human Cancer Therapy," Proceedings of the National Academy of Sciences, 1992, vol. 89 (10), pp. 4285-4289.
Casset, F., et al., "A Peptie Mimetic of an Anti-CD4 Monoclonal Antibody by Rational Design," Biochemical and Biophysical Research Communications, 2003, vol. 307 (1), pp. 198-205.
Catterall WA et al., International Union of Pharmacology. XLVIII. Nomenclature and structure-function relationships of voltage-gated calcium channels, Pharmacological reviews, 2005, 57 (4), 411-25.
Cecchini C., et al., "Increased Susceptibility to Amyloid Toxicity in Familial Alzheimer's Fibroblasts," Neurobiology of Aging, 2007, vol. 28 (6), pp. 863-876.
Cecchini M., et al., "A Molecular Dynamics Approach to the Structural Characterization of Amyloid Aggregation," Journal of Molecular Biology, 2006, vol. 357 (4), pp. 1306-1321.
Celli C.M., et al., "Origin and Pathogenesis of Antiphospholipid Antibodies," Brazilian Journal of Medical and Biological Research, 1998, vol. 31 (6), pp. 723-732.
Chacon M.A., et al., "Frizzled-1 is Involved in the Neuroprotective Effect of Wnt3a Against Abeta Oligomers," Journal of Cellular Physiology, 2008, vol. 217 (1), pp. 215-227.
Chaiken IM. , "Semisynthetic peptides and proteins," CRC Crit. Rev. Biochem, 1981, vol. 11 (3), pp. 255-301.
Chamat S., et al., "Human Monoclonal Antibodies Isolated from Spontaneous Epstein-Barr Virus-Transformed Tumors of Hu-SPL-SCID Mice and Specific for Fusion Protein Display Broad Neutralizing Activity Toward Respiratory Syncytial Virus," The Journal of Infectious Diseases, 1999, vol. 180 (2), pp. 268-277.
Chander H., et al., "Binding of Trypsin to Fibrillar Amyloid Beta-Protein," Brain Research, 2006, vol. 1082 (1), pp. 173-181.
Chang L., et al., "Femtomole Immunodetection of Synthetic and Endogenous Amyloid-Beta Oligomers and its Application to Alzheimer's Disease Drug Candidate Screening," Journal of Molecular Neuroscience, 2003, vol. 20 (3), pp. 305-313.
Chen C., "Beta-Amyloid Increases Dendritic Ca2+ Influx by Inhibiting the A-type K+ Current in Hippocampal CA1 Pyramidal Neurons," Biochemical and Biophysical Research Communications, 2005, vol. 338 (4), pp. 1913-1919.
Chen K., et al., "Cooperation Between NOD2 and Toll-like Receptor 2 Ligands in the Up-Regulation of Mouse mFPR2, a G-Protein-Coupled Abeta42 Peptide Receptor, in Microglial Cells," Journal of Leukocyte Biology, 2008, vol. 83 (6), pp. 1467-1475.
Chen Y., et al., "Selection and Analysis of an Optimized Anti-VEGF Antibody: Crystal Structure of an Affinity-Matured Fab in Complex with Antigen," Journal of Molecular Biology , 1999, vol. 293 (4), pp. 865-881.
Chen Y.R., et al., "Distinct Early Folding and Aggregation Properties of Alzheimer Amyloid-Beta Peptides Abeta40 and Abeta42: Stable Trimer or Tetramer Formation by Abeta42," The Journal of Biological Chemistry, 2006, vol. 281 (34), pp. 24414-24422.

Chiang H.C., et al., "Distinctive Roles of Different Beta-Amyloid 42 Aggregates in Modulation of Synaptic Functions," The FASEB Journal, 2009, vol. 23 (6), pp. 1969-1977.
Chiang P.K., et al., "The Many Faces of Amyloid Beta in Alzheimer's Disease," Current Molecular Medicine, 2008, vol. 8 (6), pp. 580-584.
Chiarini A., et al., "Calcium-Sensing Receptor (CaSR) in Human Brain's Pathophysiology: Roles in Late-Onset Alzheimer's Disease (LOAD)," Current Pharmaceutical Biotechnology, 2009, vol. 10 (3), pp. 317-326.
Choo-Smith L.P., et al., "The Interaction Between Alzheimer Amyloid Beta(1-40) Peptide and Ganglioside GM1-Containing Membranes," FEBS Letters, 1997, vol. 402 (2-3), pp. 95-98.
Chothia C., et al., "Canonical Structures for the Hypervariable Regions of Immunoglobulins," Journal of Molecular Biology , 1987, vol. 196 (4), pp. 901-917.
Chothia C., et al., "Conformations of Immunoglobulin Hypervariable Regions," Nature, 1989, vol. 342 (6252), pp. 877-883.
Chothia C., et al., "Structural Repertoire of the Human VH Segments," Journal of Molecular Biology, 1992, vol. 227 (3), pp. 799-817.
Chrisey La et al. , "Covalent attachment of synthetic DNA to self-assembled monolayer films," Nucleic Acids Res. , 1996, vol. 24(15), pp. 3031-3039.
Christensen D.D., "Changing the Course of Alzheimer's Disease: Anti-Amyloid Disease-Modifying Treatments on the Horizon," Primary Care Companion to the Journal of Clinical Psychiatry, 2007, vol. 9 (1), pp. 32-41.
Chromy B.A., et al., "Self-Assembly of a Beta1-42 into Globular Neurotoxins," Biochemistry, 2003, vol. 42 (44), pp. 12749-12760.
Chromy B.A., et al., "Stability of Small Oligomers of Abetal-42( ADDLs)," Society for Neuroscience Abstracts, Abstract No. 252129, 29th Annual Meeting of the Society for Neuroscience, Miami Beach, FL, 1999.
Chromy et al., "Oligomer/Conformation-Dependent Abeta Antibodies," Abstracts of the Annual Meeting of the Society for Neuroscience, 2000, vol. 26 (1-2), pp. 4.
Chung H., et al., "Degradation of Beta-Amyloid Peptide by Microglia," Society for Neuroscience Abstracts, 2000, vol. 26, 858.10.
Ciccotosto G.B., et al., "Methionine Oxidation: Implications for the Mechanism of Toxicity of the Beta-Amyloid Peptide from Alzheimer's Disease," Letters in Peptide Science, 2003, vol. 10 (5-6), pp. 413-417.
Citron M., "Alzheimer's Disease: Strategies for Disease Modification," Nature Reviews Drug Discovery, 2010, vol. 9 (5), pp. 387-398.
Clackson T., et al., "Making Antibody Fragments Using Phage Display Libraries," Nature, 1991, vol. 352 (6336), pp. 624-628.
Clark M.S., eds., "A Laboratory Manual," in: Plant Molecular Biology, Springer-Verlag Berlin Heidelberg, 1997, Table of Contents.
Cleary J.P., et al., "Cognitive Effects of Oligomeric and Fibril Aβ in Rats," Society for Neuroscience—Abstract Archive, 2002, Presentation No. 882.2.
Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Cole G.M., et al., "Alzheimer's Amyloid story finds its Star," Trends in Molecular Medicine, 2006, vol. 12 (9), pp. 395-396.
Cole G.M., et al., "Cat and Mouse," Neuron , 2006, vol. 51 (6), pp. 671-672.
Cole G.M., et al., "Docosahexaenoic Acid Protects from Amyloid and Dendritic Pathology in an Alzheimer's Disease Mouse Model," Nutrition and Health, 2006, vol. 18 (3), pp. 249-259.
Cole, M.S., et al., "Human IgG2 Variants of Chimeric Anti-CD3 Are Nonmitogenic to T Cells," J. of Immunol. , vol. 159 (7), pp. 3613-3621, 1997.

(56) References Cited

OTHER PUBLICATIONS

Colman P.M., "Effects of Amino acid Sequence Changes on Antibody-Antigen Interactions," Research in Immunology, 1994, vol. 145 (1), pp. 33-36.
Colombo R., et al., "CE can identify Small Molecules that Selectively Target Soluble Oligomers of Amyloid Beta Protein and Display Antifibrillogenic Activity," Electrophoresis, 2009, vol. 30 (8), pp. 1418-1429.
Co-Pending U.S. Appl. No. 13/862,865, filed Apr. 15, 2013.
Co-Pending U.S. Appl. No. 13/893,780, filed May 14, 2013.
Co-pending U.S. Appl. No. 14/792,500, filed Jul. 6, 2015.
Co-Pending U.S. Appl. No. 14/864,526, filed Sep. 24, 2015.
Co-Pending U.S. Appl. No. 60/126,603, filed Mar. 25, 1999.
Costantini C., et al., "The Expression of P75 Neurotrophin Receptor Protects against the Neurotoxicity of Soluble Oligomers of Beta-Amyloid," Experimental Cell Research, 2005, vol. 311 (1), pp. 126-134.
Craft J.M., et al., "Enhanced Susceptibility of S-100B Transgenic Mice to Neuroinflammation and Neuronal Dysfunction Induced by Intracerebroventricular Infusion of Human Beta-Amyloid," Glia, 2005, vol. 51 (3), pp. 209-216.
Crouch P.J., et al., "Soluble Oligomeric Amyloid Beta 1-42 Specifically Inhibits Cytochrome C Oxidase of Human Mitochondria," Mitochondrial Medicine, 2004, 4:71-472.
Crouse N.R., et al., "Oligomeric Amyloid-Beta(1-42) induces THP-1 Human Monocyte Adhesion and Maturation," Brain Research, 2009, vol. 1254, pp. 109-119.
Dahlgren K.N., et al., "Oligomeric and Fibrillar Species of Amyloid-Beta Peptides Differentially Affect Neuronal Viability," The Journal of Biological Chemistry, 2002, vol. 277 (35), pp. 32046-32053.
Das U., et al., "Interface Peptide of Alzheimer's Amyloid Beta: Application in Purification," Biochemical and Biophysical Research Communications, 2007, vol. 362 (2), pp. 538-542.
Dasilva K.A., et al., "Reduced Oligomeric and Vascular Amyloid-Beta following Immunization of TgCRDN8 Mice with an Alzheimer's DNA Vaccine," Vaccine, 2009, vol. 27 (9), pp. 1365-1376.
David et al.,, "A significant reduction in the incidence of collagen induced arthritis in mice treated with anti-TCRV-beta antibodies," Journal of Cellular Biochemistry, 1991, pp. 179.
De Almeida E.R.P., et al., "Transgenic Expreession of Two Marker Genes Under the Controlof an *Arabidopsis* rbcS Promoter: Sequences Encoding the Rubisco Transit Peptide Increase Expression Levels," Molecular and General Genetics, 1989, vol. 218, pp. 78-86.
De Chaves P., et al., "Lipid Rafts in Amyloid Beta Endocytosis and Amyloid Beta-Induced Apoptosis," Journal of Neurochemistry, 2009, vol. 110 (Suppl. 2), pp. S20-03.
De Felice F.G., et al., "Alzheimer's Disease-type Neuronal Tau Hyperphosphorylation Induced by Abeta Oligomers," Neurobiology of Aging, 2008, vol. 29 (9), pp. 1334-1347.
De Giorgi L., et al., "Induction of Foetal Lethality in Akr Offspring after Repeated Inoculations into Akr Females of Anti-Tcr/V Beta 6 Monoclonal Antibody," Immunologic Research, 1993, vol. 144 (4), pp. 245-255.
De Giorgi L., et al., "Murine Hybridomas Secreting Monoclonal Antibodies Reacting with MIse Antigens," Experimental and Clinical Immunogenetics, 1993, vol. 10 (4), pp. 219-233.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
Declaration of Andreas Muhs in support of opposition dated Oct. 10, 2014.
Declaration of Hartmut Engelmann in support of opposition dated Oct. 14, 2014.
DeMattos R.B., et al., "In Vitro and in Vivo Characterization of Beta-Amyloid Antibodies Binding to Cerebral Amyloid Angiopathy (CAA) and the Selective Exacerbation of CAA-Associated Microhemorrhage," Poster Session:Therapeutics and Therapeutic Strategies-Therapeutic strategies, Amyloid based, 2004, vol. 25, pp. S577.
DeMattos R.B., et al., "Peripheral Anti-Abeta Antibody Alters CNS and Plasma Abeta Clearance and Decreases Brain Abeta Burden in a Mouse Model of Alzheimer's Disease," Proceedings of the National Academy of Sciences, 2001, vol. 98 (15), pp. 8850-8855.
Demeester N., et al., "Comparison of the Aggregation Properties, Secondary Structure and Apoptotic Effects of Wild-Type, Flemish and Dutch N-Terminally Truncated Amyloid Beta Peptides.," European Journal of Neuroscience, 2001, vol. 13 (11), pp. 2015-2024.
DeMuro A., et al., "Calcium Dysregulation and Membrane Disruption as a Ubiquitous Neurotoxic Mechanism of Soluble Amyloid Oligomers," The Journal of Biological Chemistry, 2005, vol. 280 (17), pp. 17294-17300.
Denkewalter R.G., et al., Progress in Drug Research, 1966, vol. 10, 23 pages.
Dewachter I., et al., "Neuronal Deficiency of Presenilin 1 Inhibits Amyloid Plaque Formation and Corrects Hippocampal Long-Term Potentiation but not a Cognitive Defect of Amyloid Precursor Protein [V717I]Transgenic Mice.," Journal of Neuroscience, 2002, vol. 22 (9), pp. 3445-3453.
Dickson D.W., et al., "Correlations of Synaptic and Pathological Markers With Cognition of the Elderly," Neurobiology of Aging, 1995, vol. 16 (3), pp. 285-304.
Dillen K., et al., "A Two Decade Contribution of Molecular Cell Biology to the Centennial of Alzheimer's Disease: Are We Progressing Toward Therapy?," International Review of Cytology, 2006, vol. 254, pp. 215-300.
Ding J.D., et al., "Targeting Age-Related Macular Degeneration with Alzheimer's Disease Based Immunotherapies: Anti-Amyloid-Beta Antibody Attenuates Pathologies in an Age-Related Macular Degeneration Mouse Model," Vision Research, 2007, vol. 48 (3), pp. 339-345.
Dingledine R., et al., "Brain Slices," Plenum Press, 1984, Table of contents.
Dodel R., et al., "Naturally Occurring Autoantibodies against Beta-Amyloid: Investigating their Role in Transgenic Animal and in Vitro Models of Alzheimer's Disease," Journal of Neuro Sciences, 2011, vol. 31 (15), pp. 5847-5854.
Donnet et al., "Plasma Treatment Effect on the Surface Energy of Carbon and Carbon Fibers," Carbon, pp. 757-770, 1986, vol. 24 (6).
Dorronsoro., et al., "Peripheral and dual binding site inhibitors of acetylcholinesterase as neurodegenerative disease-modifying agents," Expert Opinion on Therapeutic Patents, 2003, vol. 13 (11), pp. 1725-1732.
Du Y., et al., "Reduced Levels of Amyloid Beta-Peptide Antibody in Alzheimer Disease," Neurology, 2001, vol. 57 (5), pp. 801-805.
Dufner P., et al., "Harnessing Phage and Ribosome Display for Antibody Optimisation," Trends in Biotechnology, 2006, vol. 24 (11), pp. 523-529.
During M, J., et al., "Controlled Release of Dopamine from a Polymeric Brain Implant: In Vivo Characterization," Annals of Neurology, 1989, vol. 25 (4), pp. 351-356.
Durocher Y., et al., "High-Level and High-Throughput Recombinant Protein Production by Transient Transfection of Suspension-Growing Human 293-EBNA1 Cells," Nucleic Acids Research, 2002, vol. 30 (2), pp. e9.
Eckenhoff R.G., et al., "Anesthetics and Neurodegenerative Disorders; a Molecular Basis for Concern?," Anesthesiology, 2003, vol. 99, pp. A848.
Eckert A., et al., "Oligomeric and Fibrillar Species of Beta-Amyloid (A Beta 42) Both Impair Mitochondrial Function in P301L tau Transgenic Mice," Journal of Molecular Medicine, 2008, vol. 86 (11), pp. 1255-1267.
Eisenberg, et al., "Analysis of membrane and surface protein sequences with the hydrophobic moment plot," J. Mol. Biol, 1984, vol. 179 (1), pp. 125-142.
EMBL Accession No. AF044238, Feb. 8, 1999.
EMBL Accession No. M12183, Jul. 16, 1988.
Englund H., et al., "Oligomerization Partially Explains the Lowering of Abeta42 in Alzheimer's Disease Cerebrospinal Fluid," Neuro-degenerative Diseases, 2009, vol. 6 (4), pp. 139-147.

(56) References Cited

OTHER PUBLICATIONS

Eren R., et al., "Human Monoclonal Antibodies Specific to Hepatitis B Virus Generated in a Human/mouse Radiation Chimera: the Trimera System," Immunology, 1998, vol. 93 (2), pp. 154-161.
Esteras-Chopo A., et al., "New Strategy for the Generation of Specific D-Peptide Amyloid Inhibitors," Journal of Molecular Biology, 2008, vol. 377 (5), pp. 1372-1381.
European Opposition of EP 06838873.5, Patent No. 1976877, by Genentech, Inc. and AC Immune SA dated Oct. 15, 2014, 35 pages.
European Patent Office Action for Application No. 11745902.4, dated Jul. 14, 2015, 5 pages.
European Search Report for Application No. 087160818, dated Dec. 22, 2011, 6 pages.
European Search Report for Application No. 101783942, dated Mar. 2, 2012, 4 pages.
European Search Report for Application No. 101783942, dated Aug. 22, 2012, 4 pages.
European Search Report for Application No. 09180982, dated May 31, 2010, 4 pages.
Evans C.G., et al., "Heat Shock Proteins 70 and 90 Inhibit Early Stages of Amyloid Beta-(1-42) Aggregation in Vitro," The Journal of Biological Chemistry, 2006, vol. 281 (44), pp. 33182-33191.
Evans et al., "Design of nonpeptidal ligands for a peptide receptor: cholecystokinin antagonists," J. Med. Chem. 1987, vol. 30, pp. 1229.
Evans N.A., et al., "Abeta(1-42) Reduces Synapse Number and Inhibits Neurite Outgrowth in Primary Cortical and Hippocampal Neurons: a Quantitative Analysis," Journal of Neuroscience Methods, 2008, vol. 175 (1), pp. 96-103.
Evin G., "Gamma-Secretase Modulators: Hopes and Setbacks for the Future of Alzheimer's Treatment," Expert Review of Neurotherapeutics, 2008, vol. 8 (11), pp. 1611-1613.
Fauchere, "Elements for the rational design of peptide drugs," Adv. Drug Research, 1986, vol. 15, pp. 29-69.
Feld M., et al., "Effect on Memory of Acute Administration of Naturally Secreted Fibrils and Synthetic Amyloid-Beta Peptides in an Invertebrate Model," Neurobiology of Learning and Memory, 2008, vol. 89 (4), pp. 407-418.
Ferrao-Gonzales A.D., et al., "Controlling {beta}-Amyloid Oligomerization by the Use of Naphthalene Sulfonates: Trapping Low Molecular Weight Oligomeric Species," The Journal of Biological Chemistry, 2005, vol. 280 (41), pp. 34747-34754.
Final Office Action dated Oct. 1, 2012 for U.S. Appl. No. 13/102,713, filed May 6, 2011.
Final Office Action dated Jul. 11, 2013 for U.S. Appl. No. 13/195,533, filed Aug. 1, 2011.
Final Office Action dated Sep. 11, 2012 for U.S. Appl. No. 13/188,034, filed Jul. 21, 2011.
Final Office Action dated Oct. 14, 2010 for U.S. Appl. No. 11/945,124, filed Nov. 26, 2007.
Final Office Action dated May 24, 2012 for U.S. Appl. No. 12/529,467, filed Jul. 27, 2010.
Final Office Action dated Nov. 26, 2013 for U.S. Appl. No. 13/085,891, filed Apr. 13, 2011.
Final Office Action dated Mar. 29, 2011 for U.S. Appl. No. 11/885,362, filed Apr. 17, 2008.
Fishwild D.M., et al., "High-Avidity Human IgGK Monoclonal Antibodies from a Novel Strain of Minilocus Transgenic Mice," Nature Biotech, 1996, vol. 14 (7), pp. 845-851.
Flink M.T., et al., "Ca2+ Channels as Targets of Neurological Disease: Lambert-Eaton Syndrome and Other Ca2+ Channelopathies," Journal of Bioenergetics and Biomembranes, 2003, vol. 35 (6), pp. 697-718.
Foote J., et al., "Antibody Framework Residues Affecting the Conformation of the Hypervariable Loops," Journal of Molecular Biology, 1992, vol. 224 (2), pp. 487-499.
Forsell C., et al., "Amyloid Precursor Protein Mutation at Codon 713 (Ala-->Val) does not Cause Schizophrenia: Non-Pathogenic Variant Found at Codon 705 (silent)," Neuroscience Letters, 1995, vol. 184 (2), pp. 90-93.
Fradinger E.A., et al., "C-Terminal Peptides Coassemble into Abeta42 Oligomers and Protect Neurons Against Abeta42-Induced Neurotoxicity," Proceedings of the National Academy of Sciences, 2008, vol. 105 (37), pp. 14175-14180.
Frenkel D., et al., "Modulation of Alzheimer's Beta-Amyloid Neurotoxicity by Site-Directed Single-Chain Antibody," Journal of Neuroimmunology, 2000, vol. 106 (1-2), pp. 23-31.
Fuchs P., et al., "Targeting Recombinant Antibodies to the Surface of Escherichia coli: Fusion to a Peptidoglycan Associated Lipoprotein," BioTechnology, 1991, vol. 9 (12), pp. 1369-1372.
Fujimuro M., et al., "Production and Characterization of Monoclonal Antibodies Specific to Multi-Ubiquitin Chains of Polyubiquitinated Proteins," FEBS Letters, 1994, vol. 349 (2), pp. 173-180.
Fujimuro M., et al., "Production of Antipolyubiquitin Monoclonal Antibodies and their Use for Characterization and Isolation of Polyubiquitinated Proteins," Methods in Enzymology, 2005, vol. 399, pp. 75-86.
Fukuchi K., et al., "Amelioration of Amyloid Load by Anti-Abeta Single-Chain Antibody in Alzheimer Mouse Model," Biochemical and Biophysical Research Communications, 2006, vol. 344 (1), pp. 79-86.
Funke S.A., et al., "Detection of Amyloid-Beta Aggregates in Body Fluids: a Suitable Method for Early Diagnosis of Alzheimer's Disease?," Current Alzheimer Research, 2009, vol. 6 (3), pp. 285-289.
Galfre G., et al., "Antibodies to Major Histocompatibility Antigens Produced by Hybrid Cell Lines," Nature, 1977, vol. 266 (5602), pp. 550-552.
Gallo M.L., et al., "The Human Immunoglobulin Loci Introduced into Mice: V (D) and J Gene Segment Usage Similar to that of Adult Humans," European Journal of Immunology, 2000, vol. 30 (2), pp. 534-540.
Garrard L.J., et al., "Fab Assembly and Enrichment in a Monovalent Phage Display System," BioTechnology, 1991, vol. 9 (12), pp. 1373-1377.
Garzon D.J., et al., "Oligomeric Amyloid Decreases Basal Levels of Brain-Derived Neurotrophic Factor (BDNF) mRNA via Specific Downregulation of BDNF Transcripts IV and V in Differentiated Human Neuroblastoma Cells," The Journal of Neuroscience, 2007, vol. 27 (10), pp. 2628-2635.
Gavilondo J.V., et al., "Antibody Engineering at the Millennium," Biotechniques, 2000, vol. 29 (1), pp. 128-145.
Gefter M.L., et al., "A Simple Method for Polyethylene Glycol-Promoted Hybridization of Mouse Myeloma Cells," Somatic Cell Genetics, 1997, vol. 3 (2), pp. 231-236.
Gellermann, et al, "Abeta-globulomers are formed independently of the fibril pathway," Neurobiology of Disease, 2008, vol. 30 (2), pp. 212-220.
Geneseq, "Anti-human Fas monoclonal antibody CH11 light chain cDNA," Accession No. AAV66736, Jan. 18, 1999.
Geneseq, "Humanized monoclonal antibody H74785-2 heavy chain," Accession No. ADX39139, 2005.
Geneseq, "Humanized monoclonal antibody Hu4785-2 partial protein," Accession No. ADX39104 2005.
Geneseq, "Humanized monoclonal antibody Hu4785-2 VH region," Accession No. ADX39143, 2005.
Geneseq, "Mouse DNA encoding antibody 3D8 heavy chain variable, region," Accession No. ABX1656922 Apr. 22, 2003.
Geneseq, "Mouse monoclonal antibody 4785 heavy chain SEQ ID 1," Accession No. ADX39100, 2005.
Geneseq, "Mouse monoclonal antibody 4785 heavy chain SEQ ID 38", Accession No. ADX39137, 2005.
Gennaro A.R., ed., Remington: The Science and Practice of Pharmacy, 19th Edition, Mack Publishing, 1995, Table of Contents.
Gervais F., et al., "Targeting Soluble Abeta Peptide with Tramiprosate for the Treatment of Brain Amyloidosis," Neurobiology of Aging, 2007, vol. 28 (4), pp. 537-547.
Ghiso J., et al., "Systemic Catabolism of Alzheimer's Abeta40 and Abeta42," The Journal of Biological Chemistry, 2004, vol. 279 (44), pp. 45897-45908.

(56) References Cited

OTHER PUBLICATIONS

Ghosal K., et al., "Alzheimer's Disease-like Pathological Features in Transgenic Mice Expressing the APP Intracellular Domain," Proceedings of the National Academy of Sciences, 2009, vol. 106 (43), pp. 18367-18372.
Giacobini E., et al., "One Hundred Years After the Discovery of Alzheimer's Disease. A Turning Point for Therapy?," Journal of Alzheimer's Disease, 2007, vol. 12 (1), pp. 37-52.
Gibbs M.E., et al., "Rescue of Abeta(1-42)-Induced Memory Impairment in Day-Old Chick by Facilitation of Astrocytic Oxidative Metabolism: Implications for Alzheimer's Disease," Journal of Neurochemistry, 2009, vol. 109 (Suppl. 1), pp. 230-236.
Giege R., et al., "An Introduction to the Crystallogenesis of Biological Macromolecules" in: Crystallization of Nucleic Acids and Proteins, Chapter 1, 2nd Edition, Ducruix A., et al., Eds., Oxford University Press, 1999, pp. 1-16.
Giliberto L., et al., "Mutant Presenilin 1 Increases the Expression and Activity of BACE1," The Journal of Biological Chemistry, 2009, vol. 284 (14), pp. 9027-9038.
Gillies S.D., et al., "High-Level Expression of Chimeric Antibodies Using Adapted cDNA Variable Region Cassettes," Journal of Immunological Methods, 1989, vol. 125 (1-2), pp. 191-202.
Giuffrida M.L., et al., "Abeta(25-35) and its C- and/or N-Blocked Derivatives: Copper Driven Structural Features and Neurotoxicity," Journal of Neuroscience Research, 2007, vol. 85 (3), pp. 623-633.
Giuffrida M.L., et al., "Beta-Amyloid Monomers are Neuroprotective," The Journal of Neuroscience, 2009, vol. 29 (34), pp. 10582-10587.
Goeddel D.V., "Systems for Heterologous Gene Expression," Methods in Enzymology, 1990, vol. 185, pp. 3-7.
Goeddel., "Gene Expression Technology" in: Methods in Enzymology 185, Academic Press, San Diego, CA, 1990.
Goldspiel B.R., et al., "Human Gene therapy" Clinical Pharmacy, 1993, vol. 12 (7), pp. 488-505.
Gong Y., et al., "Abeta-Derived Diffusible Ligands in Alzheimer's Disease Brain as Therapeutic Antibody Targets" in: Abstracts of the Annual Meeting of the Society of Neuroscience, 2002, 1 page.
Gong Y., et al., "Alzheimer's disease-affected brain: presence of oligomeric A beta ligands (ADDLs) suggests a molecular basis for reversible memory loss," Proceedings of the National Academy of Sciences, 2003, vol. 100 (18), pp. 10417-10422.
Gonzalo-Ruiz A., et al., "Oligomers of Beta-Amyloid (1-42) Peptide Induce Co-Localization of AB and Tau Proteins Associated with Calpain Activity," Journal of Neurochemistry, 2009, vol. 110 (Suppl. 2), pp. 57-58, MO08-04.
Goodson J.M., "Dental Applications" in: Medical Applications of Controlled Release, vol. 2, Chapter 6, Langer R.S., et al., eds., CRC Press, 1984, pp. 115-138.
Gowing E., et al., "Chemical Characterization of a Beta 17-42 Peptide, a Component of Diffuse Amyloid Deposits of Alzhemeimer Disease," Journal of Biological Chemistry, 1994, vol. 269 (15), pp. 10987-10988.
Grabarek, Z. and Gergely, J., "Zero-length crosslinking procedure with the use of active esters," Anal. Biochem., 1990, vol. 185 (1), pp. 131-135.
Grabowski T.J., et al., "Novel Amyloid Precursor Protein Mutation in an Lowa Family with Dementia and Severe Cerebral Amyloid Angiopathy," Annals of Neurology, 2001, vol. 49 (6), pp. 697-705.
Grace S.Y., "Abeta Induces Oxidative-Degradative Stress Through Nadph Oxidase and Phopholipase A2," Journal of Neurochemistry, 2009, vol. 110 (Suppl. 2), pp. 222, S30-02.
Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.
Grange De La, P, et al.,, "Fast DB: a website resource for the study of the expression regulation of human gene products," Nucl. Acids Res., vol. 33 (13), pp. 4276-4284, 2005.
Green L. L., et al., "Regulation of B Cell Development by Variable Gene Complexity in Mice Reconstituted with Human Immuno-globulin Yeast Artificial Chromosomes," Journal of Experimental Medicine, 1998, vol. 188 (3), pp. 483-495.
Green L.L., "Antibody Engineering via Genetic Engineering of the Mouse: XenoMouse Strains are a Vehicle for the Facile Generation of Therapeutic Human Monoclonal Antibodies," Journal of Immunological Methods, 1999, vol. 231 (1-2), pp. 11-23.
Green L.L., et al., "Antigen-Specific Human Monoclonal Antibodies from Mice Engineered with Human Ig Heavy and Light Chain YACs," Nature Genetics, 1994, vol. 7 (1), pp. 13-21.
Griffiths A.D., et al., "Human Anti-Self Antibodies with High Specificity from Phage Display Libraries," European Molecular Biology Organization, 1993, vol. 12 (2), pp. 725-734.
Guo L., et al., "APOE Down Regulates Pro-Inflammatory Responses Induced by Oligomeric Abeta in Activated Glia," Society for Neuroscience, Abstract Viewer and Itinerary Planner (2002), Abstract No. 883.12, 32nd Annual Meeting of the Society for Neuroscience, Orlando, FL, Nov. 2-7, 2002.
Guo L., et al., "Targeting Amyloid-Beta in Glaucoma Treatment," PNAS, Proceedings of the National Academy of Sciences, 2007, vol. 104 (33), pp. 13444-13449.
Ha C., et al., "Ex Situ Atomic Force Microscopy Analysis of Beta-Amyloid Self-Assembly and Deposition on a Synthetic Template," Langmuir, 2006, vol. 22 (16), pp. 6977-6985.
Ha C., et al., "Metal Ions Differentially Influence the Aggregation and Deposition of Alzheimer's Beta-Amyloid on a Solid Template," Biochemistry, 2007, vol. 46 (20), pp. 6118-6125.
Ha H., et al., "Development of Herbal Medicine for Alzheimer's Disease from Rhei Rhizoma," Journal of Neurochemistry, 2009, vol. 110 (Suppl. 2), pp. 114, TU05-06.
Haass C., et al., "Soluble Protein Oligomers in Neurodegeneration: Lessons from the Alzheimer's Amyloid Beta-Peptide," Nature Reviews. Molecular Cell Biology, 2007, vol. 8 (2), pp. 101-112.
Hachiya N.S., et al., "Oligomeric Aip2p/Dld2p Modifies the Protein Conformation of Both Properly Folded and Misfolded Substrates in Vitro," Biochemical and Biophysical Research Communications, 2004, vol. 323 (1), pp. 339-344.
Hagemeyer C.E., et al., "Single-Chain Antibodies as Diagnostic Tools and Therapeutic Agents," Thrombosis and Haemostasis, 2009, vol. 101 (6), pp. 1012-1019.
Hann, M. M., "On the double bond isostere of the peptide bond: preparation of an enkephalin analogue," J. Chem. Soc., Perkin Transactions 1, 1982, pp. 307-314.
Harding F.A., et al., "Class Switching in Human Immunoglobulin Transgenic Mice," Annals New York Academy of Sciences, 1995, vol. 764, pp. 536-546.
Hardy J., et al., "The Amyloid Hypothesis of Alzheimer's Disease: Progress and Problems on the Road to Therapeutics," Science, 2002, vol. 297 (5580), pp. 353-356.
Harlow E., et al., "Antibodies: A Laboratory Manual", Cold Spring Harbor Laboratory, 1988, Table of Contents.
Harris-White M.E., et al., Effects of Low Dose, Low Mw Soluble Amyloid Oligomers on Spatial Memory Performance Society for Neuroscience. Abstract Viewer and Itin. Plann, 2003, Abstract No. 240.11, 33rd Annual Meeting of the Society of Neuroscience, Nov. 8-12, New Orleans, 2003.
Hartley D.M., et al., "Transglutaminase Induces Protofibril-like Amyloid Beta-protein Assemblies that are Protease-resistant and Inhibit Long-term Potentiation," Journal of Biological Chemistry, 2008, vol. 283 (24), pp. 16790-16800.
Hashida S. et al., "More useful maleimide compounds for the conjugation of Fab to horseradish peroxidase through thiol groups in the hinge," J. Appl. Biochem, 1984, vol. 6, pp. 56-63.
Hashimoto M., et al., "Role of Protein Aggregation in Mitochondrial Dysfunction and Neurodegeneration in Alzheimer's and Parkinson's Diseases," Neuromolecular Medicine, 2003, vol. 4 (1-2), pp. 21-36.
Hawkins R.E., et al., "Selection of Phage Antibodies by Binding Affinity Mimicking Affinity Maturation," Journal of Molecular Biology, 1992, vol. 226 (3), pp. 889-896.
Hay B.N., et al., "Bacteriophage Cloning and *Escherichia coli* Expression of a Human IgM Fab," Human Antibodies and Hybridomas, 1992, vol. 3 (2), pp. 81-85.

(56) References Cited

OTHER PUBLICATIONS

Hayes G.M., et al., "Production of Beta-amyloid by Primary Human Foetal Mixed Brain Cell Cultures and its Modulation by Exogenous Soluble Beta-amyloid," Neuroscience, 2002, vol. 113 (3), pp. 641-646.
Head E., et al., "A Two-year Study with Fibrillar Beta-amyloid (Abeta) Immunization in Aged Canines: Effects on Cognitive Function and Brain Abeta," Journal of Neuroscience, 2008, vol. 28 (14), pp. 3555-3566.
Head E., et al., "The Effects of Immunization with Fibrillar or Oligomeric Abeta in the Brain and CSF of Aged Canines: A Pilot Study," Society for Neuroscience Abstract Viewer and Itinerary Planner (2003) Abstract No. 525.24, 33rd Annual Meeting of the Society of Neuroscience, New Orleans, LA, Nov. 8-12, 2003.
Heard C., et al., "Two Neutralizing Human Anti-RSV Antibodies: Cloning, Expression, and Characterization," Molecular Medicine, 1999, vol. 5 (1), pp. 35-45.
Heinitz K., et al., "Toxicity Mediated by Soluble Oligomers of Beta-amyloid(1-42) on Cholinergic SN56.B5.G4 Cells," Journal of Neurochemistry, 2006, vol. 98 (6), pp. 1930-1945.
Helisalmi S., et al., "Screening for Amyloid Beta Precursor Protein Codon 665, 670/671 and 717 Mutations in Finnish Patients with Alzheimer's Disease," Neuroscience Letters, 1996, vol. 205 (1), pp. 68-70.
Herz U. et al., "The Humanized (Hu-Pbmc) Scid Mouse as an in vivo Model for Human Ige Production and Allergic Inflammation of the Skin," International Archives of Allergy and Immunology, 1997, vol. 113 (1-3), 150-152.
Hess, et al., "Cooperation of Glycolytic Enzymes," J. Adv. Enzyme Reg., vol. 7, pp. 149-167, 1968.
Hicke L., "Protein Regulation by Monoubiquitin," Nature Reviews Molecular Cell Biology, 2001, vol. 2 (3), pp. 195-201.
Hieter P.A., et al., "Evolution of Human Immunoglobulin Kappa J Region Genes," Journal of Biological Chemistry, 1982, vol. 257 (3), pp. 1516-1522.
Higgins D.G., et al., "Fast and Sensitive Multiple Sequence Alignments on a Microcomputer," Computer Applications in the Biosciences, 1989, vol. 5 (2), pp. 151-153.
Higuchi R., Using PCR to Engineer DNA: PCR Technology, Erlich H.A., Stockton Press, 1989, pp. 61-70.
Hilbich C., et al., "Aggregation and Secondary Structure of Synthetic Amyloid Beta A4 Peptides of Alzheimer's Disease," Journal of Molecular Biology, 1991, vol. 218 (1), pp. 149-163.
Hillen H., et al., "Generation and Therapeutic Efficacy of Highly Oligomer-Specific Beta-Amyloid Antibodie," The Journal of Neuroscience, 2010, vol. 30 (31), pp. 10369-10379.
Hirko A.C., et al., "Peripheral Transgene Expression of Plasma Gelsolin Reduces Amyloid in Transgenic Mouse Models of Alzheimer's Disease," Molecular Therapy, 2007, vol. 15 (9), pp. 1623-1629.
Hock C., et al., "Clinical Observations with AN-1792 Using TAPIR Analyses," Neuro-degenerative Diseases, 2005, vol. 2 (5), pp. 273-276.
Holladay Man., et al., "Synthesis of Hydroxyethelene and Ketomethylene Dipeptide Isosteres," Tetrahedron Lett., 1983, vol. 24, pp. 4401-4404.
Holliger P., et al., ""Diabodies": Small Bivalent and Bispecific Antibody Fragments," Proceedings of the National Academy of Sciences, 1993, vol. 90 (14), pp. 6444-6448.
Holm P., et al., "Functional Mapping and Single Chain Construction of the Anti-Cytokeratin & Monoclonal Antibody TS1," Molecular Immunology, 2007, vol. 44, pp. 1075-1084.
Hong H.S., et al., "Combining the Rapid MTT Formazan Exocytosis Assay and the MC65 Protection Assay Led to the Discovery of Carbazole Analogs as Small Molecule Inhibitors of Abeta Oligomer-induced Cytotoxicity," Brain Research, 2007, vol. 1130 (1), pp. 223-234.
Hong H.S., et al., "Inhibition of Alzheimer's Amyloid Toxicity with a Tricyclic Pyrone Molecule in Vitro and in Vivo," Journal of Neurochemistry, 2009, vol. 108 (4), pp. 1097-1108.
Hoogenboom H.R., et al., "Designing and Optimizing Library Selection Strategies for Generating High-Affinity Antibodies," Trends in Biotechnology, 1997, vol. 15 (2), pp. 62-70.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Hoogenboom H.R., et al., "Natural and Designer Binding Sites Made by Phage Display Technology," Immunology Today, 2000, vol. 21 (8), pp. 371-378.
Hoozemans J.J., et al., "Always Around, Never the Same: Pathways of Amyloid Beta Induced Neurodegeneration throughout the Pathogenic Cascade of Alzheimer's Disease," Current Medicinal Chemistry, 2006, vol. 13 (22), pp. 2599-2605.
Hossain S., et al., "Mechanism of Docosahexaenoic Acid-induced Inhibition of in Vitro Abeta1-42 Fibrillation and Abeta1-42-induced Toxicity in SH-S5Y5 Cells," Journal of Neurochemistry, 2009, vol. 111 (2), pp. 568-579.
Howard M.A., et al., "Intracerebral Drug Delivery in Rats with Lesion-Induced Memory Deficits," Journal of Neurosurgery, 1989, vol. 71 (1), pp. 105-112.
Howlett D.R., et al., "The Pathology of APP Transgenic Mice: A Model of Alzheimer's Disease or Simply Overexpression of APP?," Histology and Histopathology, 2009, vol. 24 (1), pp. 83-100.
Hoyer W., et al., "Stabilization of a Beta-hairpin in Monomeric Alzheimer's Amyloid-beta Peptide Inhibits Amyloid Formation," Proceedings of the National Academy of Sciences, 2008, vol. 105 (13), pp. 5099-5104.
Hruby V.J., "Conformational Restrictions of Biologically Active Peptides via Amino Acid Side Chain Groups," Life Sciences, 1982, vol. 31 (3), pp. 189-199.
Hsiao K., et al., "Correlative Memory Deficits, Ap Elevation, and Amyloid Plaques in Transgenic Mice," Science, 1996, vol. 274 (5284), pp. 99-102.
Huang C. C. et al., Selective enhancement of P-type calcium currents by isoproterenol in the rat amygdala, The Journal of Neuroscience, 1998, 18(6), 2276-2282.
Huang C. et al., Isoproterenol potentiates synaptic transmission primarily by enhancing presynaptic calcium influx via P- and/or Q-type calcium channels in the rat amygdala, XP002486000, Journal of Neuroscience, 1996, 16 (3), 1026-1033.
Huang X., et al., Metal-dependence of a beta Oligamerization, Society for Neuroscience—Abstract Archive, Presentation No. 19.1, 2002.
Huse W.D., et al., "Generation of a Large Combinatorial Library of the Immunoglobulin Repertoire in Phage Lambda," Science, 1989, vol. 246 (4935), pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
Huston J.S., et al., "Protein Engineering of Single-Chain Fv Analogs and Fusion Proteins," Methods in Enzymology, 1991, vol. 203, pp. 46-88.
Hutchins W.A., et al., "Human Immune Response to a Peptide Mimic of Neisseria meningititis Serogroup C in hu- PBMC-SCID Mice," Hybridoma, 1999, vol. 18 (2), pp. 121-129.
Hyman B.T., et al., "Autoantibodies to Amyloid-beta and Alzheimer's Disease," Annals of Neurology, 2001, vol. 49 (6), pp. 808-810.
Iijima K., et al., "Abeta42 Mutants with Different Aggregation Profiles Induce Distinct Pathologies in *Drosophila*," PLoS One, 2008, vol. 3 (2), pp. e1703.
Ilan E., et al., "The Hepatitis B Virus-Trimera Mouse: A Model for Human HBV Infectoin and Evaluation of Anti-HBV Therapeutic Agents," Hepatology, 1999, vol. 29 (2), pp. 553-562.
Ingelbrecht I.L., et al., "Different 3' End Regions Strongly Influence the Level of Gene Expression in Plant Cells," Plant Cell, 1989, vol. 1 (7), pp. 671-680.
International Preliminary Report on Patentability and Written Opinion for Application No. PCT/EP2004/000927, dated Aug. 5, 2005, 11 pages.

(56) References Cited

OTHER PUBLICATIONS

International Preliminary Report on Patentability and Written Opinion for Application No. PCT/EP2006/011530, dated Jun. 3, 2008, 11 pages.
International Preliminary Report on Patentability and Written Opinion for Application No. PCT/EP2008/001548, dated Sep. 1, 2009, 11 pages.
International Preliminary Report on Patentability and Written Opinion for Application No. PCT/IB2009/006636, dated Jan. 25, 2011, 7 pages.
International Preliminary Report on Patentability and Written Opinion for Application No. PCT/US2006/046043, dated Jun. 30, 2008, 32 pages.
International Preliminary Report on Patentability and Written Opinion for Application No. PCT/US2006/046148, dated Jun. 3, 2008, 8 pages.
International Preliminary Report on Patentability and Written opinion for Application No. PCT/US2007/085932, dated Jun. 3, 2009, 5 pages.
International Preliminary Report on Patentability and Written Opinion for Application No. PCT/US2008/065199, dated Dec. 1, 2009, 10 pages.
International Preliminary Report on Patentability and Written Opinion for Application No. PCT/US2008/065205, dated Dec. 1, 2009, 6 pages.
International Preliminary Report on Patentability and Written Opinion for Application No. PCT/US2009/051721, dated Jan. 25, 2011, 7 pages.
International Search Report for Application No. PCT/EP2004/000927, dated Jun. 14, 2004, 4 pages.
International Search Report for Application No. PCT/EP2006/011530, dated Jun. 6, 2007, 7 pages.
International Search Report for Application No. PCT/EP2008/001548, dated Jul. 4, 2008, 3 pages.
International Search Report for Application No. PCT/EP2008/001549, dated Dec. 23, 2008, 6 pages.
International Search Report for Application No. PCT/IB2009/006636, dated Jan. 22, 2010, 6 pages.
International Search Report for Application No. PCT/US2006/046043, dated Jan. 21, 2008, 16 pages.
International Search Report for Application No. PCT/US2006/046148, dated Jun. 19, 2007, 5 pages.
International Search Report for Application No. PCT/US2007/085932, dated Sep. 22, 2008, 3 pages.
International Search Report for Application No. PCT/US2008/065199, dated Sep. 26, 2008, 4 pages.
International Search Report for Application No. PCT/US2008/065205, dated Oct. 31, 2008, 3 pages.
International Search Report for Application No. PCT/US2009/051721, dated Mar. 16, 2010, 6 pages.
International Search Report for Application No. PCT/US2011/047622, dated Jan. 2, 2012, 5 pages.
Invitation to Pay Fees for Application No. PCT/EP2015/065362, dated Dec. 10, 2015, 10 pages.
Jang Y.J., et al., "The Structural Basis for DNA Binding by an Anti-DNA Autoantibody," Molecular Immunology, 1998, vol. 35 (18), pp. 1207-1217.
Janssen J.C., et al., "Early Onset Familial Alzheimer's Disease: Mutation Frequency in 31 Families," Neurology, 2003, vol. 60 (2), pp. 235-239.
Jefferis R., "Glycosylation of Recombinant Antibody Therapeutics," Biotechnology Program, 2005, vol. 21 (1), pp. 11-16.
Jennings-White, C., et al., "Synthesis of ketomethylene analogs of dipeptides," Tetrahedron Lett., 1982, vol. 23 (25), pp. 2533-2534.
Jensen M.T., et al., "Lifelong Immunization with Human Beta-amyloid (1-42) Protects Alzheimer's Transgenic Mice against Cognitive Impairment throughout Aging," Neuroscience, 2005, vol. 130 (3), pp. 667-684.

Jeon D., et al., "Impaired Long-Term Memory and Long-Term Potentiation in N-type Ca2+ Channel-Deficient Mice," Genes, Brain and Behavior, 2007, vol. 6 (4), pp. 375-388.
Jiang, S., et al., "Recent Progress of Synthetic Studies to Peptide and Peptidomimetic Cyclization," Curr. Org. Chem., 2008, vol. 12 (17), pp. 1502-1542.
Joerchel S., et al., "Oligomeric Beta-amyloid(1-42) Induces the Expression of Alzheimer Disease-relevant Proteins in Cholinergic SN56.B5.G4 Cells as Revealed by Proteomic Analysis," International Journal of Developmental Neuroscience, 2008, vol. 26 (3-4), pp. 301-308.
Johansson A.S., et al., "Attenuated Amyloid-beta Aggregation and Neurotoxicity Owing to Methionine Oxidation," Neuroreport, 2007, vol. 18 (6), pp. 559-563.
Johansson A.S., et al., "Docosahexaenoic Acid Stabilizes Soluble Amyloid-beta Protofibrils and Sustains Amyloid-beta-induced Neurotoxicity in Vitro," FEBS Journal, 2007, vol. 274 (4), pp. 990-1000.
Johansson A.S. et al., "Dramatic Changes in Fibrillization Rate and Oligomer/Protofibrillar Formation of Beta-Amyloid Peptide with Oxidized Methionine: Implications for Novel Therapeutic Approaches in Alzheimer's Disease," Society for Neuroscience, Abstract Viewer and Itinerary Planner (2002), Abstract No. 123.8, 32nd Annual meeting of the Society for Neuroscience, Orlando, FL, Nov. 2-7, 2002.
Johansson A.S., et al., "Physiochemical Characterization of the Alzheimer's Disease-related Peptides A Beta 1-42Arctic and A Beta 1-42wt," FEBS Journal, 2006, vol. 273 (12), pp. 2618-2630.
Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.
Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.
Joliot A., et al., "Antennapedia Homeobox Peptide Regulates Neural Morphogenesis," Proceedings of the National Academy of Sciences, 1991, vol. 88 (5), pp. 1864-1868.
Jones C.T., et al., "Mutation in Codon 713 of the Beta Amyloid Precursor Protein Gene Presenting with Schizophrenia," Nature Genetics, 1992, vol. 1 (4), pp. 306-309.
Jones J.D., et al., "High Level Expression of Introduced Chimaeric Genes in Regenerated Transformed Plants," The EMBO Journal, 1985, vol. 4 (10), pp. 2411-2418.
Jonsson U., et al., "Introducing a Biosensor Based Technology for Real-Time Biospecific Interaction Analysis," Annales de Biologie Clinique, 1993, vol. 51 (1), pp. 19-26.
Jonsson U., et al., "Real-Time Biospecific Interaction Analysis Using Surface Plasmon Resonance and a Sensor Chip Technology," Biotechniques, 1991, vol. 11 (5), pp. 620-627.
Jungbauer L.M., et al., "Preparation of Fluorescently-labeled Amyloid-beta Peptide Assemblies: The Effect of Fluorophore Conjugation on Structure and Function," Journal of Molecular Recognition, 2009, vol. 22 (5), pp. 403-413.
Kabat E.A., et al., "Accession No. PS91-192898, Sequences of Proteins of Immunological Interest," 5th Edition, National Institutes of Health Publication No. 91-3242, 1991, Table of Contents.
Kabat E.A., et al., "Attempts to Locate Complementarity-Determining Residues in the variable Positions of Light and Heavy Chains," Annals New York Academy of Sciences, 1971, vol. 190, pp. 382-391.
Kaiser et al., "Peptide and protein synthesis by segment synthesis-condensation," Science, 1989, vol. 243, pp. 187.
Kakio A., et al., "Interactions of Amyloid Beta-Protein with various Gangliosides in Raft-like Membranes: Importance of GM1 Ganglioside-Bound form as an Endogenous Seed for Alzheimer Amyloid," Biochemistry, 2002, vol. 41 (23), pp. 7385-7390.
Kamino K., et al., "Linkage and Mutational Analysis of Familial Alzheimer Disease Kindreds for the APP Gene Region," American Journal of Human Genetics, 1992, vol. 51 (5), pp. 998-1014.

(56) References Cited

OTHER PUBLICATIONS

Kanemitsu H., et al., "Human Neprilysin is Capable of Degrading Amyloid Beta Peptide not only in the Monomeric Form but also the Pathological Oligomeric Form," Neuroscience Letters, 2003, vol. 350 (2), pp. 113-116.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Kawarabayashi T., et al., "Age-dependent Changes in Brain, CSF, and Plasma Amyloid (beta) Protein in the Tg2576 Transgenic Mouse Model of Alzheimer's Disease," Journal of Neuroscience, 2001, vol. 21 (2), pp. 372-381.
Kawarabayashi T., et al., "Dimeric Amyloid Beta Protein Rapidly Accumulates in Lipid Rafts Followed by Apolipoprotein E and Phosphorylated Tau Accumulation in the Tg2576 Mouse Model of Alzheimer's Disease," Journal of Neuroscience, 2004, vol. 24 (15), pp. 3801-3809.
Kayed R., et al., "Common Structure of Soluble Amyloid Oligomers Implies Common Mechanism of Pathogenesis," Science, 2003, vol. 300 (18), pp. 486-489.
Kellermann S.A., et al., "Antibody Discovery: The Use of Transgenic Mice to Generate Human Monoclonal Antibodies for Therapeutics," Current Opinion in Biotechnology, 2002, vol. 13 (6), pp. 593-597.
Kennett R.H., et al., eds., "Monoclonal Antibodies" in: A New Dimension in Biological Analyses, Plenum Press, 1980, Table of Contents.
Kennett R.H., Mondclonal Antibodies, In Vitro., 1980. Table of Contents.
Kent, S. B. H, "Chemical Synthesis of Peptides and Proteins," Ann. Rev. Biochem., 1988, vol. 57, pp. 957-989.
Keowkase R., et al., "Mechanism of CNS Drugs and their Combinations for Alzheimer's Disease," Central Nervous System Agents in Medicinal Chemistry, 2008, vol. 8 (4), pp. 241-248.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Kim et al., "Development of Conformation-Specific Antibodies for Neutralization of Beta-Amyloid Oligomers," Neurobiology of Aging, 2004, vol. 25 (1), pp. 5145.
Kim, N. D. et al., Putative therapeutic agents for the learning and memory deficits of people with Down syndrome, Bioorganic & Medicinal Chemistry Letters, 2006, 16 (14), 3772-3776.
Kim Y.S., et al., "Biological Tuning of Synthetic Tactics in Solid-phase Synthesis: Application to A Beta(1-42)," Journal of Organic Chemistry, 2004, vol. 69 (22), pp. 7776-7778.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kipriyanov S.M., et al., "Recombinant Single-Chain Fv Fragments Carrying C-Terminal Cysteine Residues: Production of Bivlent and Biotinylated Miniantibodies," Molecular Immunology, 1994, vol. 31 (14), pp. 1047-1058.
Kirkitadze M.D., et al., "Identification and Characterization of Key Kinetic Intermediates in Amyloid beta-protein Fibrillogenesis," Journal of Molecular Biology, 2001, vol. 312 (5), pp. 1103-1119.
Kisilevsky R., et al., "Anti-Amyloid Drugs: Potential in the Treatment of Diseases Associated with Aging," Drugs Aging, 1996, vol. 8 (2), pp. 75-83.
Kisilevsky R., et al., "Arresting Amyloidosis in Vivo Using Small-Molecule Anionic Sulphonates or Sulphates: Implications for Alzheimer's Disease," Nature Medicine, 1995, vol. 1 (2), pp. 143-148.
Kitamura Y., et al., "Stress Proteins and Regulation of Microglial Amyloid-beta Phagocytosis," Folia Pharmacologica Japonica, 2004, vol. 124 (6), pp. 407-413.
Kitchin K., et al., "Cloning, Expression, and Purification of an Anti-desipramine Single Chain Antibody in NS/O Myeloma Cells," Journal of Pharmaceutical Sciences, 1995, vol. 84 (10), pp. 1184-1189.
Klafki H.W., et al., "Electrophoretic Separation of BetaA4 Peptides (1-40) and (1-42)," Analytical Biochemistry, 1996, vol. 237 (1), pp. 24-29.
Klein W.L., "A Beta Toxicity in Alzheimers Disease; Globular Oligomers (ADDls) as New Vaccine and Drug Targets," Neurochemistry International, 2002, vol. 41 (5), pp. 345-352.
Klyubin I., et al., "Amyloid P Protein Immunotherapy Neutralizes Aβ Oligomers That Disrupt Synaptic Plasticity in Vivo," Nature Medicine, 2005, vol. 11 (5), pp. 556-561.
Klyubin L., et al., Amyloid Beta-protein (abeta) Bearing the Arctic Mutation is a More Potent Inhibitor of LTP than Wild Type ABeta, Society for Neuroscience—Abstract Archive, Presentation No. 904.13, 33rd Annual Meeting of the Society of Neuroscience, New Orleans, LA, Nov. 8-12, 2003.
Knappik A., et al., "Fully Synthetic Human Combinatorial Antibody Libraries (hUCAL)Based on Modular Consensus Frameworks and CDRs Randomized with Trinucleotides," Journal of Molecular Biology, 2000, vol. 296 (1), pp. 57-86.
Knowles J.K., et al., "The p75 Neurotrophin Receptor Promotes Amyloid-beta(1-42)-induced Neuritic Dystrophy in Vitro and in Vivo," Journal of Neuroscience, 2009, vol. 29 (34), pp. 10627-10637.
Kobayashi H., et al., "Tryptophan H33 plays an important role in pyrimidine (6-4) pyrimidone photoproduct binding by a high-affinity antibody", Protein Engineering, 1999, 12 (10), 879-884.
Koh S.H., et al., "Amyloid-beta-induced Neurotoxicity is Reduced by Inhibition of Glycogen Synthase Kinase-3," Brain Research, 2008, vol. 1188, pp. 254-262.
Kohler G., et al., "Continuous Cultures of Fused Cells Secreting Antibody of Predefined Specificity ," Nature, 1975, vol. 256 (5517), pp. 495-497.
Kokubo H., et al., "Oligomeric Proteins Ultrastructurally Localize to Cell Processes, Especially to Axon Terminals with Higher Density, But Not to Lipid Rafts in Tg2576 Mouse Brain," Brain Research, 2005, vol. 1045 (1-2), pp. 224-228.
Kontermann R., et al., eds., Antibody Engineering, Springer-Verlag Berlin Heidelberg, 2001, Table of Contents.
Kooistra J., et al., "A New Function of Human HtrA2 as an Amyloid-beta Oligomerization Inhibitor," Journal of Alzheimer's Disease, 2009, vol. 17 (2), pp. 281-294.
Kortekaas P., et al., "Development of HVA and LVA calcium currents in pyramidal CA1 neurons in the hippocampus of the rat," Developmental Brain Research, 1997, vol. 101 (1-2), pp. 139-147.
Kranenburg O., et al., "Beta-amyloid (Abeta) Causes Detachment of N1E-115 Neuroblastoma Cells by Acting as a Scaffold for Cell-associated Plasminogen Activation," Molecular and Cellular Neurosciences, 2005, vol. 28 (3), pp. 496-508.
Kriegler M., Gene Transfer and Expression: A Laboratory Manual, Stockton Press, 1990, Table of Contents.
Kumar A., et al., "Neuropathology and Therapeutic Management of Alzheimer's Disease—An Update," Drugs of the Future, 2008, vol. 33 (5), pp. 433-446.
Kumar S., et al., "Molecular Cloning and Expression of the Fabs of Human Autoantibodies in Escherichia coli. Determination of the Heavy or Light Chain Contribution to the Anti-Dna/-Cardiolipin Activity of the Fab," The Journal of Biological Chemistry, 2000, vol. 275 (45), pp. 35129-35136.
Kumar-Singh, S. et al., "Dense-Core Senile Plaques in the Flemish Variant of Alzheimer's Disease Are Vasocentric," Am J Pathol, vol. 161 (2), pp. 507-520, 2002.
Kundrot C.E., "Which Strategy for a Protein Crystallization Project", Cellular and Molecular Life Sciences, 2004, vol. 61 (5), pp. 525-536.
Kuo Y.M., et al., "Water-soluble A3 ( N-40, N-42) Oligomers in Normal and Alzheimer Disease Brains," Journal of Biological Chemistry, 1996, vol. 271 (8), pp. 4077-4081.
Kwon Y.E., et al., "Synthesis, in Vitro Assay, and Molecular Modeling of New Piperidine Derivatives Having Dual Inhibitory Potency Against Acetylcholinesterase and Abeta1-42 Aggregation

(56) References Cited

OTHER PUBLICATIONS for Alzheimer's Disease Therapeutics," Bioorganic and Medicinal Chemistry, 2007, vol. 15 (20), pp. 6596-6607.
Lacor P.N., et al., "Synaptic targeting by Alzheimer's-related amyloid beta oligomers," Journal of Neuroscience, 2004, vol. 24 (45), pp. 10191-10200.
Laemmli U.K., et al., "Cleavage of Structural Proteins During the Assembly of the Head of Bacteriophage T4," Nature, 1970, vol. 227 (5259), pp. 680-685.
Lahiri D.K., et al., "Lethal Weapon: Amyloid Beta-peptide, Role in the Oxidative Stress and Neurodegeneration of Alzheimer's Disease," Neurobiology of Aging, 2004, vol. 25 (5), pp. 581-587.
Lam A.R., et al., "Effects of the Arctic (E22-->G) Mutation on Amyloid Beta-protein Folding: Discrete Molecular Dynamics Study," Journal of the American Chemical Society, 2008, vol. 130 (51), pp. 17413-17422.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Lambert M.P., et al., "Diffusible, Nonfibrillar Ligands Derived from Ar3, 42 are Potent Central Nervous System Neurotoxins," Proceedings of the National Academy of Sciences USA, 1998, vol. 95 (11), pp. 6448-6453.
Lambert M.P., et al., "Monoclonal Antibodies that Target Pathological Assemblies of a Beta," Journal of Neurochemistry, 2007, vol. 100 (1), pp. 23-35.
Lambert M.P., et al., "Vaccination with Soluble Abeta Oilgerm Generates Toxicity-Neutralizing Antibodies," Journal of Neurochemistry, 2001, vol. 79 (3), pp. 595-605.
Langdon S.D., et al., "Germline Sequences of V(H)7183 Gene Family Members in C57bl/6 Mice Demonstrate Natural Selection of Particular Sequences during Recent Evolution," Immunogenetics, 2000, vol. 51 (3), pp. 241-245.
Langer, et al., eds., International Journal of Biological Macromolecules, 1983, vol. 23, pp. 61-127.
Langer R., et al., "Chemical and Physical Structure of Polymers as Carriers for Controlled Rlease of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.
Lanni C., et al., Studies and Screening of Molecules Interacting with Beta Amyloid and Other Amyloidogenic Proteins, Society for Neuroscience—Abstract Archive, Presentation No. 841.1, 2003.
Lashuel H.A., et al., "Neurodegenerative Disease: Amyloid Pores from Pathogenic Mutationg," Nature, 2002, vol. 418 (6895), pp. 291.
Lau T.L., et al., "Cholesterol and Clioquinol Modulation of Abeta(1-42) Interaction with Phospholipid Bilayers and Metals," Biochimica et Biophysica Acta, 2007, vol. 1768 (12), pp. 3135-3144.
Lauren J., et al., "Cellular Prion Protein Mediates Impairment of Synaptic Plasticity by Amyloid-beta Oligomers," Nature, 2009, vol. 457 (7233), pp. 1128-1132.
Lazo N.D, et al., "On the Nucleation of Amyloid Beta-protein Monomer Folding," Protein Science, 2005, vol. 14 (6), pp. 1581-1596.
Leader K.A., et al., "Antibody Responses to the Blood Group Antigen D in SCID Mice Reconstituted with Human Blood Mononuclear Cells," Immunology, 1992, vol. 76 (2), pp. 229-234.
Lecanu L., et al., "Caprospinol: Moving from a Neuroactive Steroid to a Neurotropic Drug," Expert Opinion on Investigational Drugs, 2009, vol. 18 (3), pp. 265-276.
Lee C.C., et al., "Insulin Rescues Amyloid Beta-induced Impairment of Hippocampal Long-term Potentiation," Neurobiology of Aging, 2009, vol. 30 (3), pp. 377-387.
Lee D.H., et al., "Differential Physiologic Responses of Alpha7 Nicotinic Acetylcholine Receptors to Beta-amyloid1-40 and Beta-amyloid1-42," Journal of Neurobiology, 2003, vol. 55 (1), pp. 25-30.
Lee E.B., et al., "Secretion and Intracellular Generation of Truncated Ar3 in (3-Site Amyloid-13 Precursor Protein-cleaving Enzyme Expressing Human Neurons," Journal of Biological Chemistry, 2003, vol. 278 (7), pp. 4458-4466.
Lee E.B., et al., "Targeting Amyloid-Beta Peptide (Abeta) Oligomers by Passive Immunization with a Conformationselective Monoclonal Antibody Improves Learning and Memory in Abeta Precursor Protein (APP) Transgenic Mice," The Journal of Biological Chemistry, 2006, vol. 281 (7), pp. 4292-4299.
Lee H.K., et al., "The Insulin/Akt Signaling Pathway is Targeted by Intracellular Beta-amyloid," Molecular Biology of the Cell, 2009, vol. 20 (5), pp. 1533-1544.
Lee T.Y., et al., "Artificial Proteases toward Catalytic Drugs for Amyloid Diseases," Pure and Applied Chemistry, 2009, vol. 81 (2), pp. 255-262.
Lee U.H., et al., "Molecular Cloning of Agonistic and Antagonistic Monoclonal Antibodies against Human 4-1BB," European Journal of Immunogenetics, 2002, vol. 29 (5), pp. 449-452.
Lemere C.A., "Developing Novel Immunogens for a Safe and Effective Alzheimer's Disease Vaccine," Progress in Brain Research, 2009, vol. 175, pp. 83-93.
Lemere C.A., et al., "Amyloid-beta Immunotherapy for the Prevention and Treatment of Alzheimer Disease: Lessons from Mice, Monkeys, and Humans," Rejuvenation Research, 2006, vol. 9 (1), pp. 77-84.
Lerner E.A., "How to Make a Hybridoma," The Yale Journal of Biology & Medicine, 1981, vol. 54 (5), pp. 387-402.
Leveillea F., et al., "Influence of Oligomeric Forms of the Amyloid Beta 1-42 on Neuronal Viability," Rev Neural (Paris), 2007, vol. 163 (11 pt 2), pp. 4S23.
Levine H., et al., "4,4(')-Dianilino-1,1(')-Binaphthyl-5,5(')-Disulfonate: Report on Non-Beta-Sheet Conformers of Alzheimer's Peptide Beta(1-40)," Archives of Biochemistry and Biophysics, 2002, vol. 404 (1), pp. 106-115.
Levine H III., "Alzheimer's Beta-peptide Oligomer Formation at Physiologic Concentrations," Analytical Biochemistry, 2004, vol. 335 (1), pp. 81-90.
Levitt M., "Molecular Dynamics of Native Protein. I. Computer Simulation of Trajectories," Journal of Molecular Biology, 1983, vol. 168 (3), pp. 595-617.
Levy R.D., et al., "Inhibition of Calcification of Bioprosthetic Heart Valves by Local Controlled-Release Diphosphonate," Science, 1985, vol. 228 (4696), pp. 190-192.
Lewis H., et al, "Quantification of Alzheimer Pathology in Ageing and Dementia: Age-related Accumulation of Amyloid-beta(42) Peptide in Vascular Dementia," Neuropathology and Applied Neurobiology, 2006, vol. 32 (2), pp. 103-118.
Li H., et al., "SAR and Mechanistic Studies of Tetra-Peptide Inhibitors of ABeta42-Induced Neuro-Toxicity," Biopolymers, Young Investigators Abstracts, 2009, vol. 92 (4), p. 077, pp. 324.
Liao Y.J., et al., "Anti-Ca2+ Channel Antibody Attenuates Ca2+ Currents and Mimics Cerebellar Ataxia in Vivo," Proceedings of the National Academy of Sciences, 2008, vol. 105 (7), pp. 2705-2710.
Lindberg C., et al., "Beta-amyloid Protein Structure Determines the Nature of Cytokine Release from Rat Microglia," Journal of Molecular Neuroscience, 2005, vol. 27 (1), pp. 1-12.
Lipscombe D., et al., "Functional Diversity in Neuronal Voltage-Gated Calcium Channels by Alternative Splicing of Ca(v)alpha1 ," Molecular Neurobiology, 2002, vol. 26 (1), pp. 21-44.
Little M., et al., "Of Mice and Men: Hybridoma and Recombinant Antibodies," Immunology Today, 2000, vol. 21 (8), pp. 364-370.
Liu M., et al., "Progress in Soluble Abeta Oligomers in Alzheimer's Disease and Drugs Targeting Abeta Oligomers," Chinese Pharmacological Bulletin, 2008, vol. 24 (12), pp. 1554-1557.
Liu Q., et al., "A Novel Nicotinic Acetylcholine Receptor Subtype in Basal Forebrain Cholinergic Neurons with High Sensitivity to Amyloid Peptides," Journal of Neuroscience, 2009, vol. 29 (4), pp. 918-929.
Liu R., et al., "Single Chain Variable Fragments against Beta-Amyloid (Abeta) can Inhibit Abeta Aggregation and Prevent Abeta-Induced Neurotoxicity," Biochemistry, 2004, vol. 43 (22), pp. 6959-6967.

(56) References Cited

OTHER PUBLICATIONS

Liu R., et al., "Residues 17-20 and 35-35 of Beta-Amyloid Play Critical Roles in Aggregation," Journal of Neuroscience Research, 2004, vol. 75 (2), pp. 162-171.

Liu R., et al., "Trehalose Differentially Inhibits Aggregation and Neurotoxicity of Beta-amyloid 40 and 42," Neurobiology of Disease, 2005, vol. 20 (1), pp. 74-81.

Lonberg N., et al., "Antigen-Specific Human Antibodies From Mice Comprising Four Distinct Genetic Modifications," Nature, 1994, vol. 368, pp. 856-859.

Lonberg N., et al., "Human Antibodies from Transgenic Mice," International Reviews of Immunology, 1995, vol. 13 (1), pp. 65-93.

Lue L.F., et al., "Soluble Amyloid 13 Peptide Concentration as a Predictor of Synaptic Change in Alzheimer's Disease," American Journal of Pathology, 1999, vol. 155 (3), 853-862.

Luhrs T., et al., "3D Structure of Alzheimer's Amyloid-beta(1-42) Fibrils," Proceedings of the National Academy of Sciences, 2005, vol. 102 (48), pp. 17342-17347.

Lund J., et al., "Oligosaccharide-Protein Interactions in IgG can Modulate Recognition by Fc Gamma Receptors," The FASEB Journal, 1995, vol. 9 (1), pp. 115-119.

Lunn M.P., et al., "High-Affinity Anti-Ganglioside IgG Antibodies Raised in Complex Ganglioside Knockout Mice: Reexamination of GD1a Immunolocalization," Journal of Neurochemistry, 2000, vol. 75 (1), pp. 404-412.

Ma B., et al., "Polymorphic C-Terminal-Sheet Interactions Determine the Formation of Fibril or Amyloid-Derived Diffusible Ligand-Like Globulomer for the Alzheimer A42 Dodecamer," The Journal of Biological Chemistry, 2010, vol. 285 (47), pp. 37102-37110.

Ma Q.L., et al., "p21-Activated Kinase-Aberrant Activation and Translocation in Alzheimer Disease Pathogenesis," The Journal of Biological Chemistry, 2008, vol. 283 (20), pp. 14132-14143.

Macao B., et al., "Recombinant Amyloid Beta-peptide Production by Coexpression with an Affibody Ligand," BMC Biotechnology, 2008, vol. 8, pp. 82.

Maccallum R.M., et al., "Antibody-Antigen Interactions: Contact Analysis and Binding Site Topography," Journal of Molecular Biology, 1996, vol. 262 (5), pp. 732-745.

Maccioni R.B., et al., "What have we Learned From the Tau Hypothesis? Current Hypothesis and Research Milestones in Alzheimer's Disease Current Hypotheses and Research Milestones in Alzheimer's Disease" in: International Summitt Meeting on Current Hypotheses on Alzheimer Disease, 2007.

Macquitty J.J., et al., "GenPharm's Knockout Mice," Science, 1992, vol. 257 (5074), pp. 1188.

Mader C. et al., "Interaction of the crystalline bacterial cell surface layer protein SbsB and the secondary cell wall polymer of Geobacillus stearothermophilus PV72 assessed by real-time surface plasmon resonance biosensor technology," J. Bacterial, 2004.

Madrigal J.L., et al., "Neuroprotective Actions of Noradrenaline: Effects on Glutathione Synthesis and Activation of Peroxisome Proliferator Activated Receptor Delta," Journal of Neurochemistry, 2007, vol. 103 (5), pp. 2092-2101.

Maier M., et al., "Short Amyloid-Beta Immunogens Reduce Cerebral in an Alzheimer'S Disease Mouse Model in the Absence of an Amyloid-Beta-Specific Cellular Immune Response," Journal of Neuroscience, 2006, vol. 26 (18), pp. 4717-4728.

Maliga, P., et al., Methods in Plant Molecular Biology—A Laboratory Manual, Tbl. of Cont., 1995.

Mandal P.K., et al., "Alzheimer's Disease: Halothane Induces Abeta Peptide to Oligomeric Form—Solution NMR Studies," Neurochemical Research, 2006, vol. 31 (7), pp. 883-890.

Manelli A.M., et al., "Abeta42 Neurotoxicity in Primary Co-Cultures: Effect of apoE Isoform and Abeta Conformation," Neurobiology of Aging, 2007, vol. 28 (8), pp. 1139-1147.

Manelli A.M., et al., "ApoE and Abeta1-42 Interactions: Effects of Isoform and Conformation on Structure and Function," Journal of Molecular Neuroscience, 2004, vol. 23 (3), pp. 235-246.

Manelli A.M., et al., Glial Activation by Oligomeric Versus Fibrillar Aβ1-42, Society for Neuroscience—Abstract Archive: 2000-2005, Presentation No. 193.9, 2002.

Marchalonis J.J., et al., "Evolutionary Factors in the Emergence of the Combinatorial Germline Antibody Repertoire," Advances in Experimental Medicine and Biology, 2001, vol. 484, pp. 13-30.

Maria T.J., et al., "Upregulation of p21(Cip1) in Activated Glial Cells," Glia, 2009, pp. 57524-57534.

Mariette X., et al., "Nucleotidic Sequence Analysis of the Variable Domains of Four Human Monoclonal IgM with an Antibody Activity to Myelin-Associated Glycoprotein," European Journal of Immunology, 1993, vol. 23 (4), pp. 846-851.

Marlow L., et al., "APH1, PEN2, and Nicastrin Increase Abeta Levels and Gamma-Secretase Activity," Biochemical and Biophysical Research Communications, 2003, vol. 305 (3), pp. 502-509.

Masliah E., et al., "Progress in the Development of New Treatments for Combined Alzheimer's and Parkinson's Diseases," Drug Development Research, 2002, vol. 56, pp. 282-292.

Masman M.F., et al., "In Silico Study of Full-Length Amyloid Beta 1-42 Tri- and Penta-Oligomers in Solution," The Journal of Physical Chemistry B, 2009, vol. 113 (34), pp. 11710-11719.

Masters C.L., et al., "Amyloid Plaque Core Protein in Alzheimer Disease and Down Syndrome," Proceedings of the National Academy of Sciences, 1985, vol. 82 (12), 4245-4249.

Mastrangelo I.A., et al., "High-Resolution Atomic Force Microscopy of Soluble Abeta42 Oligomers," Journal of Molecular Biology, 2006, vol. 358 (1), pp. 106-119.

Masuda Y., et al., "Identification of Physiological and Toxic Conformations in Abeta42 Aggregates," Chembiochem, 2009, vol. 10 (2), pp. 287-295.

Mathura V.S., et al., "Model of Alzheimer's Disease Amyloid-Beta Peptide Based on a RNA Binding Protein," Biochemical and Biophysical Research Communications, 2005, vol. 332 (2), pp. 585-592.

Mattson et al., "A practical approach to crosslinking," Molecular Biology Reports, 1993, vol. 17, pp. 167-183.

Mattson M.P., et al., "Pathways Towards and Away from Alzheimer'S Disease," Nature, 2004, vol. 431 (7004), pp. 107.

Mattson M.P., "Pathways Towards and Away from Alzheimer's Disease," Nature, 2004, vol. 430 (7000), pp. 631-839.

Maurer MH et al., The proteome of neural stem cells from adult rat hippocampus, Proteome Science, 2003, 1 (1), 4.

May K., "Buying a New Immnoassay System?," BioTechnology-TIBTECH, 1993, vol. 11, pp. 272-273.

McCafferty J., et al., "Phage Antibodies: Filamentous Phage Displaying Antibody Variable Domains," Nature, 1990, vol. 348 (6301), pp. 552-554.

McKinnon S.J., et al., "Caspase Activation and Amyloid Precursor Protein Cleavage in Rat Ocular Hypertension," Investigative Ophthalmology & Visual Science, 2002, vol. 43 (4), pp. 1077-1087.

McLaurin J., et al., "Inositol Stereoisomers Stabilize an Oligomeric Aggregate of Alzheimer Amyloid Beta Peptide and Inhibit Abeta-Induced Toxicity," The Journal of Biological Chemistry, 2000, vol. 275 (24), pp. 18495-18502.

McLaurin J., et al., "Review Modulating Factors in Amyloid-Beta Fibril Formation," Journal Structural Biology, 2000, vol. 130 (2-3), 259-270.

McLaurin J., et al., "Therapeutically Effective Antibodies against Amyloid-Beta Peptide Target Amyloid-Beta Residues 4-10 and Inhibit Cytotoxicity and Fibrillogenesis," Nature Medicine, 2002, vol. 8 (11), pp. 1263-1269.

McLean C.A., et al., "Soluble Pool of A-beta Amyloid as a Determinant of Severity of Neurodegeneration in Alzheimer's Disease," American Neurological Association, 1999, vol. 46 (6), 860-866.

McPherson A., et al., "Current Approaches to Macromolecular Crystallization," European Journal of Biochemistry, 1990, vol. 189 (1), pp. 1-23.

Meijer et al., Biochemical and cellular effects of roscovitine, a potent and selective inhibitor of the cyclin-dependent kinases cdc2, cdk2 and cdk5, Eur. J. Biochem, 1997, 243 (1-2), 527-536.

(56) References Cited

OTHER PUBLICATIONS

Meli G., et al., "Direct in Vivo Intracellular Selection of Conformation-Sensitive Antibody Domains Targeting Alzheimer's Amyloid-Beta Oligomers," Journal of Molecular Biology, 2009, vol. 387 (3), pp. 584-606.
Mendez M.J., et al., "Functional Transplant of Megabase Human Immunoglobulin Loci Recapitulates Human Antibody Response in Mice," Nature Genetics, 1997, vol. 15 (2), pp. 146-156.
Merrifield B., "Solid Phase Synthesis," 1986, vol. 232, pp. 342.
Merrifield J., "The total synthesis of an enzyme with ribonuclease A activity," J. Am. Chem. Soc, 1969, vol. 91, Academic Press, Inc. pp. 501-502.
Miller Y., et al., "Polymorphism of Alzheimer's Abeta17-42 (p3) Oligomers: the Importance of the Turn Location and its Conformation," Biophysical Journal, 2009, vol. 97 (4), pp. 1168-1177.
Minkeviciene R., et al., "Amyloid Beta-Induced Neuronal Hyperexcitability Triggers Progressive Epilepsy," The Journal of Neuroscience, 2009, vol. 29 (11), pp. 3453-3462.
Miscellaneous Communication dated Aug. 11, 2011 for U.S. Appl. No. 11/574,844, filed Sep. 30, 2008.
Mizushima S., et al., "pEF-BOS, a Powerful Mammalian Expression Vector," Nucleic Acids Research, 1990, vol. 18 (17), pp. 5322.
Moechars D., et al., "Early Phenotypic Changes in Transgenic Mice that Overexpress Different Mutants of Amyloid Precursor Protein in Brain," Journal of Biological Chemistry, 1999, vol. 274 (10), pp. 6483-6492.
Moir R.D., et al., "Autoantibodies to Redox-Modified Oligomeric Abeta are Attenuated in the Plasma of Alzheimer's Disease Patients," The Journal of Biological Chemistry, 2005, vol. 280 (17), pp. 17458-17463.
Monien B.H., et al., "A Novel Approach to Alzheimer's Disease Therapy: Inhibition of Aβ42 Oligomerization by C-Terminal Aβ42 Fragments," Journal of Peptide Science, 2006.
Moretto N., et al., "Conformation-Sensitive Antibodies against Alzheimer Amyloid-Beta by Immunization with a Thioredoxin-Constrained B-Cell Epitope Peptide," The Journal of Biological Chemistry, 2007, vol. 282 (15), pp. 11436-11445.
Morgan R.A., et al., "Human Gene Therapy," Annual Review of Biochemistry, 1993, vol. 62, 191-217.
Morgan T.E., et al., "Abeta-Derived Diffusible Ligands (ADDLs): Clusterin (apo J), Congo Red Binding and Toxicity," Society for Neuroscience Abstracts, 29th Annual Meeting of the Society for Neuroscience, Miami Beach, FL, Abstract No. 252130, 1999.
Morley J.S., "Modulation of the Action of Regulatory Peptides by Structural Modification," TIPS, 1980, pp. 463-468.
Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.
Morrison S.L., "Transfectomas Provide Novel Chimeric Antibodies," Science, 1985, vol. 229 (4719), pp. 1202-1207.
Mueller W., et al., "Apolipoprotein E Isoforms Increase Intracellular Ca2+ Differentially Through a Omega-Agatoxin Iva-Sensitive Ca2+-Channel.," Brain pathology, 1998, vol. 8 (4), pp. 641-653.
Mullan M., et al., "A Locus for Familial Early-onset Alzheimer's Disease on the Long Arm of Chromosome 14, Proximal to the Alpha 1-antichymotrypsin Gene," Nature Genetics, 1992, vol. 2 (4), pp. 340-342.
Mullan M., et al., "A Pathogenic Mutation for Probable Alzheimer's Disease in the APP Gene at the N-terminus of Beta-amyloid," Nature Genetics, 1992, vol. 1 (5), pp. 345-347.
Muller W., et al., "Apolipoprotein E Isoforms Increase Intracellular Ca2+ Differentially Through a Omega-Agatoxin IVa-Sensitive Ca2+-Channel," Brain Pathology, 1998, vol. 8 (4), pp. 641-653.
Muller W. et al., Impaired Ca-signaling in astrocytes from the Ts16 mouse model of Down syndrome, Neuroscience Letters, 1997, 223 (2), 81-84.
Mulligan R.C., "The Basic Science of Gene Therapy," Science, 1993, vol. 260 (5110), pp. 926-932.

Mullis K., et al., "Specific Enzymatic Amplification of DNA In Vitro: The Polymerase Chain Reaction," Cold Spring Harbor Symposia on Quantitative Biology, 1986, vol. 51 (Pt 1), pp. 263-273.
Munter L.M., et al., "GxxxG Motifs within the Amyloid Precursor Protein Transmembrane Sequence are Critical for the Etiology of Abeta42," The EMBO Journal, 2007, vol. 26 (6), pp. 1702-1712.
Murphy W.J., et al., "CD40 Stimulation Promotes Human Secondary Immunoglobulin Responses in HuPBL-SCID Chimeras," Clinical Immunology, 1999, vol. 90 (1), pp. 22-27.
Murphy W.J., et al., "The HuPBL-SCID Mouse as a Means to Examine Human Immune Function in Vivo," Seminars in Immunology, 1996, vol. 8 (4), pp. 233-241.
Murray M.M., et al., "Amyloid Beta Protein: Abeta40 Inhibits Abeta42 Oligomerization," Journal of the American Chemical Society, 2009, vol. 131 (18), pp. 6316-6317.
Myagkova M.A., et al., "Autoantibodies to Beta-Amyloid and Neurotransmitters in Patients With Alzheimer'S Disease and Senile Dementia of the Alzheimer Type.," Bulletin of Experimental Biology and Medicine, 2001, vol. 131 (2), pp. 127-129.
Nagele R.G., et al., "Contribution of Glial Cells to the Development of Amyloid Plaques in Alzheimer's Disease," Neurobiology of Aging, 2004, vol. 25 (5), pp. 663-674.
Naslund J., et al., "Relative Abundance of Alzheimer A B Amyloid Peptide Variants in Alzheimer Disease and Normal Aging," The Proceedings of the National Academy of Sciences of the United States of America, 1994, vol. 91 (18), pp. 8378-8382.
Nath A., et al., "Autoantibodies to Amyloid Beta-peptide (Abeta) are Increased in Alzheimer's Disease Patients and Abeta Antibodies can Enhance Abeta Neurotoxicity," Neuromolecular Medicine, 2003, vol. 3 (1), pp. 29-39.
NCBI Accession No. AAA92933, Mar. 23, 2002.
NCBI Accession No. AAA96779, Apr. 11, 1996.
NCBI Accession No. AAL92941, Mar. 23, 2002.
NCBL Accession No. AAA38584, Aug. 30, 1993.
Needleman S.B., et al., "A General Method Applicable to the Search for Similarities in the Amino Acid Sequence of Two Proteins," Journal of Molecular Biology, 1970, vol. 48 (3), pp. 443-453.
Nemes Z., et al., "Cross-Linking of Ubiquitin, Hsp27, Parkin, and Alpha-Synuclein by Gamma-Glutamyl-Epsilon-Lysine Bonds in Alzheimer's Neurofibrillary Tangles," The FASEB Journal, 2004, vol. 18 (10), pp. 1135-1137.
Nerelius C., et al., "Alpha-Helix Targeting Reduces Amyloid-Beta Peptide Toxicity," Proceedings of the National Academy of Sciences, 2009, vol. 106 (23), pp. 9191-9196.
Neuberger M.S., et al., "Recombinant Antibodies Possessing Novel Effector Functions," Nature, 1984, vol. 312 (5995), pp. 604-608.
Nguyen H., et al., "Production of Human Monoclonal Antibodies in SCID Mouse," Microbiology and Immunology, 1997, vol. 41 (12), pp. 901-907.
Nicholas M.R., et al., "Different Amyloid-ent Amyloid-Beta Aggregation States Induced Monocyte Differentiation or Activation," Journal of Neurochemistry, 10867, 40th Annual Meeting of the American Society for Neurochemistry, Charleston, South Carolina, 2009.
Nicolau C., et al., "A Liposome-Based Therapeutic Vaccine against Beta-Amyloid Plaques on the Pancreas of Transgenic Norba Mice," Proceedings of the National Academy of Sciences, 2002, vol. 99 (4), pp. 2332-2337.
Nielsen H.M., et al., "Preferential Uptake of Amyloid Beta 1-42 Oligomers by Primary Human Astrocytes in Vitro: Influence of SAP and C1q, OP116," Molecular Immunology, 2009, vol. 46, pp. 2860.
Nilges, M. et al., "Determination of Three-Dimensional Structures of Proteins From Interproton Distance Data by Hybrid Distance Geometry-Dynamical Simulated Annealing Calculations," FEBSLetters, 1989, 229 (2), 317-324.
Nimmrich V., et al., "Amyloid Beta Oligomers (A beta(1-42) Globulomer) Suppress Spontaneous Synaptic Activity by Inhibition of P/Q-type Calcium Currents," Journal of Neuroscience, 2008, vol. 28 (4), pp. 788-797.
Nimmrich V., et al., "Is Alzheimer's Disease a Result of Presynaptic Failure? Synaptic Dysfunctions Induced by Oligomeric Beta-Amyloid," Reviews in the Neurosciences, 2009, vol. 20 (1), pp. 1-12.

(56) References Cited

OTHER PUBLICATIONS

Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Nomura I., et al., "Mechanism of Impairment of Long-Term Potentiation by Amyloid Beta is Independent of NMDA Receptors or Voltage-Dependent Calcium Channels in Hippocampal CA1 Pyramidal Neurons," Neuroscience Letters, 2005, vol. 391 (1-2), pp. 1-6.
Non-Final Office Action dated Jan. 3, 2012 for U.S. Appl. No. 13/188,034, filed Jul. 21, 2011.
Non-Final Office Action dated Mar. 3, 2010 for U.S. Appl. No. 11/945,124, filed Nov. 26, 2007.
Non-Final Office Action dated Dec. 6, 2011 for U.S. Appl. No. 12/529,467, filed Jul. 27, 2010.
Non-Final Office Action dated Jun. 6, 2012 for U.S. Appl. No. 12/509,315, filed Jul. 24, 2009.
Non-Final Office Action dated Jun. 6, 2012 for U.S. Appl. No. 12/509,325, filed Jul. 24, 2009.
Non-Final Office Action dated Feb. 10, 2011 for U.S. Appl. No. 11/574,844, filed Sep. 30, 2008.
Non-Final Office Action dated Nov. 13, 2012 for U.S. Appl. No. 13/195,533, filed Aug. 1, 2011.
Non-Final Office Action dated Feb. 14, 2014 for U.S. Appl. No. 12/529,467, filed Jul. 27, 2010.
Non-Final Office Action dated Jul. 14, 2011 for U.S. Appl. No. 11/574,847, filed Dec. 31, 2008.
Non-Final Office Action dated Nov. 15, 2012 for U.S. Appl. No. 11/574,876, filed Feb. 25, 2009.
Non-Final Office Action dated Apr. 18, 2013 for U.S. Appl. No. 13/085,891, filed Apr. 13, 2011.
Non-Final Office Action dated Apr. 19, 2012 for U.S. Appl. No. 13/102,713, filed May 6, 2011.
Non-Final Office Action dated Jul. 22, 2010 for U.S. Appl. No. 11/885,362, filed Apr. 17, 2008.
Non-Final Office Action dated Jan. 23, 2012 for U.S. Appl. No. 11/574,876, filed Feb. 25, 2012.
Non-Final Office Action dated Feb. 24, 2014 for U.S. Appl. No. 13/195,533, filed Aug. 1, 2011.
Non-Final Office Action dated Sep. 26, 2013 for U.S. Appl. No. 11/885,362, filed Apr. 17, 2008.
Notice of Allowance dated Feb. 3, 2016 for U.S. Appl. No. 13/862,865, filed Apr. 15, 2013.
Notice of Allowance dated Apr. 4, 2011 for U.S. Appl. No. 11/945,124, filed Nov. 26, 2007.
Notice of Allowance dated Oct. 4, 2012 for U.S. Appl. No. 11/574,847, filed Dec. 31, 2008.
Notice of Allowance dated Mar. 5, 2012 for U.S. Appl. No. 11/945,124, filed Nov. 26, 2007.
Notice of Allowance dated Jul. 9, 2014 for U.S. Appl. No. 12/529,467, filed Jul. 27, 2010.
Notice of Allowance dated May 9, 2012 for U.S. Appl. No. 11/574,844, filed Sep. 30, 2008.
Notice of Allowance dated Oct. 9, 2012 for U.S. Appl. No. 11/945,124, filed Nov. 26, 2007.
Notice of Allowance dated Feb. 10, 2010 for U.S. Appl. No. 14/513,837, filed Oct. 14, 2014.
Notice of Allowance dated Feb. 10, 2012 for U.S. Appl. No. 11/574,847, filed Dec. 31, 2008.
Notice of Allowance dated Aug. 11, 2011 for U.S. Appl. No. 11/574,844, filed Sep. 30, 2008.
Notice of Allowance dated Feb. 11, 2015 for U.S. Appl. No. 13/988,307, filed Mar. 7, 2014.
Notice of Allowance dated Mar. 14, 2014 for U.S. Appl. No. 13/102,713, filed May 6, 2011.
Notice of Allowance dated Jun. 24, 2014 for U.S. Appl. No. 13/102,713, filed May 6, 2011.
Notice of Allowance dated Jun. 25, 2015 for U.S. Appl. No. 13/195,533, filed Aug. 1, 2011.
Notice of Allowance dated Oct. 29, 2014 for U.S. Appl. No. 13/085,891, filed Apr. 13, 2011.
Notice of Allowance dated Sep. 30, 2013 for U.S. Appl. No. 11/574,876, filed Feb. 25, 2009.
Notice of Opposition for Europen Patent No. EP1861422 dated Nov. 24, 2010.
Notice of Opposition dated Nov. 24, 2010 for European Application No. 06707413 filed Mar. 3, 2006.
Office Action dated Feb. 1, 2016 for U.S. Appl. No. 14/514,168, filed Oct. 14, 2014.
Office Action dated Dec. 3, 2014 for U.S. Appl. No. 13/195,533, filed Aug. 1, 2011.
Office Action dated Jun. 4, 2015 for U.S. Appl. No. 13/862,865, filed Apr. 15, 2013.
Office Action dated Oct. 5, 2015 for U.S. Appl. No. 13/893,780.
Office Action dated Jan. 9, 2015 for U.S. Appl. No. 13/893,780, filed May 14, 2013.
Office Action dated Nov. 9, 2015 for U.S. Appl. No. 14/513,837, filed Oct. 14, 2014.
Office Action dated Oct. 10, 2014 for U.S. Appl. No. 11/715,837, filed Apr. 13, 2011.
Office Action dated Jul. 21, 2014 for U.S. Appl. No. 10/179,255, filed Feb. 2, 2004.
Office Action dated Jul. 21, 2014 for U.S. Appl. No. 10/179,281, filed Feb. 2, 2004.
Office Action dated Jul. 21, 2014 for U.S. Appl. No. 10/179,297, filed Feb. 2, 2004.
Office Action dated Jul. 31, 2015 for U.S Appl. No. 14/303,300, filed Jun. 12, 2014.
Oi V.T., et al., "Chimeric Antibodies," BioTechniques, 1985, vol. 4 (3), pp. 214-215.
Okamuro J.K., et al., "Regulation of Plant Gene Expression: General Principles" in: The Biochemistry of Plants: A Comprehensive Treatise, vol. 15, Marcus A., ed., Academic Press Limited, 1989, pp. 1-82.
Ono K., et al., "Effects of Grape Seed-derived Polyphenols on Amyloid Beta-protein Self-assembly and Cytotoxicity," Journal of Biological Chemistry, 2008, vol. 283 (47), pp. 32176-32187.
Opazo C., et al., "Metalloenzyme-like Activity of Alzheimer's Disease Beta-amyloid, Cu-dependent Catalytic Conversion of Dopamine, Cholesterol, and Biological Reducing Agents to Neurotoxic $H(2)O(2)$.," Journal of Biological Chemistry, 2002, vol. 277 (43), pp. 40302-40308.
Orgogozo J.M., et al., "Subacute Meningoencephalitis in a Subset of Patients with AD after Abeta42 Immunization," Neurology, 2003, vol. 61 (1), pp. 46-54.
Origlia N., et al., "Abeta-dependent Inhibition of LTP in Different Intracortical Circuits of the Visual Cortex: The Role of RAGE," Journal of Alzheimer's Disease, 2009, vol. 17 (1), pp. 59-68.
Otto M., et al., "Neurochemical Approaches of Cerebrospinal Fluid Diagnostics in Neurodegenerative Diseases," Methods, 2008, vol. 44 (4), pp. 289-298.
Padlan E.A., "A Possible Procedure for Recucing the Immunogenicity of Antibody Variable Domains While Preserving Their Ligand-Binding Properties," Molecular Immunology, 1991, vol. 28 (4-5), pp. 489-498.
Padlan E.A., et al., "Identification of Specificity-determining Residues in Antibodies," FASEB Journal, 1995, vol. 9 (1), pp. 133-139.
Padlan E.A., et al., "Structure of an Antibody-antigen Complex: Crystal Structure of the HyHEL-10 Fab-lysozyme Complex," Proceedings of the National Academy of Sciences, 1989, vol. 86 (15), pp. 5938-5942.
Palmer J.C., et al., "Endothelin-converting Enzyme-2 is Increased in Alzheimer's Disease and Up-regulated by Abeta," American Journal of Pathology, 2009, vol. 175 (1), pp. 262-270.
Pan X.D., et al., "Tripchlorolide Protects Neuronal Cells from Microglia-mediated Beta-amyloid Neurotoxicity through Inhibiting NF-kappaB and JNK Signaling," Glia, 2009, vol. 57 (11), pp. 1227-1238.
Partis M. D. et al., "Crosslinking of proteins by omega-maleimido alkanoyl N-hydroxysuccinimide esters," J. Protein. Chem, 1983, vol. 2, pp. 263-277.

(56) References Cited

OTHER PUBLICATIONS

Pastor A.T., et al., "Amyloid Toxicity is Independent of Polypeptide Sequence, Length and Chirality," Journal of Molecular Biology, 2008, vol. 375 (3), pp. 695-707.
Paul W.E., ed., Fv Structure and Diversity in Three Dimensions:Fundamental Immunology, 3rd Edition, Raven Press, Ltd., 1993, pp. 292-295.
Paul W.E., Ed., "Structure and Function of Immunoglobulins," in: Fundamental Immunology, 1993, 3rd Edition and Chapter 9, Raven Press Ltd., New York, pp. 292-295.
Peacock M.L., et al., "Novel Amyloid Precursor Protein Gene Mutation (codon 665Asp) in a Patient with Late-onset Alzheimer's Disease," Annals of Neurology, 1994, vol. 35 (4), pp. 432-438.
Peacock M.L., et al., "Novel Polymorphism in the A4 Region of the Amyloid Precursor Protein Gene in a Patient without Alzheimer's Disease," Neurology, 1993, vol. 43 (6), pp. 1254-1256.
Pearson W.R., et al., "Improved Tools for Biological Sequence Comparison," Proceedings of the National Academy of Sciences, 1988, vol. 85 (8), pp. 2444-2448.
Pellicano M., et al., "The Sea Urchin Embryo: A Model to Study Alzheimer's Beta Amyloid Induced Toxicity," Archives of Biochemistry and Biophysics, 2009, vol. 483 (1), pp. 120-126.
Perouansky M., "Liaisons Dangereuses? General Anaesthetics and Long-term Toxicity in the CNS," European Journal of Anaesthesiology, 2007, vol. 24 (2), pp. 107-115.
Persic L., et al., "An Integrated Vector System for the Eukaryotic Expression of Antibodies or their Fragments After Selection from Phage Display Libraries," Gene, 1997, vol. 187 (1), pp. 9-18.
Petrushina I., et al., "Alzheimer'S Disease Peptide Epitope Vaccine Reduces Insoluble but not Soluble/Oligomeric Abeta Species in Amyloid Precursor Protein Transgenic Mice," Journal of Neuroscience, 2007, vol. 27 (46), pp. 12721-12731.
Pfeifer M., et al., "Cerebral Hemorrhage After Passive Anti-ABeta Immunotherapy," Science, 2002, vol. 298 (5597), pp. 1379.
Phu J., et al., "Fluorescence Resonance Energy Transfer Analysis of Apolipoprotein E C-terminal Domain and Amyloid Beta Peptide (1-42) Interaction," Journal of Neuroscience Research, 2005, vol. 80 (6), pp. 877-886.
Pike C.J., et al., "Structure-activity Analyses of beta-amyloid Peptides: Contributions of the beta 25-35 Region to Aggregation and Neurotoxicity," Journal of Neurochemistry, 1995, vol. 64 (1), pp. 253-265.
Plant L.D., et al., "The Production of Amyloid p Peptide Is a Critical Requirement for the Viability of Central Neurons," Journal of Computational Neuroscience, 2003, vol. 23 (13), pp. 5531-5535.
Podlisny M.B., et al., "Aggregation of Secreted Amyloid Beta-protein into Sodium Dodecyl Sulfate-stable Oligomers in Cell Culture," Journal of Biological Chemistry, 1995, vol. 270 (16), pp. 9564-9570.
Poljak R.J., "Production and Structure of Diabodies," Structure, 1994, vol. 2 (12), pp. 1121-1123.
Portelius A., et al., "Targeted Proteomics in Alzheimer's Disease: Focus on Amyloid-beta," Expert Review of Proteomics, 2008, vol. 5 (2), pp. 225-237.
Portolano S., et al., "High Affinity, Thyroid-specific Human Autoantibodies Displayed on the Surface of Filamentous Phage Use V Genes Similar to Other Autoantibodies," Journal of Immunology, 1993, vol. 151 (5), pp. 2839-2851.
Presta L.G., et al., "Humanization of an Antibody Directed Against IgE," Journal of Immunology, 1993, vol. 151 (5), pp. 2623-2632.
Putney P.W., eds., Calcium Signaling, CRC Press Inc, 2nd Edition, 2005, Table of Contents.
Puzzo D., et al., "Picomolar Amyloid-beta Positively Modulates Synaptic Plasticity and Memory in Hippocampus," Journal of Neuroscience, 2008, vol. 28 (53), pp. 14537-14545.
Qian J., et al., "Presynaptic Ca2+ Channels and Neurotransmitter Release at the Terminal of a Mouse Cortical Neuron," Journal of Neuroscience, 2001, vol. 21 (11), pp. 3721-3728.
Qiu W., "Anaspec poster at 20th American Peptide Society Annual Meeting," 2008.
Qiu, W. et al., "Convenient, Large-Scale Asymmetric Synthesis of Eriantiomerically Pure Trans-Cinnamylglycine and- Alpha-Alanine," Tetrahedron, 2000, vol. 56, pp. 2577-2582.
Qiu W., "Facile Synthesis of Hydrocarbon-Stapled Peptides," Anaspec Poster at 20th American Peptide Society Annual Meeting, 2008.
Qiu W.Q., et al., "Degradation of Amyloid Beta-protein by a Metalloprotease Secreted by Microglia and Other Neural and Non-neural Cells," Journal of Biological Chemistry, 1997, vol. 272 (10), pp. 6641-6646.
Qiu W.Q., et al., "Insulin-degrading Enzyme Regulates Extracellular Levels of Amyloid Beta-protein by Degradation," Journal of Biological Chemistry, 1998, vol. 273 (49), pp. 32730-32738.
Racke M.M., et al., "Exacerbation of Cerebral Amyloid Angiopathy-Associated Microhemmorrhage in Amyloid Precursor Protein Transgenic Mice by Immunotherapy Is Dependent on Antibody Recognition of Deposited Forms of Amyloid 13," The Journal of Neuroscience, 2005, vol. 25 (3), pp. 629-636.
Rahimi F., et al., "Photo-induced Cross-linking of Unmodified Proteins (PICUP) Applied to Amyloidogenic Peptides," Journal of Visualized Experiments, 2009, vol. 23.
Rahimi F., et al., "Structure-function Relationships of Pre-fibrillar Protein Assemblies in Alzheimer's Disease and Related Disorders," Current Alzheimer Research, 2008, vol. 5 (3), pp. 319-341.
Rambaldi D.C., et al., "In vitro Amyloid Abeta(1-42) Peptide Aggregation Monitoring by Asymmetrical Flow Field-flow Fractionation with Multi-angle Light Scattering Detection," Analytical and Bioanalytical Chemistry, 2009, vol. 394 (8), pp. 2145-2149.
Rangachari V., et al., "Amyloid-beta(1-42) Rapidly Forms Protofibrils and Oligomers by Distinct Pathways in Low Concentrations of Sodium Dodecylsulfate," Biochemistry, 2007, vol. 46 (43), pp. 12451-12462.
Rangachari V., et al., "Secondary Structure and Interfacial Aggregation of Amyloid-beta(1-40) on Sodium Dodecyl Sulfate Micelles," Biochemistry, 2006, vol. 45 (28), pp. 8639-8648.
Rangachari V., et al., "Rationally Designed Dehydroalanine (DeltaAla)-containing Peptides Inhibit Amyloid-beta (Abeta) Peptide Aggregation," Biopolymers, 2009, vol. 91 (6), pp. 456-465.
Ravault S., et al., "Fusogenic Alzheimer's Peptide Fragment Abeta (29-42) in Interaction with Lipid Bilayers: Secondary Structure, Dynamics, and Specific Interaction with Phosphatidyl Ethanolamine Polar Heads as Revealed by Solid-state NMR," Protein Science, 2005, vol. 14 (5), pp. 1181-1189.
Ravetch J.V., et al., "Structure of the Human Immunoglobulin mu Locus: Characterization of Embryonic and Rearranged J and D Genes," Cell, 1981, vol. 27 (3 Pt 2), pp. 583-591.
Reisner Y., et al., "The Trimera Mouse: Generating Human Monoclonal Antibodies and an Animal Model for Human Diseases," Trends in Biotechnology, 1998, vol. 16 (6), pp. 242-246.
Remington: The science and Practice of Pharmacy, 19th Edition, 1995, pp. 287-289.
Resende R., et al., "ER Stress is Involved in Abeta-induced GSK-3beta Activation and Tau Phosphorylation," Journal of Neuroscience Research, 2008, vol. 86 (9), pp. 2091-2099.
Resende R., et al., "Neurotoxic Effect of Oligomeric and Fibrillar Species of Amyloid-beta Peptide 1-42: Involvement of Endoplasmic Reticulum Calcium Release in Oligomer-induced Cell Death," Neuroscience, 2008, vol. 155 (3), pp. 725-737.
Riechmann L., et al., "Reshaping Human Antibodies for Therapy," Nature, 1988, vol. 332 (6162), pp. 323-327.
Robert R., et al., "Engineered Antibody Intervention Strategies for Alzheimer's Disease and Related Dementias by Targeting Amyloid and Toxic Oligomers," Protein Engineering, Design & Selection, 2009, vol. 22 (3), pp. 199-208.
Roberts R.W., et al., "RNA-peptide, Fusions for the in Vitro Selection of Peptides and Proteins," Proceedings of the National Academy of Sciences, 1997, vol. 94 (23), pp. 12297-12302.
Robinson J.R., Sustained and Controlled Release Drug Delivery Systems, Marcel Dekker, Inc., 1978, Table of Contents.
Roes J., et al., "Mouse Anti-mouse IgD Monoclonal Antibodies Generated in IgD-deficient Mice," Journal of Immunological Methods, 1995, vol. 183 (2), pp. 231-237.

(56) References Cited

OTHER PUBLICATIONS

Roguska M.A., et al., "Humanization of Murine Monoclonal Antibodies through Variable Domain Resurfacing," Proceedings of the National Academy of Sciences, 1994, vol. 91 (3), pp. 969-973.
Roher A.E., et al., "Morphology and Toxicity of Abeta-(1-42) Dimer Derived from Neuritic and Vascular Amyloid Deposits of Alzheimer's Disease," Journal of Biological Chemistry, 1996, vol. 272 (34), pp. 20631-20635.
Roher A.E., et al., "Oligomerizaiton and Fibril Assembly of the Amyloid-beta Protein," Biochimic et Biophysica Acta, 2000, vol. 1502 (1), pp. 31-43.
Ronicke R., et al., "Abeta Mediated Diminution of MTT Reduction—An Artefact of Single Cell Culture?," PLoS One, 2008, vol. 3 (9), pp. e3236.
Rossi G., et al., "A Family with Alzheimer Disease and Strokes Associated with A713T Mutation of the APP Gene," Neurology, 2004, vol. 63 (5), pp. 910-912.
Rouillard J.M., et al., "Gene2Oligo: Oligonucleotide Design for in Vitro Gene Synthesis," Nucleic Acids Research, 2004, vol. 32 (Web Server Issue), pp. W176-W180.
Rovira C., et al., "Abeta(25-35) and Abeta(1-40) Act on Different Calcium Channels in CA1 Hippocampal Neurons," Biochemical and Biophysical Research Communications, 2002, vol. 296 (5), pp. 1317-1321.
Rudikoff S., et al., "Single Amino Acid Substitution Altering Antigen-Binding Specificity," PNAS, Proceedings of the National Academy of Sciences, 1982, vol. 79 (6), pp. 1979-1983.
Russo C., et al., "Presenilin-1 Mutations in Alzheimer's Disease," Nature, 2000, vol. 405 (6786), pp. 531-532.
Rzepecki P., et al, "Prevention of Alzheimer's Disease-Associated Abeta Aggregation by Rationally Designed Nonpeptidic Beta-Sheet Ligands," The Journal of Biological Chemistry, 2004, vol. 279 (46), pp. 47497-47505.
Sabella S., et al., "Capillary Electrophoresis Studies on the Aggregation Process of Beta-amyloid 1-42 and 1-40 Peptides," Electrophoresis, 2004, vol. 25 (18-19), pp. 3186-3194.
Saido T.C., et al., "Dominant and Differential Deposition of Distinct Beta-amyloid Peptide Species, ABeta N3(pE), in Senile Plaques," Neuron, 1995, vol. 14 (2), pp. 457-466.
Sakmann B et al., "Single-Channel Recording" in: Antibodies, 2nd Edition, 1995, Springe, Table of Contents.
Salomon A.R., et al., "Nicotine Inhibits Amyloid Formation by the Beta-Peptide," Biochemistry, 1996, vol. 35 (42), pp. 13568-13578.
Sambamurti K., et al., "A Partial Failure of Membrane Protein Turnover may cause Alzheimer's Disease: a New Hypothesis," Current Alzheimer Research, 2006, vol. 3 (1), pp. 81-90.
Sambrook J., et al., "Expression of Cloned Genes in *Escherichia coli*," in: Molecular Cloning: A Laboratory Manual, Second Edition, TOC, Cold Spring Harbor Laboratory Press, 1989.
Sambrook J., et al., "Molecular Cloning," A Laboratory Manual, Second Edition, Cold Spring Harbor Laboratory Press,1989, Table of Contents.
Sambrook J., "Expression of Cloned Genes in *Escherichia coli*" in: Molecular Cloning, 2nd Edition, Cold Spring Harbor Laboratory Press, 1989, Chap. 17.2-17.9.
Samoszuk M. K. et al., "A peroxide-generating immunoconjugate directed to eosinophil peroxidase is cytotoxic to Hodgkin's disease cells in vitro," Antibody, Immunoconjugates and Radiopharmaceuticals, 1989, vol. 2, pp. 37-45.
Sandberg A., et al., "Stabilization of Neurotoxic Alzheimer Amyloid-Beta Oligomers by Protein Engineering," Proceedings of the National Academy of Sciences, 2010, vol. 107 (35), pp. 15595-15600.
Sankaranarayanan S., "Genetically Modified Mice Models for Alzheimer's Disease," Current Topics in Medicinal Chemistry, 2006, vol. 6 (6), pp. 609-627.
Santos A.N., et al., "A Method for the Detection of Amyloid-Beta1-40, Amyloid-Beta1-42 and Amyloid-Beta Oligomers in Blood using Magnetic Beads in Combination with Flow Cytometry and its Application in the Diagnostics of Alzheimer's Disease," Journal of Alzheimer's Disease, 2008, vol. 14 (2), pp. 127-131.
Sanz-Blasco S., et al., "Mitochondrial Ca2+ Overload Underlies Abeta Oligorners Neurotoxicity Providing an Unexpected Mechanism of Neuroprotection by NSAIDs," PLoS One, 2008, vol. 3 (7), pp. e2718.
Sato J., et al., "Design of Peptides that form Amyloid-like Fibrils Capturing Amyloid Beta1-42 Peptides," Chemistry, 2007, vol. 13 (27), pp. 7745-7752.
Sato N., et al., "Development of New Screening System for Alzheimer Disease, In Vitro Abeta Sink Assay, to Identify the Dissociation of Soluble Abeta from Fibrils," Neurobiology of Disease, 2006, vol. 22 (3), pp. 487-495.
Saudek C.D., et al., "A Preliminary Trial of the Programmable Implantable Medication System for Insulin Delivery," The New England Journal of Medicine, 1989, vol. 321 (9), pp. 574-579.
Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.
Schafmeister et al., "An all-hydrocarbon cross-linking system for enhancing the helicity and metabolilc stability of peptides," J. Am. Chem. Soc, 2000, vol. 122, pp. 5891-5892.
Schäble K.F., et al., "Characteristics of the Immunoglobulin Vkappa Genes, Pseudogenes, Relics and Orphans in the Mouse Genome," European Journal of Immunology, 1999, vol. 29 (7), pp. 2082-2086.
Schenk D., "Amyloid-Beta Immunotherapy for Alzheimer's Disease: The End of the Beginning," Nature Reviews. Neuroscience, 2002, vol. 3 (10), pp. 824-828.
Schenk D., et al., "Current Progress in Beta-Amyloid Immunotherapy," Current Opinion in Immunology, 2004, vol. 16 (5), pp. 599-606.
Schenk D., et al., "Immunization with Amyloid-Beta Attenuates Alzheimer-Disease-Like Pathology in the PDAPP Mouse," Nature, 1999, vol. 400 (6740), pp. 173-177.
Schilling S., et al., "On the Seeding and Oligomerization of pGlu-Amyloid Peptides (in vitro)," Biochemistry, 2006, vol. 45 (41), pp. 12393-12399.
Scholtzova H., et al., "Induction of Toll-like Receptor 9 Signaling as a Method for Ameliorating Alzheimer's Disease-Related Pathology," The Journal of Neuroscience, 2009, vol. 29 (6), pp. 1846-1854.
Schott J.M., et al., "New Developments in Mild Cognitive Impairment and Alzheimer's Disease," Current Opinion in Neurology, 2006, vol. 19 (6), pp. 552-558.
Schuck P., "Size distribution analysis of macromolecules by sedimentation velocity ultracentrifugation and Lamm equation modeling," Biophysical Journal, 2000, vol. 78, pp. 1606-1619.
Sciarretta K.L., et al., "Abeta40-Lactam(D23/K28) Models a Conformation Highly Favorable for Nucleation of Amyloid," Biochemistry, 2005, vol. 44 (16), pp. 6003-6014.
Sefton M.V., et al., "Implantable Pumps," Critical Reviews in Biomedical Engineering, 1987, vol. 14 (3), pp. 201-240.
Selenica M.L., et al., "Cystatin C Reduces the in Vitro Formation of Soluble Abeta1-42 Oligomers and Protofibrils," Scandinavian Journal of Clinical & Laboratory Investigation, 2007, vol. 67 (2), pp. 179-190.
Selkoe D.J., "Alzheimer's Disease: Genes, Proteins, and Therapy," Physiological Reviews, 2001, vol. 81 (2), pp. 741-766.
Selkoe D.J., "Clearing the Brain's Amyloid Cobwebs," Neuron, 2001, vol. 32 (2), pp. 177-180.
Sergeant N., et al., "Truncated Beta Amyloid Peptide Species in Pre Alzheimer Diseases as New Targets for the Vaccination Approach," Journal of Neurochemistry, 2003, vol. 85 (6), pp. 1581-1591.
Shankar G.M., et al., "Natural Oligomers of the Alzheimer Amyloid-Beta Protein Induce Reversible Synapse Loss by Modulating an NMDA-type Glutamate Receptor-Dependent Signaling Pathway," Journal of Neuroscience, 2007, vol. 27 (11), pp. 2866-2875.
Shapiro G.S., et al., "DNA Target Motifs of Somatic Mutagenesis in Antibody Genes," Critical Reviews in Immunology, 2002, vol. 22 (3), pp. 183-200.

(56) References Cited

OTHER PUBLICATIONS

Shields R.L., et al., "Lack of Fucose on Human IgG1 N-Linked Oligosaccharide Improves Binding to Human Fcgamma RII and Antibody-Dependent Cellular Toxicity," The Journal of Biological Chemistry, 2002, vol. 277 (30), pp. 26733-26740.
Shimizu E., et al., "IL-4-Induced Selective Clearance of Oligomeric Beta-Amyloid Peptide(1-42) by Rat Primary Type 2 Microglia," Journal of Immunology, 2008, vol. 181 (9), pp. 6503-6513.
Shu L., et al., "Secretion of a Single-Gene-Encoded Immunoglobulin from Myeloma Cells," Proceedings of the National Academy of Sciences, 1993, vol. 90 (17), pp. 7995-7999.
Shughrue P.J., et al., "Anti-ADDL Antibodies Differentially Block Oligomer Binding to Hippocampal Neurons," Neurobiology of Aging, 2010, vol. 31 (2), pp. 189-202.
Sikorski P., et al., "Structure and Texture of Fibrous Crystals Formed by Alzheimer's Abeta(11-25) Peptide Fragment," Structure, 2003, vol. 11 (8), pp. 915-926.
Sims M.J., et al, "A Humanized CD18 Antibody can Block Function without Cell Destruction," Journal of Immunology, 1993, vol. 151 (4), pp. 2296-2308.
Sinz A., "Chemical cross-linking and mass spectrometry for mapping three-dimensional structures of proteins and protein complexes," J. Mass Spectrom, 2003, vol. 38, pp. 1225-1237.
Sjogren M., et al., "Cholesterol and Alzheimer's Disease—is there a Relation?," Mechanisms of Ageing and Development, 2006, vol. 127 (2), pp. 133-147.
Sjogren M., et al., "The Link Between Cholesterol and Alzheimer's Disease," The World Journal of Biological Psychiatry, 2005, vol. 6 (2), pp. 85-97.
Skerra A., et al., "Assembly of a Functional Immunoglobulin Fv Fragment in *Escherichia coli*," Science, 1988, vol. 240 (4855), pp. 1038-1041.
Smith D.P., et al., "Concentration Dependent Cu2+ Induced Aggregation and Dityrosine Formation of the Alzheimer's Disease Amyloid-Beta Peptide," Biochemistry, 2007, vol. 46 (10), pp. 2881-2891.
Smith N.W., et al., "Amphotericin B Interactions with Soluble Oligomers of Amyloid Abeta1-42 Peptide," Bioorganic & Medicinal Chemistry, 2009, vol. 17 (6), pp. 2366-2370.
Smith T.F., et al., "Comparison of Biosequences," Advances in Applied Mathematics, 1981, vol. 2, pp. 482-489.
Smith-Gill S.J., et al., "Contributions of Immunoglobulin Heavy and Light Chains to Antibody Specificity for Lysozyme and Two Haptens," Journal of Immunology, 1987, vol. 139 (12), pp. 4135-4144.
Smithson S.L., et al., "Molecular Analysis of the Heavy Chain of Antibodies that Recognize the Capsular Polysaccharide of Neisseria Meningitidis in hu-PBMC Reconstituted SCID Mice and in the Immunized Human Donor," Molecular Immunology, 1999, vol. 36 (2), pp. 113-124.
Smolen V.F., et al., eds., Controlled Drug Bioavailability: Drug Product Design and Performance, vol. 1, John Wiley & Sons, 1984, Table of Contents.
Solomon B., et al., "Disaggregation of Alzheimer Beta-Amyloid by Site-Directed mAb," PNAS, Proceedings of the National Academy of Sciences, 1997, vol. 94 (8), pp. 4109-4112.
Solomon B., et al., "Monoclonal Antibodies Inhibit in Vitro Fibrillar Aggregation of the Alzheimer Beta-Amyloid Peptide," PNAS, Proceedings of the National Academy of Sciences, 1996, vol. 93 (1), pp. 452-455.
Solorzano-Vargas R.S., et al., "Epitope Mapping and Neuroprotective Properties of a Human Single Chain FV Antibody that Binds an Internal Epitope of Amyloid-Beta 1-42," Molecular Immunology, 2008, vol. 45 (4), pp. 881-886.
Sondag C.M., et al., "Beta Amyloid Oligomers and Fibrils Stimulate Differential Activation of Primary Microglia," Journal of Neuroinflammation, 2009, vol. 6:1.

Song M.K., et al., "Light Chain of Natural Antibody Plays a Dominant Role in Protein Antigen Binding," Biochemical and Biophysical Research Communications, 2000, vol. 268 (2), pp. 390-394.
Song Y.K., et al., "Antibody Mediated Lung Targeting of Long-Circulating Emulsions," PDA Journal of Pharmaceutical Science & Technology, 1995, vol. 50 (6), pp. 372-377.
Soos K., et al., "An Improved Synthesis of Beta-Amyloid Peptides for in Vitro and in Vivo Experiments," Journal of Peptide Science, 2004, vol. 10, pp. 136.
Sorensen K., et al., "ApoE Counteracts the Impairment of Mitochondrial Activity Induced by Oligomeric Abeta 1-42," European Journal of Neurology, 2008, vol. 15, pp. 45.
Spatola A. F. et al., "Chemistry and Biochemistry of Amino Acids, Peptides, and Proteins," Science, 1983, Marcel Dekker, pp. 267-357.
Spatola A. F. et al., "Structure-activity relationships of enkephalins containing serially replaced thiomethylene amide bond surrogates," Life Sci , 1986, vol. 38, pp. 1243-1249.
Spencer B., et al., "Novel Strategies for Alzheimer's Disease Treatment," Expert Opinion on Biological Therapy, 2007, vol. 7 (12), pp. 1853-1867.
Stan, R. V., "Multiple PV1 dimers reside in the same stomatal or fenestral diaphragm," Am. J. Physiol, Heart Circ. Physiol, 2004, vol. 286 (4), pp. H1347-H1353.
Standridge J.B., "Vicious Cycles within the Neuropathophysiologic Mechanisms of Alzheimer's Disease," Current Alzheimer Research, 2006, vol. 3 (2), pp. 95-107.
Staros et al., "Enhancement by N-hydroxysulfosuccinimide of water-soluble carbodiimide-mediated coupling reactions," Anal. Biochem., 1986, vol. 156 (1), pp. 220-222.
Stewart J.M., et al., Solid-Phase Peptide Synthesis, 2nd Edition, Pierce Chemical Company, 1984, Table of Contents.
Stine W.B., et al., "Antibodies Specific for Toxic Abeta Oligomers," Society for Neuroscience, 2003.
Stine W.B. Jr., et al., "In Vitro Characterization of Conditions for Amyloid-Beta Peptide Oiigomerization and Fibrillogenesis," The Journal of Biological Chemistry, 2003, vol. 278 (13), pp. 11612-11622.
Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.
Supplementary European Search Report for Application No. EP07864914, dated Apr. 28, 2010, 5 pages.
Supplementary European Search Report for Application No. EP2303920, dated Sep. 26, 2011, 3 pages.
Suram A., et al., "A New Evidence for DNA Nicking Property of Amyloid Beta-Peptide (1-42): Relevance to Alzheimer's Disease," Archives of Biochemistry and Biophysics, 2007, vol. 463 (2), pp. 245-252.
Tabaton M., "Coffee "Breaks" Alzheimer's Disease," Journal of Alzheimer's Disease, 2009, vol. 17 (3), pp. 699-700.
Tabaton M., et al., "Role of Water-Soluble Amyloid-Beta in the Pathogenesis of Alzheimer's Disease," International Journal of Experimental Pathology, 2005, vol. 86 (3), pp. 139-145.
Taguchi J., et al., "Different Expression of Calreticulin and Immunoglobulin Binding Protein in Alzheimer's Disease Brain," Acta Neuropathologica, 2000, vol. 100 (2), pp. 153-160.
Takano K., "Amyloid Beta Conformation in Aqueous Environment," Current Alzheimer Research, 2008, vol. 5 (6), pp. 540-547.
Takata K., et al., "High Mobility Group Box Protein-1 Enhances Amyloid Beta Neurotoxicity," Journal of Pharmaceutical Sciences, 2006, pp. 154p.
Takata K., et al., "Possible Involvement of Small Oligomers of Amyloid-Beta Peptides in 15-Deoxy-Delta 12,14 Prostaglandin J2-Sensitive Microglial Activation," Journal of Pharmacological Sciences, 2003, vol. 91 (4), pp. 330-333.
Takeda S., et al., "Construction of Chimaeric Processed Immunoglobulin Genes Containing Mouse Variable and Human Constant Region Sequences," Nature, 1985, vol. 314 (6010), pp. 452-454.
Tamagno E., et al., "The Various Aggregation States of Beta-Amyloid 1-42 Mediate Different Effects on Oxidative Stress,

(56) References Cited

OTHER PUBLICATIONS

Neurodegeneration, and BACE-1 Expression," Free Radical Biology & Medicine, 2006, vol. 41 (2), pp. 202-212.
Tamura, et al., "Structural correlates of an anti-carcionma antibody: identification of specificity-determining residues(SDRs) and development of a minimally immunogenic antibody variant by retention of SDRs only," J. immunol, 2000, vol. 164, pp. 1432-1441.
Taniguchi A., et al., ""Click peptide": pH-Triggered in Situ Production and Aggregation of Monomer Abeta1-42," ChemBioChem, 2009, vol. 10 (4), pp. 710-715.
Taniuchi M. et al., "Induction of nerve growth factor receptor in Schwann cells after axotomy," Proc. Natl. Acad. Sci, 1986, vol. 83, pp. 4094-4098.
Tanzi R., "Alzheimer Research Forum Discussion: Gain or Loss of Function—Time to Shake up Assumptions on Gamma-Secretase in Alzheimer Disease?," Journal of Alzheimer's Disease, 2007, vol. 11 (3), pp. 409.
Tanzi R.E., "Novel Therapeutics for Alzheimer's Disease," Neurotherapeutics, 2008, vol. 5 (3), pp. 377-380.
Tarozzi A., et al., "Cyanidin 3-O-Glucopyranoside Protects and Rescues SH-SY5Y Cells Against Amyloid-Beta Peptide-Induced Toxicity," NeuroReport, 2008, vol. 19 (15), pp. 1483-1486.
Taylor L.D., et al., "A Transgenic Mouse that Expresses a Diversity of Human Sequence Heavy and Light Chain Immunoglobulins," Nucleic Acids Research, 1992, vol. 20 (23), pp. 6287-6295.
Tenno T., et al., "Structural Basis for Distinct Roles of Lys63- and Lys48-Linked Polyubiquitin Chains," Genes to Cells, 2004, vol. 9 (10), pp. 865-875.
Teplow D.B., et al., "Effects of Structural Modifications in A β on its Oligomer Size Distribution," Society for Neuroscience, Presentation No. 91.20, 2002, Abstract.
Terry R.D., et al., "Physical Basis of Cognitive Alterations in Alzheimer's Disease: Synapse Loss is the Major Correlate of Cognitive Impairment," Annals of Neurology, 1991, vol. 30 (4), pp. 572-580.
Terryberry J.W., et al., "Autoantibodies in Neurodegenerative Diseases: Antigen-Specific Frequencies and Intrathecal Analysis," Neurobiology Aging, 1998, vol. 19 (3), pp. 205-216.
Tew D.J., et al., "Stabilization of Neurotoxic Soluble Beta-Sheet-Rich Conformations of the Alzheimer's Disease Amyloid-Beta Peptide," Biophysical Journal, 2008, vol. 94 (7), pp. 2752-2766.
Thal D.R., et al., "Fleecy Amyloid Deposits in the Internal Layers of the Human Entorhinal Cortex are Comprised of N-Terminal Truncated Fragments of Abeta," Journal of Neuropathology and Experimental Neurology, 1999, vol. 58 (2), pp. 210-216.
Tijssen P., "Hybridization with Nucleic Acid Probes—Part II: Probe Labeling and Hybridzation Techniques," Laboratory Techniques in Biochemistry and Molecular Biology, 1993, vol. 24:iii-vi, pp. 269-613.
Tolstoshev P., "Gene Therapy, Concepts, Current Trials and Future Directions," Annual Review of Pharmacology and Toxicology, 1993, vol. 32, pp. 573-596.
Tomaselli S., et al., "The Alpha-to-Beta Conformational Transition of Alzheimer's Abeta-(1-42) Peptide in Aqueous Media is Reversible: a Step by Step Conformational Analysis Suggests the Location of Beta Conformation Seeding," ChemBioChem, 2006, vol. 7 (2), pp. 257-267.
Tomidokoro Y., et al., "Familial Danish Dementia: Co-Existence of Danish and Alzheimer Amyloid Subunits (ADan and A{beta}) in the Absence of Compact Plaques," The journal of Biological Chemistry, 2005, vol. 280 (44), pp. 36883-36894.
Tomidokoro Y., et al., "Familial Danish Dementia: The Relationship of two Different Amyloids (ADAN/ABETA) Deposited in the Brain," Society for Neuroscience Abstract Viewer and Itinerary Planner, Annual Meeting of the Society of Neuroscience, 2002 Abstract No. 328.9, 32nd , Orlando, FL, 2002.
Tomiyama T., et al., "A New Amyloid Beta Variant Favoring Oligomerization in Alzheimer's-type Dementia," Annals of Neurology, 2008, vol. 63 (3), pp. 377-387.
Tsubuki S., et al., "Dutch, Flemish, Italian, and Arctic Mutations of APP and Resistance of Abeta to Physiologically Relevant Proteolytic Degradation," Lancet, 2003, vol. 361 (9373), pp. 1957-1958.
Turner R., et al., "The Potential Exploitation of Plant Viral Translational Enhancers in Biotechnology for Increased Gene Expression," Molecular Biotechnology, 1995, vol. 3 (3), pp. 225-236.
Tusell J.M., et al., "Upregulation of p21Cip1 in Activated Glial Cells," Glia, 2009, vol. 57 (5), pp. 524-534.
Ueki et al., "Solid phase synthesis and biological activities of [Arg8]-vasopressin methylenedithioether," Bioorg. Med. Chem. Lett., 1999, vol. 9, pp. 1767-1772.
Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.
Urbanc B., et al., "Computer Simulations of Alzheimer's Amyloid Beta-protein Folding and Assembly," Current Alzheimer Research, 2006, vol. 3 (5), pp. 493-504.
Urbanc B., et al., "In Silico Study of Amyloid Beta-protein Folding and Oligomerization," Proceedings of the National Academy of Sciences, 2004, vol. 101 (50), pp. 17345-17350.
Urbanc B., et al., "Molecular Dynamics Simulation of Amyloid Beta Dimer Formation," Biophysical Journal, 2004, vol. 87 (4), pp. 2310-2321.
Urlaub G., et al., "Isolation of Chinese Hamster Cell Mutants Deficient in Dihydrofolate Reductase Activity," Proceedings of the National Academy of Sciences, 1980, vol. 77 (7), pp. 4216-4220.
Uto L. et al., "Determination of urinary Tamm-Horsfall protein by ELISA using a maleimide method for enzyme-antibody conjugation," J. Immunol. Methods, 1991, vol. 138, pp. 87-94.
Vajdos F.F., et al., "Comprehensive Functional Maps of the Antigen-binding Site of an Anti-ErbB2 Antibody Obtained with Shotgun Scanning Mutagenesis," Journal of Molecular Biology, 2002, vol. 320 (2), pp. 415-428.
Valincius G., et al., "Soluble Amyloid Beta-oligomers Affect Dielectric Membrane Properties by Bilayer Insertion and Domain Formation: Implications for Cell Toxicity," Biophysical Journal, 2008, vol. 95 (10), pp. 4845-4861.
Van Broeck B., et al., "Current Insights into Molecular Mechanisms of Alzheimer Disease and their Implications for Therapeutic Approaches," Neuro-degenerative Diseases, 2007, vol. 4 (5), pp. 349-365.
Van Broeckhoven C., et al., "Amyloid Beta Protein Precursor Gene and Hereditary Cerebral Hemorrhage with Amyloidosis (Dutch)," Science, 1990, vol. 248 (4959), pp. 1120-1122.
Van Gool W.A., et al., "Concentrations of Amyloid-Beta Protein in Cerebrospinal Fluid Increase With Age in Patients Free From Neurodegenerative Disease," Neuroscience Letters, 1994, vol. 172 (1-2), pp. 122-124.
Vattemi G., et al., "Amyloid-beta42 is Preferentially Accumulated in Muscle Fibers of Patients with Sporadic Inclusion-body Myositis," Acta Neuropathologica, 2009, vol. 117 (5), pp. 569-574.
Veber D.F., et al., "The Design of Metabolically-Stable Peptide Analogs," TINS, 1985, pp. 392-396.
Verhoeyen M., et al., "Engineering of Antibodies," BioEssays, 1988, vol. 8 (2), pp. 74-78.
Vestergaard M., et al., "Detection of Alzheime's Amyloid Beta Aggregation by Capturing Molecular Trails of Individual Assemblies," Biochemical and Biophysical Research Communications, 2008, vol. 377 (2), pp. 725-728.
Vickers J.C., "A Vaccine against Alzheimer's Disease: Developments to Date," Drugs and Aging, 2002, vol. 19 (7), pp. 487-494.
Viola K.L., et al., ADDLs Bind Selectively to Nerve Cell Surfaces in Receptor-like Puncta, Society for Neuroscience—Abstract Archive, Presentation No. 91.9, 2002.
Viola K.L., et al., Immunolocalization of Oligomeric ABeta42 Binding to Primary Mouse Hippocampal Cells and B103 Rat Neuroblastoma Cells, Society for Neuroscience Abstracts, 1999, vol. 25, Part 2, 852.7.
Wahlstrom A., et al., "Secondary Structure Conversions of Alzheimer's Abeta(1-40) Peptide Induced by Membrane-mimicking Detergents," The FEBS Journal, 2008, vol. 275 (20), pp. 5117-5128.

(56) References Cited

OTHER PUBLICATIONS

Wakutani Y., et al., "Novel Amyloid Precursor Protein Gene Missense Mutation (D678N) in Probable Familial Alzheimer's Disease," Journal of Neurology, Neurosurgery and Psychiatry, 2004, vol. 75 (7), pp. 1039-1042.
Walensky et al., "Activation of apoptosis in vivo by a hydrocarbon-stapled BH3 helix," Science, 2004, vol. 305, pp. 1466-1470.
Wallick S.C., et al., "Glycosylation of a VH Residue of a Monoclonal Antibody against Alpha (1-6) Dextran Increases its Affinity for Antigen," Journal of Experimental Medicine, 1988, vol. 168 (3), pp. 1099-1109.
Wang H., et al., "Direct and Selective Elimination of Specific Prions and Amyloids by 4,5-dianilinophthalimide and Analogs," Proceedings of the National Academy of Sciences, 2008, vol. 105 (20), pp. 7159-7164.
Wang H.W., et al., Differential Effect of ABeta1-42 Conformation and ApoE Isoform on LTP, Society for Neuroscience—Abstract Archive, 2001, 752.18.
Wang H.W., et al., "Soluble Oligomers of Beta Amyloid (1-42) Inhibit Long-term Potentiation But not Long-term Depression in Rat Dentate Gyrus," Brain Research, 2002, vol. 924 (2), pp. 133-140.
Wang H.W., et al., Soluble Oligomers of ABeta(1042) Impair LTP in Rat Hippocampal Dentate Gyrus, Society for Neuroscience Abstracts, 2000, vol. 30, Part 2, 663.18.
Wang J., et al., "Development and Characterization of a TAPIR-like Mouse Monoclonal Antibody to Amyloid-beta," Journal of Alzheimer's Disease, 2008, vol. 14 (2), pp. 161-173.
Wang R., et al., "The Profile of Soluble Amyloid Beta Protein in Cultured Cell Media. Detection and Quantification of Amyloid Beta Protein and Variants by Immunoprecipitation-Mass Spectrometry," The Journal of Biological Chemistry, 1996, vol. 271 (50), pp. 31894-31902.
Wang Z., et al., "Per-6-substituted-per-6-deoxy Beta-cyclodextrins Inhibit the Formation of Beta-amyloid Peptide Derived Soluble Oligomers," Journal of Medicinal Chemistry, 2004, vol. 47 (13), pp. 3329-3333.
Ward E.S., et al., "Binding Activities of a Repertoire of Single Immunoglobulin Variable Domains Secreted from *Escherichia coli*," Nature, 1989, vol. 341 (6242), pp. 544-546.
Weaver-Feldhaus J.M., et al., "Yeast Mating for Combinatorial Fab Library Generation and Surface Display," FEBS Letters, 2004, vol. 564 (1-2), pp. 24-34.
Weggen S., et al., "Evidence that Nonsteroidal Anti-inflammatory Drugs Decrease Amyloid Beta 42 Production by Direct Modulation of Gamma-secretase Activity," Journal of Biological Chemistry, 2003, vol. 278 (34), pp. 31831-31837.
Weksler M. E., et al., "Patients with Alzheimer Disease have Lower Levels of Serum Anti-amyloid Peptide Antibodies than Healthy Elderly Individuals," Experimenal Gerontology, 2002, vol. 37 (7), pp. 943-948.
Wels B. et al., "Synthesis of a novel potent cyclic peptide MC4-ligand by ring-closing metathesis," Bioorg. Med. Chem, 2005, vol. 13, pp. 4221-4227.
Werner, et al., "Glossary of Terms Used in Medicinal Chemistry," Pure and Applied Chemistry, 1998, vol. 70, pp. 1129-1143.
Westlind-Danielsson A., et al., "Spontaneous in Vitro Formation of Supramolecular Beta-amyloid Structures, 'Betaamy Balls', by Beta-amyloid 1-40 Peptide," Biochemistry, 2001, vol. 40 (49), pp. 14736-14743.
White J.A., et al., "Differential Effects of Oligomeric and Fibrillar Amyloid-beta 1-42 on Astrocyte-mediated Inflammation," Neurobiology of Disease, 2005, vol. 18 (3), pp. 459-465.
Wilcock D.M., et al., "Intracranially Administered Anti-Abeta Antibodies Reduce Beta-amyloid Deposition by Mechanisms both Independent of and Associated with Microglial Activation," Journal of Neuroscience, 2003, vol. 23 (9), pp. 3745-3751.
Wilcock D.M., et al., "Passive Immunotherapy against Abeta in Aged APP-transgenic Mice Reverses Cognitive Deficits and Depletes Parenchymal Amyloid Deposits in Spite of Increased Vascular Amyloid and Microhemorrhage," Journal of Neuroinflammation, 2004, vol. 1 (1), pp. 24.
Williamson M.P., et al., "Binding of Amyloid Beta-peptide to Ganglioside Micelles is Dependent on Histidine-13," Biochemical Journal, 2006, vol. 397 (3), pp. 483-490.
Wilson D.M., et al., "Free Fatty Acids Stimulate the Polymerization of Tau and Amyloid Beta Peptides. In Vitro Evidence for a Common Effector of Pathogenesis in Alzheimer's Disease," American Journal of Pathology, 1997, vol. 150 (6), pp. 2181-2195.
Wiltfang J., et al., "Highly Conserved and Disease-specific Patterns of Carboxyterminally Truncated Abeta Peptides 1-37/38/39 in Addition to 1-40/42 in Alzheimer's Disease and in Patients with Chronic Neuroinflammation," Journal of Neurochemistry, 2002, vol. 81 (3), pp. 481-496.
Windisch M., et al., "The Role of Alpha-synuclein in Neurodegenerative Diseases: A Potential Target for New Treatment Strategies?," Neuro-degenerative Diseases, 2008, vol. 5 (3-4), pp. 218-221.
Winnaker E.L., From Genes to Clones: Introduction to Gene Technology, VCH Publishers, 1987, Table of Contents.
Wong P.T., et al., "Amyloid-beta Membrane Binding and Permeabilization are Distinct Processes Influenced Separately by Membrane Charge and Fluidity," Journal of Molecular Biology, 2009, vol. 386 (1), pp. 81-96.
Woodhouse A., et al., "Vaccination Strategies for Alzheimer's Disease: A New Hope?," Drugs and Aging, 2007, vol. 24 (2), pp. 107-119.
Wright A., et al., "Antibody Variable Region Glycosylation: Position Effects on Antigen Binding and Carbohydrate Structure," The EMBO Journal, 1991, vol. 10 (10), pp. 2717-2723.
Written Opinion for Application No. PCT/US2011/047622, dated Jan. 2, 2012, 6 pages.
Wu C., et al., "The Structure of Abeta42 C-terminal Fragments Probed by a Combined Experimental and Theoretical Study," Journal of Molecular Biology, 2009, vol. 387 (2), pp. 492-501.
Wu G., et al., "Delivery Systems for Gene Therapy," Biotherapy, 1991, vol. 3 (1), pp. 87-95.
Wu G.Y., et al., "Receptor-mediated in Vitro Gene Transformation by a Soluble DNA Carrier System," Journal of Biological Chemistry, 1987, vol. 262 (10), pp. 4429-4432.
Wu H. et al., "Humanization of a Murine Monoclonal Antibody by Simultaneous Optimization of Framework and CDR Residues," Journal of Molecular Biology, 1999, vol. 294 (1), pp. 151-162.
Wurth C., et al., "Mutations that Reduce Aggregation of the Alzheimer's Abeta42 Peptide: An Unbiased Search for the Sequence Determinants of Abeta Amyloidogenesis," Journal of Molecular Biology, 2002, vol. 319 (5), pp. 1279-1290.
Xia W., et al., "A Specific Enzyme-linked Immunosorbent Assay for Measuring Beta-amyloid Protein Oligomers in Human Plasma and Brain Tissue of Patients with Alzheimer Disease," Archives of Neurology, 2009, vol. 66 (2), pp. 190-199.
Xia W., et al., "Enhanced Production and Oligomerization of the 42-residue Amyloid Beta-protein by Chinese Hamster Ovary Cells Stably Expressing Mutant Presenilins," Journal of Biological Chemistry, 1997, vol. 272 (12), pp. 7977-7982.
Xiao-Dong P., et al., "Effect of Inflammatory Responses in Microglia Induced by Oligomeric Beta-Amyloid1-42 on Neuronal Cells," Acta Anatomica Sinica, 2008, vol. 39 (6), pp. 804-809.
Xu X., "Gamma-secretase Catalyzes Sequential Cleavages of the AbetaPP Transmembrane Domain," Journal of Alzheimer's Disease, 2009, vol. 16 (2), pp. 211-224.
Yamamoto N., et al., "Environment and Mutation-dependent Aggregation Behavior of Alzheimer Amyloid Beta-protein," Journal of Neurochemistry, 2004, vol. 90 (1), pp. 62-69.
Yamin G., et al., "Amyloid Beta-protein Assembly as a Therapeutic Target of Alzheimer's Disease," Current Pharmaceutical Design, 2008, vol. 14 (30), pp. 3231-3246.
Yamin G., "NMDA Receptor-dependent Signaling Pathways that Underlie Amyloid Beta-protein Disruption of LTP in the Hippocampus," Journal of Neuroscience Research, 2009, vol. 87 (8), pp. 1729-1736.

(56) References Cited

OTHER PUBLICATIONS

Yan Y., et al., "Protection Mechanisms Against Abeta42 Aggregation," Current Alzheimer Research, 2008, vol. 5 (6), pp. 548-554.

Yan Z., et al., "Roscovitine: A Novel Regulator of P10-Type Calcium Channels and Transmitter Release in Central Neurons," The Journal of Physiology, 2002, vol. 540 (Pt 3), pp. 761-770.

Yang M., et al., "Amyloid Beta-Protein Monomer Folding: Free-Energy Surfaces Reveal Alloform-Specific Differences," Journal of Molecular Biology, 2008, vol. 384 (2), pp. 450-464.

Yang X.D., et al., "Fully Human Anti-Interleukin-8 Monoclonal Antibodies: Potential Therapeutics for the Treatment of Inflammatory Disease States," Journal of Leukocyte Biology, 1999, vol. 66 (3), pp. 401-410.

Ye C.P., et al., "Protofibrils of Amyloid Beta-Protein Inhibit Specific K+ Currents in Neocortical Cultures," Neurobiology of Disease, 2003, vol. 13 (3), pp. 177-190.

Yeh M.Y., et al., "A Cell-surface Antigen Which is Present in the Ganglioside Fraction and Shared by Human Melanomas," International Journal of Cancer, 1982, vol. 29 (3), pp. 269-275.

Yeh M.Y., et al., "Cell Surface Antigens of Human Melanoma Identified by Monoclonal Antibody," Proceedings of the National Academy of Sciences, 1979, vol. 76 (6), pp. 2927-2931.

Yoshinari K., et al., "Differential Effects of Immunosuppressants and Antibiotics on Human Monoclonal Antibody Production is SCID Mouse Ascites by Five Heterohybridomas," Hybridoma, 1998, vol. 17 (1), pp. 41-45.

Yoshitake et al., "Mild and Efficient Conjugation of Rabbit Fab' and Horseradish Peroxidase Using a Maleimide Compound and Its Use for Enzyme Immunoassay," J. Biochem., 1982, 92 (5), 1413-1424.

Young K.F., et al., "Oligomeric Amyloid Beta 1-42 Activities Extracellular Signal Regulated Kinases Erk1 and Erk2 of the Mitogen Activated Protein Kinase Pathway in SH-SY5YCells," Neurobiology, 2004, vol. 25, pp. S150.

Youssef I., et al., "N-Truncated Amyloid-Beta Oligomers Induce Learning Impairment and Neuronal Apoptosis," Neurobiology of Aging, 2008, vol. 29 (9), pp. 1319-1333.

Yu L., et al., "Structural Characterization of a Soluble Amyloid Beta-Peptide Oligomer," Biochemistry, 2009, vol. 48 (9), pp. 1870-1877.

Yun S., et al., "Role of Electrostatic Interactions in Amyloid Beta-Protein (A Beta) Oligomer Formation: A Discrete Molecular Dynamics Study," Biophysical Journal, 2007, vol. 92 (11), pp. 4064-4077.

Yun S.H., et al., "Amyloid-Beta1-42 Reduces Neuronal Excitability in Mouse Dentate Gyrus," Neuroscience Letters, 2006, vol. 403 (1-2), pp. 162-165.

Zameer A., et al., "Anti-Oligomeric Abeta Single-Chain Variable Domain Antibody Blocks Abeta-Induced Toxicity Against Human Neuroblastoma Cells," Journal of Molecular Biology, 2008, vol. 384 (4), pp. 917-928.

Zarandi M., et al., "Synthesis of Abeta[1-42] and its Derivatives with Improved Efficiency," Journal of Peptide Science, 2007, vol. 13 (2), pp. 94-99.

Zhao J.H., et al., "Molecular Dynamics Simulations to Investigate the Aggregation Behaviors of the Abeta(17-42) Oligomers," Journal of Biomolecular Structure and Dynamics, 2009, vol. 26 (4), pp. 481-490.

Zhao W., et al., "Identification of Antihypertensive Drugs which Inhibit Amyloid-Beta Protein Oligomerization," Journal of Alzheimer's Disease, 2009, vol. 16 (1), pp. 49-57.

Zheng J., et al., "Annular Structures as Intermediates in Fibril Formation of Alzheimer Abeta17-42," The Journal of Physical Chemistry B, 2008, vol. 11.2 (22), pp. 6856-6865.

Zhu D., et al., "Phospholipases A2 Mediate Amyloid-Beta Peptide-Induced Mitochondrial Dysfunction," The Journal of Neuroscience, 2006, vol. 26 (43), pp. 11111-11119.

Zlokovic B.V., "Clearing Amyloid through the Blood-Brain Barrier," Journal of Neurochemistry, 2004, vol. 89 (4), pp. 807-811.

Zou K., et al., "A Novel Function of Monomeric Amyloid Beta-Protein Serving as an Antioxidant Molecule Against Metal-Induced Oxidative Damage," The Journal of Neuroscience, 2002, vol. 22 (12), pp. 4833-4841.

Zou K., et al., "Amyloid Beta-Protein (Abeta)1-40 Protects Neurons from Damage Induced by Abeta1-42 in Culture and in Rat Brain," Journal of Neurochemistry, 2003, vol. 87 (3), pp. 609-619.

\* cited by examiner

| patient number | diagnosis | gender | age at death | post-mortem time | Braak & Braak index | CERAD index | brain sample region |
|---|---|---|---|---|---|---|---|
| RZ55 | AD | male | 80 | 12 | V | C | frontal cortex |
| RZ119 | AD | male | 76 | 24 | VI | C | frontal cortex |
| RZ122 | AD | female | 83 | 14 | V-VI | C | frontal cortex |
| RZ296 | AD | male | 88 | 4 | V | C | frontal cortex |
| RZ307 | AD | female | 78 | 21 | VI | C | frontal cortex |
| ABS 0504009 | AD | male | 88 | 3 | n.d. | n.d. | frontal cortex |
| RZ145 | non-demented | female | 86 | 20 | I | 0 | frontal cortex |
| RZ342 | non-demented | female | 84 | 22 | II | 0 | frontal cortex |

FIG. 2A

| SELDI-MS analysis | Alzheimer's disease brain | | | | | | | | | | | | age matched control brain | | | |
|---|---|---|---|---|---|---|---|---|---|---|---|---|---|---|---|---|
| | RZ55 | | RZ119 | | RZ122 | | RZ296 | | RZ307 | | ABS 0504009 | | RZ145 | | RZ342 | |
| | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] | Aβ(1-40) [a.u.] | Aβ(1-42) [a.u.] |
| 6E10 | 6074 | 686 | 370 | 626 | 284 | 1101 | 161 | 1030 | 6736 | 1688 | 66 | 933 | 38 | 272 | 76 | 491 |
| 3C5 | 1667 | 110 | 13 | 21 | 58 | 652 | 32 | 507 | 2046 | 233 | 17 | 110 | 2 | 4 | 15 | 54 |
| 10F4 | 2655 | 303 | 17 | 47 | 69 | 684 | 39 | 618 | 4012 | 856 | 46 | 395 | 2 | 34 | 47 | 286 |
| IgG2b | 10 | 1 | 2 | 3 | 2 | 10 | 2 | 4 | 9 | 4 | 3 | 9 | 1 | 4 | 1 | 1 |

| SELDI-MS analysis | Alzheimer's disease brain | | | | | | | | | | | | Age matched control brain | | | |
|---|---|---|---|---|---|---|---|---|---|---|---|---|---|---|---|---|
| | RZ255 | | RZ119 | | RZ122 | | RZ296 | | RZ307 | | ABS 0504009 | | RZ145 | | RZ342 | |
| | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP | % Aβ(1-40) of 6E10 IP | % Aβ(1-42) of 6E10 IP |
| 3C5 | 27 | 16 | 4 | 3 | 20 | 59 | 20 | 49 | 30 | 14 | 26 | 12 | 5 | 1 | 20 | 11 |
| 10F4 | 44 | 44 | 5 | 8 | 24 | 62 | 24 | 60 | 60 | 51 | 70 | 42 | 5 | 13 | 62 | 58 |
| IgG2b | 0 | 0 | 1 | 0 | 1 | 1 | 1 | 0 | 0 | 0 | 5 | 1 | 3 | 1 | 1 | 0 |

FIG. 2D

| Western Blot analysis | Alzheimer's disease brain | | | | | | age matched control brain | |
|---|---|---|---|---|---|---|---|---|
| | RZ255 Aβ [a.u.] | RZ119 Aβ [a.u.] | RZ122 Aβ [a.u.] | RZ296 Aβ [a.u.] | RZ307 Aβ [a.u.] | ABS 0504009 Aβ [a.u.] | RZ145 Aβ [a.u.] | RZ342 Aβ [a.u.] |
| 6E10 | 229402 | 146045 | 151948 | 172822 | 242537 | 123837 | 42788 | 61855 |
| 3C5 | 44195 | 5624 | 35957 | 49785 | 47228 | 10662 | 169 | 3993 |
| 10F4 | 97036 | 44398 | 88681 | 103612 | 120196 | 44366 | 963 | 29300 |
| IgG2b | 754 | 109 | 601 | 1594 | 233 | 111 | 45 | 91 |

FIG. 2E

| Western Blot analysis | Alzheimer's disease brain | | | | | | age matched control brain | |
|---|---|---|---|---|---|---|---|---|
| | RZ255 % Aβ of 6E10 IP | RZ119 % Aβ of 6E10 IP | RZ122 % Aβ of 6E10 IP | RZ296 % Aβ of 6E10 IP | RZ307 % Aβ of 6E10 IP | ABS 0504009 % Aβ of 6E10 IP | RZ145 % Aβ of 6E10 IP | RZ342 % Aβ of 6E10 IP |
| 3C5 | 19 | 4 | 24 | 29 | 19 | 9 | 0 | 6 |
| 10F4 | 42 | 30 | 58 | 60 | 50 | 36 | 2 | 47 |
| IgG2b | 0 | 0 | 0 | 1 | 0 | 0 | 0 | 0 |

| | | trace OD x mm [a.u.] | antibody bound to fibrils[%] |
|---|---|---|---|
| 6E10 | supernatant | 0.007 | 97 |
| | pellet | 0.233 | |
| 3C5 | supernatant | 0.111 | 34 |
| | pellet | 0.057 | |
| 10F4 | supernatant | 0.160 | 23 |
| | pellet | 0.047 | |

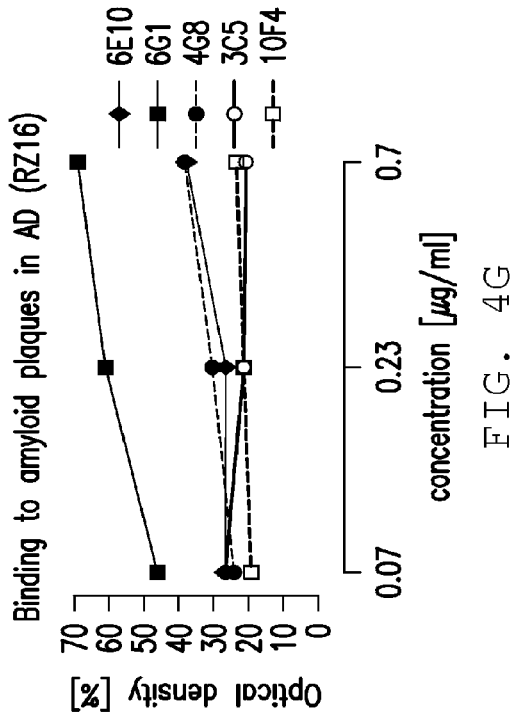
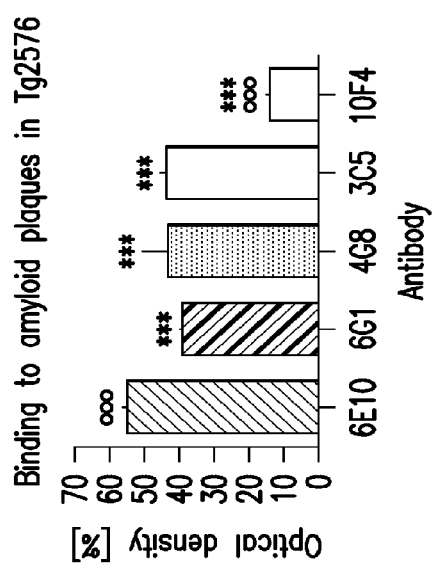
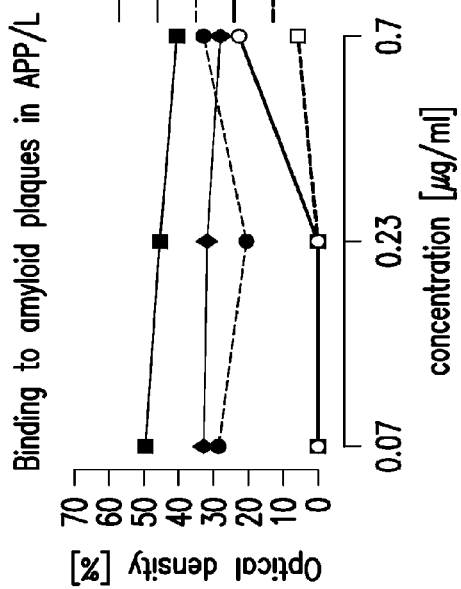

| patient # | antibody | % Aβ(1-40) of 6E10 IP | % Aβ(1-42) of 6E10 IP |
|---|---|---|---|
| ABS 0504009 | 8F5 | 29 | 55 |
| | 10F4 | 0 | 0 |
| | 3C5 | 5 | 38 |

| patient # | antibody | % Aβ(1-40) of 6E10 IP | % Aβ(1-42) of 6E10 IP |
|---|---|---|---|
| 30027 | 8F5 | 47 | 34 |
| | 10F4 | 0 | 0 |
| | 3C5 | 2 | 5 |

| patient # | antibody | % Aβ(1-40) of 6E10 IP | % Aβ(1-42) of 6E10 IP |
|---|---|---|---|
| 30026 | 8F5 | 27 | 112 |
| | 10F4 | 4 | 56 |
| | 3C5 | 1 | 9 |

| patient # | antibody | % Aβ(1-40) of 6E10 IP | % Aβ(1-42) of 6E10 IP |
|---|---|---|---|
| 26748015 | 8F5 | 28 | 58 |
| | 10F4 | 3 | 13 |
| | 3C5 | 2 | 17 |

| patient | diagnosis | gender | post-mortem CSF sample | | pre-mortem CSF sample | Mini Mental State Examination (MMSE) score |
| --- | --- | --- | --- | --- | --- | --- |
| | | | patient age at death | post mortem time (h) | patient age at sample taken | |
| ABS 0504009 | AD | male | 88 | 3 | n.a. | n.d. |
| 30027 | AD | male | n.a. | n.a. | 72 | 14 |
| 30026 | AD | male | n.a. | n.a. | 70 | 22 |
| 26748015 | AD | female | n.a. | n.a. | 48 | 11 |

FIG. 5I

SEQ ID NO:1 (VH ML45-3C5)

GATGTGCAGCTTCAGGAGTCGGGACCTGGCCTGGTGAAACCTTCTCAGTCTCTGT
CCCTCACCTGCACTGTCGCTGGCTCCTCAATCACCAGTCATTATGCCTGGAACTGG
ATCCGGCAGTTTCCAGGAAACAAACTGGAGTGGATGGGCTACATAGACTATAGT
GGTAGCACTCGCTACCTCCCCTCTCTCAAAAGTCGAATCTCTATCACTCGAGACA
CATCCAAGAACCAGTTCTTCCTGCAGTTGAATTCTGTGACTACTGAGGACACAGC
CACATATTACTGTGCAAGGGGTAGTGGTTATTTCTATGGTATGGACTACTGGGGT
CAAGGAACCTCAGTCACCGTCTCCTCA

FIG. 6A

SEQ ID NO:2 (VL ML45-3C5)

GACATCCAGATGAACCAGTCTCCATCCAGTCTGTCTCCATCCCTTGGAGACACAA
TTACCATCACTTGCCATGCCAGTCAGAACATTAATGTCTGGTTAAGCTGGTACCA
GCAGAAACCAGGAAATATTCCTAAACTATTGATCTATAAGGCTTCCAACTTGCAC
ACAGGCGTCCCATCAAGGTTTAGTGGCAGTGGATCTGGAATAGGTTTTACATTAA
CCATCCGCAGCCTGCAGCCTGAAGACATTGCCACTTACTTCTGTCAACAGGGTCA
AAGTTATCCGTACACGTTCGGAGGGGGGACTAAGCTGGAAATAAAACGG

FIG. 6B

SEQ ID NO:3 (VH ML43-10F4)

CAGGTCCAGCTGCAGCAGTCTGGAGCTGAGCTGGTAAGGCCTGGGACTTCAGTGA
GGGTGTCCTGCAAGGCTTCTGGATACGCCTTCACTAATTACTTGATAGAGTGGGT
AAAGCAGAGGCCTGGACAGGGCCTTGAGTGGATTGGAGTGATTAATCCTGGAAG
TGGTGATACTAACTACAATGAGAATTTCAAGGGCAAGGCAACACTGACTGCAGA
CAAATCCTCCAGCACTGCCTACATGCACCTCAGCAGCCTGACATCTGATGACTCT
GCGGTCTATTTCTGTACAAGAGGCGTGATTACGACGGGTTTTGACTACTGGGGCC
AAGGCACCACTCTCACAATCTCCTCA

FIG. 6C

SEQ ID NO:4 (VL ML43-10F4)

GACATCCAGATGACTCAGTCTCCAGCCTCCCTATCTGCATCTGTGGGAGAAACTG
TCACCATCACATGTCGAGCAAGTGGGAATATTCACAATTATTTAGCATGGTATCA
GCAGAAACAGGGAAAATCTCCTCAGCTCCTGGTCTATAATGCAAAAACCTTAGCA
GATGGTGTGCCATCAAGGTTCAGTGGCAGTGGATCAGGAACACAATATTCTCTCA
AGATCAACAGCCTGCAGCCTGAAGATTTTGGGAGTTATTACTGTCAACATTTTTG
GAGTAGTCCTCGGACGTTCGGTGGAGGCACCAAGCTGGAAATCAAACGG

FIG. 6D

SEQ ID NO:5 (VH ML45-3C5)

DVQLQESGPGLVKPSQSLSLTCTVAGSSIT<u>SHYAWN</u>WIRQFPGNKLEWMG<u>YIDYSGS
TRYLPSLKSR</u>ISITRDTSKNQFFLQLNSVTTEDTATYYCAR<u>GSGYFYGMDY</u>WGQGTS
VTVSS

FIG. 7A

SEQ ID NO:6 (VL ML45-3C5)

DIQMNQSPSSLSPSLGDTITITC<u>HASQNINVWLS</u>WYQQKPGNIPKLLIY<u>KASNLHT</u>GVP
SRFSGSGSGIGFTLTIRSLQPEDIATYFC<u>QQGQSYPYT</u>FGGGTKLEIKR

FIG. 7B

SEQ ID NO:7 (VH ML43-10F4)

QVQLQQSGAELVRPGTSVRVSCKASGYAFT<u>NYLIE</u>WVKQRPGQGLEWIG<u>VINPGSGD
TNYNENFKG</u>KATLTADKSSSTAYMHLSSLTSDDSAVYFCT<u>RGVITTGFDY</u>WGQGTTL
TISS

FIG. 7C

SEQ ID NO:8 (VL ML43-10F4)

DIQMTQSPASLSASVGETVTITC<u>RASGNIHNYLA</u>WYQQKQGKSPQLLVY<u>NAKTLAD</u>G
VPSRFSGSGSGTQYSLKINSLQPEDFGSYYC<u>QHFWSSPRT</u>FGGGTKLEIKR

FIG. 7D

Aβ CONFORMER SELECTIVE ANTI-Aβ GLOBULOMER MONOCLONAL ANTIBODIES

CROSS-REFERENCE TO RELATED APPLICATIONS

This is a divisional of U.S. patent application Ser. No. 14/513,837, filed on Oct. 14, 2014, which is a divisional of U.S. patent application Ser. No. 13/102,713, now U.S. Pat. No. 8,877,190, filed on May 6, 2011, which is a divisional of U.S. patent application Ser. No. 11/945,124, now U.S. Pat. No. 8,455,626, filed on Nov. 26, 2007, which claims priority to U.S. Patent Application No. 60/872,156, filed on Nov. 30, 2006, the entire contents of all of which are fully incorporated herein by reference.

BACKGROUND OF THE INVENTION

Technical Field

The subject invention relates to monoclonal antibodies that may be used in the treatment and diagnosis of Alzheimer's Disease. In particular, the present invention relates to monoclonal antibodies referred to as 10F4 and 3C5 and to other monoclonal antibodies (e.g., murine, human or humanized) having similar properties thereto.

Background Information

In 1907, the physician Alois Alzheimer first described the neuropathological features of a form of dementia subsequently named in his honor as Alzheimer's disease (AD). In particular, AD is the most frequent cause for dementia among the aged, with an incidence of about 10% of the population in those above 65 years of age. With increasing age, the probability of disease also rises. Globally, there are about 15 million people affected with the disease and further increases in life expectancy are expected to increase the number of people affected with the disease to about threefold over the next decades.

From a molecular point of view, Alzheimer's disease (AD) is characterized by a deposit of abnormally aggregated proteins. In the case of extra-cellular amyloid plaques, these deposits consist mostly of amyloid-β-peptide filaments, and in the case of the intracellular neurofibrillary tangles (NFTs), mostly of the tau protein. The amyloid β (Aβ) peptide arises from the β-amyloid precursor protein by proteolytic cleavage. This cleavage is effected by the cooperative activity of several proteases named α-, β- and γ-secretase. Cleavage leads to a number of specific fragments of differing length. The amyloid plaques consist mostly of peptides with a length of 40 or 42 amino acids (Aβ40, Aβ42). The dominant cleavage product is Aβ40; however, Aβ42 has a much stronger toxic effect. Cerebral amyloid deposits and cognitive impairments very similar to those observed in Alzheimer's disease are also hallmarks of Down's syndrome (trisomy 21), which occurs at a frequency of about 1 in 800 births.

The amyloid cascade hypothesis of Hardy and Higgins postulated that increased production of Aβ(1-42) would lead to the formation of protofibrils and fibrils (i.e., the principal components of Aβ plaques), these fibrils being responsible for the symptoms of Alzheimer's disease. Despite the poor correlation between severity of dementia and Aβ plaque burden deposited, this hypothesis was favored until recently. The discovery of soluble Aβ forms in AD brains, which correlates better with AD symptoms than plaque load does, has led to a revised amyloid-cascade-hypothesis.

Active immunization with Aβ peptides leads to a reduction in the formation as well as to partial dissolution of existing plaques. At the same time, it leads to alleviation of cognitive defects in APP transgenic mouse models. For passive immunization with antibodies directed to Aβ peptides, a reduction of an Aβ plaque burden was also found. The results of a phase IIa trial (ELAN Corporation Plc, South San Francisco, Calif., USA and Dublin, UK) of active immunization with AN-1792 (Aβ(1-42) peptide in fibrillary condition of aggregation) suggest that immunotherapy directed to Aβ peptide was successful. In a subgroup of 30 patients, the progression of disease was significantly reduced in patients with positive anti-Aβ antibody titer, measured by MMSE and DAD index. However, this study was stopped because of serious side effects in the form of a meningoencephalitis (Bennett and Holtzman, 2005, Neurology, 64, 10-12). In particular, meningoencephalitis was characterized by neuroinflammation and infiltration of T-cells into the brain. Presumably, this was due to a T-cell immune response induced by injection of Aβ(1-42) as antigen. Such an immune response is not to be expected after passive immunization. To date, there are no clinical data with reference to this available. However, with reference to such a passive approach to immunization, concerns about the side effect profile were voiced because of preclinical studies in very old APP23 mice which received an antibody directed against an N-terminal epitope of Aβ(1-42) once a week over 5 months. In particular, these mice showed an increase in the number and severity of microhemorrhages compared to control animals treated with saline (Pfeifer et al., 2002, Science, 298, 1379). A comparable increase in microhaemorrhages was also described in very old (>24 months) Tg2576 and PDAPP mice (Racke et al., 2005, J Neurosci, 25, 629-636; Wilcock et al. 2004, J. Neuroinflammation, 1(1):24; De Mattos et al., 2004, Neurobiol. Aging 25(S2):577). In both mouse strains, antibody injection led to a significant increase in microhemorrhages. In contrast, an antibody directed against the central region of the Aβ(1-42) peptide did not induce microhemorrhages (de Mattos et al., supra). The lack of inducing microhemorrhages was associated with an antibody treatment which did not bind to aggregated Aβ peptide in the form of CAA (Racke et al., J Neurosci, 25, 629-636). Yet, the exact mechanism leading to microhemorrhages in mice transgenic for APP has not been understood. Presumably, cerebral amyloid angiopathy (CAA) induces or at least aggravates cerebral hemorrhages. CAA is present in nearly every Alzheimer's disease brain and about 20% of the cases are regarded as "severe CAA". Passive immunization should therefore aim at avoiding microhemorrhages by selecting an antibody which recognizes the central or the carboxy terminal region of the Aβ peptide.

International Patent Application Publication No. WO2004/067561 describes stable Aβ(1-42) oligomers (Aβ (1-42) globulomers) and antibodies directed specifically against the globulomers. Digestion with unspecific proteases shows that the Aβ globulomer may be digested beginning with the hydrophilic N-terminus protruding from the globular core structure (Barghorn et al., 2005, J Neurochem, 95, 834-847). Such N-terminal truncated Aβ globulomers (Aβ (12-42) and Aβ(20-42) globulomers) represent the basic structural unit of this oligomeric Aβ and are a very potent antigen for active immunization of rabbits and mice leading to high antibody titers (WO2004/067561). The putative pathological role of N-terminally truncated Aβ forms in vivo has been suggested by several recent reports of their existence in AD brains (Sergeant et al., 2003, J Neurochem, 85, 1581-1591; Thal et al., 1999, J Neuropathol. Exp Neurol, 58, 210-216). During in vivo digestion, certain proteases found in brain, e.g. neprilysin (NEP 24.11) or insulin degrading enzyme (IDE), may be involved (Selkoe, 2001, Neuron, 32, 177-180).

In view of the above, there is a tremendous and immediate need for a treatment for Alzheimer's Disease which has few, if any, side effects (e.g., microhemmorhages). With such treatment, affected patients may be able to maintain a functional and active lifestyle for many years beyond that which is possible without such treatment. Thus, not only are there financial implications for such a treatment but "quality of life" implications as well, not only for the patients but also for their caregivers.

All patents and publications referred to herein are hereby incorporated in their entirety by reference.

1. Aβ(1-42) monomer, 0.1% NH$_4$OH
2. Aβ(1-40) monomer, 0.1% NH$_4$OH
3. Aβ(1-42) monomer, 0.1% NaOH
4. Aβ(1-40) monomer, 0.1% NaOH
5. Aβ(1-42) globulomer
6. Aβ(12-42) globulomer
7. Aβ(20-42) globulomer
8. Aβ(1-42) fibril preparation
9. sAPPα (Sigma) (first dot: 1 pmol)

Figures 1A, 1B:
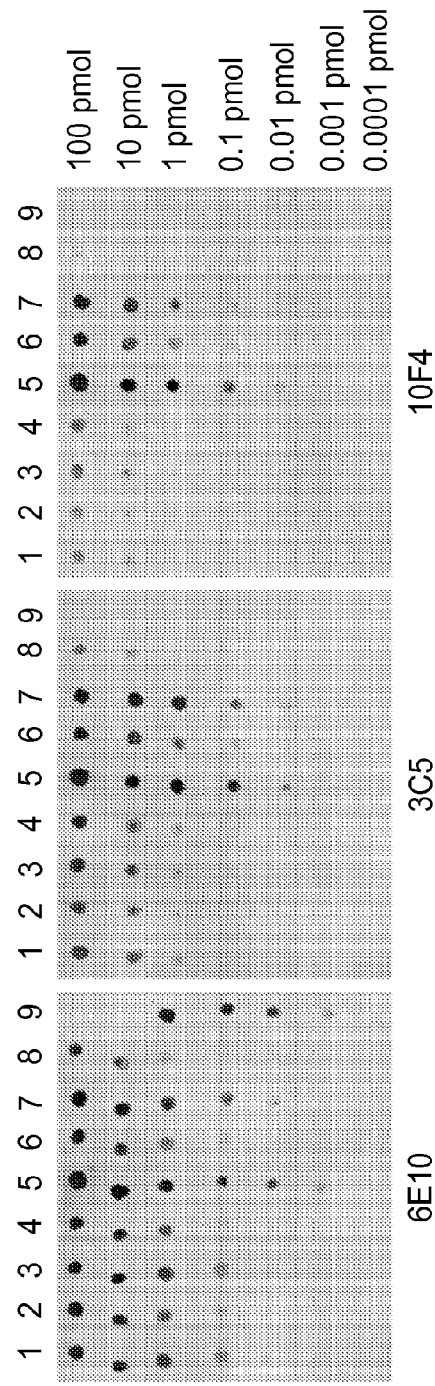
FIG. 1A shows a dot blot analysis of the specificity of different anti-Aβ antibodies (-6E10, -3C5, 10F4). The monoclonal antibodies tested here were obtained by active immunization of mice with Aβ(12-42) globulomer (prepared as described in Example I) followed by selection of the fused hybridoma cells (except for the commercially available 6E10, Signet, Cat. No.: 9320). The individual Aβ forms were applied in serial dilutions and incubated with the respective monoclonal antibodies for immune reaction.

FIG. 1B illustrates a quantitative evaluation which was done using a densitometric analysis of the intensity. For each Aβ form, only the dot corresponding to the lowest antigen concentration was evaluated provided that it had a relative density of greater than 20% of the relative density of the last optically unambiguously identified dot of the Aβ(1-42) globulomer (threshold). This threshold value was determined for every dot-blot independently. The value indicates the relationship between recognition of Aβ(1-42) globulomer and the respective Aβ form for the antibody given.

FIG. 2A-FIG. 2E illustrate the results of Aβ-peptide immunoprecipitated from Alzheimer's disease brain tissue.

FIG. 2A represents a detailed description of the patient material that was used for analysis.

FIG. 2B illustrates the immunoprecipitated amount of Aβ(1-40)-peptide and Aβ(1-42)-peptide as quantified by SELDI-MS analysis for the different patient and control brain samples with the antibodies 6E10, 3C5, 10F4 and the control antibody IgG2b.

FIG. 2C illustrates the relative immunoprecipitated amount of Aβ(1-40)-peptide and Aβ(1-42)-peptide as quantified by SELDI-MS analysis for the different patient and control brain samples with the antibodies 3C5, 10F4 and the control antibody IgG2b compared to the pan-Aβ-antibody 6E10 in percent. The total amount of Aβ-peptide immunoprecipitated by antibody 6E10 was set to 100%.

FIG. 2D illustrates the immunoprecipitated amount of Aβ-peptide as quantified by Western blot analysis for the different patient and control brain samples with the antibodies 6E10, 3C5, 10F4 and the control antibody IgG2b.

FIG. 2E illustrates the relative immunoprecipitated amount of Aβ-peptide as quantified by Western blot analysis for the different patient and control brain samples with the antibodies 3C5, 10F4 and the control antibody IgG2b compared to the pan-Aβ-antibody 6E10 in percent. The total amount of Aβ-peptide immunoprecipitated by antibody 6E10 was set to 100%.

Figures 3A, 3B:
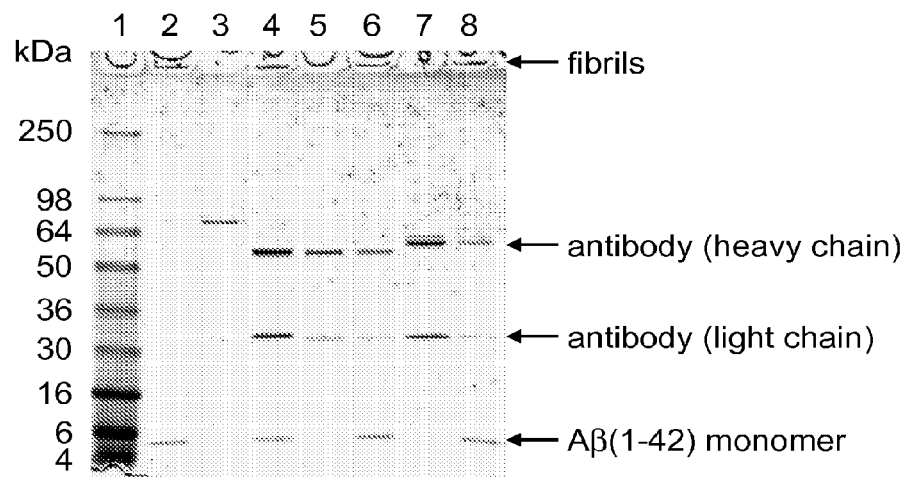

FIG. 3A shows a Coomassie stained SDS PAGE of:
1) standard proteins (molecular marker proteins)
2) Aβ(1-42) fibril preparation; control
3) Aβ(1-42) fibril preparation+mAb 6E10, 20 h, 37° C., supernatant
4) Aβ(1-42) fibril preparation+mAb 6E10, 20 h, 37° C., pellet
5) Aβ(1-42) fibril preparation+mAb 3C5, 20 h, 37° C., supernatant
6) Aβ(1-42) fibril preparation+mAb 3C5, 20 h 37° C., pellet
7) Aβ(1-42) fibril preparation+mAb 10F4, 20 h, 37° C., supernatant
8) Aβ(1-42) fibril preparation+mAb 10F4, 20 h 37° C., pellet FIG. 3B shows the densitometric quantitative analysis of in vitro antibody binding to Aβ-fibrils.

Figure 4A:
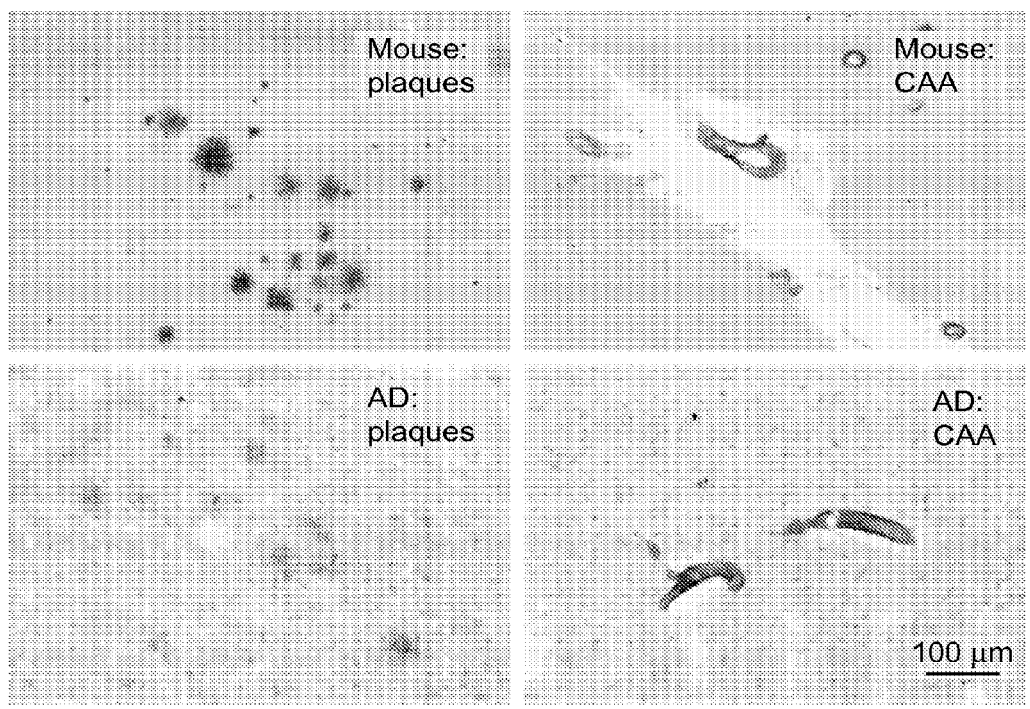
Figure 4B:
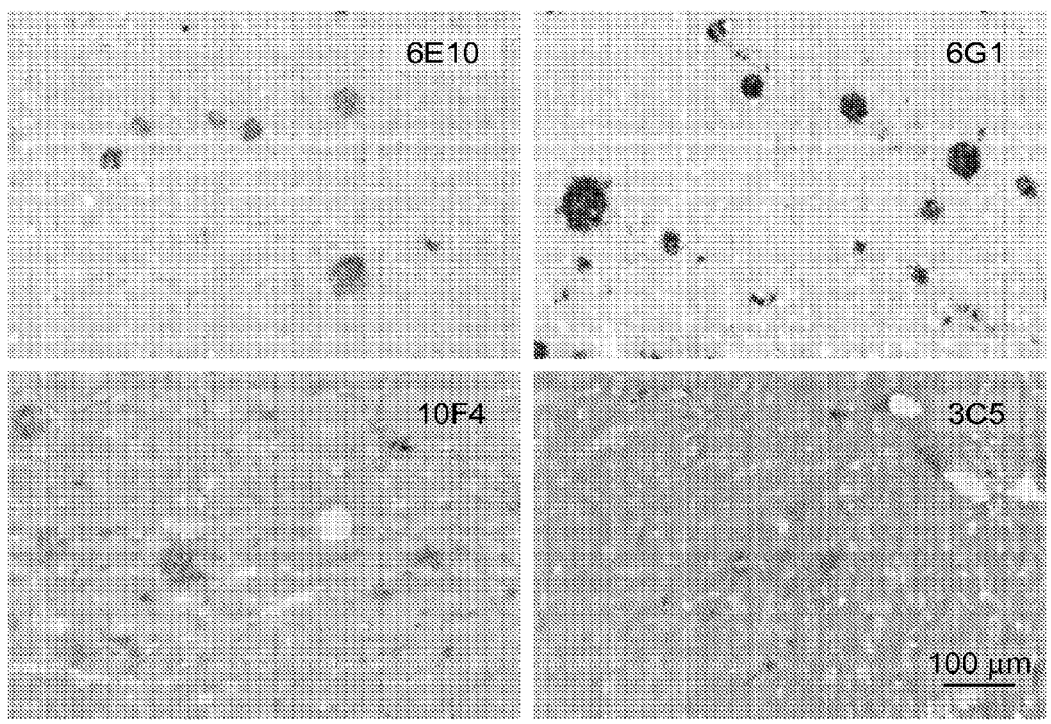
Figure 4C:
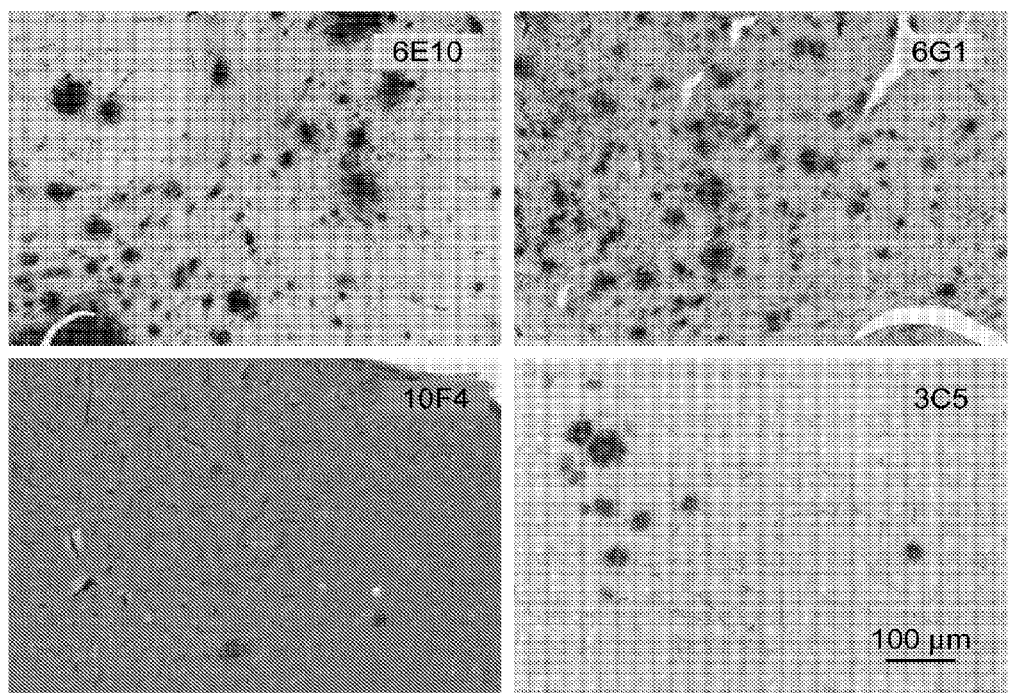

FIG. 4A-FIG. 4C shows the binding of antibodies at different concentrations to transversal sections of the neocortices of Alzheimer's disease (AD) patients or old APP transgenic mice.

FIG. 4A represents the verification of amyloid deposits by Congo Red staining as plaques in brain tissue and as cerebral amyloid angiopathy (CAA) in brain vessels in the APP transgenic mouse line Tg2576 and in an AD patient (RZ55).

FIG. 4B shows the strong staining of parenchymal deposits of Aβ (amyloid plaques) in an AD patient (RZ16) occurs only with 6G1 and the commercially available antibody 6E10 while 10F4 and 3C5 show considerably weaker staining. All antibodies were tested at a concentration of 0.7 µg/mL.

FIG. 4C shows the strong staining of parenchymal deposits of Aβ (amyloid plaques) in TG2576 mice occurs only with 6G1 and the commercially available antibody 6E10 while 10F4 and 3C5 show considerably weaker staining. All antibodies were tested at a concentration of 0.7 µg/mL.

FIG. 4D-FIG. 4G show the quantification of the analysis of Aβ plaque staining in the histological images using image analysis. Optical density values (0%=no staining) were calculated from the greyscale values of plaques subtracted by greyscale values of background tissue. (FIG. 4D shows the binding of 0.7 µg/mL antibody in Tg2576 mice. FIG. 4E shows the binding of 0.07-0.7 µg/mL antibody in APP/L mice. FIG. 4F shows the binding of 0.7 µg/mL antibody in an AD patient (RZ55), and FIG. 4G shows the binding of 0.07-0.7 µg/mL antibody in an AD patient (RZ16).) The differences between staining of the commercially available antibodies 6E10 (starts) and 4G8 (circles) and antibodies 6G1, 10F4 and 3C5 (one asterisk/circle: p<0.05, two asterisks/circles: p<0.01, and three asterisks/circles: p<0.001 versus control; post-hoc Bonferroni's t-test after ANOVA with p<0.001) were statistically evaluated (FIG. 4D and FIG. 4E). In FIG. 4E and FIG. 4G, the antibodies 10F4 and 3C5 showed always significantly less staining than the commercially available antibodies 6E10 and 4G8 (p<0.05 in post-hoc t-test after p<0.001 in ANOVA).

Figure 4H:
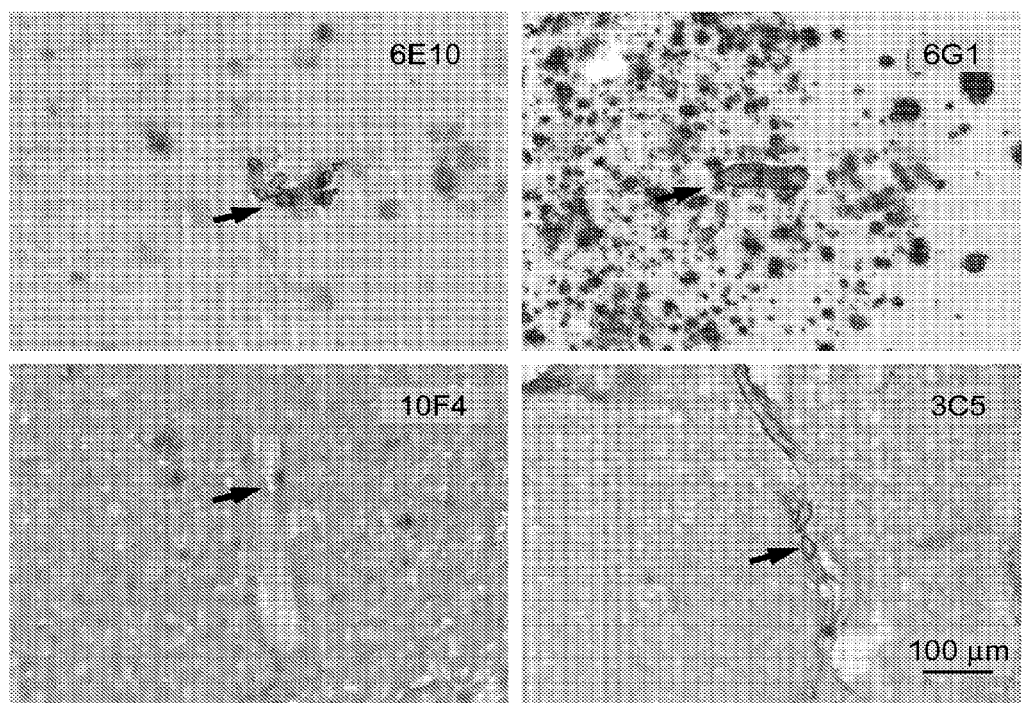

FIG. 4H shows the strong staining of vascular deposits of Aβ (arrows) occurs only with 6G1 and the commercially available antibody 6E10 while staining with 8F5 or 8C5 was much weaker. All antibodies were tested at a concentration of 0.7 μg/mL. A qualitatively similar situation was found in Tg2576 mice (not shown here).

FIG. 5A, FIG. 5C, FIG. 5E, and FIG. 5G show the amount of Aβ(1-40) and Aβ(1-42) peptide immunoprecipitated from Alzheimer's disease patient CSF by the monoclonal antibodies 6E10, 10F4, 3C5 and 8F5. Results for 4 individual Alzheimer's disease CSF samples are shown ((a)=Alzheimer's disease patient #0504009; (c)=Alzheimer's disease patient #30027; (e)=Alzheimer's disease patient #30026; (g)=Alzheimer's disease patient #26748015).

Figures 5A, 5B:
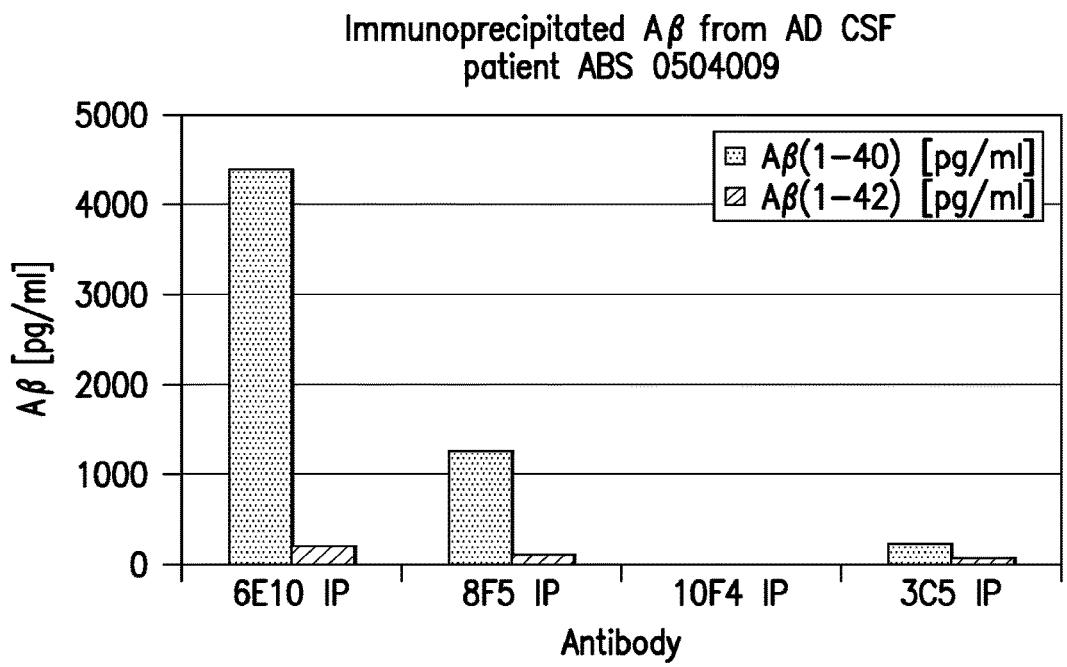
Figures 5C, 5D:
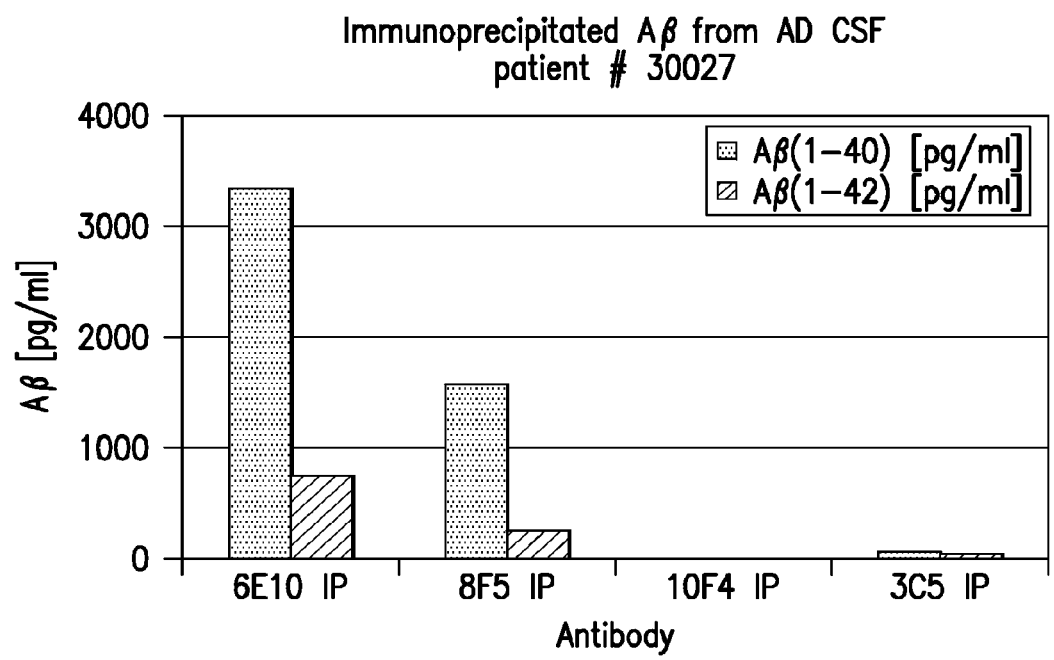
Figures 5E, 5F:
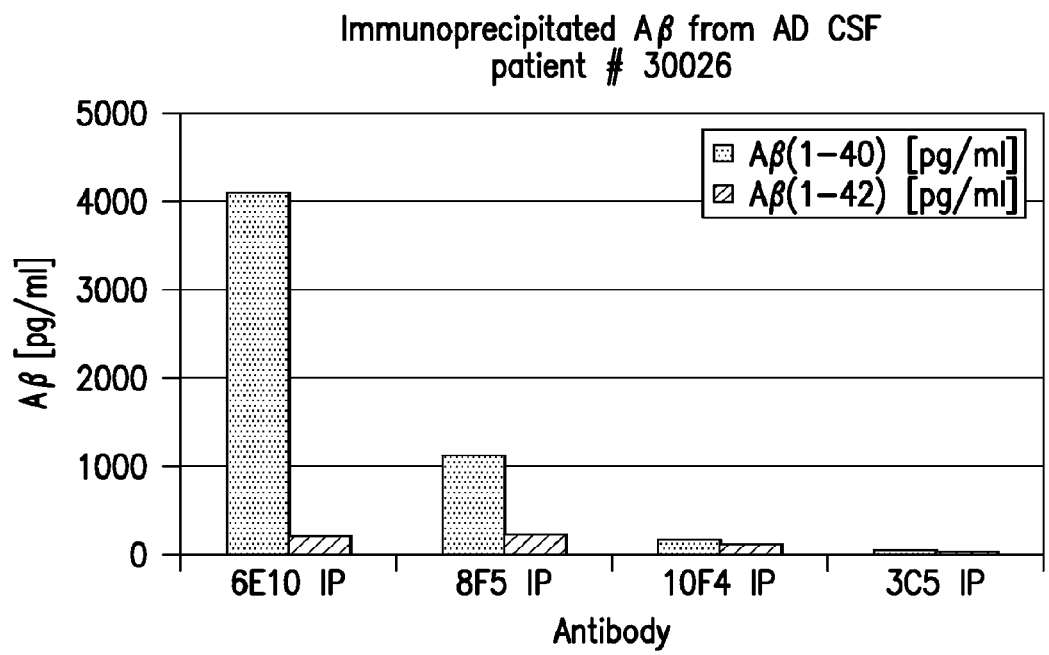
Figures 5G, 5H:
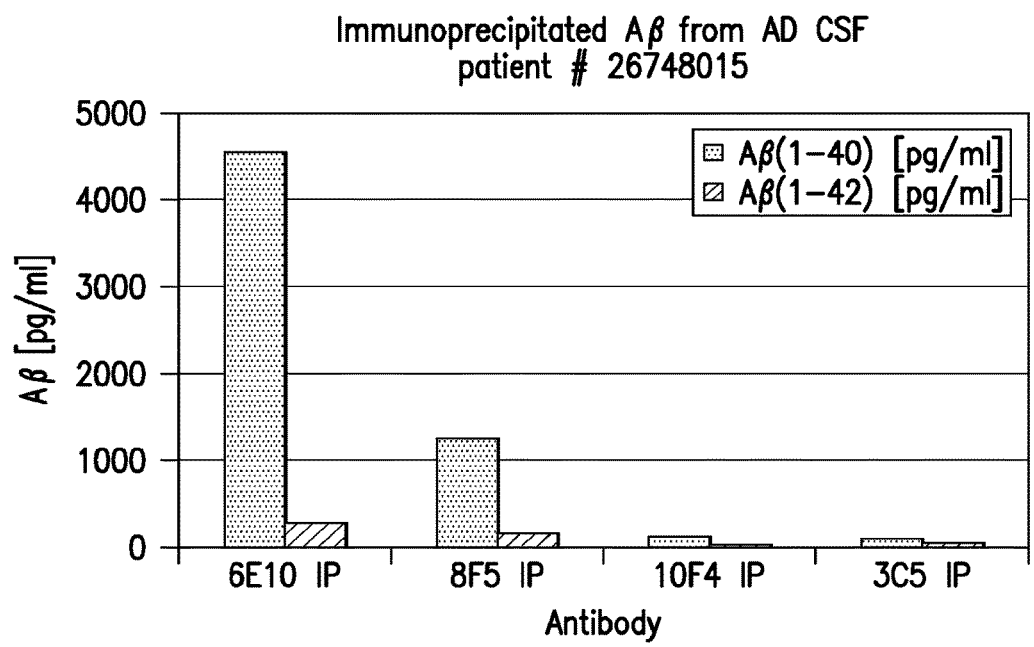

FIG. 5B shows the relative amount of Aβ(1-40) and Aβ(1-42) peptide immunoprecipitated from Alzheimer's disease patient CSF by the antibodies 10F4, 3C5 and 8F5 compared to the amount of Aβ-peptide immunoprecipitated by the antibody 6E10 in percent. The total amount of Aβ-peptide immunoprecipitated by mAb 6E10 antibody was set to 100%. Results for 4 individual Alzheimer's disease CSF samples are shown ((b)=Alzheimer's disease patient #0504009; (d)=Alzheimer's disease patient #30027; (f)=Alzheimer's disease patient #30026; (h)=Alzheimer's disease patient #26748015).

FIG. 5I represents a detailed description of the Alzheimer's disease patient CSF material that was used for analysis in FIG. 5A-FIG. 5I.

FIG. 6A illustrates the DNA sequence (SEQ ID NO:1) of the variable heavy chain encoding the monoclonal antibody referred to herein as "3C5".

FIG. 6B illustrates the DNA sequence (SEQ ID NO:2) of the variable light chain encoding the monoclonal antibody referred to herein as "3C5".

FIG. 6C illustrates the DNA sequence (SEQ ID NO:3) of the variable heavy chain encoding the monoclonal antibody referred to herein as "10F4".

FIG. 6D illustrates the DNA sequence (SEQ ID NO:4) of the variable light chain encoding the monoclonal antibody referred to herein as "10F4".

FIG. 7A illustrates the amino acid sequence (SEQ ID NO:5) of the variable heavy chain encoding the monoclonal antibody referred to herein as "3C5".

FIG. 7B illustrates the amino acid sequence (SEQ ID NO:6) of the variable light chain encoding the monoclonal antibody referred to herein as "3C5".

FIG. 7C illustrates the amino acid sequence (SEQ ID NO:7) of the variable heavy chain encoding the monoclonal antibody referred to herein as "10F4".

FIG. 7D illustrates the amino acid sequence (SEQ ID NO:8) of the variable light chain encoding the monoclonal antibody referred to herein as "10F4". (Complementarity determining regions (CDRs) are underlined in each described sequence.)

SUMMARY OF THE INVENTION

The present invention encompasses antibodies, directed against Aβ globulomers, which improve the cognitive performance of a patient in immunotherapy, while at the same time reacting only with a small portion of the entire amount of Aβ peptide in the brain. Such properties prevent a substantial disturbance of cerebral Aβ balance and lead to less side effects. (For instance, a therapeutically questionable reduction of brain volume has been observed in the study of active immunization with Aβ peptides in fibrillary condition of aggregation (ELAN Corporation Plc, South San Francisco, Calif., USA and Dublin, UK) of active immunization with AN-1792 (Aβ(1-42) peptide in fibrillary condition of aggregation). Moreover, in this trial, severe side effects in form of a meningoencephalitis were observed.)

In particular, the present invention solves the above-noted side effect issues by providing Aβ globulomer antibodies possessing high affinity for Aβ globulomers. These antibodies are capable of discriminating other forms of Aβ peptides, particularly monomers, fibrils and sAPPα. Further, the antibodies of the present invention also discriminate against amyloid beta in the cerebrospinal fluid (CSF) by binding only to non-CSF amyloid beta. Additionally, the antibodies of the present invention (e.g., 10F4 and 3C5) bind less to Aβ-plaques and vascular Aβ compared to a known antibody (i.e., 6E10).

In particular, the present invention encompasses an isolated antibody having a higher affinity to Aβ(1-42) globulomer than to at least one amyloid beta protein selected from the group consisting of Aβ(1-42) peptide present in cerebrospinal fluid (CSF) and b) Aβ(1-40) peptide present in CSF.

The present invention also includes an isolated antibody having a binding affinity to Aβ(1-42) globulomer which is greater than the binding affinity to at least one amyloid beta protein selected from the group consisting of a) Aβ(1-42) monomer, b) Aβ(1-40) monomer, c) Aβ(1-42) fibril and d) soluble amyloid precursor protein-alpha (sAPPα). This antibody binds with greater affinity to amyloid beta protein present in non-CSF than to amyloid beta protein present in CSF.

The above-described antibodies may be, for example, murine, monoclonal, recombinant, human and/or humanized. Further, any one of more of the antibodies of the present invention may bind to at least one epitope, which is the same epitope or epitopes, to which the monoclonal antibody 10F4 (obtainable from a hybridoma designated by American Type Culture Collection deposit number PTA-7808) or the monoclonal antibody 3C5 (obtainable from a hybridoma designated by American Type Culture Collection deposit number PTA-7406) binds.

Additionally, the present invention includes an isolated antibody comprising SEQ ID NO:5, an isolated antibody comprising SEQ ID NO:6 and an isolated antibody comprising both SEQ ID NO:5 and SEQ ID NO:6.

Further, the present invention encompasses an isolated antibody comprising SEQ ID NO:7, an isolated antibody comprising SEQ ID NO:8 and an isolated antibody comprising both SEQ ID NO:7 and SEQ ID NO:8.

The above-described antibodies of the present invention may comprise at least one amino acid sequence selected from the group consisting of: a) the amino acid sequence of the heavy chain CDR3 and the amino acid sequence of the light chain CDR3 of monoclonal antibody (10F4) (obtainable from a hybridoma designated by American Type Culture Collection deposit number PTA-7808) and b) the amino acid sequence of the heavy chain CDR3 and the amino acid sequence of the light chain CDR3 of monoclonal antibody (3C5) (obtainable from a hybridoma designated by American Type Culture Collection deposit number PTA-7406).

Further, the above-described antibodies of the present invention may comprise at least one amino acid sequence selected from the group consisting of: a) the amino acid sequence of the heavy chain CDR2 and the amino acid sequence of the light chain CDR2 of a monoclonal antibody (10F4) (obtainable from a hybridoma designated by American Type Culture Collection deposit number PTA-7808) and b) the amino acid sequence of the heavy chain CDR2 and the amino acid sequence of the light chain CDR2 of a monoclonal antibody (3C5) (obtainable from a hybridoma designated by American Type Culture Collection deposit number PTA-7406).

Also, the antibodies of the present invention may comprise at least one amino acid sequence selected from the group consisting of: a) the amino acid sequence of the heavy chain CDR1 and the amino acid sequence of the light chain CDR1 of a monoclonal antibody (10F4) (obtainable from a hybridoma designated by American Type Culture Collection deposit number PTA-7808) and b) the amino acid sequence of the heavy chain CDR1 and the amino acid sequence of the light chain CDR1 of a monoclonal antibody (3C5) (obtainable from a hybridoma designated by American Type Culture Collection deposit number PTA-7406).

Moreover, the present invention also includes an isolated antibody comprising at least one CDR selected from the group consisting of amino acid sequence: a) SHYAWN; b) YIDYSGSTRYLPSLKS; c) GSGYFYGMDY; d) HASQN-INVWLS; e) KASNLHT; f) QQGQSYPYT; g) NYLIE; h) VINPGSGDTNYNENFKG; i) GVITTGFDY; j) RAS-GNIHNYLA; k) NAKTLAD and l) QHFWSSPRT.

Additionally, the present invention encompasses a hybridoma designated by American Type Culture Collection deposit number PTA-7808 as well as a monoclonal antibody (10F4) obtainable from or produced by a hybridoma designated by American Type Culture Collection deposit number PTA-7808.

The invention also includes a hybridoma designated by American Type Culture Collection deposit number PTA-7406 as well as a monoclonal antibody (3C5) obtainable from or produced by a hybridoma designated by American Type Culture Collection deposit number PTA-7406.

Furthermore, the present invention includes an isolated nucleic acid molecule encoding the antibodies described above. The nucleotide sequence of this molecule may comprise at least one sequence selected from the group consisting of SEQ ID NO:1, SEQ ID NO:2, SEQ ID NO:3 and SEQ ID NO:4. Also, the present invention includes a vector comprising the isolated nucleic acid molecule as well as a host cell comprising the vector.

Additionally, the present invention includes a method of producing an antibody, comprising culturing the host cell described above in a culture medium for a time and under conditions suitable for production of any one of the antibodies described above. The antibody produced in accordance with this method is also included within the scope of the present invention.

Also, the present invention includes a composition comprising any one or more of the antibodies described above. This composition may further comprise a pharmaceutically acceptable carrier.

Further, the present invention encompasses a monoclonal antibody comprising an amino acid sequence encoded by at least one nucleotide sequence selected from the group consisting of SEQ ID NO:1, SEQ ID NO:2, SEQ ID NO:3 and SEQ ID NO:4. This antibody may be selected from the group consisting of a monoclonal antibody produced by a hybridoma designated by American Type Culture Collection deposit number PTA-7406 and a monoclonal antibody produced by a hybridoma designated by American Type Culture Collection deposit number PTA-7808. Also, the antibody may comprise at least one amino acid sequence selected from the group consisting of SEQ ID NO:5, SEQ ID NO:6, SEQ ID NO:7 and SEQ ID NO:8.

The invention also includes a method for treating or preventing an amyloidosis in a patient in need of such treatment or prevention. This method comprises administering one or more of the above-described antibodies (via passive immunization) to the patient in an amount sufficient to effect treatment or prevention. The amyloidosis may be, for example, Alzheimer's disease or the amyloidosis of Down's syndrome.

Also, the present invention encompasses an isolated antibody which binds to at least one epitope of amyloid beta protein in the brain of a patient having amyloidosis. This antibody may be produced, for example, by a hybridoma having an ATCC deposit number selected from the group consisting of PTA-7406 and PTA-7808.

The present invention also includes a method of diagnosing Alzheimer's Disease in a patient suspected of having this disease. This method comprises the steps of isolating a biological sample (for example, a CSF sample or brain tissue sample) from the patient, contacting the biological sample with one or more of the antibodies described above for a time and under conditions sufficient for formation of antigen/antibody complexes, and detecting presence of the antigen/antibody complexes in the sample, presence of the complexes indicating a diagnosis of Alzheimer's Disease in the patient. The antigen of the complex may be, for example, a globulomer.

Additionally, the present invention encompasses another method of diagnosing Alzheimer's Disease in a patient suspected of having this disease. This method comprises the steps of isolating a biological sample from the patient, contacting the biological sample with an antigen for a time and under conditions sufficient for the formation of antibody/antigen complexes, adding a conjugate to the resulting antibody/antigen complexes for a time and under conditions sufficient to allow the conjugate to bind to the bound antibody (wherein the conjugate comprises an isolated antibody of the present invention attached to a signal generating compound capable of generating a detectable signal), and detecting the presence of an antibody which may be present in the biological sample by detecting a signal generated by the signal generating compound, the signal indicating a diagnosis of Alzheimer's Disease in the patient. The antigen used in the assay may be, for example, a globulomer.

Further, the present invention includes an additional method of diagnosing Alzheimer's Disease in a patient suspected of having Alzheimer's Disease. This method comprises the steps of isolating a biological sample from the patient, contacting the biological sample with an anti-antibody (wherein the anti-antibody is specific for one or more of the antibodies of the present invention), for a time and under conditions sufficient to allow for formation of anti-antibody/antibody complexes, the complexes containing antibody present in the biological sample, adding a conjugate to the resulting anti-antibody/antibody complexes for a time and under conditions sufficient to allow the conjugate to bind to bound antibody (wherein the conjugate comprises an antigen, which binds to a signal generating compound capable of generating a detectable signal), and detecting a signal generated by the signal generating compound, this signal indicating a diagnosis of Alzheimer's Disease in the patient.

Additionally, the present invention includes a vaccine comprising one or more of the antibodies of the present invention and a pharmaceutically acceptable adjuvant.

Further, the present invention encompasses a method of identifying compounds suitable for active immunization of a patient predicted to develop Alzheimer's Disease. This method comprises the steps of exposing one or more compounds of interest to one or more of the antibodies of the present invention, for a time and under conditions sufficient for the one or more compounds to bind to the one or more antibodies and then identifying those compounds which bind to the one or more antibodies, the identified compounds to be used in active immunization in a patient predicated to develop Alzheimer's Disease.

Also, the present invention includes a kit comprising one or more of the antibodies of the present invention and a conjugate comprising an antibody attached to a signal-generating compound, wherein the antibody of the conjugate is different from the one or more antibodies within the kit. A package insert may also be included in the kit which describes the procedure to be utilized in carrying out the assay as well as the components of the kit.

The present invention also includes another kit comprising an anti-antibody to one or more antibodies of the present invention and a conjugate comprising an antigen attached to a signal-generating compound. The antigen may be, for example, a globulomer. Again, a package insert may be included which describes the steps to be utilized in carrying out the assay as well as the components of the kit.

DETAILED DESCRIPTION OF THE INVENTION

The antibodies of the present invention were designed from immunization with the truncated globulomer Aβ(12-42) as described in Example 1. In particular, monoclonal antibodies 3C5 and 10F4 were generated against the truncated (12-42)-globulomer (in contrast to monoclonal antibodies 8F5 and 8C5 which have been made against the Aβ(1-42) globulomer). This Aβ (12-42) globulomer was made directly from Aβ 12-42 peptide in contrast to the procedure described in Barghorn et al. (J. Neurochem, 95, 834-847) and in Example 3, Section 6, wherein the (12-42) globulomer was made from pre-existing 1-42-globulomer by limited proteolysis. These two Aβ(12-42) globulomer variants differ in their final aggregation pattern. The one made from Aβ(12-42) peptide shows only the intermediate globulomer forms ("oligomer A" as described in WO2004/067561) and the one made from the pre-existing Aβ(1-42)-globulomer is the mature globulomer ("oligomer B" as described in WO2004/067561).

It is an object of the present invention to provide antibodies directed against Aβ globulomers which improve the cognitive performance of a patient in immunotherapy while at the same time reacting only with a small portion of the entire amount of Aβ peptide in brain. This is expected to prevent a substantial disturbance of cerebral Aβ balance and lead to less side effects. (For instance, as noted above, a therapeutically questionable reduction of brain volume has been observed in the study of active immunization with Aβ peptides in fibrillary condition of aggregation (ELAN trial with AN1792). Moreover, in this trial severe side effects in form of a meningoencephalitis were observed. The present invention solves this problem by providing globulomer-specific antibodies possessing high affinity for Aβ globulomers. These antibodies are capable of discriminating other forms of Aβ peptides, particularly monomers and fibrils. Further, these antibodies do not bind (or bind with a lower affinity compared to commercially available antibodies (such as 6E10) (Signet Cat. no.: 9320)) to amyloid beta in cerebral spinal fluid. Consequently, the present invention relates to an antibody having a binding affinity to Aβ globulomer The term "Aβ(X-Y)" herein refers to the amino acid sequence from amino acid position X to amino acid position Y of the human amyloid β protein including both X and Y, in particular to the amino acid sequence from amino acid position X to amino acid position Y of the amino acid sequence DAEFRHDSGY EVHHQKLVFF AEDVGSNKGA IIGLMVGGVV IAT (corresponding to amino acid positions 1 to 43) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both position X and position Y or a sequence with up to three additional amino acid substitutions, none of which may prevent globulomer formation, preferably with no additional amino acid substitutions in the portion from amino acid 12 or X, whichever number is higher, to amino acid 42 or Y, whichever number is lower, more preferably with no additional amino acid substitutions in the portion from amino acid 20 or X, whichever number is higher, to amino acid 42 or Y, whichever number is lower, and most preferably with no additional amino acid substitutions in the portion from amino acid 20 or X, whichever number is higher, to amino acid 40 or Y, whichever number is lower, an "additional" amino acid substation herein being any deviation from the canonical sequence that is not found in nature.

The term "Aβ(1-42)" herein refers to the amino acid sequence from amino acid position 1 to amino acid position 42 of the human amyloid β protein including both 1 and 42, in particular to the amino acid sequence DAEFRHDSGY EVHHQKLVFF AEDVGSNKGA IIGLMVGGVV IA or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both 1 and 42 or a sequence with up to three additional amino acid substitutions none of which may prevent globulomer formation, preferably with no additional amino acid substitutions in the portion from amino acid 20 to amino acid 42. Likewise, the term "Aβ(1-40)" here refers to the amino acid sequence from amino acid position 1 to amino acid position 40 of the human amyloid β protein including both 1 and 40, in particular to the amino acid sequence DAEFRHDSGY EVHHQKLVFF AEDVGSNKGA IIGLMVGGVV or any of its naturally occurring variants, in particular those with at least one mutation selected from the group consisting of A2T, H6R, D7N, A21G ("Flemish"), E22G ("Arctic"), E22Q ("Dutch"), E22K ("Italian"), and D23N ("Iowa") wherein the numbers are relative to the start of the Aβ peptide, including both 1 and 40 or a sequence with up to three additional amino acid substitutions none of which may prevent globulomer formation, preferably with no additional amino acid substitutions in the portion from amino acid 20 to amino acid 40.

The term "Aβ(12-42)" here refers to the amino acid sequence from amino acid position 12 to amino acid position 42 of the human amyloid β protein including both 12 and 42, in particular to the amino acid sequence VHHQKLVFF AEDVGSNKGA IIGLMVGGVV IA or any of its naturally occurring variants, in particular, those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 12 and 42 or a sequence with up to three additional amino acid substitutions none of which may prevent globulomer formation, preferably with no additional amino acid substitutions in the portion from amino acid 20 to amino acid 42.

The term "Aβ(20-42)" herein refers to the amino acid sequence from amino acid position 20 to amino acid position 42 of the human amyloid β protein including both 20 and 42, in particular, to the amino acid sequence F AEDVGSNKGA IIGLMVGGVV IA or any of its naturally occurring variants, in particular those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 20 and 42 or a sequence with up to three additional amino acid substitutions none of which may prevent globulomer formation, preferably without any additional amino acid substitutions.

The term "Aβ(X-Y) globulomer" (Aβ(X-Y) globular oligomer) herein refers to a soluble, globular, non-covalent association of Aβ (X-Y) peptides as defined above, possessing homogeneity and distinct physical characteristics. According to one aspect, the Aβ(X-Y) globulomers are stable, non-fibrillar, oligomeric assemblies of Aβ (X-Y) peptides which are obtainable by incubation with anionic detergents. In contrast to monomers and fibrils, these globulomers are characterized by defined assembly numbers of subunits (e.g. early assembly forms, n=4-6, "oligomers A", and late assembly forms, n=12-14, "oligomers B", as described in WO2004/067561). The globulomers have a 3-dimensional globular type structure ("molten globule", see Barghorn et al., 2005, J Neurochem, 95, 834-847). They may be further characterized by one or more of the following features:

cleavability of N-terminal amino acids X-23 with promiscuous proteases (such as thermolysin or endoproteinase GluC) yielding truncated forms of globulomers;

non-accessibility of C-terminal amino acids 24-Y with promiscuous proteases and antibodies;

truncated forms of these globulomers maintain the 3-dimensional core structure of said globulomers with a better accessibility of the core epitope Aβ(20-Y) in its globulomer conformation.

According to the invention and, in particular, for the purpose of assessing the binding affinities of the antibodies of the present invention, the term "Aβ(X-Y) globulomer" herein refers, in particular, to a product which is obtainable by a process as described, for example, in Example I presented below. (See also WO 04/067561.) Such a process may be used to obtain Aβ(1-42) globulomers, Aβ(12-42) globulomers, and Aβ(20-42) globulomers. Preferably, the globulomer shows affinity to neuronal cells. Preferably, the globulomer also exhibits neuromodulating effects. According to another aspect of the invention, the globulomer consists of 11 to 16, and most preferably, of 12 to 14 Aβ(X-Y) peptides.

According to another aspect of the invention, the term Aβ(X-Y) globulomer" herein refers to a globulomer consisting essentially of Aβ(X-Y) subunits, where it is preferred if on average at least 11 of 12 subunits are of the Aβ(X-Y) type, more preferred if less than 10% of the globulomers comprise any non-Aβ(X-Y) peptides, and most preferred if the content of non-Aβ(X-Y) peptides is below the detection threshold. More specifically, the term "Aβ(1-42) globulomer" herein refers to a globulomer consisting essentially of Aβ(1-42) units as defined above; the term "Aβ(12-42) globulomer" herein refers to a globulomer consisting essentially of Aβ(12-42) units as defined above; and the term "Aβ(20-42) globulomer" herein refers to a globulomer consisting essentially of Aβ(20-42) units as defined above.

The term "cross-linked Aβ(X-Y) globulomer" as used herein refers to a molecule obtainable from an Aβ(X-Y) globulomer as described above by cross-linking, preferably chemically cross-linking, more preferably, aldehyde cross-linking, most preferably, glutardialdehyde cross-linking of the constituent units of the globulomer. In another aspect of the invention, a cross-linked globulomer is essentially a globulomer in which the units are at least partially joined by covalent bonds, rather than being held together by non-covalent interactions only. For the purposes of the present invention, a cross-linked Aβ(1-42) globulomer is, in particular, a cross-linked Aβ(1-42) oligomer.

The term "Aβ(X-Y) globulomer derivative" as used herein refers, in particular, to a globulomer that is labelled by being covalently linked to a group that facilitates detection, preferably, a fluorophore, e.g., fluorescein isothiocyanate, phycoerythrin, *Aequorea victoria* fluorescent protein, Dictyosoma fluorescent protein or any combination or fluorescence-active derivative thereof; a chromophore; a chemoluminophore, e.g., luciferase, preferably *Photinus pyralis* luciferase, *Vibrio fischeri* luciferase, or any combination or chemoluminescence-active derivative thereof; an enzymatically active group, e.g., peroxidase, e.g., horseradish peroxidase, or any enzymatically active derivative thereof; an electron-dense group, e.g., a heavy metal containing group, e.g., a gold containing group; a hapten, e.g., a phenol derived hapten; a strongly antigenic structure, e.g., peptide sequence predicted to be antigenic, e.g., predicted to be antigenic by the algorithm of Kolaskar and Tongaonkar; an aptamer for another molecule; a chelating group, e.g., hexahistidinyl; a natural or nature-derived protein structure mediating further specific protein-protein interactions, e.g., a member of the fos/jun pair; a magnetic group, e.g., a ferromagnetic group; or a radioactive group, e.g., a group comprising $^1$H, $^{14}$C, $^{32}$P, $^{35}$S, or $^{125}$I or any combination thereof; or to a globulomer flagged by being covalently or by non-covalent high-affinity interaction, preferably covalently linked to a group that facilitates inactivation, sequestration, degradation and/or precipitation, preferably flagged with a group that promotes in vivo degradation, more preferably with ubiquitin, where is particularly preferred if this flagged oligomer is assembled in vivo; or to a globulomer modified by any combination of the above. Such labelling and flagging groups and methods for attaching them to proteins are known in the art. Labelling and/or flagging may be performed before, during or after globulomerization. In another aspect of the invention, a globulomer derivative is a molecule obtainable from a globulomer by a labelling and/or flagging reaction. Correspondingly, term "Aβ(X-Y) monomer derivative" herein refers, in particular, to an Aβ monomer that is labelled or flagged as described for the globulomer.

The term "greater affinity" herein refers to a degree of interaction where the equilibrium between unbound antibody and unbound globulomer on the one hand and antibody-globulomer complex on the other is further in favor of the antibody-globulomer complex. Likewise, the term "smaller affinity" herein refers to a degree of interaction where the equilibrium between unbound antibody and unbound globulomer on the one hand and antibody-globulomer complex on the other is further in favour of the unbound antibody and unbound globulomer. The term "greater affinity" is synonymous with the term "higher affinity" and term "smaller affinity" is synonymous with the term "lower affinity".

The term "Aβ(X-Y) monomer" herein refers to the isolated form of the Aβ(X-Y) peptide, preferably, a form of the Aβ(X-Y) peptide which is not engaged in essentially non-covalent interactions with other Aβ peptides. Practically, the Aβ(X-Y) monomer is usually provided in the form of an aqueous solution. In a particularly preferred embodiment of the invention, the aqueous monomer solution contains 0.05% to 0.2%, more preferably, about 0.1% NH$_4$OH. In another particularly preferred embodiment of the invention, the aqueous monomer solution contains 0.05% to 0.2%, more preferably, about 0.1% NaOH. When used (for instance, for determining the binding affinities of the antibodies of the present invention), it may be expedient to dilute said solution in an appropriate manner. Further, it is usually expedient to use said solution within 2 hours, in particular, within 1 hour, and especially within 30 minutes after its preparation.

The term "fibril" herein refers to a molecular structure that comprises assemblies of non-covalently associated, individual Aβ(X-Y) peptides, which show fibrillary structure in the electron microscope, which bind Congo red and then exhibit birefringence under polarized light and whose X-ray diffraction pattern is a cross-β structure. In another aspect of the invention, a fibril is a molecular structure obtainable by a process that comprises the self-induced polymeric aggregation of a suitable Aβ peptide in the absence of detergents, e.g., in 0.1 M HCl, leading to the formation of aggregates of more than 24, preferably more than 100 units. This process is well known in the art. Expediently, Aβ(X-Y) fibrils are used in the form of an aqueous solution. In a particularly preferred embodiment of the invention, the aqueous fibril solution is made by dissolving the Aβ peptide in 0.1% NH$_4$OH, diluting it 1:4 with 20 mM NaH$_2$PO$_4$, 140 mM NaCl, pH 7.4, followed by readjusting the pH to 7.4, incubating the solution at 37° C. for 20 h, followed by centrifugation at 10000 g for 10 min and resuspension in 20 mM NaH$_2$PO$_4$, 140 mM NaCl, pH 7.4.

The term "Aβ(X-Y) fibril" herein refers to a fibril consisting essentially of Aβ(X-Y) subunits, where it is preferred if on average at least 90% of the subunits are of the Aβ(X-Y) type, more preferred, if at least 98% of the subunits are of the Aβ(X-Y) type and, most preferred, if the content of non-Aβ(X-Y) peptides is below the detection threshold.

The present invention also relates to antibodies having a similar binding profile to that of any one of said monoclonal antibodies, 10F4 and 3C5. Antibodies having a binding profile similar to that of any one of said monoclonal antibodies include antibodies which bind to the same epitope as monoclonal antibody 10F4 and 3C5.

The present invention also relates to antibodies which are capable of competing with at least one, preferably all, antibodies selected from the group consisting of 10F4 and 3C5. The term "competing antibodies" herein refers to any number of antibodies targeting the same molecular or stably but non-covalently linked supermolecular entity, preferably, the same molecule, wherein at least one is capable of specifically reducing the measurable binding of another, preferably, by sterically hampering the other's access to its target epitope or by inducing and/or stabilizing a conformation in the target entity that reduces the target's affinity for the other antibody, more preferably, by directly blocking access to the other's target epitope by binding to an epitope in sufficiently close vicinity of the former, overlapping with the former or identical to the former, most preferably, overlapping or identical, in particular identical. Two epitopes are said to be "overlapping" if they share part of their chemical structures, preferably their amino acid sequences, and to be "identical" if their chemical structures, preferably their amino acid sequences, are identical. Thus, the present invention also relates to antibodies whose target epitopes are overlapping with, preferably identical to, the target epitope of at least one of the antibodies selected from the group consisting of 10F4 and 3C5. Antibodies having a similar binding profile to that of any one of said monoclonal antibodies 10F4 and 3C5 thus further include antibodies which comprise at least a portion of the antigen-binding moiety of any one of said monoclonal antibodies. Preferably, said portion comprises at least one complementary determining region (CDR) of any one of said monoclonal antibodies. Thus, according to a further particular embodiment, the present invention relates to antibodies comprising the amino acid sequence of the heavy chain CDR3 and/or the amino acid sequence of the light chain CDR3 of monoclonal antibody 10F4 or 3C5, respectively. Specific examples of such antibodies include those which also comprise the amino acid sequence of the heavy chain CDR2 and/or the amino acid sequence of the light chain CDR2 of monoclonal antibody 10F4 or 3C5, respectively. Even more specifically, such antibodies include those which also comprise the amino acid sequence of the heavy chain CDR1 and/or the amino acid sequence of the light chain CDR1 of monoclonal antibody 10F4 or 3C5, respectively. In one aspect, the present invention thus relates to antibodies comprising a heavy chain wherein the CDR3, CDR2 and/or CDR1 domain comprises the amino acid sequence of the heavy chain CDR3, CDR2 and/or CDR1 of monoclonal antibody 10F4 or 3C5. In a further aspect, the present invention thus relates to antibodies comprising a light chain wherein the CDR3, CDR2 and/or CDR1 domain comprises the amino acid sequence of the light chain CDR3, CDR2 and/or CDR1, respectively, of monoclonal antibody 10F4 or 3C5.

In one embodiment the antibody of the invention comprises at least two variable domain CDR sets. More preferably, the two variable domain CDR sets are selected from the group consisting of: VH 10F4 CDR Set & VL 10F4 CDR Set; VH 3C5 CDR Set & VL 3C5 CDR Set (see FIGS. 7a-7d).

In another embodiment the antibody disclosed above further comprises a human acceptor framework. In a preferred embodiment, the antibody is a CDR grafted antibody. Preferably, the CDR grafted antibody comprises one or more of the CDRs disclosed above. Preferably the CDR grafted antibody comprises a human acceptor framework.

In a preferred embodiment the antibody is a humanized antibody. Preferably, the humanized antibody comprises one or more of the CDRs disclosed above. More preferably, the humanized antibody comprises three or more of the CDRs disclosed above. Most preferably, the humanized antibody comprises six CDRs disclosed above. In a particular embodiment, the CDRs are incorporated into a human antibody variable domain of a human acceptor framework. Preferably, the human antibody variable domain is a consensus human variable domain. More preferably, the human acceptor framework comprises at least one framework region amino acid substitution at a key residue, wherein the key residue is selected from the group consisting of a residue adjacent to a CDR; a glycosylation site residue; a rare residue; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. Preferably, the human acceptor framework human acceptor framework comprises at least one framework region amino acid substitution, wherein the amino acid sequence of the framework is at least 65% identical to the sequence of said human acceptor framework and comprises at least 70 amino acid residues identical to said human acceptor framework. In yet a further aspect, the present invention relates to antibodies comprising both the heavy and light chain as defined above. Preferably, the antibody comprises at least one variable domain as described above. More preferably, the antibody comprises two variable domains as described above, wherein said two variable domains have amino acid sequences as noted in FIG. 7.

In another aspect, the antibodies of the present invention comprise a heavy chain constant region selected from the group consisting of IgG1, IgG2, IgG3, IgG4, IgM, IgA, IgD, IgE and human IgG1 Ala234 Ala235 mutant constant regions. In particular, the antibodies comprise a human constant region. Antibodies comprising an IgG1 heavy chain constant region are preferred.

In another embodiment the antibody is glycosylated. Preferably the glycosylation pattern is a human glycosylation pattern or a glycosylation pattern produced by any one of the eukaryotic cells disclosed herein, in particular CHO cells.

The present invention also relates to an antigen-binding moiety of an antibody of the present invention. Such antigen-binding moieties include, but are not limited to, Fab fragments, F(ab')$_2$ fragments and single chain Fv fragments of the antibody. Further antigen-binding moieties are Fab' fragments, Fv fragments, and disulfide linked Fv fragments.

The invention also provides an isolated nucleic acid encoding any one of the antibodies disclosed herein. A further embodiment provides a vector comprising the isolated nucleic acid disclosed herein. The vector may in particular be selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic acids Research* Vol 18, No. 17); pBV; pJV; and pBJ.

In another aspect, a host cell is transformed with the vector disclosed herein. Preferably, the host cell is a prokaryotic cell. More preferably, the host cell is *E. coli*. In a related embodiment, the host cell is an eukaryotic cell. Preferably, the eukaryotic cell is selected from the group consisting of a protist cell, an animal cell, a plant cell and a fungal cell. More preferably, the host cell is a mammalian cell including, but not limited to, CHO and COS; or a fungal cell such as *Saccharomyces cerevisiae*; or an insect cell such as Sf9.

Another aspect of the invention provides a method of producing an antibody of the invention, comprising culturing any one of the host cells or a hybridoma disclosed herein in a culture medium under conditions suitable to produce the antibody. Another embodiment provides an antibody that is obtainable by the method disclosed herein. Antibodies of the present invention can be obtained in a manner known per se. B lymphocytes which, in totality, contain an antibody repertoire composed of hundreds of billions of different antibody specificities are a part of the mammalian immune system. A normal immune response to a particular antigen means selection of one or more antibodies of said repertoire which specifically bind to said antigen, and the success of an immune response is based at least partially on the ability of said antibodies to specifically recognize (and ultimately to eliminate) the stimulating antigen and to ignore other molecules in the environment of said antibodies. The usefulness of antibodies which specifically recognize one particular target antigen has led to the development of monoclonal antibody technology. Standardized hybridoma technology now allows the production of antibodies with a single specificity for an antigen of interest. More recently, recombinant antibody techniques such as in-vitro screening of antibody libraries have been developed. These techniques likewise allow antibodies having a single specificity for an antigen of interest to be produced.

In the method of the invention, the antigen of interest may be allowed to act on the antibody repertoire either in vivo or in vitro. According to one embodiment, the antigen is allowed to act on the repertoire by immunizing an animal in vivo with said antigen. This in-vivo approach may furthermore comprise establishing from the lymphocytes of an animal a number of hybridomas and selecting a particular hybridoma which secretes an antibody specifically binding to said antigen. The animal to be immunized may be, for example, a mouse, rat, rabbit, chicken, camelid or sheep or may be a transgenic version of any of the animals mentioned above, for example, a transgenic mouse with human immunoglobulin genes, which produces human antibodies after an antigenic stimulus. Other types of animals which may be immunized include mice with severe combined immunodeficiency (SCID) which have been reconstituted with human peripheral mononuclear blood cells (chimeric hu-PBMC SCID mice) or with lymphoid cells or precursors thereof, as well as mice which have been treated with a lethal total body irradiation, then protected against radiation with bone marrow cells from a mouse with severe combined immunodeficiency (SCID) and subsequently transplanted with functional human lymphocytes (the "Trimera" system). Another type of an animal to be immunized is an animal (e.g., a mouse) in whose genome an endogenous gene encoding the antigen of interest has been switched off (knocked out), for example, by homologous recombination, so that after immunization with the antigen, said animal recognizes said antigen as foreign. The polyclonal or monoclonal antibodies produced by this method are characterized and selected by using known screening methods which include, but are not limited to, ELISA and dot blot techniques.

According to another embodiment, the antigen is allowed to act on the antibody repertoire in vitro by screening a recombinant antibody library with said antigen. The recombinant antibody library may be expressed, for example, on the surface of bacteriophages or on the surface of yeast cells or on the surface of bacterial cells. In a variety of embodiments, the recombinant antibody library is an scFv library or an Fab library, for example. According to another embodiment, antibody libraries are expressed as RNA-protein fusions.

Another approach to producing antibodies of the invention comprises a combination of in vivo and in vitro approaches. For example, the antigen may be allowed to act on the antibody repertoire by immunizing an animal in vivo with said antigen and then screening in vitro with said antigen a recombinant antibody library prepared from lymphoid cells of said animal or a single domain antibody library (e.g., containing heavy and/or light chains). According to another approach, the antigen is allowed to act on the antibody repertoire by immunizing an animal in vivo with said antigen and then subjecting a recombinant antibody library or single domain library produced from lymphoid cells of said animal to affinity maturation. According to another approach, the antigen is allowed to act on the antibody repertoire by immunizing an animal in vivo with said antigen, then selecting individual antibody-producing cells secreting an antibody of interest and obtaining from said selected cells cDNAs for the variable region of the heavy and light chains (e.g., by means of PCR) and expressing said variable regions of the heavy and light chains in mammalian host cells in vitro (this being referred to as selected lymphocyte antibody method or SLAM), thereby being able to further select and manipulate the selected antibody gene sequences. Moreover, monoclonal antibodies may be selected by expression cloning by expressing the antibody genes for the heavy and light chains in mammalian cells and selecting those mammalian cells which secrete an antibody having the desired binding affinity.

The methods of the invention for producing antibodies can be used to produce various types of antibodies. These include monoclonal, in particular recombinant antibodies, especially essentially human antibodies, chimeric antibodies, humanized antibodies and CDR graft antibodies, and also antigen-binding moieties thereof.

The present invention further relates to a hybridoma that is capable of producing (secreting) a monoclonal antibody of the present invention. Hybridomas of the present invention include those designated by an American Type Culture Collection deposit number selected from the group consisting of PTA-7808 and PTA-7406 and those producing monoclonal antibodies 10F4 and 3C5.

It is noted that the antibodies of the present invention may also be reactive with, i.e., bind to, Aβ forms other than the Aβ globulomers described herein. These antigens may or may not be oligomeric or globulomeric. Thus, the antigens to which the antibodies of the present invention bind include any Aβ form that comprises the globulomer epitope with which the antibodies of the present invention are reactive. Such Aβ forms include truncated and non-truncated Aβ(X-Y) forms (with X and Y being defined as above), such as Aβ(20-42), Aβ(20-40), Aβ(12-42), Aβ(12-40), Aβ(1-42), and Aβ(1-40) forms, provided that said forms comprise the globulomer epitope.

The present invention also relates to a composition comprising an antibody of the invention or an antigen-binding moiety thereof, as defined above. According to a particular embodiment, said composition is a pharmaceutical composition which comprises the antibody of the invention or the antigen-binding moiety and a pharmaceutical acceptable carrier. The antibody of the invention or the antigen-binding moiety, as defined above, is preferably capable of neutralizing, both in vitro and in vivo, the activity of Aβ globulomer or a derivative thereof to which it binds. Said antibody or antigen-binding moiety may therefore be used for inhibiting the activity of said globulomer or derivative thereof, for example, in a preparation containing said globulomer or derivative thereof or in human individuals or other mammals in which said globulomer or derivative thereof is present.

According to one embodiment, the invention relates to a method of inhibiting the activity of said globulomer or derivative thereof which method comprises allowing an antibody of the invention or an antigen-binding moiety thereof to act on a globulomer or derivative thereof so as to inhibit the activity of said globulomer or derivative thereof. Said activity may be inhibited in vitro, for example. For instance, the antibody of the invention or the antigen-binding moiety may be added to a preparation such as a sample derived from a subject or a cell culture which contains or is suspected to contain said globulomer or derivative thereof, in order to inhibit the activity of said globulomer or derivative thereof in said sample. Alternatively, the activity of the globulomer or derivative thereof may be inhibited in an individual in vivo. Thus, the present invention further relates to the use of an antibody or an antigen-binding moiety as defined above for preparing a pharmaceutical composition for treating or preventing an amyloidosis, in particular, an amyloidosis selected from the group consisting of Alzheimer's disease and the amyloidosis of Down's syndrome. One aspect of said use of the invention is therefore a method of treating or preventing an amyloidosis, in particular, Alzheimer's disease or the amyloidosis of Down's syndrome, in a subject in need thereof, which comprises administering an antibody or an antigen-binding moiety as defined above to the subject. Using said antibody or antigen-binding moiety for treating and especially preventing the amyloidosis, in particular, Alzheimer's disease or the amyloidosis of Down's syndrome, is in particular for passive immunization. Accordingly, in the method of treating or preventing an amyloidosis, in particular Alzheimer's disease or the amyloidosis of Down's syndrome, in a subject in need thereof one purpose of administering the antibody or antigen-binding moiety to the subject is passively immunizing the subject against the amyloidosis, in particular, Alzheimer's disease or the amyloidosis of Down's syndrome.

The antibody of the invention or the antigen-binding moiety as defined above is preferably capable of detecting, both in vitro and in vivo, an Aβ globulomer or derivative thereof to which it binds. Said antibody or the antigen-binding moiety may therefore be used for detecting said globulomer or derivative thereof, for example, in a preparation containing said globulomer or derivative thereof or in human individuals or other mammals in which said globulomer or derivatives thereof is present.

According to one embodiment, the invention relates to a method of detecting said globulomer or derivative thereof, which method comprises allowing an antibody of the invention or an antigen-binding moiety thereof to act on a globulomer or derivative thereof so as to bind to said globulomer or derivative thereof (and thereby preferably forming a complex comprising the antibody or antigen-binding moiety thereof and the globulomer or derivative thereof). The globulomer may be detected in vitro, for example. For instance, the antibody of the invention or the antigen-binding moiety may be added to a preparation, for instance, a sample derived from a subject or a cell culture which contains or is suspected to contain said globulomer or derivative thereof, in order to detect said globulomer or derivative thereof in said preparation. Alternatively, the globulomer or derivative thereof may be detected in an individual in vivo. Thus, the present invention further relates to the use of an antibody or an antigen-binding moiety as defined above for preparing a composition for diagnosing an amyloidosis, in particular Alzheimer's disease or the amyloidosis of Down's syndrome. One aspect of said use of the invention is a method of diagnosing an amyloidosis, in particular, Alzheimer's disease or the amyloidosis of Down's syndrome, in a subject suspected of having the amyloidosis, in particular Alzheimer's disease or the amyloidosis of Down's syndrome, which comprises administering to the subject an antibody or an antigen-binding moiety as defined above and detecting the formation of a complex comprising the antibody or the antigen-binding moiety with the antigen, the presence of the complex indicating the amyloidosis, in particular Alzheimer's disease or the amyloidosis of Down's syndrome, in the subject. A second aspect of said use of the invention is a method of diagnosing an amyloidosis, in particular, Alzheimer's disease or the amyloidosis of Down's syndrome, in a subject suspect of having the amyloidosis, in particular, Alzheimer's disease or the amyloidosis of Down's syndrome, which comprises providing a sample from the subject, contacting the sample with an antibody or an antigen-binding moiety (as defined) above and detecting the formation of a complex comprising the antibody or the antigen-binding moiety with the antigen, the presence of the complex indicating the amyloidosis, in particular, Alzheimer's disease or the amyloidosis of Down's syndrome, in the subject.

The binding affinities of the antibodies of the invention may be evaluated by using standardized in-vitro immunoassays such as ELISA, dot blot or BIAcore analyses (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277. According to a particular embodiment, the affinities defined herein refer to the values obtained by performing a dot blot and evaluating it by densitometry. According to a particular embodiment of the invention, determining the binding affinity by dot blot comprises the following: a certain amount of the antigen (e.g. the Aβ(X-Y) globulomer, Aβ(X-Y) monomer or Aβ(X-Y) fibrils, as defined above) or, expediently, an appropriate dilution thereof, for instance in 20 mM $NaH_2PO_4$, 140 mM NaCl, pH 7.4, 0.2 mg/mL BSA to an antigen concentration of, for example, 100 pmol/μL, 10 pmol/μL, 1 pmol/μL, 0.1 pmol/μL and 0.01 pmol/μL, is dotted onto a nitrocellulose membrane, the membrane is then blocked with milk to prevent unspecific binding and washed, then contacted with the antibody of interest followed by detection of the latter by means of an enzyme-conjugated secondary antibody and a colorimetric reaction; at defined antibody concentrations, the amount of antibody bound allows affinity determination. Thus the relative affinity of two different antibodies to one target, or of one antibody to two different targets, is here defined as the relation of the respective amounts of target-bound antibody observed with the two antibody-target combinations under otherwise identical dot blot conditions. Unlike a similar approach based on Western blotting, the dot blot approach will determine an antibody's affinity to a given target in the latter's natural conformation; unlike the ELISA approach, the dot blot approach does not suffer from differences in the affinities between different targets and the matrix, thereby allowing for more precise comparisons between different targets.

The term "$K_d$", as used herein, is intended to refer to the dissociation constant of a particular antibody-antigen interaction as is known in the art.

The antibodies of the present invention are preferably isolated antibodies. An isolated antibody" means an antibody having the binding affinities as described above and which is essentially free of other antibodies having different binding affinities. The term "essentially free" here refers to an antibody preparation in which at least 95% of the antibodies, preferably at least 98% of the antibodies and more preferably at least 99% of the antibodies have the desired binding affinity. Moreover, an isolated antibody may be substantially free of other cellular material and/or chemicals.

The isolated antibodies of the present invention include monoclonal antibodies. A "monoclonal antibody" as used herein is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several novel technologies like phage, bacteria, yeast or ribosomal display, as well as by classical methods exemplified by hybridoma-derived antibodies (e.g., an antibody secreted by a hybridoma prepared by hybridoma technology, such as the standard Kohler and Milstein hybridoma methodology ((1975) Nature 256:495-497). Thus, a non-hybridoma-derived antibody with uniform sequence is still referred to as a monoclonal antibody herein although it may have been obtained by non-classical methodologies, and the term "monoclonal" is not restricted to hybridoma-derived antibodies but used to refer to all antibodies derived from one nucleic acid clone. Thus, the monoclonal antibodies of the present invention include recombinant antibodies. The term "recombinant" as used herein refers to any artificial combination of two otherwise separated segments of sequence, e.g., by chemical synthesis or by the manipulation of isolated segments of nucleic acids by genetic engineering techniques. In particular, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al. (1992) *Nucl. Acids Res.* 20:6287-6295); or antibodies which are produced, expressed, generated or isolated in any other way in which particular immunoglobulin gene sequences (such as human immunoglobulin gene sequences) are assembled with other DNA sequences. Recombinant antibodies include, for example, chimeric, CDR graft and humanized antibodies. The person skilled in the art will be aware that expression of a conventional hybridoma-derived monoclonal antibody in a heterologous system will require the generation of a recombinant antibody even if the amino acid sequence of the resulting antibody protein is not changed or intended to be changed.

In a particular embodiment of the invention, the antibody is a humanized antibody. According to a multiplicity of embodiments, the antibody may comprise an amino acid sequence derived entirely from a single species, such as a human antibody or a mouse antibody. According to other embodiments, the antibody may be a chimeric antibody or a CDR graft antibody or another form of a humanized antibody.

The term "antibody" is intended to refer to immunoglobulin molecules consisting of 4 polypeptide chains, two heavy (H) chains and two light (L) chains. The chains are usually linked to one another via disulfide bonds. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

The term "antigen-binding moiety" of an antibody (or simply "antibody moiety") refers to one or more fragments of an antibody of the invention, said fragment(s) still having the binding affinities as defined above. Fragments of a complete antibody have been shown to be able to carry out the antigen-binding function of an antibody. In accordance with the term "antigen-binding moiety" of an antibody, examples of binding fragments include (i) an Fab fragment, i.e. a monovalent fragment composed of the VL, VH, CL and CH1 domains; (ii) an F(ab')$_2$ fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; (v) a dAb fragment (Ward et al., (1989) *Nature* 341:544-546) consisting of a VH domain or of VH, CH1, CH2, DH3, or VH, CH2, CH3; and (vi) an isolated complementarity-determining region (CDR). Although the two domains of the Fv fragment, namely VL and VH, are encoded by separate genes, they may further be linked to one another using a synthetic linker, e.g. a poly-G$_4$S amino acid sequence, and recombinant methods, making it possible to prepare them as a single protein chain in which the VL and VH regions combine in order to form monovalent molecules (known as single chain Fv (ScFv); see, for example, Bird et al. (1988) *Science* 242:423-426; and Huston et al. (1988) *Proc. Natl. Acad. Sci. USA* 85:5879-5883). The term "antigen-binding moiety" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art.

Furthermore, an antibody of the present invention or antigen-binding moiety thereof may be part of a larger immunoadhesion molecule formed by covalent or noncovalent association of said antibody or antibody moiety with one or more further proteins or peptides. Relevant to such immunoadhesion molecules are the use of the streptavidin core region in order to prepare a tetrameric scFv molecule (Kipriyanov, S. M., et al. (1995) *Human Antibodies and Hybridomas* 6:93-101) and the use of a cystein residue, a marker peptide and a C-terminal polyhistidinyl, e. g. hexahistidinyl, tag in order to produce bivalent and biotinylated scFv molecules (Kipriyanov, S. M., et al. (1994) *Mol. Immunol.* 31:1047-1058).

The term "human antibody" refers to antibodies whose variable and constant regions correspond to or are derived from immunoglobulin sequences of the human germ line, as described, for example, by Kabat et al. (see Kabat, et al. (1991) *Sequences of Proteins of Immunological Interest, Fifth Edition*, U.S. Department of Health and Human Services, NIH Publication No. 91-3242). However, the human antibodies of the invention may contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies of the invention have variable regions and may also contain constant regions derived from immunoglobulin sequences of the human germ line (see Kabat, E. A., et al. (1991) *Sequences of Proteins of Immunological Interest, Fifth Edition*, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which contain sequences of the variable region of heavy and light chains from a nonhuman species (e.g. mouse, rat, rabbit, chicken, camelid, sheep or goat) but in which at least one part of the VH and/or VL sequence has been altered in order to be more "human-like", i.e. to be more similar to variable sequences of the human germ line. One type of a humanized antibody is a CDR graft antibody in which human CDR sequences have been inserted into nonhuman VH and VL sequences to replace the corresponding nonhuman CDR sequences.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and Kabat, E. A., et al. (1991) *Sequences of Proteins of Immunological Interest, Fifth Edition*, U.S. Department of Health and Human Services, NIH Publication No. 91-3242).

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues not occurring at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and of the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, in spite of great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined using different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the finding that germline antibody genes are more likely than mature antibody genes are to conserve essential amino acid sequence structures characteristic of individuals in the species, hence less likely to be recognized as non-self when used in that species.

As used herein, the term "key" residues refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (which can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" specifically refers to an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain. The humanized antibody can be selected from any class of immunoglobulins, including IgM, IgG, IgD, IgA and IgE, and any subclass, including without limitation IgG 1, IgG2, IgG3 and IgG4. The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond exactly to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones, Verlagsgesellschaft, Weinheim, Germany 1987). In a family of immunoglobulins, each position in the consensus sequence is occupied by the amino acid occurring most frequently at that position in the family. Where two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "epitope" includes any polypeptide determinant capable of specific binding to an immunoglobulin. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or any combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is connected in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, also to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct which is stably and operably integrated into the genome of a cell from which a transgenic organism develops, directing the expression of an encoded gene product in one or more cell types or tissues of the transgenic organism.

Methods of producing antibodies of the invention are described below. A distinction is made here between in-vivo approaches, in-vitro approaches or a combination of both.

In-Vivo Approaches:

Depending on the type of the desired antibody, various host animals may be used for in-vivo immunization. A host expressing itself an endogenous version of the antigen of interest may be used. Alternatively, it is possible to use a host which has been made deficient in an endogenous version of the antigen of interest. For example, mice which had been made deficient in a particular endogenous protein via homologous recombination at the corresponding endogenous gene (i.e., knockout mice) have been shown to generate a humoral response to the protein with which they have been immunized and therefore to be able to be used for production of high-affinity monoclonal antibodies to the protein (see, for example, Roes, J. et al. (1995) *J. Immunol. Methods* 183:231-237; Lunn, M. P. et al. (2000) *J. Neurochem.* 75:404-412).

A multiplicity of nonhuman mammals are suitable hosts for antibody production in order to produce nonhuman antibodies of the invention. They include, for example, mice, rats, chickens, camelids, rabbits, sheep and goats (and knockout versions thereof), although preference is given to mice for the production of hybridoma. Furthermore, a nonhuman host animal expressing a human antibody repertoire may be used for producing essentially human antibodies to a human antigen with dual specificity. Nonhuman animals of this kind include transgenic animals (e.g., mice) bearing human immunoglobulin transgenes (chimeric hu-PBMC SCID mice) and human/mouse irradiation chimeras which are described in more detail below.

According to one embodiment, the animal immunized is a nonhuman mammal, preferably a mouse, which is transgenic due to human immunoglobulin genes so that said nonhuman mammal makes human antibodies upon antigenic stimulation. Typically, immunoglobulin transgenes for heavy and light chains with human germ line configuration are introduced into such animals which have been altered such that their endogenous heavy and light chain loci are inactive. If such animals are stimulated with antigen (e.g., with a human antigen), antibodies derived from the human immunoglobulin sequences (human antibodies) are produced. It is possible to make from the lymphocytes of such animals human monoclonal antibodies by means of standardized hybridoma technology. For a further description of transgenic mice with human immunoglobulins and their use in the production of human antibodies, see, for example, U.S. Pat. No. 5,939,598, WO 96/33735, WO 96/34096, WO 98/24893 and WO 99/53049 (Abgenix Inc.), and U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, U.S. Pat. No. 5,814,318, U.S. Pat. No. 5,877,397 and WO 99/45962 (Genpharm Inc.); see also MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N. (1995) *Ann. N.Y. Acad. Sci.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188:483-495; Green, L. L. (1999) *J. Immunol. Methods* 231:11-23; Yang, X. D. et al. (1999) *J. Leukoc. Biol.* 66:401-410; Gallo, M. L. et al. (2000) *Eur. J. Immunol.* 30:534-540.

According to another embodiment, the animal which is immunized may be a mouse with severe combined immunodeficiency (SCID), which has been reconstituted with human peripheral mononuclear blood cells or lymphoid cells or precursors thereof. Such mice which are referred to as chimeric hu-PBMC SCID mice produce human immunoglobulin responses upon antigenic stimulation, as has been proved. For a further description of these mice and of their use for generating antibodies, see, for example, Leader, K. A. et al. (1992) *Immunology* 76:229-234; Bombil, F. et al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. et al. (1997) *J. Immunol.* 159:1393-1403; Nguyen, H. et al. (1997) *Microbiol. Immunol.* 41:901-907; Arai, K. et al. (1998) *J. Immunol. Methods* 217:79-85; Yoshinari, K. and Arai, K. (1998) *Hybridoma* 17:41-45; Hutchins, W. A. et al. (1999) *Hybridoma* 18:121-129; Murphy, W. J. et al. (1999) *Clin. Immunol.* 90:22-27; Smithson, S. L. et al. (1999) *Mol.*

*Immunol.* 36:113-124; Chamat, S. et al. (1999) *J. Infect. Diseases* 180:268-277; and Heard, C. et al. (1999) *Molec. Med.* 5:35-45.

According to another embodiment, the animal which is immunized is a mouse which has been treated with a lethal does of total body irradiation, then protected from radiation with bone marrow cells from mice with severe combined immunodeficiency (SCID) and subsequently transplanted with functional human lymphocytes. This type of chimera, referred to as the Trimera system, is used in order to produce human monoclonal antibodies by immunizing said mice with the antigen of interest and then producing monoclonal antibodies by using standardized hybridoma technology. For a further description of these mice and of their use for generating antibodies, see, for example, Eren, R. et al. (1998) *Immunology* 93:154-161; Reisner, Y and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

Starting from the in-vivo generated antibody-producing cells, monoclonal antibodies may be produced by means of standardized techniques such as the hybridoma technique originally described by Kohler and Milstein (1975, *Nature* 256:495-497) (see also Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology of producing monoclonal antibody hybridomas is sufficiently known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortalized cell line (typically a myeloma) is fused with lymphocytes (typically splenocytes or lymph node cells or peripheral blood lymphocytes) of a mammal immunized with the Aβ globulomer of the invention or derivative thereof, and the culture supernatants of the resulting hybridoma cells are screened in order to identify a hybridoma which produces a monoclonal antibody of the present invention. Any of the many well known protocols for fusing lymphocytes and immortalized cell lines can be applied for this purpose (see also G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the skilled worker will appreciate that there are diverse variations of such methods, which are likewise useful. Typically, the immortalized cell line (e.g., a myeloma cell line) is derived from the same mammalian species as the lymphocytes. For example, murine hybridomas may be established by fusing lymphocytes from a mouse immunized with an immunogenic preparation of the invention with an immortalized mouse cell line. Preferred immortalized cell lines are mouse myeloma cell lines which are sensitive to culture medium containing hypoxanthine, aminopterine and thymidine (HAT medium). Any of a number of myeloma cell lines may be used by default as fusion partner, for example the P3-NS1/1-Ag4-1, P3-x63-Ag8.653 or Sp2/O-Ag14 myeloma lines. These myeloma cell lines are available from the American Type Culture Collection (ATCC), Manassas, Va. Typically, HAT-sensitive mouse myeloma cells are fused to mouse splenocytes using polyethylene glycol (PEG). Hybridoma cells resulting from the fusion are then selected using HAT medium, thereby killing unfused and unproductively fused myeloma cells (unfused splenocytes die after several days because they are not transformed). Hybridoma cells producing monoclonal antibodies of the invention are identified by screening the hybridoma culture supernatants for such antibodies, for example, by using a dot blot assay in order to select those antibodies which have the binding affinities as defined above. The monoclonal antibodies 10F4 and 3C5 all have been generated using the above-described in-vivo approach and thereof are obtainable from a hybridoma as defined herein.

Likewise, said hybridoma can be used as a source of nucleic acid encoding light and/or heavy chains in order to recombinantly produce antibodies of the present invention, as is described below in further detail.

In-Vitro Approaches:

As an alternative to producing antibodies of the invention by immunization and selection, antibodies of the invention may be identified and isolated by screening recombinant combinatorial immunoglobulin libraries to thereby isolate immunoglobulin library members which have the required binding affinity. Kits for generating and screening display libraries are commercially available (e.g. the Pharmacia Recombinant Phage Antibody System, catalog No. 27-9400-01; and the Stratagene SurfZAP® Phage Display Kit, catalog No. 240612). In many embodiments, the display library is an scFv library or an Fab library. The phage display technique for screening recombinant antibody libraries has been adequately described. Examples of methods and compounds which can be used particularly advantageously for generating and screening antibody display libraries can be found, for example, in McCafferty et al. WO 92/01047, U.S. Pat. No. 5,969,108 and EP 589 877 (describes in particular scFv display), Ladner et al. U.S. Pat. No. 5,223,409, U.S. Pat. No. 5,403,484, U.S. Pat. No. 5,571,698, U.S. Pat. No. 5,837,500 and EP 436 597 (describes pIII fusion, for example); Dower et al. WO 91/17271, U.S. Pat. No. 5,427,908, U.S. Pat. No. 5,580,717 and EP 527 839 (describes in particular Fab display); Winter et al. International Publication WO 92/20791 and EP 368,684 (describes in particular the cloning of sequences for variable immunoglobulin domains); Griffiths et al., U.S. Pat. No. 5,885,793 and EP 589 877 (describes in particular isolation of human antibodies to human antigens by using recombinant libraries); Garrard et al. WO 92/09690 (describes in particular phage expression techniques); Knappik et al. WO 97/08320 (describes the human recombinant antibody library HuCal); Salfeld et al. WO 97/29131, (describes production of a recombinant human antibody to a human antigen (human tumor necrosis factor alpha) and also in-vitro affinity maturation of the recombinant antibody) and Salfeld et al., U.S. Provisional Patent Application No. 60/126,603 and the patent applications based hereupon (likewise describes production of recombinant human antibodies to human antigen (human interleukin-12), and also in-vitro affinity maturation of the recombinant antibody).

Further descriptions of screenings of recombinant antibody libraries can be found in scientific publications such as Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clarkson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; Barbas et al. (1991) *PNAS* 88:7978-7982; McCafferty et al. *Nature* (1990) 348:552-554; and Knappik et al. (2000) *J. Mol. Biol.* 296:57-86.

As an alternative to using bacteriophage display systems, recombinant antibody libraries may be expressed on the surface of yeast cells or of bacterial cells. WO 99/36569 describes methods of preparing and screening libraries expressed on the surface of yeast cells. WO 98/49286 describes in more detail methods of preparing and screening libraries expressed on the surface of bacterial cells. In all in vitro approaches, a selection process for enriching recombinant antibodies with the desired properties form an integral part of the process, which is generally referred to as "panning" and often takes the form of affinity chromatography over columns to whose matrix the target structure has been attached. Promising candidate molecules are then subjected to individual determination of their absolute and/or relative affinities, preferably by means of a standardized dot blot assay.

Once an antibody of interest of a combinatorial library has been identified and sufficiently characterized, the DNA sequences encoding the light and heavy chains of said antibody are isolated by means of standardized molecular-biological techniques, for example, by means of PCR amplification of DNA from the display package (e.g., the phage) which has been isolated during library screening. Nucleotide sequences of genes for light and heavy antibody chains, which may be used for preparing PCR primers, are known to one of ordinary skill in the art. A multiplicity of such sequences are described, for example, in Kabat, E. A., et al. (1991) *Sequences of Proteins of Immunological Interest, Fifth Edition*, U.S. Department of Health and Human Services, NIH Publication No. 91-3242 and in the database of sequences of the human germ line VBASE.

An antibody or antibody moiety of the invention may be produced by recombinantly expressing the genes for light and heavy immunoglobulin chains in a host cell. In order to recombinantly express an antibody, a host cell is transfected with one or more recombinant expression vectors carrying DNA fragments encoding the light and heavy immunoglobulin chains of said antibody, thereby expressing the light and heavy chains in the host cell and secreting them preferably into the medium in which said host cells are cultured. The antibodies can be isolated from this medium. Standardized recombinant DNA methods are used in order to obtain genes for heavy and light antibody chains, to insert said genes into recombinant expression vectors and to introduce said vectors into host cells. Methods of this kind are described, for example, in Sambrook, Fritsch and Maniatis (eds.), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

Once DNA fragments encoding VH and VL segments of the antibody of interest have been obtained, said DNA fragments may be further manipulated using standardized recombinant DNA techniques, for example, in order to convert the genes for variable regions to genes for full length antibody chains, to genes for Fab fragments or to an scFv gene. These manipulations comprise linking a VL- or VH-encoding DNA fragment operatively to another DNA fragment encoding another protein, for example a constant antibody region or a flexible linker. The term "operatively linked" is to be understood here as meaning that the two DNA fragments are linked in such a way that the amino acid sequences encoded by said two DNA fragments remain in frame. The isolated DNA encoding the VH region may be converted to a gene for a full length heavy chain by operatively linking the VH-region encoding DNA with another DNA molecule encoding heavy chain constant regions (CH1, CH2 and CH3). The sequences of human heavy chain constant region genes are well known (see, for example, Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The heavy chain constant region may be a constant region from IgG1, IgG2, IgG3, IgG4, IgM, IgA, IgE or IgD, with preference being given to a constant region from IgG, in particular IgG1 or IgG4. To obtain a gene for a heavy chain Fab fragment, the VH-encoding DNA may be operatively linked to another DNA molecule encoding merely the heavy chain constant region CH1. The isolated DNA encoding the VL region may be converted to a gene for a full length light chain (and a gene for an Fab light chain) by operatively linking the VL-encoding DNA to another DNA molecule encoding the light chain constant region CL. The sequences of genes of the constant region of human light chain are well known (see Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The light chain constant region may be a constant kappa or lambda region, a constant kappa region being preferred.

In order to generate an scFv gene, the VH- and VL-encoding DNA fragments may be operatively linked to another fragment encoding a flexible linker, for example the amino acid sequence $(Gly_4\text{-}Ser)_3$ so that the VH and VL sequences are expressed as a continuous single-chain protein, with the VL and VH regions being linked to one another via said flexible linker (see Bird et al. (1988) *Science* 242:423-426; Huston et al. (1988) *Proc. Natl. Acad. Sci. USA* 85:5879-5883; McCafferty et al., *Nature* (1990) 348:552-554).

Single domain VH and VL having the binding affinities as described above may be isolated from single domain libraries by the above-described methods. Two VH single-domain chains (with or without CH1) or two VL chains or a pair of one VH chain and one VL chain with the desired binding affinity may be useful as described herein for the antibodies of the invention.

In order to express the recombinant antibodies or antibody moieties of the invention, the DNAs encoding partial or full length light and heavy chains may be inserted into expression vectors so as to operatively link the genes to appropriate transcriptional and translational control sequences. In this context, the term "operatively linked" is to be understood to mean that an antibody gene is ligated in a vector in such a way that transcriptional and translational control sequences within the vector fulfill their intended function of regulating transcription and translation of said antibody gene. Expediently, the expression vector and the expression control sequences are chosen so as to be compatible with the expression host cell used. The gene for the antibody light chain and the gene for the antibody heavy chain may be inserted into separate vectors or both genes are inserted into the same expression vector, this being the usual case. The antibody genes are inserted into the expression vector by means of standardized methods (for example by ligation of complementary restriction cleavage sites on the antibody gene fragment and the vector, or by ligation of blunt ends, if no restriction cleavage sites are present). The expression vector may already carry sequences for antibody constant regions prior to insertion of the sequences for the light and heavy chains. For example, one approach is to convert the VH and VL sequences to full length antibody genes by inserting them into expression vectors already encoding the heavy and, respectively, light chain constant regions, thereby operatively linking the VH segment to the CH segment(s) within the vector and also operatively linking the VL segment to the CL segment within the vector.

Additionally or alternatively, the recombinant expression vector may encode a signal peptide which facilitates secretion of the antibody chain from the host cell. The gene for said antibody chain may be cloned into the vector, thereby linking the signal peptide in frame to the N terminus of the gene for the antibody chain. The signal peptide may be an immunoglobulin signal peptide or a heterologous signal peptide (i.e. a signal peptide from a non-immunoglobulin protein). In addition to the genes for the antibody chain, the expression vectors of the invention may have regulatory sequences controlling expression of the genes for the antibody chain in a host cell.

The term "regulatory sequence" is intended to include promoters, enhancers and further expression control elements (e.g. polyadenylation signals) which control transcription or translation of the genes for the antibody chain. Regulatory sequences of this kind are described, for example, in Goeddel; *Gene Expression Technology: Methods in Enzymology* 185, Academic Press, San Diego, Calif. (1990). The skilled worker will appreciate that the expression vector design which includes selection of regulatory sequences may depend on factors such as the choice of the host cell to be transformed, the desired strength of expression of the protein, etc. Preferred regulatory sequences for expression in mammalian host cells include viral elements resulting in strong and constitutive protein expression in mammalian cells, such as promoters and/or enhancers derived from cytomegalovirus (CMV) (such as the CMV promoter/enhancer), simian virus 40 (SV40) (such as the SV40 promoter/enhancer), adenovirus (e.g., the adenovirus major late promoter (AdMLP)) and polyoma. For a further description of viral regulatory elements and sequences thereof, see, for example, U.S. Pat. No. 5,168,062 to Stinski, U.S. Pat. No. 4,510,245 to Bell et al. and U.S. Pat. No. 4,968,615 to Schaffner et al.

Apart from the genes for the antibody chain and the regulatory sequences, the recombinant expression vectors of the invention may have additional sequences such as those which regulate replication of the vector in host cells (e.g., origins of replication) and selectable marker genes. The selectable marker genes facilitate the selection of host cells into which the vector has been introduced (see, for example, U.S. Pat. Nos. 4,399,216, 4,634,665 and 5,179,017, all to Axel et al.). For example, it is common for the selectable marker gene to render a host cell into which the vector has been inserted resistant to cytotoxic drugs such as G418, hygromycin or methotrexate. Preferred selectable marker genes include the gene for dihydrofolate reductase (DHFR) (for use in dhfr⁻ host cells with methotrexate selection/amplification) and the neo gene (for G418 selection).

For expression of the light and heavy chains, the expression vector(s) encoding said heavy and light chains is(are) transfected into a host cell by means of standardized techniques. The various forms of the term "transfection" are intended to comprise a multiplicity of techniques customarily used for introducing exogenous DNA into a prokaryotic or eukaryotic host cell, for example electroporation, calcium phosphate precipitation, DEAE-dextran transfection, and the like. Although it is theoretically possible to express the antibodies of the invention either in prokaryotic or eukaryotic host cells, preference is given to expressing the antibodies in eukaryotic cells and, in particular, in mammalian host cells, since the probability of a correctly folded and immunologically active antibody being assembled and secreted is higher in such eukaryotic cells and in particular mammalian cells than in prokaryotic cells. Prokaryotic expression of antibody genes has been reported as being ineffective for production of high yields of active antibody (Boss, M. A. and Wood, C. R. (1985) *Immunology Today* 6:12-13).

Preferred mammalian host cells for expressing recombinant antibodies of the invention include CHO cells (including dhfr⁻ CHO cells described in Urlaub and Chasin, (1980) *Proc. Natl. Acad. Sci. USA* 77:4216-4220, which are used together with a DHFR-selectable marker, as described, for example, in R. J. Kaufman and P. A. Sharp (1982) *Mol. Biol.* 159:601-621), NS0 myeloma cells, COS cells and SP2 cells. When introducing recombinant expression vectors encoding the antibody genes into mammalian host cells, the antibodies are produced by culturing the host cells until the antibody is expressed in said host cells or, preferably, the antibody is secreted into the culture medium in which the host cells grow. The antibodies may then be isolated from the culture medium by using standardized protein purification methods. It is likewise possible to use host cells in order to produce moieties of intact antibodies, such as Fab fragments or scFv molecules. Variations of the above-described procedure are of course included in the invention. For example, it may be desirable to transfect a host cell with DNA encoding either the light chain or the heavy chain (but not both) of an antibody of the invention. If either light or heavy chains are present which are not required for binding of the antigen of interest, then the DNA encoding either such a light or such a heavy chain or both may be removed partially or completely by means of recombinant DNA technology. Molecules expressed by such truncated DNA molecules are likewise included in the antibodies of the invention. In addition, it is possible to produce bifunctional antibodies in which a heavy chain and a light chain are an antibody of the invention and the other heavy chain and the other light chain have specificity for an antigen different from the antigen of interest, by crosslinking an antibody of the invention to a second antibody by means of standardized chemical methods.

In a preferred system for recombinant expression of an antibody of the invention or an antigen-binding moiety thereof, a recombinant expression vector encoding both the antibody heavy chain and the antibody light chain is introduced into dhfr⁻ CHO cells by means of calcium phosphate-mediated transfection. Within the recombinant expression vector, the genes for the heavy and light antibody chains are in each case operatively linked to regulatory CMV enhancer/AdMLP-promoter elements in order to effect strong transcription of said genes. The recombinant expression vector also carries a DHFR gene which can be used for selecting dhfr⁻ CHO cells transfected with the vector by using methotrexate selection/amplification. The selected transformed host cells are cultured so that the heavy and light antibody chains are expressed, and intact antibody is isolated from the culture medium. Standardized molecular-biological techniques are used in order to prepare the recombinant expression vector, to transfect the host cells, to select the transformants, to culture said host cells, and to obtain the antibody from the culture medium. Thus, the invention relates to a method of synthesizing a recombinant antibody of the invention by culturing a host cell of the invention in a suitable culture medium until a recombinant antibody of the invention has been synthesized. The method may further comprise isolating said recombinant antibody from said culture medium.

As an alternative to screening recombinant antibody libraries by phage display, other methods known to the skilled worker may be used for screening large combinatorial libraries to identify the antibodies of the invention. Basically, any expression system in which a close physical linkage between a nucleic acid and the antibody encoded thereby is established and may be used to select a suitable nucleic acid sequence by virtue of the properties of the antibody it encodes may be employed. In one type of an alternative expression system, the recombinant antibody library is expressed in the form of RNA-protein fusions, as described in WO 98/31700 to Szostak and Roberts, and in Roberts, R. W. and Szostak, J. W. (1997) Proc. Natl. Acad. Sci. USA 94:12297-12302. In this system, in-vitro translation of synthetic mRNAs carrying on their 3' end puromycin, a peptidyl acceptor antibiotic, generates a covalent fusion of an mRNA and the peptide or protein encoded by it. Thus, a specific mRNA of a complex mixture of mRNAs (e.g. a combinatorial library) may be concentrated on the basis of the properties of the encoded peptide or protein (e.g. of the antibody or a moiety thereof), such as binding of said antibody or said moiety thereof to Aβ(12-42) globulomer or a derivative thereof. Nucleic acid sequences which encode antibodies or moieties thereof and which are obtained by screening of such libraries may be expressed by recombinant means in the above-described manner (e.g. in mammalian host cells) and may, in addition, be subjected to further affinity maturation by either screening in further rounds mRNA-peptide fusions, introducing mutations into the originally selected sequence(s), or using other methods of in-vitro affinity maturation of recombinant antibodies in the above-described manner.

Combinations of In-Vivo and In-Vitro Approaches

The antibodies of the invention may likewise be produced by using a combination of in-vivo and in-vitro approaches such as methods in which Aβ(12-42) globulomer or a derivative thereof is first allowed to act on an antibody repertoire in a host animal in vivo to stimulate production of Aβ(12-42) globulomer or derivative-binding antibodies and then further antibody selection and/or antibody maturation (i.e., optimization) are accomplished with the aid of one or more in-vitro techniques. According to one embodiment, a combined method of this kind may comprise firstly immunizing a nonhuman animal (e.g., a mouse, rat, rabbit, chicken, camelid, sheep or goat or a transgenic version thereof or a chimeric mouse) with said Aβ (12-42) globulomer or derivative thereof to stimulate an antibody response to the antigen and then preparing and screening a phage display antibody library by using immunoglobulin sequences of lymphocytes which have been stimulated in vivo by the action of said Aβ (12-42) globulomer or derivative. The first step of this combined procedure may be carried out in the manner described above in connection with the in-vivo approaches, while the second step of this procedure may be carried out in the manner described above in connection with the in-vitro approaches. Preferred methods of hyperimmunizing nonhuman animals with subsequent in-vitro screening of phage display libraries prepared from said stimulated lymphocytes include those described by BioSite Inc., see, for example, WO 98/47343, WO 91/17271, U.S. Pat. No. 5,427,908 and U.S. Pat. No. 5,580, 717.

According to another embodiment, a combined method comprises firstly immunizing a nonhuman animal (e.g., a mouse, rat, rabbit, chicken, camelid, sheep, goat or a knockout and/or transgenic version thereof, or a chimeric mouse) with an Aβ (12-42) globulomer of the invention or derivative thereof to stimulate an antibody response to said Aβ (12-42) globulomer or derivative thereof and selecting the lymphocytes which produce the antibodies having the desired specificity by screening hybridomas (prepared, for example, from the immunized animals). The genes for the antibodies or single domain antibodies are isolated from the selected clones (by means of standardized cloning methods such as reverse transcriptase polymerase chain reaction) and subjected to in-vitro affinity maturation in order to improve thereby the binding properties of the selected antibody or the selected antibodies. The first step of this procedure may be conducted in the manner described above in connection with the in-vivo approaches, while the second step of this procedure may be conducted in the manner described above in connection with the in-vitro approaches, in particular by using methods of in-vitro affinity maturation, such as those described in WO 97/29131 and WO 00/56772.

In a further combined method, the recombinant antibodies are generated from individual isolated lymphocytes by using a procedure which is known to the skilled worker as selected lymphocyte antibody methods (SLAM) and which is described in U.S. Pat. No. 5,627,052, WO 92/02551 and Babcock, J. S. et al. (1996) Proc. Natl. Acad. Sci. USA 93:7843-7848. In this method, a nonhuman animal (e.g., a mouse, rat, rabbit, chicken, camelid, sheep, goat, or a transgenic version thereof, or a chimeric mouse) is firstly immunized in vivo with Aβ (12-42) globulomer or a derivative thereof to stimulate an immune response to said oligomer or derivative, and then individual cells secreting antibodies of interest are selected by using an antigen-specific haemolytic plaque assay. To this end, the globulomer or derivative thereof or structurally related molecules of interest may be coupled to sheep erythrocytes, using a linker such as biotin, thereby making it possible to identify individual cells secreting antibodies with suitable specificity by using the haemolytic plaque assay. Following the identification of cells secreting antibodies of interest, cDNAs for the variable regions of the light and heavy chains are obtained from the cells by reverse transcriptase PCR, and said variable regions may then be expressed in association with suitable immunoglobulin constant regions (e.g., human constant regions) in mammalian host cells such as COS or CHO cells. The host cells transfected with the amplified immunoglobulin sequences derived from in vivo-selected lymphocytes may then be subjected to further in-vitro analysis and in-vitro selection by spreading out the transfected cells, for example, in order to isolate cells expressing antibodies with the binding affinity. The amplified immunoglobulin sequences may furthermore be manipulated in vitro.

Antibodies having the required affinities defined herein can be selected by performing a dot blot essentially as described above. Briefly, the antigen is attached to a solid matrix, preferably dotted onto a nitrocellulose membrane, in serial dilutions. The immobilized antigen is then contacted with the antibody of interest followed by detection of the latter by means of an enzyme-conjugated secondary antibody and a colorimetric reaction; at defined antibody and antigen concentrations, the amount of antibody bound allows affinity determination. Thus the relative affinity of two different antibodies to one target, or of one antibody to two different targets, is here defined as the relation of the respective amounts of target-bound antibody observed with the two antibody-target combinations under otherwise identical dot blot conditions. Antibodies which bind to the same epitope as monoclonal antibody 10F4 or 3C5 can be obtained in a manner known per se.

In the same way as antibodies may be competing, described above, different target structures are herein said to be "competing" for a particular antibody if at least one of these structures is capable of specifically reducing the measurable binding of another, preferably by offering an overlapping or identical epitope, more preferably an identical epitope. Competing target entities are useful for directly selecting antibodies by virtue of their relative affinity to such target structures. Relative affinities may thus be determined directly by using a competition assay in which distinguishable forms of the competing entities, e.g., differently labelled competing structures, are contacted with the antibody of interest, and the relative affinity of the antibody to each of these entities is deduced from the relative amounts of these entities which are bound by the antibody. Such competition may be used to directly enrich for antibodies possessing a desired relative affinity to the target entity, by attaching the entity towards which greater affinity is desired to a solid matrix support and adding a suitable amount, preferably a molar excess, of the competing entity towards which smaller affinity is desired to the medium. Thus, the antibodies displaying the desired relative affinities will tend to bind to the matrix more strongly than others and may be obtained after washing out the less desirable forms, e.g., by washing out at low salt concentrations and then harvesting the bound antibody by reversibly detaching it from its target by using high salt concentrations. If desired, several rounds of enrichment may be performed. In a particular embodiment of the invention, where the genotype underlying an antibody is physically linked to this antibody, e.g., in a pool of hybridomas or antigen-displaying phages or yeast cells, the corresponding phenotype may be rescued.

In another embodiment of the invention, a modified dot blot is used where the immobilized antigen competes with a solved entity for antibody binding, so that the relative affinity of the antibody can be deduced from the percentage bound to the immobilized antigen. Antibody moieties such as Fab and $F(ab')_2$ fragments may be produced from whole antibodies by using conventional techniques such as digestion with papain or pepsin. In addition, antibodies, antibody moieties and immunoadhesion molecules may be obtained by using standardized recombinant DNA techniques.

The present invention also relates to pharmaceutical agents (compositions) comprising an antibody of the invention and, optionally, a pharmaceutically suitable carrier. Pharmaceutical compositions of the invention may furthermore contain at least one additional therapeutic agent, for example one or more additional therapeutic agents for the treatment of a disease for whose relief the antibodies of the invention are useful. If, for example, the antibody of the invention binds to a globulomer of the invention, the pharmaceutical composition may furthermore contain one or more additional therapeutic agents useful for the treatment of disorders in which the activity of said globulomer is important. Pharmaceutically suitable carriers include any solvents, dispersing media, coatings, antibacterial and antifungal agents, isotonic and absorption-delaying agents, and the like, as long as they are physiologically compatible. Pharmaceutically acceptable carriers include, for example, water, saline, phosphate-buffered saline, dextrose, glycerol, ethanol and the like, and combinations thereof. In many cases, preference is given to using isotonic agents, for example sugars, polyalcohols such as mannitol or sorbitol, or sodium chloride in addition. Pharmaceutically suitable carriers may furthermore contain relatively small amounts of auxiliary substances such as wetting agents or emulsifiers, preservatives or buffers, which increase the half life or efficacy of the antibodies. The pharmaceutical compositions may be suitable for parenteral administration, for example. Here, the antibodies are prepared preferably as injectable solutions with an antibody content of 0.1-250 mg/mL. The injectable solutions may be prepared in liquid or lyophilized form, the dosage form being a flint glass or vial, an ampoule or a filled syringe. The buffer may contain L-histidine (1-50 mM, preferably 5-10 mM) and have a pH of 5.0-7.0, preferably of 6.0. Further suitable buffers include, without being limited thereto, sodium succinate, sodium citrate, sodium phosphate or potassium phosphate buffers. Sodium chloride may be used in order to adjust the tonicity of the solution to a concentration of 0-300 mM (preferably 150 mM for a liquid dosage form). Cryoprotectants, for example sucrose (e.g., 0-10%, preferably 0.5-1.0%) may also be included for a lyophilized dosage form. Other suitable cryoprotectants are trehalose and lactose. Fillers, for example mannitol (e.g., 1-10%, preferably 2-4%) may also be included for a lyophilized dosage form. Stabilizers, for example L-methionine (e.g., 51-50 mM, preferably 5-10 mM) may be used both in liquid and lyophilized dosage forms. Further suitable fillers are glycine and arginine. Surfactants, for example, polysorbate 80 (e.g., 0-0.05%, preferably 0.005-0.01%), may also be used. Further surfactants are polysorbate 20 and BRIJ surfactants.

The compositions of the invention may have a multiplicity of forms. These include liquid, semisolid and solid dosage forms, such as liquid solutions (e.g., injectable and infusible solutions), dispersions or suspensions, tablets, pills, powders, liposomes and suppositories. The preferred form depends on the intended type of administration and on the therapeutic application. Typically, preference is given to compositions in the form of injectable or infusible solutions, for example compositions which are similar to other antibodies for passive immunization of humans. The preferred route of administration is parenteral (e.g., intravenous, subcutaneous, intraperitoneal or intramuscular). According to a preferred embodiment, the antibody is administered by intravenous infusion or injection. According to another preferred embodiment, the antibody is administered by intramuscular or subcutaneous injection. Therapeutic compositions must typically be sterile and stable under preparation and storage conditions. The compositions may be formulated as solutions, microemulsions, dispersions, liposomes or other ordered structures suitable for high concentrations of active substance. Sterile injectable solutions may be prepared by introducing the active compound (i.e., the antibody) in the required amount into a suitable solvent, where appropriate with one or a combination of the above-mentioned ingredients, as required, and then sterile-filtering said solution. Dispersions are usually prepared by introducing the active compound into a sterile vehicle containing a basic dispersion medium and, where appropriate, other required ingredients. In the case of a sterile lyophilized powder for preparing sterile injectable solutions, vacuum drying and spray drying are preferred methods of preparation, which produces a powder of the active ingredient and, where appropriate, of further desired ingredients from a previously sterile-filtered solution. The correct flowability of a solution may be maintained by using, for example, a coating such as lecithin, by maintaining, in the case of dispersions the required particle size or by using surfactants. A prolonged absorption of injectable compositions may be achieved by additionally introducing into the composition an agent which delays absorption, for example monostearate salts and gelatine.

The antibodies of the invention may be administered by a multiplicity of methods known to the skilled worker, although the preferred type of administration for many therapeutic applications is subcutaneous injection, intravenous injection or infusion. The skilled worker will appreciate that the route and/or type of administration depend on the result desired. According to particular embodiments, the active compound may be prepared with a carrier which protects the compound against rapid release, such as, for example, a formulation with sustained or controlled release, which includes implants, transdermal plasters and microencapsulated release systems. Biologically degradable biocompatible polymers such as ethylene vinyl acetate, polyanhydrides, polyglycolic acid, collagen, polyorthoesters and polylactic acid may be used. The methods of preparing such formulations are well known to the skilled worker; see, for example, *Sustained and Controlled Release Drug Delivery Systems*, J. R. Robinson, ed., Marcel Dekker, Inc., New York, 1978.

According to particular embodiments, an antibody of the invention may be administered orally, for example, in an inert diluent or a metabolizable edible carrier. The antibody (and further ingredients, if desired) may also be enclosed in a hard or soft gelatine capsule, compressed to tablets or added directly to food. For oral therapeutic administration, the antibodies may be mixed with excipients and used in the form of oral tablets, buccal tablets, capsules, elixirs, suspensions, syrups and the like. If it is intended to administer an antibody of the invention via a route other than the parenteral one, it may be necessary to choose a coating from a material which prevents its inactivation.

The present invention also relates to a method of inhibiting the activity of globulomers of the invention in an individual which suffers from a disorder in which the amyloid β protein is involved and in which in particular the activity of said globulomers of the invention is important. Said method comprises the administration of at least one antibody of the invention to the individual with the aim of inhibiting the activity of the globulomer to which the antibody binds. Said individual is preferably a human being. An antibody of the invention may be administered for therapeutic purposes to a human individual. In addition, an antibody of the invention may be administered to a nonhuman mammal for veterinary purposes or within the framework of an animal model for a particular disorder. Such animal models may be useful for evaluating the therapeutic efficacy of antibodies of the invention (for example for testing dosages and time courses of administration).

Disorders in which the globulomers of the invention play a part include, in particular, disorders in whose development and/or progression a globulomer of the invention is involved. These are in particular those disorders in which globulomers of the invention are evidently or presumably responsible for the pathophysiology of said disorder or are a factor which contributes to the development and/or progression of said disorder. Accordingly, those disorders are included here in which inhibition of the activity of globulomers of the invention can relieve symptoms and/or progression of the disorder. Such disorders can be verified, for example, by an increased concentration of globulomers of the invention in a biological fluid of an individual suffering from a particular disorder (e.g., increased concentration in serum, plasma, CSF, urine, etc.). This may be detected, for example, by using an antibody of the invention. The globulomers of the invention play an important part in the pathology associated with a multiplicity of disorders in which neurodegenerative elements, cognitive deficiencies, neurotoxic elements and inflammatory elements are involved.

In another aspect of the invention, disorders that can be treated or prevented include those associated with amyloidoses. The term "amyloidoses" herein denotes a number of disorders characterized by abnormal folding, clumping, aggregation and/or accumulation of particular proteins (amyloids, fibrous proteins and their precursors) in various tissues of the body. In Alzheimer's disease and Down's syndrome, nerve tissue is affected, and in cerebral amyloid angiopathy (CAA) blood vessels are affected.

The pharmaceutical compositions of the invention may include a "therapeutically effective amount" or a "prophylactically effective amount" of an antibody or antibody moiety of the invention. A "therapeutically effective amount" refers to an amount effective, at dosages and for periods of time necessary, to achieve the desired therapeutic result. A therapeutically effective amount of the antibody or antibody moiety may be determined by a person skilled in the art and may vary according to factors such as the disease state, age, sex, and weight of the individual, and the ability of the antibody or antibody moiety to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Moreover, the present invention includes a further method of preventing or treating Alzheimer's disease in a patient in need of such prevention or treatment. This method comprises the step of administering the vaccine noted above to the patient in an amount sufficient to effect the prevention or treatment.

Further, the present invention encompasses a method of identifying compounds suitable for active immunization of a patient predicted to develop an amyloidosis, e.g. Alzheimer's disease. This method comprises: 1) exposing one or more compounds of interest to one or more of the antibodies described above for a time and under conditions sufficient for the one or more compounds to bind to the antibody or antibodies; 2) identifying those compounds which bind to the antibody or antibodies, the identified compounds to be used in active immunization in a patient predicated to develop an amyloidosis, e.g., Alzheimer's disease.

Within the framework of diagnostic usage of the antibodies, qualitative or quantitative specific globulomer determination serves in particular to diagnose disease-relevant amyloid β forms. In this context, specificity means the possibility of being able to detect a particular globulomer or a derivative thereof, or a mixture thereof with sufficient sensitivity. The antibodies of the invention advantageously have detection threshold concentrations of less than 10 ng/mL of sample, preferably of less than 1 ng/mL of sample and particularly preferably of less than 100 μg/mL of sample, meaning that at least the concentration of globulomer per mL of sample, indicated in each case, advantageously also lower concentrations, can be detected by the antibodies of the invention. The detection is carried out immunologically. This may be carried out, in principle, by using any analytical or diagnostic assay method in which antibodies are used, including agglutination and precipitation techniques, immunoassays, immunohistochemical methods and immunoblot techniques, for example Western blotting or, preferably, dot blot methods. In vivo methods, for example imaging methods, are also included here.

The use in immunoassays is advantageous. Competitive immunoassays, i.e., assays where antigen and labelled antigen (tracer) compete for antibody binding, and sandwich immunoassays, i.e., assays where binding of specific antibodies to the antigen is detected by a second, usually labelled antibody, are both suitable. These assays may be either homogeneous, i.e., without separation into solid and liquid phases, or heterogeneous, i.e., bound labels are separated from unbound ones, for example, via solid phase-bound antibodies. Depending on labelling and method of measurement, the various heterogeneous and homogeneous immunoassay formats can be classified into particular classes, for example RIAs (radioimmunoassays), ELISA (enzyme-linked immunosorbent assay), FIA (fluorescence immunoassay), LIA (luminescence immunoassay), TRFIA (time-resolved FIA), IMAC (immunoactivation), EMIT (enzyme-multiplied immune test), TIA (turbidometric immunoassay), I-PCR (immuno-PCR).

For the globulomer quantification of the invention, preference is given to competitive immunoassays in which a defined amount of labelled globulomer derivative serving as tracer competes with the globulomer of the sample (containing an unknown amount of unlabelled globulomers) to be quantified for binding to the antibody used. The amount of antigen, i.e., the amount of globulomer, in the sample can be determined from the amount of the displaced tracer with the aid of a standard curve.

Of the labels available for these purposes, enzymes have proved advantageous. Systems based on peroxidases, in particular, horseradish peroxidase, alkaline phosphatase and β-D-galactosidase, may be used, for example. Specific substrates whose conversion can be monitored photometrically, for example, are available for these enzymes. Suitable substrate systems are based on p-nitrophenyl phosphate (p-NPP), 5-bromo-4-chloro-3-indolyl phosphate/nitroblue tetrazolium (BCIP/NPT), Fast-Red/naphthol-AS-TS phosphate for alkaline phosphatase; 2,2-azinobis(3-ethylbenzothiazoline-6-sulfonic acid) (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazolinehydrazone (MBTH) for peroxidases; o-nitrophenyl-β-D-galactoside (o-NPG), p-nitrophenyl-β-D-galactoside and 4-methylumbelliphenyl-β-D-galactoside (MUG) for β-D-galactosidase. In many cases, these substrate systems are commercially available in a ready-to-use form, for example in the form of tablets which may also contain further reagents such as appropriate buffers and the like. The tracers used may be labelled globulomers. In this sense, a particular globulomer can be determined by labelling the globulomer to be determined and using it as tracer. The coupling of labels to globulomers for preparing tracers may be carried out in a manner known per se. The comments above on derivatization of globulomers of the invention are referred to by analogy. In addition, a number of labels appropriately modified for conjugation to proteins are available, for example biotin-, avidin-, extravidin- or streptavidin-conjugated enzymes, maleimide-activated enzymes and the like. These labels may be reacted directly with the oligomer or, if required, with the appropriately derivatized globulomer to give the tracer. If, for example, a streptavidin-peroxidase conjugate is used, then this firstly requires biotinylation of the globulomer. This applies correspondingly to the reverse order. Suitable methods to this end are also known to the skilled worker.

If a heterogeneous immunoassay format is chosen, the antigen-antibody complex may be separated by binding it to the support, for example via an anti-idiotypical antibody coupled to said support, e.g. an antibody directed against rabbit IgG. Appropriate supports, in particular microtiter plates coated with appropriate antibodies, are known and partly commercially available.

The present invention further relates to immunoassay sets having at least one antibody as described above and further components. Said sets are, usually in the form of a packaging unit, a combination of means for carrying out a globulomer determination of the invention. For the purpose of as easy handling as possible, said means are preferably provided in an essentially ready-to-use form. An advantageous arrangement offers the immunoassay in the form of a kit. A kit usually comprises multiple containers for separate arrangement of components. All components may be provided in a ready-to-use dilution, as a concentrate for diluting or as a dry substance or lyophilisate for dissolving or suspending; individual or all components may be frozen or stored at room temperature until use. Sera are preferably shock-frozen, for example at −20° C. so that in these cases an immunoassay has to be kept preferably at temperatures below freezing prior to use. Further components supplied with the immunoassay depend on the type of said immunoassay. Usually, standard protein, tracer which may or may not be required and control serum are supplied together with the antiserum. Furthermore, microtiter plates, preferably antibody-coated, buffers, for example, for testing, for washing or for conversion of the substrate, and the enzyme substrate itself may also be included.

General principles of immunoassays and generation and use of antibodies as auxiliaries in laboratory and hospital can be found, for example, in Antibodies, A Laboratory Manual (Harlow, E., and Lane, D., Ed., Cold Spring Harbor Laboratory, Cold Spring Harbor, N.Y., 1988).

The present invention also includes a method of diagnosing an amyloidosis, e.g., Alzheimer's disease, in a patient suspected of having this disease. This method comprises the steps of: 1) isolating a biological sample from the patient; 2) contacting the biological sample with at least one of the antibodies described above for a time and under conditions sufficient for formation of antigen/antibody complexes; and 3) detecting presence of the antigen/antibody complexes in said sample, presence of the complexes indicating a diagnosis of an amyloidosis, e.g., Alzheimer's disease, in the patient. The antigen may be, for example, an globulomer or a portion or fragment thereof which has the same functional properties as the full globulomer (e.g., binding activity).

Further, the present invention includes another method of diagnosing an amyloidosis, e.g., Alzheimer's disease in a patient suspected of having this disease. This method comprising the steps of: 1) isolating a biological sample from the patient; 2) contacting the biological sample with an antigen for a time and under conditions sufficient for the formation of antibody/antigen complexes; 3) adding a conjugate to the resulting antibody/antigen complexes for a time and under conditions sufficient to allow the conjugate to bind to the bound antibody, wherein the conjugate comprises one of the antibodies described above, attached to a signal generating compound capable of generating a detectable signal; and 4) detecting the presence of an antibody which may be present in the biological sample, by detecting a signal generated by the signal generating compound, the signal indicating a diagnosis of an amyloidosis, e.g., Alzheimer's disease in the patient. The antigen may be a globulomer or a portion or fragment thereof having the same functional properties as the full globulomer (e.g., binding activity).

The present invention includes an additional method of diagnosing an amyloidosis, e.g., Alzheimer's disease, in a patient suspected of having an amyloidosis, e.g., Alzheimer's disease. This method comprises the steps of: 1) isolating a biological sample from said patient; 2) contacting the biological sample with anti-antibody, wherein the anti-antibody is specific for one of the antibodies described above, for a time and under conditions sufficient to allow for formation of anti-antibody/antibody complexes, the complexes containing antibody present in the biological sample; 2) adding a conjugate to resulting anti-antibody/antibody complexes for a time and under conditions sufficient to allow the conjugate to bind to bound antibody, wherein the conjugate comprises an antigen, which binds to a signal generating compound capable of generating a detectable signal; and 3) detecting a signal generated by the signal generating compound, the signal indicating a diagnosis of an amyloidosis, e.g., Alzheimer's disease, in the patient.

Also, the present invention includes a kit comprising: a) at least one of the antibodies described above and b) a conjugate comprising an antibody attached to a signal-generating compound, wherein the antibody of the conjugate is different from the isolated antibody.

The present invention also encompasses a kit comprising: a) an anti-antibody to one of the antibodies described above and b) a conjugate comprising an antigen attached to a signal-generating compound. The antigen may be a globulomer or a fragment or portion thereof having the same functional characteristics as the globulomer (e.g., binding activity).

In one diagnostic embodiment of the present invention, an antibody of the present invention, or a portion thereof, is coated on a solid phase (or is present in a liquid phase). The test or biological sample (e.g., whole blood, cerebrospinal fluid, serum, etc.) is then contacted with the solid phase. If antigen (e.g., globulomer) is present in the sample, such antigens bind to the antibodies on the solid phase and are then detected by either a direct or indirect method. The direct method comprises simply detecting presence of the complex itself and thus presence of the antigens. In the indirect method, a conjugate is added to the bound antigen. The conjugate comprises a second antibody, which binds to the bound antigen, attached to a signal-generating compound or label. Should the second antibody bind to the bound antigen, the signal-generating compound generates a measurable signal. Such signal then indicates presence of the antigen in the test sample. Examples of solid phases used in diagnostic immunoassays are porous and non-porous materials, latex particles, magnetic particles, microparticles (see U.S. Pat. No. 5,705,330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful. Examples of biological fluids which may be tested by the above immunoassays include plasma, whole blood, dried whole blood, serum, cerebrospinal fluid or aqueous or organo-aqueous extracts of tissues and cells.

The present invention also encompasses a method for detecting the presence of antibodies in a test sample. This method comprises the steps of: (a) contacting the test sample suspected of containing antibodies with anti-antibody specific for the antibodies in the patient sample under time and conditions sufficient to allow the formation of anti-antibody/antibody complexes, wherein the anti-antibody is an antibody of the present invention which binds to an antibody in the patient sample; (b) adding a conjugate to the resulting anti-antibody/antibody complexes, the conjugate comprising an antigen (which binds to the anti-antibody) attached to a signal generating compound capable of detecting a detectable signal; and (d) detecting the presence of the antibodies which may be present in the test sample by detecting the signal generated by the signal generating compound. A control or calibrator may be used which comprises antibody to the anti-antibody.

Kits are also included within the scope of the present invention. More specifically, the present invention includes kits for determining the presence of antigens (e.g., globulomers) in a patient suspected of having Alzheimer's disease or another condition characterized by cognitive impairment. In particular, a kit for determining the presence of antigens in a test sample comprises a) an antibody as defined herein or moiety thereof; and b) a conjugate comprising a second antibody (having specificity for the antigen) attached to a signal generating compound capable of generating a detectable signal. The kit may also contain a control or calibrator which comprises a reagent which binds to the antigen as well as a package insert describing the procedure to be used when conducting the assay.

The present invention also includes a kit for detecting antibodies in a test sample. The kit may comprise a) an anti-antibody specific (for example, one of the subject invention) for the antibody of interest, and b) an antigen or portion thereof as defined above. A control or calibrator comprising a reagent which binds to the antigen may also be included. More specifically, the kit may comprise a) an anti-antibody (such as the one of the present invention) specific for the antibody and b) a conjugate comprising an antigen (e.g., globulomer) attached to a signal generating compound capable of generating a detectable signal. Again, the kit may also comprise a control of calibrator comprising a reagent which binds to the antigen as well as a package insert describing the components of the kits and how they are to be utilized. The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

It should also be noted that the subject invention not only includes the full length antibodies described above but also moieties or fragments thereof, for example, the Fab portion thereof. Additionally, the subject invention encompasses any antibody having the same properties of the present antibodies in terms of, for example, binding specificity, structure, etc.

Advantages of the Invention:

By immunization with Aβ(12-42) globulomer (as described in Example I), different monoclonal antibodies may be obtained which differ in their tolerance or recognition of different Aβ(1-42) oligomers and Aβ(X-42) oligomers, as determined by comparative dot blotting as described above. This allows development of an antibody directed to Aβ oligomers which possesses an optimal relation between cognition enhancing effect, desired specificity over other Aβ forms and minimal side effect profile. The same holds true for monoclonal antibodies for use in passive immunization. The advantage of such a specific strategy for immunization (active and passive) is that it will not induce an immune response against Aβ monomers, Aβ peptides in fibrillary states of aggregation or sAPPα. This is advantageous in several ways:

1) In the form of insoluble Aβ plaques, Aβ peptides in fibrillary states of aggregation amount to the major part of the entire Aβ peptide pool in AD brains. A massive release of Aβ by dissolution of Aβ plaques induced by reaction of anti-Aβ antibodies with these plaques is to be regarded as detrimental. This massive release of Aβ would then cross the blood-brain barrier, enter the bloodstream and potentially increase the risk of microhaemorrhages. In addition, in the ELAN trial mentioned above, this very strategy of immunization with fibrillary Aβ peptide forms required cancellation of the trial due to 6% of cases with an onset of meningoencephalitis.
2) Immune responses directed to monomeric Aβ peptide forms are undesirable, as it could be shown that the latter may exert cognition-enhancing effects. 3) Immune responses directed to s reaction. Moreover, sAPPα was also shown to exert cognition-enhancing effects.
4) A response directed to vascular Aβ peptide in the form of CAA is to be avoided in order to eschew the undesirable side effect of microhaemorrhages (i.e., antibodies against the central portion of Aβ and which in addition do not bind to Aβ-peptides aggregated in the form of CAA induce fewer microhaemorrhages when compared to such against the N-terminus, see above).
5) Antibodies which specifically react with Aβ oligomers will have higher bioavailability with regard to the pathophysiologically relevant Aβ species, as they will not be bound to, e.g., fibrillary or monomeric Aβ and thus made unavailable for therapeutic effect.

Again, it should be noted that the antibodies of the present invention and, in particular, 10F4 and 3C5, do not (or with a lower binding affinity compared to commercially available antibodies like 6E10 (Signet Cat. no.: 9320)) detect amyloid beta in the cerebrospinal fluid. Thus, due to the high turnover rates of amyloid beta in the CSF, this lack of binding by the antibodies to the amyloid beta in the CSF prevents the waste of antibodies, as well as creates a more efficacious and selective system in comparison to those antibodies which bind to all amyloid beta found in the body (e.g., brain and CSF). Further, this property of the antibodies of the present invention allows one to reduce the amount of antibody to be administered (in connection with passive immunization), reduces the risk of side effects since the dose is lower thereby restricting antibodies to the target, increases efficacy, and also increases the therapeutic index. Furthermore, the risk of microhemmorrhages is also reduced. Additionally, since the antibodies do not detect fibrillar forms of amyloid beta, the risks associated with such complex formation are also reduced.

Deposit Information:

The hybridoma (ML45-3C5.5C10) which produces monoclonal antibody 3C5 was deposited with the American Type Culture Collection, 10801 University Boulevard, Manassas, Va. 20110 on Feb. 28, 2006 under the terms of the Budapest Treaty and was assigned ATCC No. PTA-7406. Hybridoma (ML43-10F4.3H8) which produces monoclonal antibody 10F4 was deposited with the American Type Culture Collection, 10801 University Boulevard, Manassas, Va. 20110 on Aug. 16, 2006 under the terms of the Budapest Treaty and was assigned ATCC No. PTA-7808.

The present invention may be illustrated by use of the following non-limiting examples:

Example I

Preparation of Aβ(12-42) Globulomer for Immunization

The Aβ(12-42) synthetic peptide (AnaSpec Inc.; Lot #40443) was suspended in 100% (v/v) 1,1,1,3,3,3-hexafluoro-2-propanol (HFIP) at 40 mg/mL (5 mg in 125 μL HFIP) and incubated for complete solubilization under shaking at 37° C. for 1 h. The HFIP acts as a hydrogen-bond breaker and is used to eliminate pre-existing structural inhomogeneities in the Aβ peptide. After centrifugation at 10000 g for 10 min the supernatant of the HFIP-dissolved Aβ(12-42) was diluted with 6.1 mL phosphate-buffered saline (PBS) (20 mM $NaH_2PO_4$, 140 mM NaCl, pH 7.4) and 625 μL 2% (w/v) sodium dodecyl sulfate (SDS) (in $H_2O$) were added (final concentration of 0.2% (w/v) SDS) and incubated for 3 h at 37° C. Once more, 625 μL 2% (w/v) sodium dodecyl sulfate (SDS) (in $H_2O$) were added (final concentration of 0.4% (w/v) SDS) and further incubated for 3 h at 37° C. The solution was diluted with 7 mL $H_2O$ and incubated for 16 h at 37° C. After centrifugation at 3000 g for 10 min the supernatant was further diluted with 15 mL PBS (20 mM $NaH_2PO_4$, 140 mM NaCl, pH 7.4) and concentrated by ultrafiltration (5 kDa cut-off) to 0.65 mL, dialysed against 20 mM $NaH_2PO_4$, 140 mM NaCl, 0.05% (w/v) SDS, pH 7.4 for 16 h at room temperature, centrifuged at 10000 g for 10 min and the supernatant comprising the Aβ(12-42) globulomer withdrawn. The samples were aliquoted and stored at −80° C. until further use.

Example II

Production of Monoclonal Antibodies 3C5 and 10F4

Balb/c mice were immunized sub-cutaneous with 50 μg of Aβ (12-42) globulomer as described in Example I in CFA (Sigma) and boosted twice at one month intervals. Spleens were collected and spleen cells fused with mouse myeloma SP2/0 cells at 5:1 ratio by a PEG procedure. Fusion cells were plated in 96-well dishes in Azaserine/Hypoxanthine selection media at 2×105 cells/mL, 200 mL per well. Cells were allowed to grow to form visible colonies and supernatants assayed for Aβ oligomer reactivity by a direct ELISA assay. Hybridomas secreting antibodies to Aβ oligomers were subcloned by limiting dilution, until antibody expression appeared stable.

Example III

Dot-Blot Profile of the Selectivity of the Anti-Aβ Globulomer Antibodies

In order to characterize the selectivity of the monoclonal anti-Aβ globulomer antibodies, they were probed for recognition with different Aβ-forms. To this end, serial dilutions of the individual Aβ forms ranging from 100 pmol/μL to 0.01 pmol/μL in PBS supplemented with 0.2 mg/mL BSA were made. 1 μL of each sample was blotted onto a nitrocellulose membrane. For detection, the corresponding antibody was used (0.2 μg/mL). Immunostaining was done using peroxidase conjugated anti-mouse-IgG and the staining reagent BM Blue POD Substrate (Roche).

Aβ-Standards for Dot-Blot:

1. Aβ(1-42) monomer, 0.1% NH$_4$OH 1 mg Aβ(1-42) (Bachem Inc., Cat. no.: H-1368) were dissolved in 0.5 mL 0.1% NH$_4$OH in H$_2$O (freshly prepared) (=2 mg/mL) and immediately shaken for 30 sec at room temperature to obtain a clear solution. The sample was stored at −20° C. for further use.

2. Aβ(1-40) monomer, 0.1% NH$_4$OH 1 mg Aβ(1-40) (Bachem Inc., cat. no. H-1368) were dissolved in 0.5 mL 0.1% NH$_4$OH in H$_2$O (freshly prepared) (=2 mg/mL) and immediately shaken for 30 sec. at room temperature to obtain a clear solution. The sample was stored at −20° C. for further use.

3. Aβ(1-42) monomer, 0.1% NaOH 2.5 mg Aβ(1-42) (Bachem Inc., cat. no. H-1368) were dissolved in 0.5 mL 0.1% NaOH in H$_2$O (freshly prepared) (=5 mg/mL) and immediately shaken for 30 sec. at room temperature to obtain a clear solution. The sample was stored at −20° C. for further use.

4. Aβ(1-40) monomer, 0.1% NaOH 2.5 mg Aβ(1-40) (Bachem Inc., cat. no. H-1368) were dissolved in 0.5 mL 0.1% NaOH in H$_2$O (freshly prepared) (=5 mg/mL) and immediately shaken for 30 sec. at room temperature to obtain a clear solution. The sample was stored at −20° C. for further use.

5. Aβ(1-42) globulomer

The Aβ(1-42) synthetic peptide (H-1368, Bachem, Bubendorf, Switzerland) was suspended in 100% 1,1,1,3,3,3-hexafluoro-2-propanol (HFIP) at 6 mg/mL and incubated for complete solubilization under shaking at 37° C. for 1.5 h. The HFIP acts as a hydrogen-bond breaker and is used to eliminate pre-existing structural inhomogeneities in the Aβ peptide. HFIP was removed by evaporation in a SpeedVac and Aβ(1-42) resuspended at a concentration of 5 mM in dimethylsulfoxide and sonicated for 20 s. The HFIP-pretreated Aβ(1-42) was diluted in phosphate-buffered saline (PBS) (20 mM NaH$_2$PO$_4$, 140 mM NaCl, pH 7.4) to 400 μM and 1/10 volume 2% sodium dodecyl sulfate (SDS) (in H$_2$O) added (final concentration of 0.2% SDS). An incubation for 6 h at 37° C. resulted in the 16/20-kDa Aβ(1-42) globulomer (short form for globular oligomer) intermediate. The 38/48-kDa Aβ(1-42) globulomer was generated by a further dilution with three volumes of H$_2$O and incubation for 18 h at 37° C. After centrifugation at 3000 g for 20 min the sample was concentrated by ultrafiltration (30-kDa cut-off), dialysed against 5 mM NaH$_2$PO$_4$, 35 mM NaCl, pH 7.4, centrifuged at 10000 g for 10 min and the supernatant comprising the 38/48-kDa Aβ(1-42) globulomer withdrawn. As an alternative to dialysis the 38/48-kDa Aβ(1-42) globulomer can also be precipitated by a ninefold excess (v/v) of ice-cold methanol/acetic acid solution (33% methanol, 4% acetic acid) for 1 h at 4° C. The 38/48-kDa Aβ(1-42) globulomer is then pelleted (10 min at 16200 g), resuspended in 5 mM NaH$_2$PO$_4$, 35 mM NaCl, pH 7.4, and the pH adjusted to 7.4.

6. Aβ(12-42) globulomer 2 mL of an Aβ(1-42) globulomer preparation prepared according to Example 3.5 (see above) are admixed with 38 mL buffer (5 mM sodium phosphate, 35 mM sodium chloride, pH 7.4) and 150 μl of a 1 mg/mL GluC endoproteinase (Roche) in H$_2$O. The reaction mixture is stirred for 6 h at RT, and a further 150 μL of a 1 mg/mL GluC endoproteinase (Roche) in H$_2$O are subsequently added. The reaction mixture is stirred at RT for another 16 h, followed by addition of 8 μL of a 5 M DIFP (Diisopropylfluorphosphate) solution. The reaction mixture is concentrated to approx. 1 mL via a 15 mL 30 kDa Centriprep tube. The concentrate is admixed with 9 mL of buffer (5 mM sodium phosphate, 35 mM sodium chloride, pH 7.4) and again concentrated to 1 mL. The concentrate is dialyzed at 6° C. against 1 L of buffer (5 mM sodium phosphate, 35 mM NaCl) in a dialysis tube for 16 h. The dialysate is adjusted to an SDS content of 0.1% with a 1% strength SDS solution in H$_2$O. The sample is removed by centrifugation at 10000 g for 10 min and the supernatant is removed.

7. Aβ(20-42) globulomer 1.59 mL of Aβ(1-42) globulomer preparation prepared according to Example 2.5 (see above) are admixed with 38 mL of buffer (50 mM MES/NaOH, pH 7.4) and 200 μL of a 1 mg/mL thermolysin solution (Roche) in H$_2$O. The reaction mixture is stirred at RT for 20 h. Then 80 μl of a 100 mM EDTA solution, pH 7.4, in H$_2$O are added and the mixture is furthermore adjusted to an SDS content of 0.01% with 400 μl of a 1% strength SDS solution. The reaction mixture is concentrated to approx. 1 mL via a 15 mL 30 kDa Centriprep tube. The concentrate is admixed with 9 mL of buffer (50 mM MES/NaOH, 0.02% SDS, pH 7.4) and again concentrated to 1 mL. The concentrate is dialyzed at 6° C. against 1 L of buffer (5 mM sodium phosphate, 35 mM NaCl) in a dialysis tube for 16 h. The dialysate is adjusted to an SDS content of 0.1% with a 2% strength SDS solution in H$_2$O. The sample is removed by centrifugation at 10000 g for 10 min and the supernatant is removed.

8. Aβ(1-42) fibrils 1 mg Aβ(1-42) (Bachem Inc. Cat. no.: H-1368) were solved in 500 μL aqueous 0.1% NH$_4$OH (Eppendorff tube) and the sample was stirred for 1 min at room temperature. 100 μL of this freshly prepared Aβ(1-42) solution were neutralized with 300 μL 20 mM NaH$_2$PO$_4$; 140 mM NaCl, pH7.4. The pH was adjusted to pH 7.4 with 1% HCl. The sample was incubated for 24 h at 37° C. and centrifuged (10 min at 10000 g). The supernatant was discarded and the fibril pellet resuspended with 400 μL 20 mM NaH$_2$PO$_4$; 140 mM NaCl, pH 7.4 by vortexing for 1 min.

9. sAPPα

Supplied by Sigma (cat. no. 59564; 25 μg in 20 mM NaH$_2$PO$_4$; 140 mM NaCl; pH 7.4). The sAPPα was diluted to 0.1 mg/mL (=1 pmol/μL) with 20 mM NaH$_2$PO$_4$, 140 mM NaCl, pH 7.4, 0.2 mg/mL BSA.

Materials for Dot Blot:

Aβ-standards:
Serial dilution of Aβ antigens in 20 mM $NaH_2PO_4$, 140 mM NaCl, pH 7.4+0.2 mg/mL BSA
1) 100 pmol/μL
2) 10 pmol/μL
3) 1 pmol/μL
4) 0.1 pmol/μL
5) 0.01 pmol/μL Nitrocellulose:
Trans-Blot Transfer medium, Pure Nitrocellulose Membrane (0.45 μm); BIO-RAD Anti-Mouse-POD:
Cat. No: 715-035-150 (Jackson Immuno Research)

Detection reagent:
BM Blue POD Substrate, precipitating (Roche)

Bovine Serum Albumin, (BSA):
Cat. No.: A-7888 (SIGMA)

Blocking reagent:
5% low fat milk in TBS

Buffer solutions:
TBS
25 mM Tris/HCl buffer pH 7.5
+150 mM NaCl
TTBS
25 mM Tris/HCl—buffer pH 7.5
+150 mM NaCl
+0.05% Tween 20
PBS+0.2 mg/mL BSA
20 mM $NaH_2PO_4$ buffer pH 7.4
+140 mM NaCl
+0.2 mg/mL BSA Antibody solution I:
0.2 μg/mL antibody diluted in 20 mL 1% low fat milk in TBS Antibody solution II:
1:5000 dilution
Anti-Mouse-POD in 1% low fat milk in TBS Dot Blot Procedure:
1) 1 μL each of the different Aβ-standards (in their 5 serial dilutions) were dotted onto the nitrocellulose membrane in a distance of approximately 1 cm from each other.
2) The Aβ-standards dots were allowed to dry on the nitrocellulose membrane on air for at least 10 min at room temperature (RT) (=dot blot).
3) Blocking:
The dot blot was incubated with 30 mL 5% low fat milk in TBS for 1.5 h at RT.
4) Washing:
The blocking solution was discarded and the dot blot incubated under shaking with 20 mL TTBS for 10 min at RT.
5) Antibody solution I:
The washing buffer was discarded and the dot blot incubated with antibody solution I for 2 h at RT.
6) Washing:
The antibody solution I was discarded and the dot blot incubated under shaking with 20 mL TTBS for 10 min at RT.
The washing solution was discarded and the dot blot incubated under shaking with 20 mL TTBS for 10 min at RT.
The washing solution was discarded and the dot blot incubated under shaking with 20 mL TBS for 10 min at RT.
7) Antibody solution II:
The washing buffer was discarded and the dot blot incubated with antibody solution II overnight at RT.
8) Washing:
The antibody solution II was discarded and the dot blot incubated under shaking with 20 mL TTBS for 10 min at RT.
The washing solution was discarded and the dot blot incubated under shaking with 20 mL TTBS for 10 min at RT.
The washing solution was discarded and the dot blot incubated under shaking with 20 mL TBS for 10 min at RT.
9) Development:
The washing solution was discarded. The dot blot was developed with 10 mL BM Blue POD Substrate for 10 min. The development was stopped by intense washing of the dot blot with $H_2O$. Quantitative evaluation was done using a densitometric analysis (GS800 densitometer (BioRad) and software package Quantity one, Version 4.5.0 (BioRad)) of the dot-intensity. Only dots were evaluated that had a relative density of greater than 20% of the relative density of the last optically unambiguously identified dot of the Aβ(20-42) globulomer. This threshold value was determined for every dot-blot independently. The calculated value indicates the relation between recognition of Aβ(1-42) globulomer and the respective Aβ form for the antibody given.

The monoclonal antibodies tested were obtained (except for 6E10) by active immunization of mice with Aβ(12-42) globulomer (prepared as described in Example I), followed by selection of the fused hybridoma cells. The individual Aβ forms were applied in serial dilusions and incubated with the respective antibodies for immune reaction.
1. Aβ(1-42) monomer, 0.1% $NH_4OH$
2. Aβ(1-40) monomer, 0.1% $NH_4OH$
3. Aβ(1-42) monomer, 0.1% NaOH
4. Aβ(1-40) monomer, 0.1% NaOH
5. Aβ(1-42) globulomer
6. Aβ(12-42) globulomer
7. Aβ(20-42) globulomer
8. Aβ(1-42) fibril preparation
9. sAPPα (Sigma); (first dot: 1 pmol)

Results are shown in FIG. 1.

Based upon an analysis of the dot blot results, the anti-Aβ globulomer mAbs 10F4 and 3C5 have a high affinity for Aβ-globulomer forms such as the Aβ(1-42) globulomer, Aβ(12-42) globulomer and Aβ (20-42) globulomer). They discriminate other Aβ forms such as Aβ-monomers to a certain extent and do not significantly recognize Aβ(1-42) fibrils or sAPPα. The antibodies 10F4 and 3C5 can therefore be coined 'anti-Aβ globulomer antibodies'.

Example IV

Detection of Aβ-Globulomer Epitopes in Alzheimer's Disease Brain by 10F4 and 3C5

A: Extraction Procedure
Reagent List:
3% SDS-buffer:
50 mM Tris/HCl, 150 mM NaCl, 0.5% Triton X100, 1 mM EGTA, 3% SDS, 1% Na-desoxycholate, pH7.4
Complete Protease Inhibitor Cocktail:
dissolve 1 tablet complete inhibitor cocktail (Roche Diagnostics GmbH; Cat. no.: 1697498) in 1 mL $H_2O$; freshly prepared PMSF-solution:
500 mM PMSF in methanol
3% SDS extraction-buffer:
  add ¹⁄₁₀₀ complete inhibitor cocktail solution to the 3% SDS-buffer
  add ¹⁄₅₀₀ PMSF solution to the 3% SDS-buffer
  prepare extraction buffer immediately before use at room temperature
Antibodies:
  mAb 10F4
  mAb 3C5
  mAb 6E10 (Signet; Cat. no.: 9320)
  mAb IgG2b (control antibody, generated against a synthetical hapten, Dianova, clone NCG2B.01, Cat. No: DLN-05812)
Procedure:
0.2 g of −80° C. frozen post mortem human AD and aged match control brain tissue samples were added to 1.8 mL freshly prepared 3% SDS-extraction buffer at room temperature. The sample was immediately homogenized on ice by a glass potter. The homogenized sample was transferred to a reaction vial and centrifuged at 10000 g for 5 min. The supernatant (=3% SDS-brain extract) was collected carefully and stored in a reaction vial at −80° C. for further use.

B: Activation of Dynabeads with Monoclonal Mouse Antibodies
  the stock-suspension of dynabeads (Dynabeads M-280 Sheep anti-Mouse IgG, Invitrogen; Cat. no.: 112.02) was shaken carefully to prevent foaming
  1 mL was aseptically removed and transferred to a 1.5 mL reaction vial
  the dynabeads were washed 3 times 5 min with 1 mL immunoprecipitation (IP)-wash buffer (IP-wash-buffer: PBS (20 mM $NaH_2PO_4$, 140 mM NaCl, pH 7.4), 0.1% BSA). During the washing procedure the supernatant was carefully removed while the dynabeads were immobilized at the side of the reaction vial with a magnetic separator stand (MSS)
  the washed dynabeads were incubated with 40 µg Aβ-antibody in 1 mL PBS, 0.1% BSA
  the activation was carried out by overnight incubation under shaking at 4° C.
  the activated dynabeads were washed 4 times 30 min (again using the MSS) with 1 mL IP-wash buffer (PBS (20 mM $NaH_2PO_4$, 140 mM NaCl, pH 7.4), 0.1% BSA)
  the activated dynabeads were resuspended with 1 mL PBS, 0.1% BSA, 0.02% Na-Azide; vortexed and centrifuged briefly
  the antibody activated dynabeads were stored at 4° C. until further use C: Immunoprecipitation (IP)
  25 µL 3% SDS-brain extract were diluted with 975 µL 20 mM $NaH_2PO_4$, 140 mM NaCl; 0.05% Tween 20, pH 7.5 (=1:40 dilution).
  25 µL of each antibody activated dynabeads of the following list were incubated with 1 mL of the 1:40 diluted 3% SDS-brain extract:
    6E10-Dynabeads
    3C5-Dynabeads
    10F4-Dynabeads
    IgG2b-Dynabeads
  the immunoprecipitation was carried out by overnight incubation (~20 h) under shaking at 6° C.
  the dynabeads were immobilized with the MPS
  the supernatant was carefully removed and discarded
  the dynabeads were washed as follows:
    2 times 5 minutes with 500 µL 20 mM $NaH_2PO_4$, 140 mM NaCl, pH 7.5+0.1% BSA
    1 time 3 minutes with 500 µL 2 mM $NaH_2PO_4$, 14 mM NaCl, pH 7.5
    important: after the last removal of the washing buffer the reaction vials were centrifuged, placed back in the MSS and the remaining drops of fluid carefully removed
  10 µL 50% $CH_3CN$, 0.5% TFA in $H_2O$ were added to the reaction vial and vortexed
  the reaction vials were incubated 10 minutes at RT under shaking
  the dynabeads were immobilized with the MSS
  the supernatant comprising the immunoprecipitated eluted Aβ species was carefully withdrawn (=IP-eluate)

D: Surface-Enhanced Laser Desorption Ionization-Mass Spectrometry (SELDI-MS):
  1 µL IP-eluate was spotted onto a H4 Protein Chip Array (Ciphergen; Cat. no. C573-0028).
  the spots were allowed to dry on a warm incubator plate
  CHCA-solution:
    5 mg CHCA were dissolved in 150 µL acetonitrile+150 µL 1% TFA=stock solution; stored at −20° C.
    of the stock solution 10 µL were diluted with 20 µL acetonitrile and 20 µL 1% TFA=working CHCA-solution
  2 µL of the working CHCA-solution was applied onto the spots
  the spots were allowed to dry on a warm incubator plate and analysed by SELDI-MS (Surface-Enhanced Laser Desorption Ionization-Mass Spectrometry)
  conditions: laser intensity 200; sensitivity 6; mass range 800 Da-10000 Da; position 20-80; collect 5
  analysis: the MZ area of the respective Aβ-mass peaks was quantified E. Western Blot Analysis of Imuunoprecipitated AD-Brain Extract:
SDS-PAGE:
  SDS-sample buffer:
    0.3 g SDS
    4 mL 1 M Tris/HCl pH 6.8
    8 mL glycerol
    70 µL 1% bromphenolblue in ethanol
    add $H_2O$ to 50 mL
  Running buffer:
    7.5 g Tris
    36 g Glycine
    2.5 g SDS
    add $H_2O$ to 2.5 L
  SDS-PAGE gel system:
    18% Tris/Glycine Gel: (Invitrogen Inc., Cat. no.: EC65055BOX)
  5 µL IP-eluate were added to 13 µL sample buffer (300 µL SDS-sample buffer+10 µL 1 M Tris-solution in $H_2O$+20 µL 85% glycerol). The resulting 18 µL sample are loaded onto a 18% Tris/Glycin Gel (Invitrogen Inc., Cat. no.: EC65055BOX). The SDS-PAGE is conducted at a constant current of 20 mA.
Western Blot Procedure:
  Subsequent to electrophoresis, the gel was blotted for 45 minutes at 75 mA onto a nitrocellulose membrane (7.5 cm×9 cm, 0.2 µm, BioRad) using a semi-dry blotting chamber (BioRad).
  Blot-buffer:
    6 g Tris
    28.1 g glycine 500 mL methanole
add H$_2$O to 2.5 L Western Blot Immunostaining:

Materials:
Anti-Aβ antibody 6E10 (Signet; Cat. No. 9320)
Anti-Mouse-POD (Jackson ImmunoResearch, Cat. no.: 715-035-150)
Detection reagent:
Super Signal West Pico Substrat (Pierce, Cat. no.: 34077)
Bovine Serum Albumin (BSA, Serva, Cat. no.: 11926)
low fat milk powder (Lasana)
Blocking reagent:
2% BSA in PBST
TBS:
25 mM Tris/HCl
150 mM NaCl Puffer, pH 7.5
TTBS:
25 mM Tris/HCl
150 mM NaCl Puffer
0.05% Tween 20, pH 7.5
PBS:
20 mM NaH$_2$PO$_4$ buffer
140 mM NaCl buffer, pH 7.5
PBST:
20 mM NaH$_2$PO$_4$ buffer
140 mM NaCl buffer
0.05% Tween 20, pH 7.5
Antibody solution I:
1 µg/mL 6E10=1:1000 in 20 mL 3% low fat milk in TBS
Antibody solution II:
1:10000 diluted anti-mouse-POD in 20 mL 3% low fat milk in TBS Procedure:
1) The Western blot was boiled for 10 minutes in PBS.
2) Blocking:
The Western blot was incubated for 16 h at 6° C. with 50 mL blocking reagent.
3) Washing:
The blocking solution was discarded and the Western blot washed with 50 mL TTBS for 10 minutes at room temperature.
The blocking solution was discarded and the Western blot washed with 50 mL TBS for 10 minutes at room temperature.
4) Antibody solution I:
The washing solution was discarded and the Western blot incubated with antibody solution I for 4 h at room temperature.
5) Washing:
The blocking solution was discarded and the Western blot washed with 50 mL TTBS for 10 minutes at room temperature.
The blocking solution was discarded and the Western blot washed with 50 mL TTBS for 10 minutes at room temperature.
The blocking solution was discarded and the Western blot washed with 50 mL TBS for 10 minutes at room temperature.
6) Antibody solution II:
The washing solution was discarded and the Western blot incubated with antibody solution II for 1 h at room temperature.
7) Washing:
The blocking solution was discarded and the Western blot washed with 50 mL TTBS for 10 minutes at room temperature.
The blocking solution was discarded and the Western blot washed with 50 mL TTBS for 10 minutes at room temperature.
The blocking solution was discarded and the Western blot washed with 50 mL TBS for 10 minutes at room temperature.
8) Development and quantitative analysis:
The washing solution was discarded.
Two mL Super Signal West Pico Substrate Enhancer and 2 mL Peroxide Solution were mixed.
The resulting 4 mL solution were added to the Western blot and the blot was incubated for 5 minutes in the dark.
The blot was analyzed using a chemoluminescence imaging system (VersaDoc, BioRad). Five pictures at were taken at 30, 97.5, 165, 232.5 and 300 seconds acquisition time.
The picture at which no saturation of the trace (intensity×mm) of the Aβ-protein bands occurred was quantitatively analyzed using the software package Quantity one, Version 4.5.0 (BioRad).

The results are shown in FIG. 2. The extraction procedure with 3% (w/v) used herein is thought to extract soluble forms of the total Aβ-peptide pool in the brain because the buffer composition is not sufficient to solubilize Aβ-peptide in the aggregated fibrillar form. The Aβ-peptide that is bound in the Alzheimer's disease brain extract by the monoclonal antibodies 3C5 and 10F4 is therefore soluble Aβ-peptide. These soluble Aβ-species are thought to be the Alzheimer's disease relevant species, as they correlate better with the severity of the disease than fibrillar Aβ in the form of Aβ-plaques found in AD brain (Kuo et al. 1996, J. Biol. Chem. 271, 4077-4081; Lue et al., 1999, Am. J. Pathol. 155, 853-862). Therefore, the antibodies 10F4 and 3C5 target the disease relevant Aβ-species. Moreover, in comparison to the pan-Aβ-antibody 6E10, the monoclonal antibodies 3C5 and 10F4 bind only a to subfraction of the total soluble Aβ-pool in the Alzheimer's disease brain extract. The remaining Aβ-forms obviously do not possess the Aβ-globulomer epitope recognized by 3C5 and 10F4. Due to the fact that these Aβ-forms are not thought to be neuropathogenic, it is advantageous not to attack them by the treatment antibody to reduce side effects and not to reduce the effective concentration of antibodies circulating in the CNS. Therefore, the dosing of the treatment antibody can be reduced resulting in a better therapeutic index.

Example V

Semi-Quantitative Analysis Visualized by SDS-Page of the Discrimination of Anti-Aβ Globulomer Antibodies for Aβ(1-42) Fibrils Aβ(1-42) Fibril Preparation:
1 mg of Aβ(1-42) (Bachem, Cat. No.: H-1368) was dissolved in 500 µL 0.1% NH$_4$OH in H$_2$O and agitated for 1 min at ambient temperature. The sample was centrifuged for 5 min at 10000 g. The supernatant was collected. Aβ(1-42) concentration in the supernatant was determined according to Bradford's method (BIO-RAD Inc. assay procedure).
100 µL of Aβ(1-42) in 0.1% NH$_4$OH were mixed with 300 µL of 20 mM NaH$_2$PO$_4$, 140 mM NaCl, pH 7.4 and adjusted to pH 7.4 with 2% HCl. The sample was then incubated at 37° C. for 20 hours. Following which, the sample was centrifuged for 10 min at 10000 g. The supernatant was discarded, and the residue was mixed with 400 µL of 20 mM NaH₂PO₄, 140 mM NaCl, pH 7.4, resuspended by vigorous agitation ("vortexing") for 1 min and centrifuged for 10 min at 10000 g. The supernatant was discarded, and the residue was mixed with 400 µL of 20 mM NaH₂PO₄, 140 mM NaCl, pH 7.4, resuspended by vigorous agitation ("vortexing") for 1 min and centrifuged for 10 min at 10000 g once more. The supernatant was discarded. The residue was resuspended in 380 µL of 20 mM NaH₂PO₄, 140 mM NaCl, pH 7.4 and prompted by vigorous agitation ("vortexing").

Binding of Anti-Aβ Antibodies to Aβ(1-42) Fibrils:

40 µL of Aβ(1-42) fibril preparation were diluted with 160 µL of 20 mM NaH₂PO₄, 140 mM NaCl, 0.05% Tween 20, pH 7.4 and agitated 5 min at ambient temperature, and then the sample was centrifuged for 10 min at 10000 g. The supernatant was discarded, and the residue was resuspended in 95 µL of 20 mM NaH₂PO₄, 140 mM NaCl, 0.05% Tween 20, pH 7.4. Resuspension was prompted by vigorous agitation ("vortexing"). Aliquots of 10 µL of the fibril preparation were each mixed with:
 a) 10 µL 20 mM NaH₂PO₄, 140 mM NaCl, pH 7.4
 b) 10 µL 0.5 µg/µL of 3C5 in 20 mM NaH₂PO₄, 140 mM NaCl, pH 7.4
 c) 10 µL 0.5 µg/µL of 10F4 in 20 mM NaH₂PO₄, 140 mM NaCl, pH 7.4
 d) 10 µL 0.5 µg/µL of 6E10 (Signet Cat. Nr.: 9320) in 20 mM NaH₂PO₄, 140 mM NaCl, pH 7.4

The samples were incubated at 37° C. for 20 hours, and then centrifuged for 10 min at 10000 g. The supernatants were collected and mixed with 20 µL of SDS-PAGE sample buffer. The residues were mixed with 50 µL of 20 mM NaH₂PO₄, 140 mM NaCl, 0.025% Tween 20, pH 7.4 and resuspended by "vortexing". Then, the samples were centrifuged for 10 min at 10000 g. The supernatants were discarded, and the residues were mixed with 20 µL 20 mM NaH₂PO₄, 140 mM NaCl, 0.025% Tween 20, pH 7.4, then with 20 µL of SDS-PAGE sample buffer. The samples were applied to a 4-20% Tris/glycine gel for electrophoresis.

Parameters for SDS-PAGE:
 SDS sample buffer: 0.3 g SDS
 4 mL 1M Tris/HCl pH 6.8
 8 mL glycerine
 1 mL 1% bromphenol blue in ethanol
 Fill with H₂O ad 50 mL
 4-20% Tris/Glycine Gel: (Invitrogen Cat. no.: EC6025BOX)
 Electrophoresis buffer: 7.5 g Tris
 36 g Glycine
 2.5 g SDS
 Fill with H₂O ad 2.5 L
 The gel is run at a constant current of 20 mA.
 Staining of the gels: Coomassie Blue R250

Results are shown in FIG. 3.

Semiquantitative analysis of different anti-Aβ antibodies and their discrimination of Aβ(1-42) fibrils:

Positions of antibodies, Aβ(1-42) fibrils antibody heavy chain, antibody light chain and Aβ(1-42) monomers are marked at the edge of the gel. Due to their size, Aβ(1-42) fibrils cannot enter the SDS-PAGE gel and can be seen in the gel slot.
 1. Marker
 2. Aβ(1-42) fibril preparation; control
 3. Aβ(1-42) fibril preparation; +mAb 6E10; 20 h 37° C.; supernatant
 4. Aβ(1-42) fibril preparation; +mAb 6E10; 20 h 37° C.; pellet
 5. Aβ(1-42) fibril preparation; +mAb 3C5; 20 h 37° C.; supernatant
 6. Aβ(1-42) fibril preparation; +mAb 3C5; 20 h 37° C.; pellet
 7. Aβ(1-42) fibril preparation; +mAb 10F4; 20 h 37° C.; supernatant
 8. Aβ(1-42) fibril preparation; +mAb 10F4; 20 h 37° C.; pellet The relative binding to fibril type Aβ was evaluated from SDS-PAGE analysis by measuring the Optical Density (OD) values from the Heavy Chain of the antibodies in the fibril bound (pellet-fraction) and the supernatant fractions after centrifugation. Antibodies that have bound to the Aβ fibrils should be co-pelleted with the Aβ-fibrils and therefore are found in the pellet fraction whereas non-Aβ-fibril bound (free) antibodies are found in the supernatant. The percentage of antibody bound to Aβ-fibrils was calculated according to the following formula:

$$\text{Percent antibody bound to } A\beta\text{-fibrils} = OD_{fibril\ fraction} \times 100\%/(OD_{fraction} + OD_{supernatant\ fraction}).$$

Results are shown in FIG. 3. In contrast to the commercially available antibody 6E10 (Signet Cat. no.: 9320) which recognizes and binds to a linear Aβ-epitope between AA1-17, the Aβ globulomer antibodies 3C5 and 10F4 bind to Aβ(1-42)-fibrils with a lower affinity in a co-pelleting experiment. This is evidenced by the fact that the 3C5 and 10F4 antibodies, after an incubation with Aβ(1-42) fibrils, remain mainly after a pelleting step in the supernatant and are not co-pelleted due to being bound to the Aβ(1-42) fibrils.

In the Alzheimer's disease brain, the Aβ fibrils are a major component of the total Aβ peptide pool. By attacking these fibrils by anti Aβ-antibodies, the risk of negative side effects is elevated due to a liberation of high amounts of Aβ which subsequently may increase the risk of microhaemorrhages. An increased risk for microhemorrhages was observed in an active immunization approach with fibrillar aggregates of the Aβ peptide (Bennett and Holtzman, 2005, Neurology, 64, 10-12; Orgogozo J, Neurology, 2003, 61, 46-54; Schenk et al., 2004, Curr Opin Immunol, 16, 599-606).

Example VI

In Situ Analysis of the Specific Reaction of Antibodies 10F4 and 3C5 to Fibrillar Abeta Peptide in the Form of Amyloid Plaques and Amyloid in Meningeal Vessels in Old App Transgenic Mice and Alzheimer's Disease Patients Antibodies 10F4 and 3C5 show reduced staining to fibrillar Aβ peptide deposits suggesting that their therapeutic effect is mediated by binding to soluble globulomeric forms rather than fibrillar deposited forms of Aβ peptide. Since antibody binding to fibrillar Aβ peptide can lead to fast dissolution of aggregates and a subsequent increase of soluble Aβ concentration, which in turn is thought to be neurotoxic and could lead to microhemorrhages, an antibody therapy that effects the soluble globulomer rather than the monomer is preferred.

Methods:

For these experiments, several brain material samples were used: cortical tissue from 2 AD patients (RZ16 and RZ 55) and cortical tissue from 19 month old Tg2576 mice (APPSWE #001349, Taconic, Hudson, N.Y., USA) or 12 month old APP/L mice (ReMYND, Leuven, Belgium).

The mice overexpress human APP with a familial Alzheimer's disease mutation and form β-amyloid deposits in the brain parenchyma at about 11 months of age and β-amyloid deposits in larger cerebral vessels at about 18 months of age. The animals were deeply anaesthetized and transcardially perfused with 0.1 M phosphate-buffered saline (PBS) to flush the blood. Then, the brain was removed from the cranium and divided longitudinally. One hemisphere of the brain was shock-frozen and the other fixated by immersion into 4% paraformaldehyde. The immersion-fixated hemisphere was cryoprotected by soaking in 30% sucrose in PBS and mounted on a freezing microtome. The entire forebrain was cut into 40 µm transverse sections which were collected in PBS and used for the subsequent staining procedure.

The neocortex samples from Alzheimer's disease patients were obtained from Brain-Net, Munich, Germany as frozen tissue, immersion-fixated in 4% paraformaldehyde during thawing, and subsequently treated like the mouse tissue. Individual sections were stained with Congo Red using the following protocol:

Material:
Amyloid dye Congo Red kit (Sigma-Aldrich; HT-60), consisting of alcoholic NaCl solution, NaOH solution and Congo Red solution
staining cuvettes
microscope slides SuperfrostPlus and coverslips
Ethanol, Xylol, embedding medium Reagents:
NaOH diluted 1:100 with NaCl solution yields alkaline saline
alkaline saline diluted 1:100 with Congo Red solution yields alkaline Congo Red solution (prepare no more than 15 min before use, filtrate)
mount sections on slide and allow them to dry
incubate slide in staining cuvette, first for 30-40 minutes in alkaline saline, then for 30-40 minutes in alkaline Congo Red solution
rinse three times with fresh ethanol and embed over xylol Staining was first photographed using a Zeiss Axioplan microscope (Zeiss, Jena, Germany) and evaluated qualitatively. Red colour indicated amyloid deposits both in the form of plaques and in larger meningeal vessels. Later on, evaluation of antibody staining focused on these structures. Staining was performed by incubating the sections with a solution containing 0.07-0.7 µg/ml of the respective antibody in accordance with the following protocol:

Materials:
TBST washing solution (Tris Buffered Saline with Tween 20; 10× concentrate; DakoCytomation S3306, DAKO, Hamburg, Germany) 1:10 in Aqua bidest.)
0.3% $H_2O_2$ in methanol
donkey serum (Serotec, Düsseldorf, Germany), 5% in TBST, as blocking serum
monoclonal mouse-anti-globulomer antibodies diluted at given concentrations in TBST
secondary antibody: biotinylated donkey-anti-mouse antibody (Jackson Immuno/Dianova, Hamburg, Germany; 715-065-150; diluted 1:500 in TBST)
StreptABComplex (DakoCytomation K 0377, DAKO, Hamburg, Germany)
Peroxidase Substrate Kit diaminobenzidine (=DAB; SK-4100; Vector Laboratories, Burlingame, Calif., USA)
SuperFrost Plus microscope slides and coverslips
xylol free embedding medium (Medite, Burgdorf, Germany; X-tra Kitt)

Procedure:
transfer floating sections into ice-cold 0.3% $H_2O_2$ and incubate for 30 min
wash for 5 min in TBST buffer
incubate with donkey serum/TBST for 20 minutes
incubate with primary antibody for 24 hours at room temperature
wash in TBST buffer for 5 minutes
incubate with blocking serum for 20 minutes
wash in TBST buffer for 5 minutes
incubate with secondary antibody for 60 minutes at ambient temperature
wash in TBST buffer for 5 minutes
incubate with StreptABComplex for 60 minutes at ambient temperature
wash in TBST buffer for 5 minutes
incubate with DAB for 20 minutes
mount the section on slides, air-dry slides, dehydrate slides with alcohol and embed slides Besides visual inspection of sections under the microscope, amyloid staining was additionally quantified by optically excising 10 randomly selected plaques from the histological images using the ImagePro 5.0 image analysis system and determining their average greyscale value. Optical density values (were calculated from the greyscale values by subtracting the mean background density of the stained material from the density of amyloid plaques (0%—no plaque staining above surrounding background, 100%—no transmission/maximal staining). The differences between antibodies 6E10/4G8 and 6G1, 10F4 and 3C5, respectively, were tested for statistical significance with ANOVA.

Results:
All antibody stained material described in the following proved to be congophilic amyloid deposits (FIG. 4(a)). The globulomer-preferring antibodies 10F4 and 3C5 stained parenchymal and meningeal congophilic deposits of Aβ peptide at the same concentration of 0.7 µg/mL significantly less than the antibodies 6G1 and 6E10 (FIG. 4(b,c,h)). Quantitative analysis of parenchymal amyloid plaque staining revealed binding of all antibodies to plaques (statistically significant density above control), but binding of antibody 10F4 and 3C5 was significantly lower than binding of the reference antibody 6E10 (raised to N-terminal sequence of Aβ) and equal or lower than reference antibody 4G8 (raised to N-terminal sequence of Aβ) (FIG. 4(d-g)).

Antibodies 10F4 and 3C5 bind less to amyloid deposits than antibodies which recognize Aβ monomer or part of the Aβ sequence. Treatment with antibodies binding to fibrillar Aβ peptide can lead to fast dissolution of amyloid plaques in brain tissue and a subsequent increase of soluble Aβ concentration, which in turn is thought to be neurotoxic and could lead to microhemorrhages, and/or a fast dissolution of vascular amyloid, which also could lead to microhemorrhages. Therefore, an antibody therapy that effects the soluble globulomer rather than the monomer is preferred.

Example VII

Endogenous Aβ(1-42) and Aβ(1-40) Levels in CSF of Ad Patients after Immunoprecipitation with Anti-Aβ Globulomer Antibodies 10F4 and 3C5

Immunoprecipitation (IP) of Aβ-species from AD-brain CSF with Dynabeads M-280 Sheep anti-Mouse IgG
The following mAbs were immobilized to Dynabeads M-280 Sheep anti-Mouse IgG:
mAb 6E10 (Signet Inc.; Cat. no.: 9320)
mAb 3C5 mAb 10F4
mAb 8F5

Dynabeads M-280 Sheep Anti-Mouse IgG:

Sheep anti-Mouse IgG (Invitrogen Inc., Cat. no.: 112.02) is covalently bound to magnetic beads (Dynabeads).

Activation of Dynabeads with Monoclonal Mouse Antibodies the stock-suspension of dynabeads (Dynabeads M-280 Sheep anti-Mouse IgG, Invitrogen; Prod. No. 112.02) was shaken carefully to prevent foaming 1 mL was aseptically removed and transferred to a 1.5 mL reaction vial the dynabeads were washed 3 times 5 min with 1 mL immunoprecipitation (IP)-wash buffer (IP-wash-buffer: PBS (20 mM $NaH_2PO_4$, 140 mM NaCl, pH 7.4), 0.1% (w/v) BSA). During the washing procedure the supernatant was carefully removed while the dynabeads were immobilized at the side of the reaction vial with a magnetic separator stand (MSS)

the washed dynabeads were incubated with 40 μg Aβ-antibody in 1 mL PBS, 0.1% (w/v) BSA the activation was carried out by overnight incubation under shaking at 4° C.

the activated dynabeads were washed 4 times 30 min (again using the MSS) with 1 mL IP-wash buffer (PBS (20 mM $NaH_2PO_4$, 140 mM NaCl, pH 7.4), 0.1% (w/v) BSA)

the activated dynabeads were resuspended with 1 mL PBS, 0.1% (w/v) BSA, 0.02% (w/v) Na-Azide; vortexed and centrifuged briefly the antibody activated dynabeads were stored at 4° C. until further use CSF Sample Preparation:

400 μL CSF from an Alzheimer's disease patient were added to 4 μL Complete Protease Inhibitor Cocktail (Roche Inc. Cat. no.: 1697498, 1 tablet dissolved in 1 mL water) and 0.8 μL 500 mM PMSF dissolved in methanol. After 10 min 1.6 mL 20 mM $NaH_2PO_4$, 140 mM NaCl, 0.05% Tween 20, pH 7.4 (PBST) was added.

Immunoprecipitation of Aβ Species from Human AD-CSF:

250 μL aliquot of the prepared CSF sample were added to 25 μL anti-Aβ-Dynabeads suspension Immunoprecipitation occurred under stirring at 6° C. for 16 hours. Subsequent washing of the beads was performed 3 times 5 min. with 1 mL PBS/0.1% (w/v) BSA and finally once 3 min. with 1 mL 10 mM Tris/HCL pH 7.5 buffer. During the washing procedure the supernatant was carefully removed while the dynabeads were immobilized at the side of the reaction vial with a magnetic separator stand (MSS)

The residual supernatant was thoroughly removed after the final washing step.

The Aβ peptides and the corresponding antibody were removed from the Dynabeads by adding 25 μL sample buffer without β-Mercaptoethanol (0.36 M Bistris, 0.16 M Bicine, 1% SDS (w/v), 15% (w/v) sucrose, 0.004% (w/v) Bromphenolblue) to the Eppendorff tube and heating for 5 min at 95° C. in a heating block. After cooling to room temperature the dynabeads were immobilized at the side of the reaction vial with a magnetic separator stand (MSS) and the supernatant were transferred to another Eppendorff tube (IP eluate).

Analysis of Aβ Immunoprecipitates by Urea-PAGE Followed by Western Blot Procedure:

The quantification of Aβ1-40 and Aβ1-42 species was performed by a 8 M Urea Poly-Acrylamide-Gel-Electrophoresis system and subsequent Western Blot analysis according to the procedure first described by H. W. Klafki et al., Analytical Biochemistry 237, 24-29 (1996) and later also used by J. Wiltfang et al., J. of Neurochemistry 81, 481-496, 2002. There were only two minor changes made in the experimental procedure:

1) SDS concentration in the stacking gel was adjusted to 0.25% (w/v) instead of 0.1% (w/v).
2) For the Western blot the antibody 1E8 (Senetek Drug Delivery Technologies Inc. St. Louis, Mo., USA) was replaced by Anti-Human Amyloid β (N) (82E1) Mouse IgG mAb (IBL, Cat. no.: 10323)

15 μL IP eluate aliquots of the immunoprecipitated samples were loaded onto the 8 M Urea PAGE. Electrophoresis was performed at 100 V (15 min) and continued at 60 V. The electrophoresis was stopped when the running front of the blue sample loading dye was still 0.5 cm away from the end of the gel.

Western Blot Procedure:

Western blot analysis was performed in a Semi Dry Blotting chamber (BioRad Inc., 45 min at 75 mA) onto 7.5 cm×9 cm Nitrocellulose 0.45 μm (BioRad Inc.)

Blotting buffer: 6 g Tris; 28.1 g Glycin; 500 m L Methanol; adjust to 2.5 l with water.

The Nitrocellulose blot was boiled for 10 min in PBS at 100° C. The blot was saturated by treatment with 50 mL 5% (w/v) BSA in PBST for 1 hour at RT. After removal of the fluid phase the following washing step were performed twice with: 50 mL TTBS (25 mM Tris/HCl; 150 mM NaCl Puffer; 0.05% Tween 20; pH 7.5) for 10 min at RT and subsequently with 50 mL TBS (25 mM Tris/HCl; 150 mM NaCl buffer; pH 7.5) for 10 min at RT.

For further development the final washing buffer was discarded from the blot and 15 mL antibody I solution (0.2 μg/mL 82E1=1:500 in 3% (w/v) skimmed milk powder (Lasana Inc.), in 15 mL TBS) were added for 20 hours at 6° C. Removal of buffer was followed by the three wash steps as described above. The blot was incubated with Antibody solution II (1:10000 dilution of anti-Mouse-POD in 15 mL 3% (w/v) skimmed milk powder in 15 mL TBS) for 1 hour at RT. Removal of buffer was followed by the three wash steps as described above.

After removal of the last washing buffer 2 mL Super Signal West Femto Maximum Sensitivity Substrat Enhancer and 2 mL Peroxide Solution was mixed. The freshly prepared solution was poured onto the blot which was preincubated in the dark for 5 min. Chemoluminescence was recorded using a VersaDoc Imaging system (BioRad).

Imaging Parameters:

exposure time 180 sec.

Picture records after 30 sec., 60 sec., 120 sec. and 180 sec. The results were obtained from the picture with 180 sec. exposure time.

The anti-globulomer antibodies 10F4 and 3C5 of the present invention have a lower affinity for Aβ(1-42) peptide and Aβ(1-40) peptide in the CSF of an Alzheimer's disease patient, in comparison to the commercially available antibody 6E10 (which is, in the literature, regarded to recognize all Aβ-forms regardless of their conformation). CSF Aβ-peptide forms undergo a high turnover rate (Bateman et al., Nature Medicine, 2006, 12(7):856-61) and are therefore unlikely the disease relevant species. Therefore, the CSF Aβ-forms should not be targeted in a passive immunization treatment strategy of Alzheimer's disease in order to reduce the risk of undesired side effects. It is noted that, in an earlier study (Barghorn et al., J Neurochem. 2005; 95(3):834-847), the anti Aβ-globulomer antibody 8F5 did not recognize and bind to Aβ-peptide in the CSF of an Alzheimer's disease patient. This earlier study was performed using a sandwich ELISA method. In contrast, when using the immunoprecipitation and Urea PAGE method described above, the same antibody 8F5 does recognize Aβ-peptide in the CSF of an Alzheimer's disease patient (see FIG. 5). Therefore, the sandwich ELISA method produced false negative results; hence, for the detection of Aβ-peptides in CSF, the immunoprecipitation and Urea PAGE methods described herein should be used.

What is claimed is:

1. An isolated antibody having a higher affinity to Aβ(1-42) globulomer than to at least one amyloid beta protein selected from the group consisting of a) Aβ(1-42) peptide present in cerebrospinal fluid (CSF) and b) Aβ(1-40) peptide present in CSF, wherein the antibody comprises:
   (i) the amino acid sequences of the Complementary Determining Region (CDR) 1, CDR2, and CDR3 of the heavy chain variable region (VH) of SEQ ID NO: 5 and the amino acid sequences of the CDR1, CDR2, and CDR3 of the light chain variable region (VL) of SEQ ID NO: 6, or
   (ii) the amino acid sequences of the CDR1, CDR2, and CDR3 of the heavy chain variable region (VH) of SEQ ID NO: 7 and the amino acid sequences of the CDR1, CDR2, and CDR3 of the light chain variable region (VL) of SEQ ID NO: 8.

2. An isolated antibody having a higher affinity to Aβ(1-42) globulomer than to at least one amyloid beta protein selected from the group consisting of a) Aβ(1-42) peptide present in cerebrospinal fluid (CSF), and b) Aβ(1-40) peptide present in CSF, wherein the antibody comprises:
   (i) the amino acid sequences of the VH CDR1 VH CDR2 VH CDR3 VL CDR1 VL CDR2, and VL CDR3 of a monoclonal antibody (10F4) obtainable from a hybridoma designated by American Type Culture Collection (ATCC) deposit number PTA-7808, or
   (ii) the amino acid sequences of the VH CDR1, VH CDR2, VH CDR3, VL CDR1, VL CDR2, and VL CDR3 of a monoclonal antibody (3C5) obtainable from a hybridoma designated by ATCC deposit number PTA-7406.

3. The isolated antibody of claim 1 or claim 2 wherein said antibody comprises:
   (i) the amino acid sequence of the VH CDR1 of SEQ ID NO:9, the amino acid sequence of the VH CDR2 of SEQ ID NO:10, the amino acid sequence of the VH CDR3 of SEQ ID NO:11, the amino acid sequence of the VL CDR1 of SEQ ID NO:12, the amino acid sequence of the VL CDR2 of SEQ ID NO:13, and the amino acid sequence of the VL CDR3 of SEQ ID NO:14, or
   (ii) the amino acid sequence of the VH CDR1 of SEQ ID NO:15, the amino acid sequence of the VH CDR2 of SEQ ID NO:16, the amino acid sequence of the VH CDR3 of SEQ ID NO:17, the amino acid sequence of the VL CDR1 of SEQ ID NO:18, the amino acid sequence of the VL CDR2 of SEQ ID NO:19, and the amino acid sequence of the VL CDR3 of SEQ ID NO:20.

4. The isolated antibody of claim 1 or claim 2, wherein the antibody is a monoclonal antibody.

5. The isolated antibody of claim 4, wherein the antibody is a recombinant antibody.

6. The isolated antibody of claim 1 or claim 2, wherein the antibody is humanized.

7. The isolated antibody of claim 1 or claim 2, wherein the VH of the antibody comprises the amino acid sequence of SEQ ID NO: 5 and the VL of the antibody comprises the amino acid sequence of SEQ ID NO: 6.

8. The isolated antibody of claim 7, wherein the antibody comprises a human IgG1 heavy chain constant region or a human IgG4 heavy chain constant region.

9. The isolated antibody of claim 7, wherein the antibody comprises a human kappa light chain constant region.

10. The isolated antibody of claim 1 or claim 2, wherein the VH of the antibody comprises the amino acid sequence of SEQ ID NO: 7 and the VL of the antibody comprises the amino acid sequence of SEQ ID NO: 8.

11. The isolated antibody of claim 10, wherein the antibody comprises a human IgG1 heavy chain constant region or a human IgG4 heavy chain constant region.

12. The isolated antibody of claim 10, wherein the antibody comprises a human kappa light chain constant region.

13. A composition comprising said antibody of claim 1 or said antibody of claim 2.

14. The composition of claim 13, wherein the composition is a pharmaceutical composition and further comprises a pharmaceutical acceptable carrier.

15. A vaccine comprising: a) said antibody of claim 1 or said antibody of claim 2 and b) a pharmaceutically acceptable adjuvant.

16. A kit comprising: a) said antibody of claim 1 or said antibody of claim 2 and b) a conjugate comprising an antibody attached to a signal-generating compound, wherein said antibody of said conjugate is different from said isolated antibody.

17. An isolated antibody produced by a method comprising culturing a host cell comprising a vector comprising an isolated nucleic acid molecule;
   wherein the isolated nucleic acid molecule comprises at least one sequence selected from the group consisting of SEQ ID NO:1, SEQ ID NO:2, SEQ ID NO:3 and SEQ ID NO:4;
   wherein the isolated nucleic acid molecule encodes the antibody of claim 1.

18. A method of identifying compounds suitable for active immunization of a patient predicted to develop Alzheimer's Disease comprising the steps of:
   a) exposing one or more compounds of interest to said antibody of claim 1 or said antibody of claim 2, for a time and under conditions sufficient for said one or more compounds to bind to said antibody of claim 1 or said antibody of claim 2; and
   b) identifying those compounds which bind to said isolated antibody of 1 or said antibody of claim 2, said identified compounds to be used in active immunization in a patient predicated to develop Alzheimer's Disease.

19. An isolated antibody produced by the hybridoma having ATCC deposit number PTA-7406 or PTA-7808.

* * * * *

```
                          SEQUENCE LISTING

<160> NUMBER OF SEQ ID NOS: 25

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
gatgtgcagc ttcaggagtc gggacctggc ctggtgaaac cttctcagtc tctgtccctc      60
acctgcactg tcgctggctc ctcaatcacc agtcattatg cctggaactg gatccggcag     120
tttccaggaa acaaactgga gtggatgggc tacatagact atagtggtag cactcgctac     180
ctcccctctc tcaaaagtcg aatctctatc actcgagaca catccaagaa ccagttcttc     240
ctgcagttga attctgtgac tactgaggac acagccacat attactgtgc aaggggtagt     300
ggttatttct atggtatgga ctactggggt caaggaacct cagtcaccgt ctcctca       357

<210> SEQ ID NO 2
<211> LENGTH: 324
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
gacatccaga tgaaccagtc tccatccagt ctgtctccat cccttggaga cacaattacc      60
atcacttgcc atgccagtca gaacattaat gtctggttaa gctggtacca gcagaaacca     120
ggaaatattc ctaaactatt gatctataag gcttccaact tgcacacagg cgtcccatca     180
aggtttagtg gcagtggatc tggaataggt tttacattaa ccatccgcag cctgcagcct     240
gaagacattg ccacttactt ctgtcaacag ggtcaaagtt atccgtacac gttcggaggg     300
gggactaagc tggaaataaa acgg                                             324

<210> SEQ ID NO 3
<211> LENGTH: 354
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
caggtccagc tgcagcagtc tggagctgag ctggtaaggc ctgggacttc agtgagggtg      60
tcctgcaagg cttctggata cgccttcact aattacttga tagagtgggt aaagcagagg     120
cctggacagg gccttgagtg gattggagtg attaatcctg gaagtggtga tactaactac     180
aatgagaatt tcaagggcaa ggcaacactg actgcagaca atcctccaga cactgcctac     240
atgcacctca gcagcctgac atctgatgac tctgcggtct atttctgtac aagaggcgtg     300
attacgacgg gttttgacta ctggggccaa ggcaccactc tcacaatctc ctca          354

<210> SEQ ID NO 4
```

<211> LENGTH: 324
<212> TYPE: DNA
<213> ORGANISM: Artificial Sequence
<220> FEATURE:
<223> OTHER INFORMATION: Description of Artificial Sequence: Synthetic construct

<400> SEQUENCE: 4

```
gacatccaga tgactcagtc tccagcctcc ctatctgcat ctgtgggaga aactgtcacc      60
atcacatgtc agcaagtgg gaatattcac aattatttag catggtatca gcagaaacag     120
ggaaaatctc ctcagctcct ggtctataat gcaaaaacct agcagatgg tgtgccatca     180
aggttcagtg gcagtggatc aggaacacaa tattctctca agatcaacag cctgcagcct     240
gaagattttg ggagttatta ctgtcaacat ttttggagta gtcctcggac gttcggtgga     300
ggcaccaagc tggaaatcaa acgg                                            324
```

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic construct

<400> SEQUENCE: 5

```
Asp Val Gln Leu Gln Glu Ser Gly Pro Gly Leu Val Lys Pro Ser Gln
1               5                   10                  15
Ser Leu Ser Leu Thr Cys Thr Val Ala Gly Ser Ser Ile Thr Ser His
            20                  25                  30
Tyr Ala Trp Asn Trp Ile Arg Gln Phe Pro Gly Asn Lys Leu Glu Trp
        35                  40                  45
Met Gly Tyr Ile Asp Tyr Ser Gly Ser Thr Arg Tyr Leu Pro Ser Leu
    50                  55                  60
Lys Ser Arg Ile Ser Ile Thr Arg Asp Thr Ser Lys Asn Gln Phe Phe
65                  70                  75                  80
Leu Gln Leu Asn Ser Val Thr Thr Glu Asp Thr Ala Thr Tyr Tyr Cys
                85                  90                  95
Ala Arg Gly Ser Gly Tyr Phe Tyr Gly Met Asp Tyr Trp Gly Gln Gly
            100                 105                 110
Thr Ser Val Thr Val Ser Ser
        115
```

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic construct

<400> SEQUENCE: 6

```
Asp Ile Gln Met Asn Gln Ser Pro Ser Ser Leu Ser Pro Ser Leu Gly
1               5                   10                  15
Asp Thr Ile Thr Ile Thr Cys His Ala Ser Gln Asn Ile Asn Val Trp
            20                  25                  30
Leu Ser Trp Tyr Gln Gln Lys Pro Gly Asn Ile Pro Lys Leu Leu Ile
        35                  40                  45
Tyr Lys Ala Ser Asn Leu His Thr Gly Val Pro Ser Arg Phe Ser Gly
    50                  55                  60
```

-continued

```
Ser Gly Ser Gly Ile Gly Phe Thr Leu Thr Ile Arg Ser Leu Gln Pro
 65                  70                  75                  80

Glu Asp Ile Ala Thr Tyr Phe Cys Gln Gln Gly Gln Ser Tyr Pro Tyr
                 85                  90                  95

Thr Phe Gly Gly Gly Thr Lys Leu Glu Ile Lys Arg
            100                 105

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Gln Val Gln Leu Gln Gln Ser Gly Ala Glu Leu Val Arg Pro Gly Thr
  1               5                  10                  15

Ser Val Arg Val Ser Cys Lys Ala Ser Gly Tyr Ala Phe Thr Asn Tyr
                 20                  25                  30

Leu Ile Glu Trp Val Lys Gln Arg Pro Gly Gln Gly Leu Glu Trp Ile
             35                  40                  45

Gly Val Ile Asn Pro Gly Ser Gly Asp Thr Asn Tyr Asn Glu Asn Phe
         50                  55                  60

Lys Gly Lys Ala Thr Leu Thr Ala Asp Lys Ser Ser Ser Thr Ala Tyr
 65                  70                  75                  80

Met His Leu Ser Ser Leu Thr Ser Asp Asp Ser Ala Val Tyr Phe Cys
                 85                  90                  95

Thr Arg Gly Val Ile Thr Thr Gly Phe Asp Tyr Trp Gly Gln Gly Thr
                100                 105                 110

Thr Leu Thr Ile Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Ile Gln Met Thr Gln Ser Pro Ala Ser Leu Ser Ala Ser Val Gly
  1               5                  10                  15

Glu Thr Val Thr Ile Thr Cys Arg Ala Ser Gly Asn Ile His Asn Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Asp Gly Val Pro Ser Arg Phe Ser Gly
         50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Ser Pro Arg
                 85                  90                  95

Thr Phe Gly Gly Gly Thr Lys Leu Glu Ile Lys Arg
            100                 105

<210> SEQ ID NO 9
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser His Tyr Ala Trp Asn
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ile Asp Tyr Ser Gly Ser Thr Arg Tyr Leu Pro Ser Leu Lys Ser
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Tyr Phe Tyr Gly Met Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ala Ser Gln Asn Ile Asn Val Trp Leu Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Asn Leu His Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Gly Gln Ser Tyr Pro Tyr Thr
```

```
<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Tyr Leu Ile Glu
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Ile Asn Pro Gly Ser Gly Asp Thr Asn Tyr Asn Glu Asn Phe Lys
1               5                   10                  15

Gly

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Val Ile Thr Thr Gly Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gly Asn Ile His Asn Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Ala Lys Thr Leu Ala Asp
1               5

<210> SEQ ID NO 20
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 20

Gln His Phe Trp Ser Ser Pro Arg Thr
1               5

<210> SEQ ID NO 21
<211> LENGTH: 43
<212> TYPE: PRT
<213> ORGANISM: Homo sapiens

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 22
<211> LENGTH: 42
<212> TYPE: PRT
<213> ORGANISM: Homo sapiens

<400> SEQUENCE: 22

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 23
<211> LENGTH: 40
<212> TYPE: PRT
<213> ORGANISM: Homo sapiens

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 24
<211> LENGTH: 31
<212> TYPE: PRT
<213> ORGANISM: Homo sapiens

<400> SEQUENCE: 24

Val His His Gln Lys Leu Val Phe Phe Ala Glu Asp Val Gly Ser Asn
1               5                   10                  15

Lys Gly Ala Ile Ile Gly Leu Met Val Gly Gly Val Val Ile Ala
            20                  25                  30

<210> SEQ ID NO 25
<211> LENGTH: 23
<212> TYPE: PRT
<213> ORGANISM: Homo sapiens
```

```
<400> SEQUENCE: 25

Phe Ala Glu Asp Val Gly Ser Asn Lys Gly Ala Ile Ile Gly Leu Met
1               5                   10                  15

Val Gly Gly Val Val Ile Ala
            20
```